United States Patent
Kluge et al.

(10) Patent No.: US 11,376,329 B2
(45) Date of Patent: *Jul. 5, 2022

(54) LOW MOLECULAR WEIGHT SILK COMPOSITIONS AND STABILIZING SILK COMPOSITIONS

(71) Applicant: Trustees of Tufts College, Medford, MA (US)

(72) Inventors: Jonathan A. Kluge, Southborough, MA (US); Fiorenzo G. Omenetto, Lexington, MA (US); David L. Kaplan, Concord, MA (US)

(73) Assignee: Trustees of Tufts College, Medford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/068,083

(22) Filed: Mar. 11, 2016

(65) Prior Publication Data

US 2016/0263228 A1    Sep. 15, 2016

Related U.S. Application Data

(63) Continuation of application No. 14/775,200, filed as application No. PCT/US2014/029636 on Mar. 14, 2014.

(60) Provisional application No. 61/792,161, filed on Mar. 15, 2013, provisional application No. 61/830,950, filed on Jun. 4, 2013, provisional application No. 61/883,737, filed on Sep. 27, 2013, provisional application No. 61/909,687, filed on Nov. 27, 2013.

(51) Int. Cl.
| | |
|---|---|
| *A61K 47/42* | (2017.01) |
| *A61K 9/19* | (2006.01) |
| *A61L 27/36* | (2006.01) |
| *C07K 14/435* | (2006.01) |
| *B01J 20/24* | (2006.01) |
| *C07H 21/02* | (2006.01) |
| *C07K 14/50* | (2006.01) |
| *A61K 9/08* | (2006.01) |
| *A61K 38/18* | (2006.01) |

(52) U.S. Cl.
CPC .............. *A61K 47/42* (2013.01); *A61K 9/08* (2013.01); *A61K 9/19* (2013.01); *A61K 38/1825* (2013.01); *A61L 27/3604* (2013.01); *B01J 20/24* (2013.01); *C07H 21/02* (2013.01); *C07K 14/43518* (2013.01); *C07K 14/43586* (2013.01); *C07K 14/503* (2013.01); *C07K 2319/00* (2013.01)

(58) Field of Classification Search
None
See application file for complete search history.

(56) References Cited

U.S. PATENT DOCUMENTS

| | | |
|---|---|---|
| 3,270,960 A | 9/1966 | Phillips |
| 3,773,919 A | 11/1973 | Boswell et al. |
| 3,832,253 A | 8/1974 | Di Palma et al. |
| 3,854,480 A | 12/1974 | Zaffaroni |
| 4,452,775 A | 6/1984 | Kent |
| 4,667,014 A | 5/1987 | Nestor, Jr. et al. |
| 4,675,189 A | 6/1987 | Kent et al. |
| 4,748,034 A | 5/1988 | de Rham |
| 4,806,355 A | 2/1989 | Goosen et al. |
| 5,015,476 A | 5/1991 | Cochrum et al. |
| 5,075,109 A | 12/1991 | Tice et al. |
| 5,093,489 A | 3/1992 | Diamantoglou |
| 5,133,974 A | 7/1992 | Paradissis et al. |
| 5,239,660 A | 8/1993 | Ooi |
| 5,245,012 A | 9/1993 | Lombari et al. |
| 5,263,992 A | 11/1993 | Guire |
| 5,270,419 A | 12/1993 | Domb |
| 5,407,686 A | 4/1995 | Patel et al. |
| 5,576,881 A | 11/1996 | Doerr et al. |
| 5,736,152 A | 4/1998 | Dunn |
| 5,902,800 A | 5/1999 | Green et al. |
| 5,932,462 A | 8/1999 | Harris et al. |
| 6,127,143 A | 10/2000 | Gunasekaran |

(Continued)

FOREIGN PATENT DOCUMENTS

| | | | |
|---|---|---|---|
| CN | 101445546 A | | 6/2009 |
| JP | 0200126247 | * | 9/2001 |

(Continued)

OTHER PUBLICATIONS

Wenk et al., J. Control. Rei., 2008, 132: 26-34.*
Marell et al., Biomaterials, online Oct. 6, 2011, 33: 102-108.*
Rockwood et al., Nature Protocols, 2011, 6: 1612-1631.*
Pritchard et al., Biomaterials, 2011, 32: 909-918.*
Nam et al., J. Appl. Polym. Sci., 2001, 81: 3008-3021.*

(Continued)

*Primary Examiner* — Ileana Popa
(74) *Attorney, Agent, or Firm* — Quarles & Brady, LLP

(57) ABSTRACT

The present disclosure provides certain silk-fibroin compositions with particular characteristics and/or properties. In some embodiments, the disclosure provides low molecular weight compositions. In some embodiments, the disclosure provides silk fibroin compositions that comprise an active (e.g., a biological) agent or component. In some embodiments, the disclosure provides low molecular weight silk fibroin compositions that comprise an active (e.g., a biological) agent or component. In some embodiments, an active agent is stabilized in a silk composition, e.g., for a period of time and/or against certain conditions or events. In some embodiments, a component present in a silk fibroin composition may be subject to analysis and/or characterization. In some embodiments, a component present in a silk fibroin composition may be recovered from the composition.

21 Claims, 32 Drawing Sheets

Specification includes a Sequence Listing.

(56) References Cited

U.S. PATENT DOCUMENTS

| | | |
|---|---|---|
| 6,245,537 B1 | 6/2001 | Williams et al. |
| 6,267,776 B1 | 7/2001 | O'Connell |
| 6,302,848 B1 | 10/2001 | Larson et al. |
| 6,310,188 B1 | 10/2001 | Mukherjee |
| 6,325,810 B1 | 12/2001 | Hamilton et al. |
| 6,337,198 B1 | 1/2002 | Levene et al. |
| 6,372,244 B1 | 4/2002 | Antanavich et al. |
| 6,379,690 B2 | 4/2002 | Blanchard et al. |
| 6,395,734 B1 | 5/2002 | Tang et al. |
| 7,842,780 B2 | 11/2010 | Kaplan et al. |
| 8,187,616 B2 | 5/2012 | Wang et al. |
| 8,206,774 B2 | 6/2012 | Kaplan et al. |
| 8,354,501 B2 | 1/2013 | Kaplan et al. |
| 2004/0219630 A1† | 11/2004 | Tsubouchi |
| 2004/0265260 A1 | 12/2004 | Tsubouchi et al. |
| 2007/0212730 A1 | 9/2007 | Vepari et al. |
| 2008/0085272 A1 | 4/2008 | Kaplan et al. |
| 2009/0232963 A1 | 9/2009 | Kaplan et al. |
| 2010/0028451 A1 | 2/2010 | Kaplan et al. |
| 2010/0178304 A1 | 7/2010 | Wang et al. |
| 2010/0279112 A1 | 11/2010 | Kaplan et al. |
| 2011/0046686 A1 | 2/2011 | Kaplan et al. |
| 2011/0171239 A1 | 7/2011 | Kaplan et al. |
| 2011/0305765 A1 | 12/2011 | Mathur et al. |
| 2012/0052124 A1 | 3/2012 | Kaplan et al. |
| 2012/0070427 A1 | 3/2012 | Kaplan et al. |
| 2012/0187591 A1 | 7/2012 | Wang et al. |
| 2014/0308362 A1 | 10/2014 | Bellas et al. |
| 2015/0183841 A1 | 7/2015 | Lo et al. |
| 2015/0273021 A1 | 10/2015 | Kaplan et al. |
| 2016/0046679 A1 | 2/2016 | Kluge et al. |
| 2016/0235889 A1 | 8/2016 | Lotta et al. |

FOREIGN PATENT DOCUMENTS

| | | |
|---|---|---|
| WO | WO-97/08315 A1 | 3/1997 |
| WO | WO-03/035124 A2 | 5/2003 |
| WO | WO-2004/000255 A1 | 12/2003 |
| WO | WO-2004/000915 A2 | 12/2003 |
| WO | WO-2004/062697 A2 | 7/2004 |
| WO | WO-2005/012606 A2 | 2/2005 |
| WO | WO-2005/123114 A2 | 12/2005 |
| WO | WO-2006/062685 A2 | 6/2006 |
| WO | WO-2006/076711 A2 | 7/2006 |
| WO | WO-2007/098951 A2 | 9/2007 |
| WO | WO-2008/118133 A2 | 10/2008 |
| WO | WO-2008/150861 A1 | 12/2008 |
| WO | WO-2009/023615 A1 | 2/2009 |
| WO | WO-2009/126689 A2 | 10/2009 |
| WO | WO-2010/036992 A2 | 4/2010 |
| WO | WO-2010/042798 A2 | 4/2010 |
| WO | WO-2010/057142 A2 | 5/2010 |
| WO | WO-2011/005381 A2 | 1/2011 |
| WO | WO-2011/006133 A2 | 1/2011 |
| WO | WO-2011/008842 A2 | 1/2011 |
| WO | WO-2011/011347 A2 | 1/2011 |
| WO | WO-2011/041395 A2 | 4/2011 |
| WO | WO-2011/063990 A2 | 6/2011 |
| WO | WO-2011/109691 A2 | 9/2011 |
| WO | WO-2011/130335 A2 | 10/2011 |
| WO | WO-2012/031144 A2 | 3/2012 |
| WO | WO-2012/145739 A1 | 10/2012 |
| WO | WO-2013/126799 A1 | 8/2013 |
| WO | WO-2013/142119 A1 | 9/2013 |
| WO | WO-2013/142611 A2 | 9/2013 |
| WO | WO-2013/152265 A1 | 10/2013 |
| WO | WO-2014/066884 A1 | 5/2014 |
| WO | WO-2014/145002 A2 | 9/2014 |
| WO | WO-2015/070108 A1 | 5/2015 |

OTHER PUBLICATIONS

Yoshimazu et al., J. Appl. Polym. Sci., 1990, 40: 127-134.*
Ha et al., Biomacromolecules, 2005, 6: 1722-1731.*
U.S. Appl. No. 61/613,185, filed Mar. 20, 2012, Kaplan et al.
U.S. Appl. No. 61/621,209, filed Apr. 6, 2012, Kaplan et al.
U.S. Appl. No. 61/719,146, filed Oct. 26, 2012, Kaplan et al.
U.S. Appl. No. 61/792,161, filed Mar. 15, 2013, Kluge et al.
U.S. Appl. No. 61/808,768, filed Apr. 5, 2013, Leisk et al.
U.S. Appl. No. 61/809,535, filed Apr. 8, 2013, Kaplan et al.
U.S. Appl. No. 61/830,950, filed Jun. 4, 2013, Kluge et al.
U.S. Appl. No. 61/881,653, filed Sep. 24, 2013, Kaplan et al.
U.S. Appl. No. 61/902,145, filed Nov. 8, 2013, Omenetto et al.
Acharya, C. et al., Performance evaluation of a silk protein-based matrix for the enzymatic conversion of tyrosine to $_l$-DOPA, Biotechnol. J., 3:226-233 (2008).
Adler, Am. Pharmaceutical Rev., pp. 1-9 (2012).
Altman, G.H. et al., Silk-based biomaterials, Biomaterials, 24(3):401-416 (2003).
Andreotti, M. et al., Correlation between HIV-1 viral load quantification in plasma, dried blood spots, and dried plasma spots using the Roche COBAS Taqman assay, J. Clin. Virol., 47(1):4-7 (2010).
Bayraktar, O. et al., Silk fibroin as a novel coating material for controlled release of theophylline, Eur. J. Pharm. Biopharm, 60:373-381 (2005).
Beaucage, S. L. and Iyer, R. P., The Functionalization of Oligonucleotides Via Phosphoramidite Derivatives, Tetrahedron Report No. 329, 49(10):1925-1963 (1993).
Burckbuchler, V. et al., Rheological and syringeability properties of highly concentrated human polyclonal immunoglobulin solutions, Eur. J. Pharm. Biopharm., 76(3):351-6 (2010).
Chang, M.K. et al., C-reactive protein binds to both oxidized LDL and apoptotic cells through recognition of a common ligand: Phosphorylcholine of oxidized phospholipids, Proc. Natl. Acad. Sci. U S A, 99(20): 13043-8 (2002).
Demura, M. and Asakura, T., Immobilization of glucose oxidase with Bombyx mori silk fibroin by only stretching treatment and its application to glucose sensor, Biotechnol. Bioeng., 33(5):598-603 (1989).
Dineva, M.A. et al., Sample preparation: a challenge in the development of point-of-care nucleic acid-based assays for resource-limited settings, Analyst, 132(12):1193-9 (2007).
Egholm, M. et al., Peptide Nucleic Acids (PNA). Oligonucleotide Analogues with an Achiral Peptide Backbone, J. Am. Chem. Soc. 114:1895-1897 (1992).
Egholm, M. et al., PNA hybridizes to complementary oligonucleotides obeying the Watson-Crick hydrogen-bonding rules, Nature, 365:566-568 (1993).
Extended European Search Report, Application No. 14763730.0, 8 pages, dated Sep. 16, 2016.
Guziewicz, N. et al., Lyophilized silk fibroin hydrogels for the sustained local delivery of therapeutic monoclonal antibodies, Biomaterials, 32(10):2642-50 (2011).
Hersel, U. et al., RGD modified polymers: biomaterials for stimulated cell adhesion and beyond, Biomaterials, 24(24):4385-415 (2003).
Hofmann, S. et al., Silk fibroin as an organic polymer for controlled drug delivery, Journal of Controlled Release, 111:219-227 (2006).
Hu, X. et al., Regulation of Silk Material Structure by Temperature-Controlled Water Vapor Annealing, Biomacromolecules, 12:1686-1696 (2011).
International Search Report for PCT/US2014/029636, 6 pages (dated Dec. 2, 2014).
Jin, I.J. et al., Water-Stable Silk Films with Reduced Beta-Sheet Content, Adv. Funct. Mater., 15:1241-1247 (2005).
Lee et al., A combination graft of low-molecular-weight silk fibroin with Choukroun platelet-rich fibrin for rabbit calvarial defect, Oral Surg Oral Med Oral Pathol Oral Radiol Endod, 109:e33-e38 (2010).
Letsinger, R.L. and Mungall, W.S., Phosphoramidate analogs of oligonucleotides, J. Org. Chem., 35(11):3800-3 (1970).
Li, M. et al., Study on Porous Silk Fibroin Materials. II. Preparation and Characteristics of Spongy Porous Silk Fibroin Materials, J. Applied Polymer Science, 79:2192-2199 (2001).
Lovett, M. et al., Gel spinning of silk tubes for tissue engineering, Biomaterials, 29(35):4650-4657 (2008).
Lu, Q. et al., Water-Insoluble Silk Films with Silk I Structure, Acta Biomaterials, 6(4):1380-1387 (2010).

(56) References Cited

OTHER PUBLICATIONS

Lu, S. et al., Stabilization of Enzymes in Silk Films, Biomacromolecules, 10:1032-1042 (2009).
Lucas F. et al., The silk fibroins, Advances in Protein Chemistry, 13:107-242 (1958).
Mandal, B. et al., High-strength silk protein scaffolds for bone repair, Proceedings of the National Academy of Sciences USA, 109(20):7699-7704 (2012).
Martínez-Subiela, S. and Cerón, J.J., Effects of hemolysis, lipemia, hyperbilirrubinemia, and anticoagulants in canine C-reactive protein, serum amyloid A, and ceruloplasmin assays, Can. Vet. J., 46(7):625-9 (2005).
Mei, J.V. et al., Use of filter paper for the collection and analysis of human whole blood specimens, J. Nutr., 131(5):1631S-6S (2001).
Meier, C. and Engels, J. W., Peptide Nucleic Acids (PNAs)—Unusual Properties of Nonionic Oligonucleotide Analogues, Angew. Chem. Int. Ed. Engl. 31(8):1008-1010 (1992).
Min, S. et al., Preparation and Characterization of Crosslinked Porous Silk Fibroin Gel, Sen'l Gakkaishi, 54(2):85-92 (1997).
Miyairi, S. and Sugiura, M., Properties of beta-Glucosidase Immobilized in Sericin Membrane, J. Ferment. Technol., 56(4):303-308 (1978).
Nazarov, R. et al., Porous 3-D scaffolds from regenerated silk fibroin, Biomacromolecules, 5(3):718-26 (2004).
Omenetto, F.G. and Kaplan, D.L., New Opportunities for an Ancient Material, Science, 329:528-531 (2010).
Palmer, D.S. et al., Characterization of factors affecting the stability of frozen heparinized plasma, Vox Sang., 65(4):258-70 (1993).
Pritchard, E. et al., Effect of Silk Protein Processing on Drug Delivery from Silk Films, Macromolecular Bioscience, 13:311-320 (2013).
Pritchard, E.M. and Kaplan, D.L., Silk fibroin biomaterials for controlled release drug delivery, Expert. Opin. Drug Deliv., 8(6):797-811 (2011).
Puren, A. et al., Laboratory operations, specimen processing, and handling for viral load testing and surveillance, J. Infect. Dis., 201 Suppl 1:S27-36 (2010).
Schaffner P. and Dard, M.M., Structure and function of RGD peptides involved in bone biology, Cell Mol Life Sci., 60:119-32 (2003).
Scott, C.T. et al., Personal medicine—the new banking crisis, Nat. Biotechnol., 30(2):141-7 (2012).
Scriver, C.C., A simple phenylalanine method for detecting phenylketonuria in large populations of newborn infants, by Robert Guthrie and Ada Susi, Pediatrics, 1963;32:318-343, Pediatrics, 102(1 Pt 2):236-7 (1998).
Sofia, S. et al., Functionalized silk-based biomaterials for bone formation, Journal of Biomedical Materials Research, 54(1): 139-148 (2001).
Takahashi, K. et al., Induction of Pluripotent Stem Cells from Adult Human Fibroblasts by Defined Factors, Cell, 131(5):861-872 (2007).
Urquhart, J. et al., Rate-Controlled Delivery Systems in Drug and Hormone Research, Ann. Re. Pharmacol. Toxicol., 24:199-236 (1984).
Vepari, C. and Kaplan, D.L., Silk as a Biomaterial, Prog. Polym. Sci., 32(8-9):991-1007 (2007).
Warren, L. et al., Highly efficient reprogramming to pluripotency and directed differentiation of human cells with synthetic modified mRNA, Cell Stem Cell, 7(5):618-30 (2010).
Wenk, E. et al., Silk fibroin spheres as a platform for controlled drug delivery, J. Control. Release, 24;132(1):26-34 (2008).
Written Opinion for PCT/US2014/029636, 10 pages (dated Dec. 2, 2014).
Yu, J. et al., Induced Pluripotent Stem Cell Lines Derived from Human Somatic Cells, Science 318:1917-1920 (2007).
Zhang, J. et al., Stabilization of vaccines and antibiotics in silk and eliminating the cold chain, Proc. Natl. Acad. Sci. USA, 109(30):11981-6 (2012).
Erickson, H. P., Size and Shape of Protein Molecules at the Nanometer Level Determined by Sedimentation, Gel Filtration, and Electron Microscopy, Schulin Li (ed.), Biological Procedures Online, 11(1): 32-51 (2009).
Wenk, E. et al, Microporous silk fibroin scaffolds embedding PLGA microparticles for controlled growth factor delivery in tissue engineering, Biomaterials, 30(13): 2571-81 (2009).
Zhang, Y-Q. et al, Synthesis, characterization and immunogenicity of silk-fibroin-L-asparaginase bioconjugates, Journal of Biotechnology, 120: 315-326 (2005).
Roy, I. and Gupta, M. N., Freeze-drying of proteins: some emerging concerns, Biotechnol. Appl. Biochem., 39: 165-177 (2004).

\* cited by examiner
† cited by third party

Silk Protein-Based Stabilization for Diagnostics

J.A. Kluge, F.G. Omenetto, D.L. Kaplan
Dept. Biomedical Engineering, Tufts University, Medford, MA 02155

Introduction

- Stabilization of biologic specimens for critical for
  i) population monitoring [1]
  ii) out-patient disease screening [2] and
  iii) data informatics for personalized medicine [3]
  it remains an important unmet challenge, one that is central to a variety of global health initiatives and one that could impact our ability to monitor the health status of deployed armed forces.

- Current stabilization of fluid-laden cellular elements and labile biomolecules for diagnostics requires a cold-storage condition.

- To address these challenges, a silk fibroin solid matrix material has been optimized for use in diagnostic biospecimen stabilization. Silk fibroin can be processed into a variety of material formats [4], it is mechanically robust [5], and can be used to stabilize a number of labile molecules [6].
  A New Silk Fibroin Solid Matrix

- We recently demonstrated that silk fibroin biopolymer is compatible with many factors found in blood [7]. This matrix has been further optimized to store and recover:
  i) whole blood and plasma proteins
  ii) nucleic acids Silk fibroin matrix mixed with human blood → Long term storage and on-demand resolubilization

FIG. 30A

Material and Methods

Blood Stabilization

Blood Drawing: Heparinized venous blood was freshly drawn from de-identified patients. (Research Blood Components Brighton, MA). Upon delivery, plasma was immediately isolated 1000xg. Blood and plasma solid weight fractions were calculated by measuring the residual weight of air-dryed aliquots.

Silk Film Matrix Preparation: Purified silk solutions [4] were mixed with fresh blood or isolated plasma by gentle pipetting. Samples were cast onto polydimethylsiloxane (PDMS) platforms and left to air dry at room temperature (25°C) for 6 hours. Dry samples were either analyzed for day 0 measurements or stored at room temperature and 37°C for comparisons against frozen plasma aliquots.

Blood Coupon Analysis: Blood and plasma coupons were punched out (5mm dia.) loaded (40mg total) into 2mL conical tubes mixed with 2mL of 2x phosphate buffered saline (PBS), and vortexed for 15 seconds, resulting in a homogeneous solution as shown below. All samples were then immunoassayed for a variety of cardiovascular disease (CVD) biomarkers, either by standard ELISA or LUMINEX™ multiplexed assays.

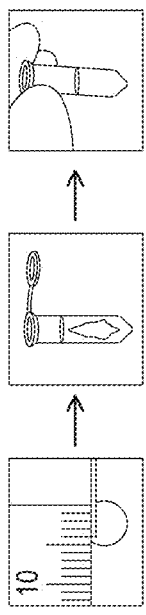

DNA/RNA Stabilization

Samples: Human genomic DNA and whole tissue RNA (Zyogen) were used for long term stability studies and GFP mRNA (Stemgent) used for transfection [8]. Stock solutions were diluted in purified silk solutions as above. Silk samples were either lyophilized following a 2-day protocol [9] or control samples were frozen at -80C.

DNA/RNA Analysis: Following lyophilization and storage, (RT, 37C, 60C) each sample was solubilized with UPW. The recovered DNA or RNA samples were mixed with 2 µL of 6X loading dye (Novagen) prior to loading into a 0.8% agarose gel for DNA samples and a 1% agarose gel for RNA samples.
RNA was analyzed using a SuperScript® III Platinum® One-Step qRT-PCR Kit (Invitrogen) and primers for GAPDH (FAM™/MGB Probe, Non-Primer Limited, Invitrogen), following manufacturer's instruction The qRT-PCR was performed on a Stratagene Mx3000P QPCR System.

FIG. 30C

Commercial Applications & Stage of Development

Proofs of Principle:
- Silk fibroin solid matrix was able to store blood samples across multiple patient samples.
  i) Both ELISA and Luminex™ immuno-based analytics were compatible
  ii) In some cases, silk stabilization outperformed frozen control benchmark
- Lyophilized silks protect both purified RNA and DNA from thermally-induced degradation
- mRNA recovered from silk remains bioactive

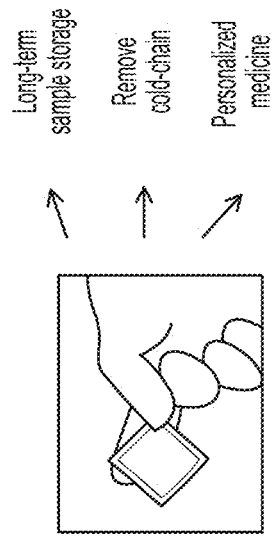

→ Long-term sample storage
→ Remove cold-chain
→ Personalized medicine

References and Acknowledgements

[1] Yang+ J.Clin. Microbiol. 2010 [2] Adam+ Clin Biochem. 2011 [3] Scott+ Nat. Biotech. 2012 [4] Rockwood+Nat. Protoc. 2011 [5] Jin+Nature 2003 [6] Pritchard+ Biopolymers 2012 [7] Seib+ Biomat. 2012 [8] Warren+ Cell Stem Cell 2010 [9] Guziewicz+ Biomat. 2011.

The work was supported by the National Institutes of Health (P41EB002520) and by the Defence Advanced Research Projects Agency (DARPA) under the program SB 112-005 (*Improved Dried Biological Specimen Materials, Recovery and Processing for Diagnostics*). Thanks to J. Curcuru and A. Tai for help in Luminex assay workup at the Tufts Clinical Translational Science institute.

FIG. 30D

LOW MOLECULAR WEIGHT SILK COMPOSITIONS AND STABILIZING SILK COMPOSITIONS

CROSS-REFERENCE TO RELATED APPLICATIONS

This application claims priority to U.S. patent application Ser. No. 14/775,200, filed on Sep. 11, 2015, which is a U.S. national phase application under 35 U.S.C. § 371 of international PCT application no. PCT/US14/29636, filed on Mar. 14, 2014, which claims the benefit of and priority to U.S. Provisional Application No. 61/909,687, filed on Nov. 27, 2013; 61/883,732, filed on Sep. 27, 2013; 61/830,950, filed on Jun. 4, 2013; and 61/792,161, filed on Mar. 15, 2013. The disclosures of each of these applications is hereby incorporated by reference.

GOVERNMENT SUPPORT

This invention was made with government support under grant no. SB 112-005 awarded by DARPA and grant no. P41 EB002520 awarded by NIH. The government has certain rights in the invention.

SEQUENCE LISTING

The instant application contains a Sequence Listing which has been submitted electronically in ASCII format and is hereby incorporated by reference in its entirety. Said ASCII copy, created on Oct. 13, 2015, is named "2016-05-27 Sequence Listing as originally filed in 2002458-0623.txt" and is 21,880 bytes in size.

BACKGROUND

Stabilization and subsequent recovery of active agents and/or biological samples is a critical feature of many applications, because the active agents and/or biological samples are usually labile and sensitive to changes in surrounding conditions, e.g., temperature, humidity and/or light. Even if an active agent or a biological sample is identified to be useful for a given reaction, its application is often hampered by a lack of long-term stability under process conditions.

Various methods to stabilize active agents (e.g., enzymes, therapeutic proteins including vaccines and/or biological samples (e.g., blood and/or blood components) have been utilized or studied, including cold-chain storage, lyophilization, covalent immobilization, and cellulose-based technologies. However, all these methods suffer drawbacks such as intense energy requirement, or poor recovery of active agents and/or biological samples. These drawbacks further limit the options in on-demand or point-of-care applications. Accordingly, there is a need for improved technologies and/or products or a new material that can stabilize active agents and/or biological samples (e.g., at ambient conditions) and permit recovery of various analytes in sufficient amounts from the stabilized samples for treatment, diagnostics, detection and/or analyses.

SUMMARY

The present disclosure provides certain silk fibroin compositions with novel and/or unexpected structural and/or functional characteristics and/or properties. The present disclosure provides methods of making and/or using such compositions, as well as articles comprised of or from them. In some embodiments, provided compositions include an active (e.g., biological) agent or component. In some embodiments, the active agent or component is stabilized in the composition as compared with otherwise comparable conditions, for example lacking the silk fibroin and/or particular of the structural and/or functional characteristics and/or properties.

Among other things, embodiments of various aspects described herein stem from the discovery that low molecular weight silk fibroin-based silk materials provide unique material properties suitable for a number of applications. As described in detail below, low molecular weight silk fibroin compositions described herein provide certain material characteristics that are distinct from or improved as compared to conventional silk fibroin-based materials. Accordingly, in one aspect, provided herein is a low molecular weight silk fibroin composition comprising a population of silk fibroin fragments having a range of molecular weights, characterized in that: no more than 15% of the total number of silk fibroin fragments in the population has a molecular weight exceeding 200 kDa, and at least 50% of the total number of the silk fibroin fragments in the population has a molecular weight within a specified range, wherein the specified range is between about 3.5 kDa and about 120 kDa, or between about 5 kDa and about 125 kDa.

Stated another way, a low molecular weight silk fibroin composition described herein can comprise a population of silk fibroin fragments having a range of molecular weights, characterized in that: no more than 15% of the total moles of silk fibroin fragments in the population has a molecular weight exceeding 200 kDa, and at least 50% of the total moles of the silk fibroin fragments in the population has a molecular weight within a specified range, wherein the specified range is between about 3.5 kDa and about 120 kDa, or between about 5 kDa and about 125 kDa.

The low molecular weight silk fibroin composition can be present in various forms. In some embodiments, the low molecular weight silk fibroin composition is an aqueous solution. The inventors have surprisingly discovered inter alia, that an agent (e.g., but not limited to, proteins, nucleic acids such as DNA, RNA and/or modifications thereof, therapeutic agents, vaccines) or a sample (e.g., a biological sample) incorporated or mixed with a low molecular weight silk fibroin solution described herein can be stabilized for a period of time under a wide range of temperatures. In some embodiments, the agent or sample incorporated or mixed with a low molecular silk fibroin solution can be stabilized for a period of time, e.g., at least 24 hours or longer, under any of a variety of conditions, including, for example an ambient condition (e.g., at room temperature) and/or an elevated temperature condition (e.g., 60° C.).

In some embodiments, the low molecular weight silk fibroin composition can be in a solid state form, e.g., a silk fibroin article. Examples of a silk fibroin article can include, but are not limited to, a film, a sheet, a gel or hydrogel, a mesh, a mat, a non-woven mat, a fabric, a scaffold, a tube, a slab or block, a fiber, a particle, a powder, a 3-dimensional construct, an implant, a foam or a sponge, a needle, a lyophilized article, and any combinations thereof. In some embodiments, the silk fibroin articles can be bioresorbable implants, tissue scaffolds, sutures, reinforcement materials, medical devices, coatings, construction materials, wound dressing, tissue sealants, fabrics, textile products, and any combinations thereof.

In some embodiments, the low molecular weight silk fibroin article is readily reconstituted into a low molecular weight silk fibroin solution for further processing. In some embodiments, the low molecular weight silk fibroin article described herein can have a solubility of at least 5% or more in an aqueous solution. That is, at least 5% or more of the total weight or volume of the low molecular weight silk fibroin article can dissolve or reconstitute in an aqueous solution. In some embodiments, the low molecular weight silk fibroin article described herein can have a solubility of more than 5% or higher, including, e.g., at least 10%, at least 20%, at least 30%, at least 40%, at least 50%, at least 60%, at least 70%, at least 80%, at least 90%, at least 95% or more, in an aqueous solution. In some embodiments, the low molecular weight silk fibroin article described herein can be soluble or reconstituted at room temperature. In some embodiments, the low molecular weight silk fibroin article described herein can be soluble or reconstituted in water such as deionized water at room temperature. In some embodiments, the low molecular weight silk fibroin article can be used in on-demand applications.

In some embodiments, the low molecular silk fibroin article described herein can have enhanced solubility in an aqueous solution relative to a reference silk fibroin composition (e.g., a conventional silk-fibroin based material). In some embodiments, the solubility of the low molecular silk fibroin article in an aqueous solution can be enhanced by at least about 5% or more, as compared to the solubility of a reference silk fibroin composition. For example, the solubility of the low molecular silk fibroin article in an aqueous solution can be enhanced by more than 5% or higher, including, e.g., at least about 10%, at least about 20%, at least about 30%, at least about 40%, at least about 50%, at least about 60%, at least about 70%, at least about 80%, at least about 90%, at least about 95% or more, as compared to the solubility of a reference silk fibroin composition. In some embodiments, the solubility of the low molecular silk fibroin article in an aqueous solution can be enhanced by at least about 1.1-fold or more, as compared to the solubility of a reference silk fibroin composition. For example, the solubility of the low molecular silk fibroin article in an aqueous solution can be enhanced by more than 1.1-fold or higher, including, e.g., at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold or higher, as compared to the solubility of a reference silk fibroin composition. In some embodiments, the aqueous solution can be water. In some embodiments, the aqueous solution can be a buffered solution, e.g., but not limited to a phosphate buffered solution.

In some embodiments, the low molecular silk fibroin article described herein can be used to entrap at least one agent or a sample (e.g., a biological sample) therein for stabilization of the agent or sample and subsequent recovery thereof. In some embodiments, a partial or original loading of the agent or sample can be recovered from at least a portion or an aliquot of the low molecular silk fibroin article by dissolving the portion or aliquot of the low molecular silk fibroin article in an aqueous solution. In some embodiments, the portion or aliquot of the low molecular silk fibroin article can be dissolved in an aqueous solution (e.g., but not limited to water such as deionized water or a buffered solution) at room temperature. In some embodiments, an active agent or a sample (e.g., a biological sample) entrapped in a low molecular silk fibroin article described herein can have a recovery of at least 5% or more in an aqueous solution. That is, at least 5% or more of the original loading of the active agent or sample can be recovered from the low molecular silk fibroin article in a solution or liquid form. In some embodiments, an active agent or a sample (e.g., a biological sample) entrapped in a low molecular silk fibroin article described herein can have a recovery of more than 5% or higher, including, e.g., at least 10%, at least 20%, at least 30%, at least 40%, at least 50%, at least 60%, at least 70%, at least 80%, at least 90%, at least 95% or more, in an aqueous solution.

In some embodiments, the low molecular silk fibroin article can provide enhanced recovery of the agent or sample entrapped therein, relative to recovery of the agent or sample entrapped in a reference silk fibroin composition. In some embodiments, recovery of an agent or a sample entrapped in the low molecular silk fibroin article can be enhanced by at least about 5% or more, as compared to recovery of the agent or sample entrapped in a reference silk fibroin composition. For example, recovery of an agent or a sample entrapped in the low molecular silk fibroin article can be enhanced by more than 5% or higher, including, e.g., at least about 10%, at least about 20%, at least about 30%, at least about 40%, at least about 50%, at least about 60%, at least about 70%, at least about 80%, at least about 90%, at least about 95% or more, as compared to recovery of the agent or sample entrapped in a reference silk fibroin composition. In some embodiments, recovery of an agent or a sample entrapped in the low molecular silk fibroin article can be enhanced by at least about 1.1-fold or more, as compared to recovery of the agent or sample entrapped in a reference silk fibroin composition. For example, recovery of an agent or a sample entrapped in the low molecular silk fibroin article can be enhanced by more than 1.1-fold or higher, including, e.g., at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold or higher, as compared to recovery of the agent or sample entrapped in a reference silk fibroin composition. In some embodiments, the aqueous solution can be a buffered solution, e.g., but not limited to a phosphate buffered solution. In some embodiments, the use of a buffered solution (e.g., but not limited to a phosphate buffered solution) to reconstitute a low molecular weight silk fibroin article described herein can improve recovery of an active agent or a sample incorporated in the low molecular weight silk fibroin article, as compared to use of a non-buffered solution (e.g., water).

In various embodiments of different aspects described herein, a reference silk fibroin composition can be a composition or mixture produced by degumming silk cocoon at an atmospheric boiling temperature for about 60 minutes or less, e.g., less than 60 minutes, less than 50 minutes, less than 40 minutes, less than 30 minutes, less than 20 minutes, less than 10 minutes or shorter. In one embodiment, a reference silk fibroin composition can be a composition or mixture produced by degumming silk cocoon at an atmospheric boiling temperature in an aqueous sodium carbonate solution for about 60 minutes or less, e.g., less than 60 minutes, less than 50 minutes, less than 40 minutes, less than 30 minutes, less than 20 minutes, less than 10 minutes or shorter.

Another aspect provided herein relates to a shelf-stable composition comprising a silk fibroin article, wherein the silk fibroin article comprises one or more embodiments of the low molecular silk fibroin composition described herein. In some embodiments, the shelf-stable composition is shelf-stable in that material properties of the silk fibroin article remain stable for at least one month or longer. In some embodiments, the shelf-stable composition can comprise the low molecular weight silk fibroin composition present in a form of particles, including powder.

In general, the present disclosure encompasses the recognition that certain silk fibroin compositions are particularly useful for the incorporation of active (e.g., biological) and/or labile entities. In some embodiments, silk compositions are provided that include an active and/or labile agent, such as a biological sample or component thereof. In some embodiments, provided silk compositions (including, for example, low molecular weight silk fibroin compositions) stabilize active and/or labile agents (e.g., stabilize biological samples or components thereof).

While the low molecular weight silk fibroin particles including powder can be produced by any art-recognized methods, in some embodiments, the low molecular weight silk fibroin particles can be produced by a process comprising subjecting a low molecular weight silk fibroin solution to lyophilization, thereby forming a lyophilized low molecular weight silk fibroin material or particles. In some embodiments, the lyophilized low molecular weight silk fibroin material or particles can be further reduced to smaller particles. In one embodiment, the lyophilized low molecular weight silk fibroin material or particles can be further milled to produce smaller particles or powder. Accordingly, another aspect provided herein is a shelf-stable reagent comprising low molecular weight silk fibroin powder. In some embodiments, the low molecular weight silk fibroin powder can be lyophilized powder. The shelf-stable reagent can be provided as part of a kit or in a container, e.g., a vial, a syringe, or a sample collection container, e.g., a blood collection container, or a multi-well plate.

Various embodiments described herein provide for a storage-stable composition comprising one or more embodiments of the low molecular weight silk fibroin composition described herein and an agent desired to be stabilized, wherein the agent is associated with or incorporated in the low molecular weight silk fibroin composition. In some embodiments, the agent desired to be stabilized can be an active agent. For example, in some embodiments, proteins, peptides, nucleic acid molecules, and/or modified nucleic acid molecules can be stabilized in the low molecular weight silk fibroin compositions. In some embodiments, the agent desired to be stabilized can be a therapeutic agent. In some embodiments, the agent desired to be stabilized can be a diagnostic marker for a disease or disorder. In some embodiments, the agent desired to be stabilized can be a sample to be assayed for one or more components present in the sample. In some embodiments, the sample can be a biological sample.

Yet another aspect provided herein relates to a silk fibroin article comprising one or more embodiments of the low molecular weight silk fibroin composition described herein and a substrate. The low molecular weight silk fibroin composition can be dispersed in the substrate, deposited on the substrate, or a combination thereof.

Another aspect provided herein is a method of forming a silk fibroin solution comprising dissolving in a liquid one or more embodiments of the low molecular weight silk fibroin composition described herein, wherein the silk fibroin solution is a homogenous solution. In one embodiment, the liquid is water, e.g., but not limited to deionized water. As used herein, the term "homogenous solution" generally refers to a solution having a uniform appearance or composition throughout the solution. For example, the size of the silk fibroin fragments or particles in a homogenous silk fibroin solution is generally too small to be seen or detected, e.g., by naked eyes. Stated another way, a homogenous silk fibroin solution is substantially free of silk fibroin aggregates (e.g., insoluble silk fibroin fragments, silk fibroin particles and/or clusters). Examples of the silk fibroin aggregates can include, but are not limited to, full-length silk fibroin molecules, larger silk fibroin fragments, silk fibroin particles or clusters formed by assembly or aggregation of smaller silk fibroin fragments, and any combinations thereof).

Another aspect provided herein relates to methods of stabilizing an agent over a period of time under certain conditions in one or more embodiments of the silk fibroin composition described herein. In some embodiments, the agent can be stabilized under ambient conditions.

A further aspect provided herein is a method of recovering at least one active agent comprising: (a) providing one or more embodiments of the low molecular weight silk fibroin composition described herein, one or more embodiments of the shelf-stable composition described herein, or one or more embodiments of the storage-stable composition described herein, wherein the at least one active agent is stabilized in the composition; and (b) dissolving at least a portion of the composition in water, thereby forming a sample solution comprising silk fibroin and a detectable or measurable amount of the at least one active agent.

Yet another aspect provided herein is a method of modulating at least one property of a silk fibroin composition comprising varying, in the silk fibroin composition, a weight ratio of silk fibroin fragments in the composition having a molecular weight exceeding 200 kDa to silk fibroin fragments in the composition having a molecular weight within a specified range, wherein the specified range is between about 3.5 kDa and about 120 kDa, or between about 5 kDa and about 125 kDa.

A still another aspect provided herein is a method of controlling the size of a silk fibroin particle comprising two steps: (a) varying, in a silk fibroin solution, a weight ratio of silk fibroin fragments in the solution having a molecular weight exceeding 200 kDa to silk fibroin fragments in the solution having a molecular weight within a specified range, wherein the specified range is between about 3.5 kDa and about 120 kDa, or between about 5 kDa and about 125 kDa; and (b) forming the silk fibroin particle from the silk fibroin solution.

Silk fibroin is an example of polypeptides having a portion or portions of an amino acid sequence that can adopt beta-sheet secondary structure. For example, silk fibroin structure generally comprises a sequence of amino acids, in which a portion or portions of the sequence are generally characterized by alternating glycine and alanine, or alanine alone. Without wishing to be bound by theory, such configuration allows fibroin molecules to self-assemble into a beta-sheet conformation. Accordingly, in yet another aspect, provided herein is a composition comprising a population of polypeptide fragments having a portion or portions of an amino acid sequence that is characterized by alternating glycine and alanine or alanine alone, and having a range of molecular weights ranging between about 3.5 kDa and about 120 kDa or between about 5 kDa and about 125 kDa. In some embodiments, the compositions is characterized in that: no more than 15% of the total number of polypeptide fragments in the population has a molecular weight exceeding 200 kDa, and at least 50% of the total number of the polypeptide fragments in the population has a molecular weight within a specified range, wherein the specified range is between about 3.5 kDa and about 120 kDa, or between about 5 kDa and about 125 kDa.

In another aspect, the silk fibroin in the compositions and/or methods described herein can be replaced with or used in combination with other non-silk polypeptides comprising a beta sheet structure or having a propensity for forming such a structure based on the amino acid sequence. Thus, provided herein also include polypeptide compositions comprising a population of beta-sheet forming polypeptide fragments. In some embodiments, the population of beta-sheet forming polypeptide fragments described herein can have a range of molecular weights, characterized in that: no more than 15% of the total number of the beta-sheet forming polypeptide fragments in the population has a molecular weight exceeding 200 kDa, and at least 50% of the total number of the beta-sheet forming polypeptide fragments in the population has a molecular weight within a specified range, wherein the specified range is between about 3.5 kDa and about 120 kDa or between about 5 kDa and about 125 kDa.

As used herein, the term "beta-sheet forming polypeptide" refers to a polypeptide having a portion or portions of an amino acid sequence that adopt the beta-sheet secondary structure. In some embodiments, the beta-sheet forming polypeptides can be selected on the basis of having a beta sheet structure or a propensity for forming such a structure based on the amino acid sequence.

In some embodiments, the beta-sheet forming polypeptides can have an amphiphilic nature (i.e., having both hydrophilic and hydrophobic properties and/or portions). The amphiphilic polypeptide can be obtained from a single source (e.g., naturally occurring proteins) and contain both a hydrophobic module or stretch and a hydrophilic module or stretch within the polypeptide, such that the single polypeptide itself is naturally amphiphilic. In some embodiments, a hydrophobic module or stretch and a hydrophilic module or stretch can be fused or coupled together to form an amphiphilic entity. Such "fusion" or "chimeric" polypeptides can be produced using recombinant techniques, chemical coupling, or both.

In some embodiments, the beta-sheet forming polypeptides can comprise a portion or portions of an amino acid sequence of polypeptides selected from the following list: fibroins, actins, collagens, catenins, claudins, coilins, elastins, elaunins, extensins, fibrillins, lamins, laminins, keratins, tublins, viral structural proteins, zein proteins (seed storage protein) and any combinations thereof.

In some embodiments, the beta-sheet forming polypeptides can comprise a regenerated (e.g., purified) protein from natural sources, recombinant proteins produced in heterologous systems, synthetic or chemically produced peptides, or combination of these.

In some embodiments, the beta-sheet forming polypeptides can comprise a portion or portions of an amino acid sequence of polypeptides corresponding to any one of the list provided above, with or without one or more sequence variations, as compared to the native or wild type counterpart. For example, in some embodiments, such variants may show at least 85% overall sequence identity as compared to a wild type sequence, e.g., at least 86%, 87%, 88%, 89%, 90%, 91%, 92%, 93%, 94%, 95%, 96%, 97%, 98%, 99% overall sequence identity

BRIEF DESCRIPTION OF THE DRAWING

This patent or application file contains at least one drawing executed in color. Copies of this patent or patent application publication with color drawing (s) will be provided by the Office upon request and payment of the necessary fee.

FIG. 2A shows a representative image of SDS-PAGE analysis for silk degummed for 10, 20, 30, 60 minutes, or 60 minutes autoclaved. FIG. 2B shows representative densiometric image analysis performed on an electrophoresis gel. The raw pixel intensity is plotted as a function of molecular weight. The percentage of each molecular weight band can be calculated by dividing the summed intensity of the specific molecular weight band by the total summed intensity of all the molecular weight bands.

FIGS. 6A and 6C show the w/v % for various boiling times and mass loadings. The dotted line indicates the maximum w/v % concentration possible based on complete theoretical solubility (2, 4, and 8%, respectively). FIGS. 6B and 6D show the molecular weight of the corresponding solutions used for lyophilzation, in which 7.5 µg of protein in solution was run under reducing conditions on a NuPAGE® Novex® 3-8% Tris-Acetate Gel (Invitrogen), using a HiMark™ Pre-Stained Protein Standard (range 30-460 kDa, Invitrogen). FIG. 6E presents data in FIGS. 6A and 6C in a different format, showing the reconstituted silk fibroin solution concentrations (mg/mL) and the percentage of solubility.

FIGS. 11A and 11B show fibrinogen recovery from (11A) silk-plasma films and (11B) silk-blood films. FIGS. 11C and 11D show C-reactive protein (CRP) recovery from (11C) silk-plasma films and (11D) silk-blood films.

In FIG. 13B, the signals from the 60 MB group are a result of a whitish coloration in the samples, giving a false positive for gelation in the absorbance readings, but these samples did not gel. FIG. 13 shows that none of the autoclaved samples gelled after a week, and none of the 60 MB groups gelled after a week.

FIGS. 30A-30D Present a summary of an embodiment of silk protein-based stabilization for diagnostics as described herein.

CERTAIN DEFINITIONS

Figure 1:
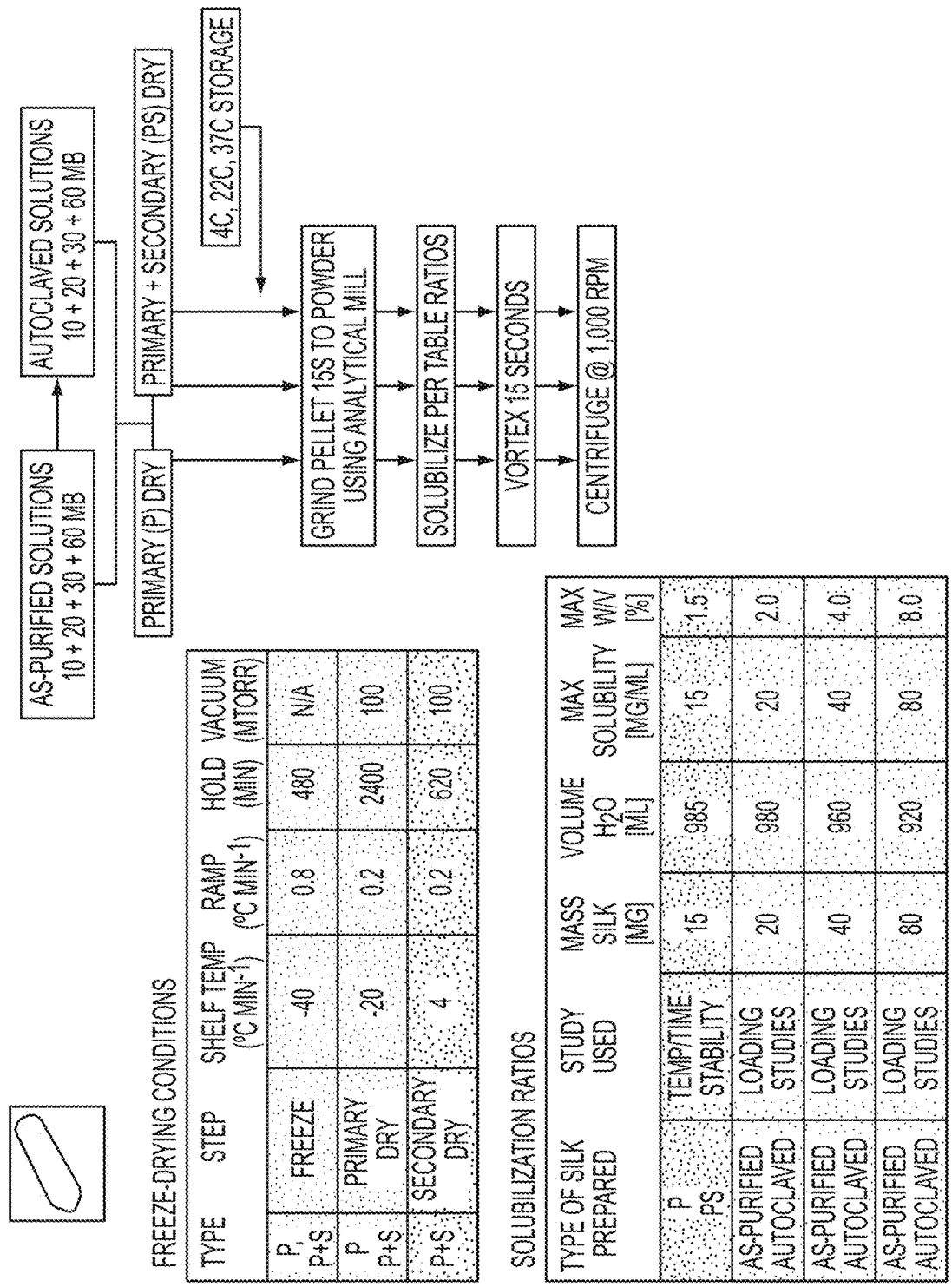
FIG. 1 shows the process flow diagram for solubility studies of silk degummed for 10, 20, 30, or 60 minutes. The freeze-drying conditions and solubilization ratios are also provided.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

A: The singular terms "a," "an," and "the" include plural referents unless context clearly indicates otherwise. Similarly, the word "or" is intended to include "and" unless the context clearly indicates otherwise.

About: Other than in the operating examples, or where otherwise indicated, all numbers expressing quantities of ingredients or reaction conditions used herein should be understood as modified in all instances by the term "about." The term "about" when used in connection with percentages may mean±5% of the value being referred to. For example, about 100 means from 95 to 105.

Ambient: As used herein, an "ambient" condition is the surrounding condition without active cooling, heating, etc. Typically, the term refers to room temperature, which generally describes common indoor temperatures, often between 20-25° C. (68-77° F.). In some embodiments, ambient temperatures are between 0° C. and 60° C., between 0° C. and 50° C., or between 0° C. and 40° C. In some embodiments, the ambient temperature is the fridge temperature (e.g., between 0 C and 15 C, inclusive). In some embodiments, the ambient temperature is the room temperature, e.g., between 20° C. and 35° C., and it can vary with geographical conditions. For example, the room temperature in warm-climate regions, e.g., Africa, can be generally warmer than that in cool-climate regions, e.g., the United States or United Kingdom. In some embodiments, the storage temperature can be at least about 37° C. or greater than 37° C.

Antigens: As used herein, the term "antigens" refers to a molecule or a portion of a molecule capable of being bound by a selective binding agent, such as an antibody, and additionally capable of being used in an animal to elicit the production of antibodies capable of binding to an epitope of that antigen. An antigen may have one or more epitopes. The term "antigen" can also refer to a molecule capable of being bound by an antibody or a T cell receptor (TCR) if presented by MEW molecules. The term "antigen", as used herein, also encompasses T-cell epitopes. An antigen is additionally capable of being recognized by the immune system and/or being capable of inducing a humoral immune response and/or cellular immune response leading to the activation of B- and/or T-lymphocytes. This may, however, require that, at least in certain cases, the antigen contains or is linked to a Th cell epitope and is given in adjuvant. An antigen can have one or more epitopes (B- and T-epitopes). The specific reaction referred to above is meant to indicate that the antigen will preferably react, typically in a highly selective manner, with its corresponding antibody or TCR and not with the multitude of other antibodies or TCRs which may be evoked by other antigens. Antigens as used herein may also be mixtures of several individual antigens.

Bioactivity: The term "bioactivity," as used herein in reference to an active agent, generally refers to the ability of an active agent to interact with a biological target and/or to produce an effect on a biological target. For example, bioactivity can include, without limitation, elicitation of a stimulatory, inhibitory, regulatory, toxic or lethal response in a biological target. The biological target can be a molecule or a cell. For example, a bioactivity can refer to the ability of an active agent to modulate the effect/activity of an enzyme, block a receptor, stimulate a receptor, modulate the expression level of one or more genes, modulate cell proliferation, modulate cell division, modulate cell morphology, or any combination thereof. In some instances, a bioactivity can refer to the ability of a compound to produce a toxic effect in a cell. Exemplary cellular responses include, but are not limited to, lysis, apoptosis, growth inhibition, and growth promotion; production, secretion, and surface expression of a protein or other molecule of interest by the cell; membrane surface molecule activation including receptor activation; transmembrane ion transports; transcriptional regulations; changes in viability of the cell; changes in cell morphology; changes in presence or expression of an intracellular component of the cell; changes in gene expression or transcripts; changes in the activity of an enzyme produced within the cell; and changes in the presence or expression of a ligand and/or receptor (e.g., protein expression and/or binding activity). Methods for assaying different cellular responses are well known to one of skill in the art, e.g., western blot for determining changes in presence or expression of an endogenous protein of the cell, or microscopy for monitoring the cell morphology in response to the active agent, or FISH and/or qPCR for the detection and quantification of changes in nucleic acids. Bioactivity can be determined in some embodiments, for example, by assaying a cellular response.

In reference to an antibody, the term "bioactivity" includes, but is not limited to, epitope or antigen binding affinity, the in vivo and/or in vitro stability of the antibody, the immunogenic properties of the antibody, e.g., when administered to a human subject, and/or the ability to neutralize or antagonize the bioactivity of a target molecule in vivo or in vitro. The aforementioned properties or characteristics can be observed or measured using art-recognized techniques including, but not limited to, scintillation proximity assays, ELISA, ORIGEN immunoassay (IGEN), fluorescence quenching, fluorescence ELISA, competitive ELISA, SPR analysis including, but not limited to, SPR analysis using a BIAcore biosenser, in vitro and in vivo neutralization assays (see, for example, International Publication No. WO 2006/062685), receptor binding, and immunohistochemistry with tissue sections from different sources including human, primate, or any other source as needed. In reference to an immunogen, the "bioactivity" includes immunogenicity, the definition of which is discussed in detail later. In reference to a virus, the "bioactivity" includes infectivity, the definition of which is discussed in detail later. In reference to a contrast agent, e.g., a dye, the "bioactivity" refers to the ability of a contrast agent when administered to a subject to enhance the contrast of structures or fluids within the subject's body. The bioactivity of a contrast agent also includes, but is not limited to, its ability to interact with a biological environment and/or influence the response of another molecule under certain conditions.

Cold chain: The phrase "cold chain" refers to a temperature-controlled supply chain. An unbroken cold chain is an uninterrupted series of storage and distribution activities which maintain a given temperature range. It is used to help extend and ensure the shelf life of products such as chemicals, biologics and pharmaceutical drugs. Cold chains are common in the food and pharmaceutical industries and also some chemical shipments. A typical temperature range for a cold chain in pharmaceutical industries is 2 to 8° C. In some cases, the specific temperature (and time at temperature) tolerances depend on the actual product being stored and/or shipped.

Component: As used herein, the phrase "a component" of a sample refers to a physical, chemical or biological entity (e.g., but not limited to proteins, peptides, nucleic acids, cells, growth factors, and/or therapeutic agents) present in a sample that can be detected or analyzed.

Comprises: Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

Comprising: As used herein the term "comprising" or "comprises" is used in reference to compositions, methods, and respective component(s) thereof, that are useful to an embodiment, yet open to the inclusion of unspecified elements, whether useful or not.

Decrease: The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

Essentially: As used interchangeably herein, the terms "essentially" and "substantially" means a proportion of at least about 60%, or preferably at least about 70% or at least about 80%, or at least about 90%, at least about 95%, at least about 97% or at least about 99% or more, or any integer between 70% and 100%. In some embodiments, the term "essentially" means a proportion of at least about 90%, at least about 95%, at least about 98%, at least about 99% or more, or any integer between 90% and 100%. In some embodiments, the term "essentially" can include 100%.

Fibroin: As used herein, the term "fibroin" includes silkworm silk fibroin and insect or spider silk protein (Lucas et al., Adv. Protein Chem 13: 107-242(1958)). Any type of silk fibroin can be used according to aspects of the present invention. There are many different types of silk produced by a wide variety of species, including, without limitation: *Antheraea mylitta; Antheraea pernyi; Antheraea yamamai; Galleria mellonella; Bombyx mori; Bombyx mandarina; Galleria mellonella; Nephila clavipes; Nephila senegalensis; Gasteracantha mammosa; Argiope aurantia; Araneus diadematus; Latrodectus geometricus; Araneus bicentenarius; Tetragnatha versicolor; Araneus ventricosus; Dolomedes tenebrosus; Euagrus chisoseus; Plectreurys tristis; Argiope trifasciata;* and *Nephila madagascariensis*. In some embodiments, fibroin is obtained from a solution containing a dissolved silkworm silk or spider silk. The silkworm silk protein is obtained, for example, from *Bombyx mori*, and the spider silk is obtained from *Nephila clavipes*. Other silks include transgenic silks, genetically engineered silks (recombinant silk), such as silks from bacteria, yeast, mammalian cells, transgenic animals, or transgenic plants, and variants thereof. See for example, WO 97/08315 and U.S. Pat. No. 5,245,012, content of both of which is incorporated herein by reference in its entirety. In some embodiments, silk fibroin can be derived from other sources such as spiders, other silkworms, bees, synthesized silk-like peptides, and bioengineered variants thereof. In some embodiments, silk fibroin can be extracted from a gland of silkworm or transgenic silkworms. See for example, WO2007/098951, content of which is incorporated herein by reference in its entirety. Although different species of silk-producing organisms, and different types of silk, have different amino acid compositions, various fibroin proteins share certain structural features. A general trend in silk fibroin structure is a sequence of amino acids that is characterized by usually alternating glycine and alanine, or alanine alone. Such configuration allows fibroin molecules to self-assemble into a beta-sheet conformation. These "Ala-rich" and "Gly-rich" hydrophobic blocks are typically separated by segments of amino acids with bulky side-groups (e.g., hydrophilic spacers). In some embodiments, core repeat sequences of the hydrophobic blocks of fibroin can be represented by the following amino acid sequences and/or formulae: (GAGAGS)5-15 (SEQ ID NO: 1); (GX)5-15 (X=V, I, A) (SEQ ID NO: 2); GAAS (SEQ ID NO: 3); (S1-2A11-13) (SEQ ID NO: 4); GX1-4 GGX (SEQ ID NO: 5); GGGX (X=A, S, Y, R, D V, W, R, D) (SEQ ID NO: 6); (S1-2A1-4)1-2 (SEQ ID NO: 7); GLGGLG (SEQ ID NO: 8); GXGGXG (X=L, I, V, P) (SEQ ID NO: 9); GPX (X=L, Y, I); (GP(GGX)1-4 Y)n (X=Y, V, S, A) (SEQ ID NO: 10); GRGGAn (SEQ ID NO: 11); GGXn (X=A, T, V, S); GAG(A)6-7GGA (SEQ ID NO: 12); and GGX GX GXX (X=Q, Y, L, A, S, R) (SEQ ID NO: 13). In some embodiments, a fibroin peptide can contain multiple hydrophobic blocks, e.g., 3, 4, 5, 6, 7, 8, 9, 10, 11, 12, 13, 14, 15, 16, 17, 18, 19 and 20 hydrophobic blocks within the peptide. In some embodiments, a fibroin peptide can contain between 4-17 hydrophobic blocks. In some embodiments of the invention, a fibroin peptide comprises at least one hydrophilic spacer sequence ("hydrophilic block") that is about 4-50 amino acids in length. Non-limiting examples of the hydrophilic spacer sequences include: TGSSGFGPYVNG-GYSG (SEQ ID NO: 14); YEYAWSSE (SEQ ID NO: 15); SDFGTGS (SEQ ID NO: 16); RRAGYDR (SEQ ID NO: 17); EVIVIDDR(SEQ ID NO: 18); TTIIEDLDITIDGAD-GPI (SEQ ID NO: 19) and TISEELTI (SEQ ID NO: 20). In certain embodiments, a fibroin peptide can contain a hydrophilic spacer sequence that is a derivative of any one of the representative spacer sequences listed above. Such derivatives are at least 75%, at least 80%, at least 85%, at least 90%, or at least 95% identical to any one of the hydrophilic spacer sequences. In some embodiments, a fibroin peptide suitable for the present invention contains no spacer. Silks are generally fibrous proteins and characterized by modular units linked together to form high molecular weight, highly repetitive proteins. These modular units or domains, each with specific amino acid sequences and chemistries, are thought to provide specific functions. For example, sequence motifs such as poly-alanine (polyA) and poly-alanine-glycine (poly-AG) are inclined to be beta-sheet-forming; GXX motifs contribute to 31-helix formation; GXG motifs provide stiffness; and, GPGXX (SEQ ID NO: 22) contributes to beta-spiral formation. These are examples of different components in various silk structures whose positioning and arrangement are tied with the end material properties of silk-based materials (reviewed in Omenetto and Kaplan (2010) Science 329: 528-531). Also see: WO 2011/130335 (PCT/US2011/032195), the contents of which are incorporated herein by reference.

Increase: The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

Inhibit: As used herein, the term "inhibit" means to prevent something from happening, to delay occurrence of something happening, and/or to reduce the extent or likelihood of something happening.

Maintain: As used herein, the terms "maintaining," "maintain," and "maintenance," when referring to compositions or active agents mean keeping, sustaining, or retaining the bioactivity of at least one active agent in a silk fibroin matrix, when the active agent is subjected to certain conditions. In some embodiments, one or more active agents distributed in a silk fibroin matrix retains at least about 30% of its original bioactivity, including at least about 40%, at least about 50%, at least about 60%, at least about 70%, at least about 80%, at least about 90% of its original bioactivity or higher.

Nanopattern: The term "nanopattern" or "nanopatterned" as used herein refers to small patterning that is provided in a silk fibroin-based matrix, e.g., film or foam, or compositions comprising such a silk fibroin-based matrix. Generally, the patterning having structural features of a size that can be appropriately measured in a nanometer scale (i.e., 10~9 meters), for instance, sizes ranging from 1 nanometer to millimeters, inclusive.

Nucleic acid: As used herein, the term "nucleic acid" or "oligonucleotide" or grammatical equivalents herein means at least two nucleotides, including analogs or derivatives thereof, which are covalently linked together. Exemplary nucleic acids include, but are not limited to, polynucleotides, oligonucleotides, genes, genes including control and termination regions, self-replicating systems such as viral or plasmid DNA, genomic DNA, cDNA, mRNA, pre-mRNA, single-stranded and double-stranded siRNAs and other RNA interference reagents (RNAi agents or iRNA agents), shRNA (short hairpin RNAs), antisense oligonucleotides, aptamers, ribozymes, microRNAs (miRNAs), pre-miRNA, and modified RNAs (e.g., locked nucleic acid). The nucleic acids can be single stranded or double stranded. The nucleic acid can be DNA, RNA or a hybrid, where the nucleic acid contains any combination of deoxyribo- and ribo-nucleotides, and any combination of uracil, adenine, thymine, cytosine and guanine. The nucleic acids can comprise one or more backbone modifications, e.g., phosphoramide (Beaucage et al., Tetrahedron 49(10):1925 (1993) and references therein; Letsinger, J. Org. Chem. 35:3800 (1970)), phosphorothioate, phosphorodithioate, O-methylphophoroamidite linkages (see Eckstein, Oligonucleotides and Analogues: A Practical Approach, Oxford University Press), or peptide nucleic acid linkages (see Egholm, J. Am. Chem. Soc. 114:1895 (1992); Meier et al., Chem. Int. Ed. Engl. 31:1008 (1992); and Nielsen, Nature, 365:566 (1993), content of all of which is herein incorporated by reference. The nucleic acids can also include modifications to nucleobase and/or sugar moieties of nucleotides. Exemplary sugar modifications at the sugar moiety include replacement of 2'-OH with halogens (e.g., fluoro), O-mehtyl, O-methoxyethyl, NH2, SH and S-methyl.

Polyethylene glycol: "PEG" means an ethylene glycol polymer that contains about 20 to about 2000000 linked monomers, typically about 50-1000 linked monomers, usually about 100-300. Polyethylene glycols include PEGs containing various numbers of linked monomers, e.g., PEG20, PEG30, PEG40, PEG60, PEG80, PEG100, PEG115, PEG200, PEG 300, PEG400, PEG500, PEG600, PEG1000, PEG1500, PEG2000, PEG3350, PEG4000, PEG4600, PEG5000, PEG6000, PEG8000, PEG11000, PEG12000, PEG2000000 and any mixtures thereof.

Prevent: As used herein, the term "preventing" when used to refer to the action of an agent to a process (e.g., pathogenesis, disease progression, etc.) means reducing extent of and/or delaying onset of such a process when the agent (e.g., a therapeutic agent) is administered prior to development of one or more symptoms or attributes associated with the process.

Ready-to-use: The phrase "ready-to-use" as in "a ready-to-use formulation" refers to a composition or product that requires no further processing (e.g., a step in manufacturing) prior to use by an end user. In some embodiments, ready-to-use formulations include injection-ready formulations (i.e., injectables). In the context of the present invention, ready-to-use formulations encompass concentrated formulations, such as stock formulations, that are designed to be diluted prior to administration.

Reference: The term "reference" is used herein to refer, for example, to a reference composition or set of conditions, etc. Those skilled in the art will understand what might be an appropriate "reference" in a particular situation, from context. In general, a "reference" shares sufficient similarity with a composition or set of conditions of interest to permit meaningful comparison. In many embodiments, a "reference composition" herein is a conventional silk-fibroin composition (e.g., not a low molecular weight silk fibroin composition).

Short hairpin RNA: The term "shRNA" as used herein refers to short hairpin RNA which functions as RNAi and/or siRNA species but differs in that shRNA species are double stranded hairpin-like structure for increased stability. The term "RNAi" as used herein refers to interfering RNA, or RNA interference molecules are nucleic acid molecules or analogues thereof for example RNA-based molecules that inhibit gene expression. RNAi refers to a means of selective post-transcriptional gene silencing. RNAi can result in the destruction of specific mRNA, or prevents the processing or translation of RNA, such as mRNA Short interfering RNA: The term "short interfering RNA" (siRNA), also referred to herein as "small interfering RNA" is defined as an agent which functions to inhibit expression of a target gene, e.g., by RNAi. An siRNA can be chemically synthesized, it can be produced by in vitro transcription, or it can be produced within a host cell. siRNA molecules can also be generated by cleavage of double stranded RNA, where one strand is identical to the message to be inactivated. The term "siRNA" refers to small inhibitory RNA duplexes that induce the RNA interference (RNAi) pathway. These molecules can vary in length (generally 18-30 base pairs) and contain varying degrees of complementarity to their target mRNA in the antisense strand. Some, but not all, siRNA have unpaired overhanging bases on the 5' or 3' end of the sense 60 strand and/or the antisense strand. The term "siRNA" includes duplexes of two separate strands, as well as single strands that can form hairpin structures comprising a duplex region.

Solution: The term "solution" broadly refers to a homogeneous mixture composed of one phase. Typically, a solution comprises a solute or solutes dissolved in a solvent or solvents. It is characterized in that the properties of the mixture (such as concentration, temperature, and density) can be uniformly distributed through the volume. In the context of the present application, therefore, a "silk fibroin solution" refers to silk fibroin protein in a soluble form, dissolved in a solvent, such as water. In some embodiments, silk fibroin solutions may be prepared from a solid-state silk fibroin material (i.e., silk matrices), such as silk films and other scaffolds. Typically, a solid-state silk fibroin material is reconstituted with an aqueous solution, such as water and a buffer, into a silk fibroin solution. It should be noted that liquid mixtures that are not homogeneous, e.g., colloids, suspensions, emulsions, are not considered solutions. To give but one example, silk fibroin microspheres or particles suspended in a solution do not themselves constitute a silk fibroin solution.

Stabilization: As used herein, "stabilization" of an agent effectuated by soluble silk fibroin refers to any effects of a silk fibroin polypeptide that favor, promote, facilitate and/or maintain the integrity of the structure (e.g., confirmation) and corresponding function or activity of the agent, such that the agent is less susceptible to degradation, misfolding, denaturation, aggregation and/or inactivation. More detailed discussions on stabilizing effects of silk fibroin matrices are provided in: PCT/US12/34643 (filed Apr. 23, 2012) and Zhang et al. (2012) Proc. Nat'l. Acad. Sci. U.S.A. 109(30): 11981-6, the contents of each of which are herein incorporated by reference in their entirety. In accordance with embodiments of various aspects described herein, at least one property of one or more components of a biological sample can be stabilized within a low molecular weight silk fibroin composition for any period of time. As used herein, the term "stabilize," "stabilizing," or "stabilization" refers to at least one property (e.g., activity, integrity and/or quantity) of a component of a biological sample being partially or completely maintained or retained in a low molecular weight silk-based material over a period of time. With respect to stabilization of activity, in some embodiments, at least about 30% or more (including at least about 40%, at least about 50%, at least about 60%, at least about 70%, at least about 80%, at least about 90% or up to 100%) of a component originally present in a biological sample can retain at least a partial or complete activity over a period of time. Stated another way, a component can retain at least about 30% or more (including at least about 40%, at least about 50%, at least about 60%, at least about 70%, at least about 80%, at least about 90% or up to 100%) of its original activity over a period of time. With respect to stabilization of integrity, at least about 30% or more (including at least about 40%, at least about 50%, at least about 60%, at least about 70%, at least about 80%, at least about 90% or up to 100%) of a component originally present in a biological sample can retain integrity over a period of time. With respect to stabilization of quantity, at least about 30% or more (including at least about 40%, at least about 50%, at least about 60%, at least about 70%, at least about 80%, at least about 90% or up to 100%) of a component originally present in a biological sample can be retained over a period of time, regardless of whether the component is active or inactive, or intact or non-intact. As used herein, the term "originally" or "original", when used in reference to original presence or original activity of a component refers to the level of a component measured immediately after a biological sample is obtained from a subject, or, alternatively, measured immediately before or after a biological sample is mixed or entrapped within a silk-based material. In some embodiments, original presence or original activity of a component refers to the level of a component in a control, e.g., a control stabilized by a non-silk approach, e.g., a frozen control.

Statistically significant: The term "statistically significant" or "significantly" refers to statistical significance and generally means at least two standard deviation (2SD) away from a reference level. The term refers to statistical evidence that there is a difference. It is defined as the probability of making a decision to reject the null hypothesis when the null hypothesis is actually true.

Subject: As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient" and "subject" are used interchangeably herein.

Susceptible: As used herein, the term "susceptible" means having an increased risk for and/or a propensity for (typically based on genetic predisposition, environmental factors, personal history, or combinations thereof) something, e.g., a disease, disorder, or condition (such as, for example, cancer) than is observed in the general population as a whole. The term takes into account that an individual "susceptible" for a condition may never be diagnosed with the condition.

Tube: The term "tube" here refers to an elongated shaft with a lumen therein. The tube can typically be an elongate hollow cylinder, but may also be a hollow shaft of other cross-sectional shapes Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

The disclosure is further illustrated by the following examples which should not be construed as limiting. The examples are illustrative only, and are not intended to limit,

DETAILED DESCRIPTION OF CERTAIN EMBODIMENTS

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

Low Molecular Weight Compositions

One aspect provided herein relates to low molecular weight silk fibroin compositions. According to one aspect of the invention, a low molecular weight silk fibroin composition comprises a population of silk fibroin fragments having a range of molecular weights, characterized in that: no more than 15% of total number of the silk fibroin fragments in the population has a molecular weight exceeding 200 kDa, and at least 50% of the total number of the silk fibroin fragments in the population has a molecular weight within a specified range, wherein the specified range is between about 3.5 kDa and about 120 kDa, or between about 5 kDa and about 125 kDa.

Stated another way, in some embodiments, a low molecular weight silk fibroin composition comprises a population of silk fibroin fragments having a range of molecular weights, characterized in that: no more than 15% of total moles of the silk fibroin fragments in the population has a molecular weight exceeding 200 kDa, and at least 50% of the total moles of the silk fibroin fragments in the population has a molecular weight within a specified range, wherein the specified range is between about 3.5 kDa and about 120 kDa, or between about 5 kDa and about 125 kDa.

In some embodiments, a low molecular weight silk fibroin composition comprises a population of silk fibroin fragments having a range of molecular weights, characterized in that: no more than 15% of total weight of the silk fibroin fragments in the population has a molecular weight exceeding 200 kDa, and at least 50% of the total weight of the silk fibroin fragments in the population has a molecular weight within a specified range, wherein the specified range is between about 3.5 kDa and about 120 kDa, or between about 5 kDa and about 125 kDa.

As used herein, the phrase "silk fibroin fragments" refers to peptide chains or polypeptides having an amino acid sequence corresponding to fragments derived from silk fibroin protein or variants thereof. In the context of the present disclosure, silk fibroin fragments generally refer to silk fibroin peptide chains or polypeptides that are smaller than the naturally occurring full length silk fibroin counterpart, such that one or more of the silk fibroin fragments within a population or composition are less than 300 kDa, less than 250 kDa, less than 200 kDa, less than 175 kDa, less than 150 kDa, less than 120 kDa, less than 100 kDa, less than 90 kDa, less than 80 kDa, less than 70 kDa, less than 60 kDa, less than 50 kDa, less than 40 kDa, less than 30 kDa, less than 25 kDa, less than 20 kDa, less than 15 kDa, less than 12 kDa, less than 10 kDa, less than 9 kDa, less than 8 kDa, less than 7 kDa, less than 6 kDa, less than 5 kDa, less than 4 kDa, less than 3.5 kDa, etc.

In some embodiments, "a composition comprising a population of silk fibroin fragments" can encompass a composition comprising non-fragmented (i.e., full-length) silk fibroin polypeptide, in addition to shorter fragments of silk fibroin polypeptides. Silk fibroin fragments described herein can be produced as recombinant proteins, or derived or isolated (e.g., purified) from a native silk fibroin protein or silk cocoons.

In some embodiments, the silk fibroin fragments can be derived by degumming silk cocoons under a specified condition selected to produce the silk fibroin fragments having the desired range of molecular weights.

In some embodiments, silk fibroin fragments can be derived by degumming silk cocoons at or close to (e.g., within 5% around) an atmospheric boiling temperature for at least about 60 minutes or longer, including, e.g., at least 70 minutes, at least 80 minutes, at least 90 minutes, at least 100 minutes, at least 110 minutes, at least about 120 minutes or longer. As used herein, the term "atmospheric boiling temperature" refers to a temperature at which a liquid boils under atmospheric pressure.

In some embodiments, silk fibroin fragments can be produced by degumming silk cocoons in an aqueous solution at about 90° C.-about 110° C. for at least 60 minutes or longer, including, e.g., at least 70 minutes or longer. In some embodiments, the silk fibroin fragments can be derived by degumming silk cocoons below an atmospheric boiling temperature for a longer period of time, e.g., more than 60 minutes or longer, e.g., longer than 70 minutes, longer than 80 minutes, longer than 90 minutes, longer than 100 minutes, longer than 110 minutes, longer than 120 minutes, longer than 130 minutes, longer than 140 minutes, longer than 150 minutes, or longer.

Without wishing to be bound by theory, the silk fibroin fragments can be produced by degumming silk cocoons at a temperature of about 70° C. for at least 60 minutes or longer, including, e.g., at least 70 minutes, at least 80 minutes, at least 90 minutes, at least 100 minutes or longer. In some embodiments, the silk fibroin fragments can be produced by a process comprising degumming silk cocoons under a specified condition and further subjecting the resultant silk fibroin solution to high temperatures and/or high pressures. For example, the silk fibroin fragments can be produced by a process comprising degumming silk cocoons around boiling temperature for about 10 minutes and then subjecting the resultant silk fibroin solution to high temperatures and/or high pressures (e.g., autoclaving).

In one embodiment, an example of a low molecular silk fibroin composition can be produced as follows: a silk fibroin preparation is processed (e.g., heated and/or boiled) in a sufficient amount to achieve fragmentation of silk fibroin polypeptides, characterized in that at least 50 wt % of the total silk fibroin present in the silk fibroin preparation show reduced molecular weights, i.e., smaller than full-length silk fibroin (e.g., silk fibroin fragments), as determined, for example, by SDS gel electrophoresis. To illustrate, for instance, for a silk fibroin preparation containing total of 1.0 gram full-length silk fibroin as a starting material, after the step of heating and/or boiling, at least 0.5 gram of the silk fibroin are now in reduced forms (smaller fragments) as compared to the starting material (e.g., full-length polypeptide). As a result, average molecular weight of silk fibroin polypeptides within the preparation will decrease upon formation of a low molecular weight silk fibroin composition.

In some embodiments, silk fibroin fragments in a low molecular weight silk fibroin composition as described herein can be substantially free of sericin. In some embodiments, the silk fibroin fragments can contain sericin of no more than 5 wt % or less of the total weight of the silk protein composition. For example, the silk fibroin fragments can contain sericin of no more than 4 wt %, no more than 3 wt %, no more than 2 wt %, no more than 1 wt %, no more than 0.5 wt %, of the total weight of the silk protein composition.

In some embodiments, the silk fibroin fragments can be modified. For example, in some embodiments, the silk fibroin fragments can be modified to include a functional group. In some embodiments, the silk fibroin fragments can be covalently or non-covalently linked or fused to an agent, including, e.g., but not limited to, a peptide, a protein, a nucleic acid molecule, a contrast agent, a therapeutic agent, a target binding ligand, cell binding ligand, an amphiphilic peptide, or any combinations thereof. In some embodiments, the amino acid sequence of the silk fibroin fragments can include a cell binding ligand and/or an amphiphilic peptide. In one embodiment, the amino acid sequence of the silk fibroin fragments can include a RGD sequence.

In embodiments of the low molecular weight silk fibroin compositions described herein, no more than 15% of the total number (or total moles) or total weight of the silk fibroin fragments in the population has a molecular weight exceeding 200 kDa. As used herein, the phrase "exceeding 200 kDa" refers to the molecular weight of the silk fibroin fragments greater than 200 kDa. In some embodiments, the phrase "exceeding 200 kDa" can encompass molecular weight of the silk fibroin fragments being about 200 kDa. In some embodiments, the silk fibroin fragments having a molecular weight exceeding 200 kDa is present in the population in an amount of no more than 10% of the total number (or total moles) or total weight of the silk fibroin fragments, including, e.g., no more than 9%, no more than 8%, no more than 7%, no more than 6%, no more than 5%, no more than 4%, no more than 3%, no more than 2%, no more than 1%, of the total number (or total moles) or total weight of the silk fibroin fragments. In one embodiment, the low molecular weight silk fibroin composition is substantially free of the silk fibroin fragments having a molecular weight exceeding 200 kDa.

In the low molecular weight silk fibroin compositions described herein, at least 50% of the total number (or total moles) or total weight of the silk fibroin fragments has a molecular weight within a specified range, wherein the specified range is between about 3.5 kDa and about 120 kDa, or between about 5 kDa and about 125 kDa. In some embodiments, more than 50%, including, e.g., at least 55%, at least 60%, at least 65%, at least 70%, at least 75%, at least 80%, at least 85%, at least 90%, at least 95% or higher, of the total number (or total moles) or total weight of the silk fibroin fragments can have a molecular weight within the specified range. In one embodiment, the low molecular weight silk fibroin composition can have a population of the silk fibroin fragments substantially having a molecular weight between about 3.5 kDa and about 120 kDa, or between about 5 kDa and about 125 kDa.

The specified range of the molecular weight distribution of the silk fibroin fragments present in at least 50% of the total number (or total moles) or total weight of the silk fibroin fragments in the population can vary between about 3.5 kDa and about 120 kDa, or between about 5 kDa and about 125 kDa. In some embodiments, the molecular weight distribution of at least about 50% of the total number (or total moles) or total weight of the silk fibroin fragments can have a lower limit of 3.5 kDa or greater, but less than 120 kDa. For example, the lower limit of the specified range can be 3.5, 5, 10, 15, 20, 25, 30, 35, 40, 45, 50, 55, 60, 65, 70, 75, 80, 85, 90, 95, 100, 105, 110, or 115 kDa. In some embodiments, the specified range of the molecular weight distribution of at least about 50% of the total number (or total moles) or total weight of the silk fibroin fragments can have a upper limit of 10 kDa or greater (including and up to 120 kDa). By way of example only, the upper limit of the specified range can be 10, 15, 20, 25, 30, 35, 40, 45, 50, 55, 60, 65, 70, 75, 80, 85, 90, 95, 100, 105, 110, 115, or 120 kDa. Examples of the specified range can include, without limitations, (i) between about 5-120 kDa; (ii) between about 10-120 kDa; (iii) between about 15-120 kDa; (iv) between 20-120 kDa; (v) between 20-110 kDa; (vi) between about 20-100 kDa; (vii) between about 20-90 kDa; (viii) between about 20-80 kDa; (ix) between about 30-120 kDa; (x) between about 30-100 kDa; (xi) between about 30-90 kDa; (xii) between about 30-80 kDa; (xiii) between about 40-120 kDa; (xiv) between about 40-110 kDa; (xv) between about 40-100 kDa; (xvi) between about 40-90 kDa, and (xvii) between about 40-80 kDa.

The silk fibroin fragments having a molecular weight distribution with the specified range as described above can exhibit a continuous or discrete molecular weight distribution. As used herein, the term "continuous molecular weight distribution" refers to a distribution of molecular weight having any sub-ranges between a specified range. As used herein, the term "discrete molecular weight distribution" refers to a distribution of molecular weight having certain sub-ranges between the specified range. By way of example only, the silk fibroin fragments having a discrete molecular weight distribution with the specified range between about 3.5 kDa and about 120 kDa, or between about 5 kDa and about 125 kDa can refer to a population of the silk fibroin fragments, in which some of the silk fibroin fragments have a molecular weight between about 3.5 kDa and 10 kDa, while at least some or the rest of the silk fibroin fragments have a molecular weight between about 110 kDa and about 120 kDa.

Accordingly, in some embodiments, at least about 50% or higher of the total number (or total moles) or total weight of the silk fibroin fragments in the population having a molecular weight within the specific range between 3.5 kDa and 120 kDa, or between about 5 kDa and about 125 kDa can be characterized as a population of the silk fibroin fragments, in which at least about 50% of the total number (or total moles) or total weight of the silk fibroin fragments in the population having a molecular weight within the specific range is comprised by one or more (e.g., 1, 2, 3, 4, 5, 6, 7, 8, 9, 10) of the following sub-ranges (i)-(x), which include: (i) silk fibroin having a molecular weight distribution of 20 kDa to 30 kDa; (ii) silk fibroin having a molecular weight distribution of 30 kDa to 40 kDa; (iii) silk fibroin having a molecular weight distribution of 40 kDa to 50 kDa; (iv) silk fibroin having a molecular weight distribution of 50 kDa to 60 kDa; (v) silk fibroin having a molecular weight distribution of 60 kDa to 70 kDa; (vi) silk fibroin having a molecular weight distribution of 70 kDa to 80 kDa; (vii) silk fibroin having a molecular weight distribution of 80 kDa to 90 kDa; (viii) silk fibroin having a molecular weight distribution of 90 kDa to 100 kDa; (ix) silk fibroin having a molecular weight distribution of 100 kDa to 110 kDa; and (x) silk fibroin having a molecular weight distribution of 110 kDa to 120 kDa.

The amount of silk fibroin fragments having a molecular weight sub-range (i) to (x) can vary from 0% to 100% of the total number (or total moles) or total weight of all of the silk fibroin fragments in the composition described herein, provided that the combined weight of the silk fibroin fragments having the molecular weight sub-ranges (i)-(x) makes up at least 50% or higher of the total number (or total moles) or total weight of all of the silk fibroin fragments in the composition. Accordingly, the low molecular weight silk fibroin compositions described herein can be configured to have any combinations of the silk fibroin fragments having the molecular weight sub-range (i) to (x). In some embodiments, the low molecular weight silk fibroin compositions can have silk fibroin fragments corresponding to one specific molecular weight sub-range defined herein. In other embodiments, the low molecular weight silk fibroin composition can have a mixture of silk fibroin fragments corresponding to two or more specific molecular weight sub-ranges defined herein.

In some embodiments, the ratio of the silk fibroin fragments having a molecular weight of 76 kDa to silk fibroin fragments having a molecular weight of 18 kDa is not 5:1 to 1.5:1. Accordingly, in some embodiments, the low molecular weight silk fibroin composition can comprise a population of silk fibroin fragments having a range of molecular weights, characterized in that: no more than 15% of total number (or total moles) or total weight of the silk fibroin fragments in the population has a molecular weight exceeding 200 kDa, and at least 50% of the total number (or total moles) or total weight of the silk fibroin fragments in the population has a molecular weight within a specified range, wherein the specified range is between about 3.5 kDa and about 120 kDa, or between about 5 kDa and about 125 kDa with a proviso that the ratio of the silk fibroin fragments having a molecular weight of 76 kDa to silk fibroin fragments having a molecular weight of 18 kDa is not 5:1 to 1.5:1.

In some embodiments, the low molecular weight silk fibroin composition can further comprise no more than 35% of the total number (or total moles) or total weight of the silk fibroin fragments having a molecular weight distribution between 120 kDa and 200 kDa. For example, in some embodiments, less than 35%, including, e.g., no more than 30%, no more than 25%, no more than 20%, no more than 15%, no more than 10%, no more than 5%, no more than 3%, no more than 1%, of the total number (or total moles) or total weight of the silk fibroin having the molecular weight distribution between 120 kDa and 200 kDa can be present in the composition described herein. In one embodiment, the composition described herein can be substantially free of silk fibroin fragments having a molecular weight distribution between 120 kDa and 200 kDa.

In some embodiments where the composition comprises silk fibroin fragments having a molecular weight distribution between 120 kDa and 200 kDa, those silk fibroin fragments can be comprised by one or more (e.g., 1, 2, 3, 4, 5, 6, 7, or 8) of the following sub-ranges (xi)-(xviii), which include: (xi) silk fibroin having a molecular weight distribution of 120 kDa to 130 kDa; (xii) silk fibroin having a molecular weight distribution of 130 kDa to 140 kDa; (xiii) silk fibroin having a molecular weight distribution of 140 kDa to 150 kDa; (xiv) silk fibroin having a molecular weight distribution of 150 kDa to 160 kDa; (xv) silk fibroin having a molecular weight distribution of 160 kDa to 170 kDa; (xvi) silk fibroin having a molecular weight distribution of 170 kDa to 180 kDa; (xvii) silk fibroin having a molecular weight distribution of 180 kDa to 190 kDa; and (xviii) silk fibroin having a molecular weight distribution of 190 kDa to 200 kDa.

In some embodiments, the composition described herein can be enriched in at least one or more of the silk fibroin fragments within the specific sub-ranges (i)-(xviii) as defined herein, relative to a reference silk fibroin composition. In some embodiments, a reference silk fibroin composition can be a composition or mixture produced by degumming silk cocoon at an atmospheric boiling temperature for about 60 minutes. In one embodiment, a reference silk fibroin composition can be a composition or mixture produced by degumming silk cocoon at an atmospheric boiling temperature in an aqueous sodium carbonate solution for about 60 minutes. In some embodiments, the composition described herein can be enriched in at least two or more (e.g., 2, 3, 4, 5, 6, 7, 8, 9, 10 or more) of the silk fibroin fragments within the specific sub-ranges (i)-(xviii) as defined herein, relative to a reference silk fibroin composition. In some embodiments, the at least one or more of the silk fibroin fragments can be enriched in the composition by at least about 10% or more, including, e.g., at least about 20%, at least about 30%, at least about 40%, at least about 50%, at least about 60%, at least about 70%, at least about 80%, at least about 90%, at least about 95% or more, relative to a reference silk fibroin composition. In some embodiments, the at least one or more of the silk fibroin fragments can be enriched in the composition by at least about 1.1-fold or more, including, e.g., at least about 1.5-fold, at least about 2-fold, at least about 3-fold, at least about 4-fold, at least about 5-fold or more, relative to a reference silk fibroin composition.

In accordance with various embodiments described herein, the low molecular weight silk fibroin compositions are distinct from so-called "hydrolyzed silk." Hydrolyzed silk is generally produced by hydrolyzing or breaking down silk proteins into smaller peptide chains, e.g., with a molecular weight of no more than 1 kDa, and/or constituent amino acids such as glycine, alanine and serine. Accordingly, the term "hydrolyzed silk" as used herein refers to silk peptide chains or amino acids with a molecular weight of less than 2 kDa, less than 1 kDa, less than 500 Da or smaller. Stated another way, the hydrolyzed silk is generally free of silk fibroin peptide chains with molecular weights of at least 3.5 kDa or higher, including, for example, at least 5 kDa, at least 10 kDa, at least 15 kDa, at least 20 kDa, at least 25 kDa, at least 30 kDa, at least 40 kDa, at least 50 kDa, At least 60 kDa, at least 70 kDa, at least 80 kDa, at least 90 kDa, at least 100 kDa or higher.

The molecular weight of the silk fibroin fragments described herein can be determined by any known methods in the art, including, e.g., but not limited to, SDS-PAGE gel, size exclusion gel chromatography, mass spectroscopy, or any combinations thereof. In some embodiments, the molecular weights of the silk fibroin fragments as referenced herein in the low molecular weight silk fibroin compositions described herein can be determined by sodium dodecyl sulfate polyacrylamide gel electrophoresis (SDS-PAGE). By way of example only, for each low molecular weight silk fibroin composition, an appropriate amount (e.g., about 7.5 µg) of the composition or silk fibroin protein can be prepared in solution and then loaded into a gel such as 3-8% Tris-Acetate gel (e.g., NuPAGE® Novex® 3-8% Tris-Acetate Gel obtained from Invitrogen). A protein standard or ladder is also loaded into the gel to provide reference molecular weights. Examples of a protein standard can include, but are not limited to, a HiMark™ unstained Protein Standard (range 30-460 kDa, Invitrogen) and a Mark12™ Protein Standard (range 30-200 kDa, Invitrogen). The gels can be run under reducing conditions following manufacturer's instructions. For example, in one embodiment, the gel can be run at about ~200 V for about 45 minutes, and then stained for visualization of the protein bands. In some embodiments, the gel can be stained with a Colloidal Blue staining kit, e.g., obtained from Invitrogen. The molecular weight distributions of the silk fibroin fragments present in the low molecular weight silk fibroin compositions can then be quantified using any art-recognized methods, for example, by taking densiometric measurements of protein bands along the length of sample lanes of the gel. In one embodiment, ImageJ (NIH, Bethesda, Md.) can be used to determine the densiometric measurements of the protein bands on the gel. In one embodiment, the "Gel Analyzer" tool within the ImageJ software can be used to perform the densiometric analysis.

Without limitation, the molecular weight as used herein can be the peak average molecular weight ($M_p$), the number average molecular weight ($M_n$), or the weight average molecular weight ($M_w$).

In some embodiments, the low molecular weight silk fibroin composition can further comprise at least one or more active agents, examples of which are described below. The active agent can be dispersed in the composition described herein by any known methods in the art. For example, the active agent can be dispersed homogenously or heterogeneously (e.g., forming a gradient of the active agent) in the composition described herein, see US Application Publication No. US20070212730 A1, the content of which is incorporated herein by reference in its entirety. In some embodiments, agents included in a low molecular weight silk fibroin composition may be stored in and/or released or recovered from such compositions, whether in liquid or solid forms. In some embodiments, included agents can be analyzed, e.g., prior to, during, or after such release or recovery.

Low Molecular Weight Solutions:

In some embodiments, a low molecular weight silk fibroin composition provided herein can be a solution (optionally including an agent, such as an agent to be stabilized and/or analyzed as described herein). Accordingly, in another aspect, provided herein is an aqueous silk fibroin solution comprising one or more embodiments of the low molecular weight silk fibroin composition described herein. In some embodiments, the aqueous silk fibroin solution can be formulated in water. In some embodiments, the aqueous silk fibroin solution can be formulated in a buffered solution. Example of a buffered solution includes, but is not limited to a phosphate buffered solution.

The silk fibroin can be present in the solution at any concentration suited to the need, e.g., injectability of the silk fibroin solution. In some embodiments, the aqueous silk fibroin solution can have silk fibroin at a concentration of about 0.1% wt/v to about 90% wt/v, 0.1% wt/v to about 75% wt/v, or 0.1% wt/v to about 50% wt/v. In some embodiments, the aqueous silk fibroin solution can have silk fibroin at a concentration of about 0.1% wt/v to about 10% wt/v, about 0.1% wt/v to about 5% wt/v, about 0.1% wt/v to about 2% wt/v, or about 0.1% wt/v to about 1% wt/v. In some embodiments, the silk fibroin solution have silk fibroin at a concentration of about 10% wt/v to about 50% wt/v, about 20% wt/v to about 50% wt/v, about 25% wt/v to about 50% wt/v, or about 30% wt/v to about 50% wt/v.

In some embodiments, the aqueous silk solution can remain stable under a specific condition for at least about 3 days or more, including, e.g., at least about 4 days, at least about 5 days, at least about 6 days, at least about 7 days, at least about 2 weeks, at least about 3 weeks, at least about 4 weeks or more. The specific condition can be characterized by one or more of the environmental parameters including, but not limited to, temperature, light, humidity, pressure, and any combinations thereof. In some embodiments, the aqueous silk solution can remain stable at about room temperature to at least about 37° C. or higher for at least about 3 days or more, including, e.g., at least about 4 days, at least about 5 days, at least about 6 days, at least about 7 days, at least about 2 weeks or longer. In some embodiments, the aqueous silk solution does not gel upon exposure of the aqueous silk fibroin solution to a certain condition for at least bout 3 days or more, including, e.g., at least about 4 days, at least about 5 days, at least about 6 days, at least about 7 days, at least about 2 weeks, at least about 3 weeks, at least about 4 weeks or more. In some embodiments, the aqueous silk solution does not gel upon exposure of the aqueous silk fibroin solution to a temperature of at least room temperature or higher (e.g., ~15° C., ~20° C., ~25° C., ~30° C., ~35° C., ~40° C. or higher) for at least bout 3 days or more, including, e.g., at least about 4 days, at least about 5 days, at least about 6 days, at least about 7 days, at least about 2 weeks, at least about 3 weeks, at least about 4 weeks or more.

In some embodiments, the low molecular weight silk fibroin solution described herein gels slower than a reference silk fibroin solution as defined herein. In some embodiments, the low molecular weight silk fibroin solution described herein gels slower than a conventional silk fibroin solution.

As used herein, the term "remain stable" refers to material properties of the aqueous silk fibroin solution remaining substantially the same upon exposure to the specific condition for a period of time. Examples of the material properties can include, but are not limited to, viscosity, particle size, opacity, and any combinations thereof. In some embodiments, a stable aqueous silk solution can be characterized by no substantial change in the viscosity upon exposure to the specific condition for a period of time. In some embodiments, a stable aqueous silk solution can be characterized as a homogenous solution as defined herein. For example, a homogenous aqueous silk fibroin solution can be characterized as an aqueous silk fibroin solution that is substantially free of silk fibroin aggregates (e.g., insoluble silk fibroin fragments, silk fibroin particles and/or clusters that are visible to naked eyes) upon exposure to a specified condition for a period of time. Examples of the silk fibroin aggregates can include, but are not limited to, full-length silk fibroin molecules, larger silk fibroin fragments, silk fibroin particles or clusters formed by assembly or aggregation of smaller silk fibroin fragments, and any combinations thereof). In some embodiments, silk fibroin aggregates can include silk fibroin particles or clusters formed by a process including, but not limited to precipitation, gelation, and/or clumping. In some embodiments, the silk fibroin aggregates can be silk fibroin particles or clusters having a size of about 1 mm or larger. In one embodiment, the silk fibroin particles or clusters can be formed by assembly or aggregation of silk fibroin fragments present in the solution.

Low Molecular Weight Articles:

In some embodiments, low molecular weight silk fibroin compositions provided herein can form a solid silk fibroin article. Examples of such solid silk fibroin articles can include, but are not limited to, a film, a sheet, a gel or hydrogel, a mesh, a mat, a non-woven mat, a fabric, a scaffold, a tube, a block, a fiber, a particle, powder, a 3-dimensional construct, an implant, a foam, a needle, a lyophilized article, and any combinations thereof. Methods for forming various forms of a solid silk fibroin articles are known in the art and some exemplary methods are described below herein.

In some embodiments, a low molecular weight silk fibroin article can be shelf-stable for at least 1 month. The term "shelf-stable" as used herein refers to material properties of the silk fibroin particles remaining substantially the same upon storage for a period of time. Material properties of the silk fibroin articles can include, but are not limited to, hardness, porosity, solubility, particle size, dryness, and any combinations thereof.

In some embodiments, a low molecular weight silk fibroin article can be resolubilized in water to form a silk fibroin solution substantially free of silk fibroin aggregates. In some embodiments, at least about 50%, at least about 60%, at least about 70%, at least about 80%, at least about 90%, at least about 95% or higher of the low molecular weight silk fibroin article can be resolubilized in water to form a silk fibroin solution substantially free of silk fibroin aggregates.

In some embodiments, no heating and/or salt addition are required to dissolve a low molecular weight silk fibroin article fabricated using one or more embodiments of the low molecular weight silk fibroin compositions described herein. Accordingly, in some embodiments, the silk fibroin article can be resolubilzed in aqueous solution at room temperature to form a silk fibroin solution. In some embodiments, a low molecular weight silk fibroin article can completely dissolve in water (e.g., deionized water) at room temperature, provided that the concentration of the dissolved silk fibroin is below saturation. In some embodiments, the saturation point of the low molecular silk fibroin composition in an aqueous solution (e.g., water) can be at least 30% w/v, at least 40% w/v, at least 50% w/v, at least 60% w/v, at least 70% w/v, at least 80% w/v or higher.

In some embodiments, the saturation point of a low molecular weight silk fibroin composition in an aqueous solution (e.g., water) can range from about 30% w/v to about 80% w/v, from about 40% w/v to about 70% w/v, from about 50% w/v to about 60% w/v. Accordingly, in some embodiments, a low molecular weight silk fibroin article can have a water-solubility of at least about 10 mg/mL or higher, including, e.g., at least about 20 mg/mL, at least about 30 mg/mL, at least about 40 mg/mL, at least bout 50 mg/mL, at least about 60 mg/mL, at least about 70 mg/mL, at least about 80 mg/mL, at least about 90 mg/mL, at least about 100 mg/mL, at least about 200 mg/mL, at least about 400 mg/mL, at least about 600 mg/mL, at least about 800 mg/mL, at least about 1000 mg/mL or higher.

In some embodiments, a low molecular weight silk fibroin article can have a dissolution rate of at least 0.01 mg/s to about 100 mg/s or about 0.1 mg/s to about 90 mg/s, or about 1 mg/s to about 80 mg/s. In some embodiments, a low molecular weight silk fibroin article can be dissolved in an aqueous solution (e.g., water such as deionized water) at room temperature at a rate of about 0.01 mg/s to about 100 mg/s or about 0.1 mg/s to about 90 mg/s, or about 1 mg/s to about 80 mg/s.

In some embodiments, a low molecular weight silk fibroin article can be used in on-demand or point-of-care applications. For example, a user (e.g., a subject or a medical provider) can apply or self-administer the silk fibroin article at any location (e.g., residence, remote village, and battlefield). For diagnostics, in some embodiments, the user can send the silk fibroin article to a hospital, a clinic or any analysis facility. Alternatively or additionally, in some embodiments, a low molecular weight silk fibroin article can be used to create stored samples (e.g., stored blood samples), which stored samples, in some embodiments, may be stable over at least a specified period of time (e.g., days, weeks, months, years, etc) and/or may be re-tested or sampled over time (e.g., to permit comparison, for example with later-obtained samples, etc)

Without wishing to be bound by theory, in some embodiments, the resolubility (i.e., the ability of a solid form of a low molecular weight silk fibroin composition to be dissolved or reconstituted into a solution or liquid form) of the silk fibroin article can be determined by length of time and/or temperature for degumming silk cocoons. For example, in some embodiments, a dissolvable silk fibroin article can be formed from a low molecular weight silk fibroin solution, which is obtained by degumming silk cocoons at or close to an atmospheric boiling point for at least 60 minutes or longer, e.g., at least 90 minutes or longer. In other embodiments, a dissolvable silk fibroin article can be formed from a low molecular weight silk fibroin solution, which is obtained by degumming silk cocoons at lower temperatures, e.g., about 60-90° C. for at least 90 minutes or longer, e.g., at least 120 minutes or longer.

In some embodiments, solid forms of the low molecular weight silk fibroin compositions described herein are highly dissolvable. Thus, in one aspect, the present invention provides highly dissolvable forms of solid silk fibroin compositions comprising low molecular weight silk fibroin fragments. As compared to conventional silk fibroin compositions previously described, the highly dissolvable forms of the solid silk fibroin compositions described herein are characterized by their high water-solubility, high rate of dissolution, as well as biocompatibility with a wide range of agents (e.g., but not limited to biological agents). From a material science point of view, low molecular weight silk fibroin compositions described herein provide greater flexibility, tunability and ease of handling and versatility in part due to the ability to better control the liquid-solid or solid-liquid transition. This is based at least in part on the finding that the solubility of silk fibroin can be finely tuned when the composition is composed predominantly of smaller fragments of silk fibroin (i.e., low molecular weight silk fibroin fragments). This added flexibility makes it possible to utilize silk-based materials in ways that are not possible with conventional silk materials comprising or made of more high molecular weight silk fibroin. Thus, unique material properties of low molecular weight silk fibroin materials include, but are not limited to: solid form silk fibroin compositions that can be easily dissolved into an aqueous solution; and liquid form silk fibroin compositions (e.g., silk fibroin solutions) that resist unwanted self-assembly or gelling while providing desirable stabilizing effects for agents incorporated or associated therein.

Accordingly, in some embodiments, the low molecular weight silk fibroin composition can be specifically formulated to behave as a fully-dissolvable form, which can be easily and rapidly reconstituted in water (e.g., pure water or deionized water) or any other water-based solutions suitable for particular use, such as buffers. In these embodiments, because low molecular weight silk fibroin compositions in solid forms described herein are readily dissolvable into an aqueous solution, one or more agents incorporated therein can be readily recovered from the soluble form of the solid low molecular weight silk fibroin compositions. For instance, a biological agent, such as a biological sample, can be "stored" in association with low molecular weight silk fibroin composition in a solid form, which can then be released into an aqueous solution to achieve almost full recovery of the agents. Once released, such agents can be readily analyzed (e.g., detected, measured, assayed, identified, isolated, etc.) by any suitable means, such as analytical tools. Alternatively or additionally, in some embodiments, an included agent (e.g., a biological agent) can be analyzed without being released from a silk fibroin composition.

Stabilizing Compositions

Stabilization and subsequent recovery of an agent desired to be stabilized (e.g., active agents and/or biological samples) is a critical feature of many applications, because the active agents and/or biological samples are usually labile and sensitive to changes in surrounding conditions, e.g., temperature, humidity and/or light. In a number of previously described methods, even if an active agent or a biological sample is identified to be useful for a given reaction, its application is often hampered by a lack of long-term stability under process conditions and/or low recovery. As further described below, various embodiments of the present inventions described herein address these short comings existed in prior art technologies.

For example, a technology capable of protecting stabilized samples against adverse temperature profiles could extend the reach of centralized testing systems to a global scale. To this end, the inventors have discovered inter alia that certain silk-based materials can protect active agents (e.g., biological samples or components thereof, therapeutic and/or diagnostic reagents, etc) from degradation of structural and/or functional features. The term "active agent" is used herein to refer to a biological sample (e.g., a sample of tissue or fluid, such as for instance blood) or a component thereof, and/or to a biologically active entity or compound, and/or to a structurally or functionally labile entity.

In some embodiments, stabilization of an active agents/biological sample's bioactivity is critical. In other embodiments, stabilizing activity or bioactivity is not always required. For example, maintaining bioactivity is often not a requirement for assaying and quantifying a stabilized biological sample.

In some particular embodiments, the present disclosure demonstrates inter alia that silk-based materials can protect human whole blood and blood components such as RNA over long durations and in the context of adverse environmental conditions. The present disclosure demonstrates, for example, that whole blood and/or donor-matched plasma can be stabilized in silk-based materials, e.g., film, by casting and air drying, and the respective plasma proteins recovered by a simple mixing protocol with water.

The present disclosure also specifically demonstrates various particular advantageous features of low molecular weight silk compositions, as described herein, for use in stabilizing included agents. For example, among other things, the present disclosure demonstrates that low molecular weight silk compositions tend to gel less quickly than higher molecular weight silk compositions. Among other things, such delayed gelling attributes could contribute, in some embodiments, to extended shelf-life. Additionally, the present disclosure demonstrates that low molecular weight silk compositions protect against sample loss even with autoclaving. In some embodiments, the present invention provides autoclaved low molecular weight silk compositions, for example comprising an included agent. In some embodiments, the present invention provides systems for reconstituting low molecular weight silk compositions (e.g., solid form low molecular weight silk compositions), including autoclaved such composition, wherein the compositions are characterized by high recovery of an included agent. In certain embodiments, such compositions and/or systems are appropriate for large scale manufacturing and/or processing (e.g., shipping) of compositions.

Stabilization effect of silk fibroin compositions as demonstrated herein have broad implications, including for example for the maintenance, storage, and/or transportation of samples (e.g., blood samples) obtained in the field. In many embodiments, therefore, provided technologies are particularly useful in settings where samples (e.g., blood draws) are obtained with limited resources and/or in contexts where downstream analyses are beyond the reach of point-of-case technologies.

The present disclosure specifically demonstrates the breadth of clinically-relevant analytical tools that can be used to measure the absolute abundance of blood analytes (or blood components) from a range of donors once recovered from the silk-based material. The work reported herein demonstrates that by using the compositions and methods of various embodiments described herein, the recovered analyte levels (or recovered component levels) are consistent with measurements performed on donor-matched fresh or frozen plasma, which is the format currently used as a gold standard for clinical workups. In some embodiments, the silk-stabilized analyte levels (or silk-stabilized component levels) were higher than their frozen counterparts, indicating the silk-based material can out-perform the current gold standard for certain applications. The inventors also demonstrated that different techniques, such as lyophilization, can be used to stabilize biological samples, e.g., RNA, in the presence of the same silk formulations for subsequent recovery using a simple aqueous reconstitution method. The recovered RNA was available at levels consistent with frozen controls and is capable of transfecting a model cell line.

Various forms of silk-based materials can protect a biological sample against widely-fluctuating temperature profiles and against mechanical perturbations encountered during shipment. A silk-based material can be specifically formulated to behave as a fully-solubilized system by reconstitution in water (e.g., in pure water or a buffer suitable for sample interactions), providing full recovery of the entrapped components or biomarkers to be analyzed by a number of clinically-relevant analytical tools. Prior to the present disclosure, no technology exists in the art that combines these unique attributes, namely i) ease of sample procurement, ii) impressive thermal/mechanical stability profiles, iii) simplicity in reconstitution/recovery. However, as demonstrated herein, the present disclosure provides compositions and methods that provide, among other things, i) ease of sample procurement, ii) impressive thermal/mechanical stability profiles, iii) simplicity in reconstitution/recovery.

Since silk fibroin is highly resistant against enzymatic/thermal/UV degradation, it is believed that entrapped biological samples can be banked for long-term storage (i.e. months-years in duration) at centralized facilities, without the need for refrigeration/freezing, in order to collect population-wide longitudinal data sets or enhance personalized medicine.

Accordingly, in one aspect, the present disclosure provides the use of silk solutions (e.g., tuned to produce silk-based materials with desirable solubility properties) and silk-based materials made from these solutions for entrapment and stabilization of a biological sample, e.g., whole blood and blood components. The silk purification and entrapment schemes provide the ability to fully reconstitute the entrapped blood components (e.g., cells, and/or nucleic acids such as circulating DNAs or RNAs). In one embodiment, a blood draw equivalent to a finger prick volume can be mixed with a silk solution, e.g., as described in the Examples section herein and, thereafter, at least partially dried silk-based material can be readily procured containing stabilized blood components.

Silk entrapment/stabilization platforms described herein are fundamentally For example, liquid silk fibroin compositions can be immediately amenable to routine liquid assays for the biological sample in the composition and can be subjected to the same validation and quality control (QC) procedures that are used for fresh whole blood or frozen samples. The solution composition can be at least partially dried or formed in to a silk fibroin article. The silk fibroin in the dried composition or the article can be resolublized thereby providing a solution which is amenable to routine liquid assays for detection of the biological sample or a component thereof.

Conversely, since DBS analytes require some level of chemical interaction with the paper substrate upon drying in order to be protected, partial sample retention in the matrix and/or damage to the analytes is expected using standard DBS recovery procedures. In turn, this imposes unique validation protocols and QC metrics on the DBS workup in order to monitor losses and non-uniformity between extractions. Second, it can be difficult to define a sample volume and then aliquot paper-based DBS samples accordingly due to the non-uniformity of the spot (from between-user variability and hematocrit sample-sample variability) both across and through the thickness of the paper substrate. This is particularly problematic with patient populations that vary widely in age or suffer from abnormal hematocrit levels (renal impairment, oncology patients, etc). Conversely, the silk-based material (e.g., low molecular weight silk fibroin compositions) described herein can provide complete recovery if desired (e.g., an entire volume, such as an entire 50 µL volume, can be reconstituted) or aliquots can be easily prepared by weight since the silk/blood complex is mixed and dried homogeneously.

Accordingly, embodiments of various aspects described herein also relate to silk-based materials for stabilization of at least one component of a biological sample mixed therewith or entrapped therewith, which permit detection of the component at a later time, as well as methods of making and using the same.

In one aspect, provided herein is a silk-based material comprising silk fibroin (e.g., a low molecular weight silk fibroin composition) and a biological sample/active agent wherein at least one property of at least one component of the biological sample is stabilized for a period of time, and/or wherein the at least one component of the biological sample/active agent is detectable after the period of time.

The property of at least one active agent (e.g., biological sample or component) that is stabilized in the silk-based material can be a physical or structural property, a chemical property, and/or a biological property. In some embodiments, said at least one property can comprise activity or bioactivity, structural integrity, structural conformation, and/or quantity of the agent. Depending on different applications (e.g., diagnostic purposes vs. therapeutic purposes), silk fibroin and/or silk silk-based material can be processed to stabilize one or more properties of at least one component of a biological sample.

In some embodiments, stabilizing activity or bioactivity of a component of a biological sample is not always required. For example, for diagnostic applications, activity of a component to be detected can be not as important as integrity and/or quantity of the component stabilized in a biological sample. In these embodiments, the component to be detected can be inactive as long as the component remains intact and/or and quantity of the component is maintained. As used interchangeably herein, the terms "activity" and "bioactivity" refer to the one or more structural and/or functional characteristics of a component, such as, for example its ability to interact with a biological target and/or to produce an effect on a biological target. For example, bioactivity can include, without limitation, elicitation of a stimulatory, inhibitory, regulatory, toxic or lethal response in a biological target. The biological target can be a molecule or a cell. For example, a bioactivity can refer to the ability of a component (e.g., a protein or a nucleic acid molecule) to modulate the effect/activity of a cell or an enzyme, block a receptor, stimulate a receptor, modulate the expression level of one or more genes, modulate cell proliferation, modulate cell division, modulate cell morphology, infect or transfect a cell, or any combination thereof. In some instances, a bioactivity can refer to the ability of a component to produce a toxic effect in a cell.

In some embodiments, it can be desirable to further stabilize activity of a component of a biological sample. By way of example only, a protein present in a biological sample can be in an active or inactive state. In this embodiment, the silk-based material can stabilize a protein present in a biological sample in its active or native form, e.g., a phosphorylated protein, or a glycosylated protein. This embodiment can be useful where the activity of a component plays a role in diagnosis of a disease or disorder.

In accordance with embodiments of various aspects described herein, at least one property of one or more components of a biological sample can be stabilized within a silk-based material for any period of time. As used herein, the term "stabilize," "stabilizing," or "stabilization" refers to at least one property (e.g., activity, integrity and/or quantity) of a component of a biological sample being partially or completely maintained or retained in a silk-based material over a period of time. With respect to stabilization of activity, in some embodiments, at least about 30% or more (including at least about 40%, at least about 50%, at least about 60%, at least about 70%, at least about 80%, at least about 90% or up to 100%) of a component originally present in a biological sample can retain at least a partial or complete activity over a period of time. Stated another way, a component can retain at least about 30% or more (including at least about 40%, at least about 50%, at least about 60%, at least about 70%, at least about 80%, at least about 90% or up to 100%) of its original activity over a period of time. With respect to stabilization of integrity, at least about 30% or more (including at least about 40%, at least about 50%, at least about 60%, at least about 70%, at least about 80%, at least about 90% or up to 100%) of a component originally present in a biological sample can retain integrity over a period of time. With respect to stabilization of quantity, at least about 30% or more (including at least about 40%, at least about 50%, at least about 60%, at least about 70%, at least about 80%, at least about 90% or up to 100%) of a component originally present in a biological sample can be retained over a period of time, regardless of whether the component is active or inactive, or intact or non-intact. As used herein, the term "originally" or "original", when used in reference to original presence or original activity of a component refers to the level of a component measured immediately after a biological sample is obtained from a subject, or, alternatively, measured immediately before or after a biological sample is mixed or entrapped within a silk-based material. In some embodiments, original presence or original activity of a component refers to the level of a component in a control, e.g., a control stabilized by a non-silk approach, e.g., a frozen control.

At least one property of one or more active agents/biological samples/components thereof can stabilized within a silk-based material for a period of time, e.g., until the component is extracted or recovered for detection. In some embodiments, at least one property can be stabilized for at least about 3 hours, at least about 6 hours, at least about 12 hours, at least about 18 hours, at least about 24 hours or longer. In some embodiments, at least one property can be stabilized for at least about 1 day, at least about 2 days, at least about 3 days, at least about 4 days, at least about 5 days, at least about 6 days, at least about 7 days, or longer. In some embodiments, at least one property can be stabilized for at least about 1 week, at least about 2 weeks, at least about 3 weeks, at least about 4 weeks, at least about 2 months, at least about 3 months, at least about 6 months, at least about 9 months, at least about 1 year, at least about 2 years, at least about 3 years, at least about 6 years or longer.

As discussed further below, a silk-based material described herein can be present in any form. For example, the silk-based material can be in a form of a solution, a film, a fiber, a particle, a gel, a hydrogel, a foam, a sponge, a mat, a mesh, a fabric, powder, a coating layer, a lyophilized form thereof, or any combinations thereof. In some embodiments, the silk-based material can be a thin film. In some embodiments, the silk-based material can be lyophilized While one or more components of a biological sample can be detected without isolating it/them from the silk-based material, a measurable or detectable level of the component(s) can be alternatively extracted or recovered from the silk-based material for subsequent processing, analysis and/or characterization. As used herein, the term "measurable or detectable level" refers to the lower limit of detection, which generally depends on the detection sensitivity of a detection and/or characterization method or assay selected for the specific component. For example, when the component to be detected is a nucleic acid molecule (e.g., RNA or DNA) and an amplification-based detection method (e.g., but not limited to polymerase chain reaction (PCR) is selected to detect the component, about 0.0001% of the nucleic acid molecules (e.g., one copy of an RNA molecule) can be extracted or recovered from the silk-based material for amplification and detection.

In some embodiments, the silk-based material can be dissolvable such that a measurable or detectable level of the component(s) can become accessible or available for subsequent processing, analysis and/or characterization. As used herein, the term "dissolvable" generally refers to solubility, dissolution or degradation of a silk-based material in a fluid. A dissolvable silk-based material can partially or completely dissolve or degrade in a fluid over a period of time. For example, at least about 5% or more of a silk-based material, including, e.g., at least about 10%, at least about 20%, at least about 30%, at least about 40%, at least about 50%, at least about 60%, at least about 70%, at least about 80%, at least about 90%, at least about 95%, or up to 100%, of the silk-based material can dissolve or degrade in a fluid (e.g., an aqueous fluid) over a period of time ranging from seconds, minutes, hours, to days. In some embodiments, a silk-based material can partially or completely (e.g., at least about 5% or more of the silk-based material) dissolve or degrade in a fluid (e.g., an aqueous fluid) within at least about 10 seconds, at least about 20 seconds, at least about 30 seconds, at least about 40 seconds, at least about 50 seconds, at least about 60 seconds or more. In some embodiments, a silk-based material can partially or completely (e.g., at least about 5% or more of the silk-based material) dissolve or degrade in a fluid (e.g., an aqueous fluid) within at least about 1 min, at least about 5 mins, at least about 10 mins, at least about 15 mins, at least about 30 mins, at least about 1 hour or more. Stated another way, a dissolvable silk-based material is a silk-based material that can dissolve or degrade in a fluid (e.g., an aqueous fluid) a sufficient portion thereof in order to recover or extract at least one active agent/sample/component present therein.

The dissolvability or solubility of the silk-based material can depend on a number of factors, including, e.g., but not limited to, composition of the silk-based material (e.g., the ratio of a biological sample to silk fibroin, the type of the biological sample (e.g., but not limited to urine, blood, and/or cerumen) mixed or entrapped with silk fibroin, and/or types of buffers/excipients employed in aiding in stabilization of the biological sample and/or at least one or more components thereof), silk purification methods (e.g., degumming condition such as boil time), methods for forming the silk-based material described herein, sterilization methods, and any combinations thereof.

In some embodiments, the dissolvability or solubility of the silk-based material can be controlled by the molecule weight/chain lengths of silk. In general, a silk-based material comprising lower molecule weight/chain length of silk fibroin can have a higher solubility in an aqueous solvent than one comprising higher molecule weight/chain lengths of silk fibroin. In one embodiment, the molecule weight/chain lengths of silk fibroin can be controlled by the degumming condition. For example, silk cocoons can be boiled in a salt solution (e.g., $Na_2CO_3$) for a pre-determined period of time, e.g., ranging from about 1 minute to about 3 hours, from about 5 minutes to about 2 hours, from about 10 minutes to about 1.5 hours, or from about 15 minutes to about 1 hour. In some embodiments, silk cocoons can be boiled in a salt solution (e.g., $Na_2CO_3$) for at least about 1 minute, at least about 10 minutes, at least about 20 minutes, at least about 30 minutes, at least about 45 minutes, at least about 1 hour, at least about 2 hours or longer. Without wishing to be bound by theory, longer boiling times can yield lower molecule weight/chain lengths of silk fibroin.

See, e.g., Pritchard E M et al. "Effect of Silk Protein Processing on Drug Delivery from Silk Films" Macromol Biosci. Epub 2013 Jan. 24, for details on effects of degumming on silk material properties, including molecular weight, viscosity, diffusivity and degradation behavior. Depending on types of biological samples and component(s) thereof to be stabilized, optimum degumming time can be determined for desired solubility of the silk-based material and thus recovery of the component, e.g., as described in the Examples. In some embodiments silk-based stabilizing compositions as described herein are low molecular weight silk compositions.

Indeed, the inventors have discovered that various forms of low molecular weight silk fibroin compositions offer particularly advantageous properties for protecting and/or stabilizing agents (e.g., biological samples) associated or incorporated therein. For example, low molecular weight silk compositions described herein can act as "a molecular stabilizer" to protect a biological sample against widely-fluctuating environmental factors, such as fluctuating temperatures profiles and/or against mechanical perturbations, for example, encountered during transportation, storage, and/or handling. Also, the inventors have discovered that compositions comprising low molecular weight silk fibroin as disclosed herein can be completely reconstituted in water. In contrast, high molecular weight silk fibroin does not fully reconstitute in water under similar conditions. The high molecular weight forms aggregates when reconstituted in water under similar conditions.

To date, no technology has been described in the art that combines these unique attributes, namely i) ease of sample procurement, ii) impressive thermal/mechanical stability profiles, iii) simplicity and yield in reconstitution/recovery. However, as demonstrated herein, the present disclosure provides compositions and methods that provides i) ease of sample procurement, ii) impressive thermal/mechanical stability profiles, iii) simplicity and yield in reconstitution/recovery. Without wishing to be bound by theory, silk fibroin is highly resistant against enzymatic/thermal/UV degradation, it is believed that entrapped agents (e.g., active agents and/or biological samples) in silk fibroin compositions can be banked for long-term storage (i.e. months-years in duration) at centralized facilities, without the need for refrigeration/freezing, and be readily recovered later whenever the agents are ready for use and/or analysis. Thus, silk fibroin compositions provided herein, and particularly low molecular weight silk fibroin compositions, can enable collection of population-wide longitudinal data sets or enhancement of personalized medicine.

The inventors have particularly discovered that incorporation of a biological sample in one or more embodiments of the low molecular weight silk fibroin compositions described herein can stabilize detectable moieties present in the biological sample for a period of time under certain conditions, which can in turn permit higher recovery of the detectable moieties thereafter, for example for subsequent analysis and/or characterization of the component, as compared to recovery of the detectable moieties from a conventional silk fibroin-based material.

In some embodiments, the present disclosure provides the use of the low molecular weight silk fibroin compositions disclosed herein (e.g., tuned to produce various soluble or solid forms of low molecular weight silk fibroin-based materials, such as solutions, films, particles or powders, scaffolds, meshes and/or fibers, with desirable properties such as enhanced solubility (relative to conventional silk fibroin-based materials), enhanced recovery of additives (relative to conventional silk fibroin-based materials, and the like) for entrapment, stabilization, and subsequent recovery of a sample. In some embodiments, the sample is a biological sample.

The amounts of silk fibroin to an active agent/biological sample in silk fibroin compositions described herein can be adjusted for a number of factors including, e.g., but not limited to, volume and/or type of the biological sample, silk fibroin concentrations, solubility of the resultant silk-based materials, abundance of a target component to be stabilized and/or detected, recovery efficiency of the components present in the biological sample, detection sensitivity of the detection/characterization methods selected for a specific component.

In some embodiments, the ratio (e.g., mass ratio, volume ratio or molar ratio) of the silk fibroin to active agent/sample/component be within a range of about 1:10000 to about 10000:1, or from about 1:1000 to about 1000:1. In some embodiments, the ratio (e.g., mass ratio, volume ratio or molar ratio) is about 1:1 to about 1000:1. In some embodiments, the ratio is about 1:1000 to about 1000:1, about 1:500 to about 500:1, about 1:250 to about 250:1, about 1:125 to about 125:1, about 1:100 to about 100:1, about 1:50 to about 50:1, about 1:25 to about 25:1, about 1:10 to about 10:1, about 1:5 to about 5:1, about 1:3 to about 3:1, or about 1:1. By way of example only, in some embodiments, the volume ratio of silk fibroin to a blood sample can be within a range of about 1:1 to about 1000:1, or from about 1:1 to about 100:1, or from about 1:1: to about 50:1, or from about 1:1 to about 25:1.

The ratio of the silk fibroin matrix to the active agent/sample/component can vary with a number of factors, including the selection of an active agent, the storage condition and duration, the concentration of the silk fibroin matrix and the form of the silk matrix. One of skill in the art can determine appropriate ratio of the silk fibroin matrix to the active agent, e.g., by measuring bioactivity of the active agent retained at various ratios described herein over a pre-defined amount of time under a defined condition, e.g., at a temperature of above 0° C. Methods for measuring the bioactivity of various active agents described herein, e.g., enzymes, vaccines, proteins, antibodies and nucleic acids, are well known in the art. By way of example, stability or bioactivity of a given active agent in silk fibroin may be determined based on combinations of time and temperature. For example, stabilization studies can be conducted for 6 months. Activity assays can be conducted, for example, after 2 weeks, 4 weeks, then monthly. Samples can be prepared to provide N=3 for each time point. The range of temperature storage conditions to be assessed include 4° C. (refrigeration), 25° C. (room temperature), 37° C. (body temperature), 45° C. and/or 50° C., inclusive. Alternatively or additionally, activity can be assayed after one, two, three or more freeze-thaw cycles. These variables can be combined exhaustively to fully characterize the optimum formulation for long-term stability of active agent(s). In some embodiments, the results of the silk-related active agent stability can be compared with e.g., lyophilized active agent preparations with the same storage conditions, with the goal of improving the stability of the manufacture-recommended storage conditions (e.g., 4° C.) of lyophilized active agent preparations.

Stabilizing silk fibroin compositions described herein can have any amount of silk fibroin provided that the amount is sufficient to stabilize at least one property of at least one component of a biological sample for a period of time, and permit detection of the active agent/sample/component after the period of time. In some embodiments, the amount of silk fibroin in the composition vary with, e.g., the type and/or volume size of the agent/sample/component as described herein, form of the silk-based material (e.g., film, vs. foam), fabrication method of any silk-based material to be formed (e.g., air drying vs. lyophilization) and/or the silk fibroin concentration used to form the initial silk fibroin composition.

To give but a few examples, a silk-based stabilizing material can be prepared from an agent-containing silk solution comprising from about 0.25% to about 50% (w/v) of silk fibroin, or from about 0.5% to about 30% (w/v), or from about 0.5% to about 15% (w/v), or from about 0.5% to about 10% (w/v). In some embodiments, the silk-based material can be a silk solution comprising a biological sample. For example, in one embodiment, a silk-based film can be prepared from a silk solution comprising from about 1% to about 15% (w/v) of silk fibroin and an active agent or biological sample/component. In another embodiment, a silk-based foam can be prepared from a silk solution comprising from about 0.1% to about 5% (w/v) of silk fibroin and an active agent/biological sample/component.

In some embodiments, the silk-based material can be a solid-state silk-based material formed from a silk solution comprising a biological sample.

In some embodiments, an agent/sample/component can be stabilized in a silk composition (e.g., in a low molecular weight based composition) over a range of storage temperatures for the period of time described herein and allow recovery and/or detection of at least one component of the biological sample for analysis. Unlike typical sub-zero storage temperatures required for biological samples (e.g., in −80° C. freezer or in liquid nitrogen), the silk-based materials described herein can permit a biological sample to be stabilized therein at storage temperatures above 0° C. or higher. In some embodiments, the storage temperatures can range from about 0° C. to about an ambient temperature. In some embodiments, the storage temperature can be at least about 40° C. or greater than 40° C. In some embodiments, the storage temperature can be at least about 45° C. or greater than 45° C.

In some embodiments, an agent/sample/component can be stabilized in a silk fibroin composition as described herein under light exposure for the period of time described herein and allow recovery and/or detection of at least one component of the biological sample for analysis. For example, in some embodiments, an agent/sample/component present in a composition can be exposed to light, e.g., light of different wavelengths and/or from different sources. In some embodiments, an agent/sample/component present in the silk-based material can be exposed to UV or infra-red irradiation. In some embodiments, the agent/sample/component present in the silk-based material can be exposed under visible lights.

In some embodiments, a biological sample can be stabilized in a provided silk fibroin composition over a range of relative humidity for the period of time described herein and allow recovery and/or detection of at least one component of the biological sample for analysis. In some embodiments, the relative humidity can be at least about 5%, at least about 10%, at least about 20%, at least about 30%, at least about 40%, at least about 50% or higher.

The term "relative humidity" as used herein is a measurement of the amount of water vapor in a mixture of air and water vapor. It is generally defined as the partial pressure of water vapor in the air-water mixture, given as a percentage of the saturated vapor pressure under those conditions.

In some embodiments, the stabilizing silk fibroin compositions described can be lyophilized, for example to decrease residual moisture during storage. In some embodiments, residual moisture is decreased by at least about 5%, at least about 10%, at least about 20%, at least about 30%, at least about 40%, at least about 50%, at least about 60%, at least about 70%, at least about 80%, at least about 90%, or at least about 95%.

In some embodiments, the compositions described herein can be maintained under or subjected to any air pressure. In some embodiments, the compositions described herein can be maintained under or subjected to about atmospheric pressure, or higher, e.g., about 1 atm, about 2 atms, about 3 atms, about 4 atms, about 5 atms, about 6 atms, about 7 atms, about 8 atms, about 9 atms or about 10 atms. In some embodiments, the compositions described herein can be maintained under or subjected to vacuum.

In some embodiments, where, while not necessary, a silk fibroin composition (e.g., a silk-based solution) is stored at sub-zero temperatures, an agent/sample/component can be stabilized in the composition upon at least one or more freeze-thaw cycles (e.g., a frozen silk-based solution to a thawed silk-based solution) and allow recovery and/or detection of at least one component of the biological sample for analysis. The term "freeze-thaw cycles" is used herein to describe a series of alternating freezing and thawing, and also encompasses a series of alternating frozen (solid) and fluid state. For example, one freeze-thaw cycle involves a change of state between a frozen (solid) state and a fluid state. The time interval between freezing and thawing, or frozen and fluid state, can be any period of time, e.g., hours, days, weeks or months. For example, once a silk-based solution has been frozen or is in a frozen state, it can be continually stored in the frozen state at sub-zero temperatures, e.g., between about −20° C. and −80° C., until it needs to be thawed for use again. Freezing of a composition can be performed rapidly, e.g., in liquid nitrogen, or gradually, e.g., in a freezing temperature, e.g., between about −20° C. and −80° C. Thawing of a frozen composition can be performed at any temperature above 0° C. rapidly, e.g., at room temperature, or gradually, e.g., on ice. Typically, a component of a biological sample, e.g., protein and/or nucleic acid, in non-silk fibroin matrix can lose its activity or integrity over one or more freeze-thaw cycles. As described herein, distributing a biological sample in a silk fibroin matrix can increase the stability of at least one component thereof and thus retain its activity or integrity during one or more freeze-thaw cycles.

In one embodiment, an agent/sample/component can be stabilized in a provided silk fibroin composition under two or more conditions described above for the period of time described herein and allow recovery and/or detection of at least one component of the agent/sample/component for analysis.

Another aspect provided herein relates to methods and compositions of maintaining or stabilizing the bioactivity of an active agent. The method includes maintaining a composition, wherein the composition comprises a silk fibroin matrix and at least one active agent distributed, mixed, or embedded therein, and wherein the at least one active agent retains or stabilizes at least about 30% of its original bioactivity when the composition is subjected to a specified condition, which inhibits or reduces the bioactivity of the active agent, for a period of time. Such conditions can include, but are not limited to, a state-changing cycle, temperatures, air pressures, humidity, and light exposure.

The term "state-changing cycle" as used herein refers to a change of a material state, including, but not limited to, from a solid state to a fluid state, or from a fluid state to a solid state. A fluid state can include, but is not limited to, liquids, gases, slurries, flowable paste, plasmas, and any combinations thereof. A solid state refers to a state that is not flowable, and it can also encompass semi-solids, e.g., a gel. The composition described herein can be maintained at a certain state for any period of time, e.g., seconds, minutes, hours, weeks, months, or years, before changing to another state. A state-changing cycle can be resulted from at least one change in an environmental condition described herein, e.g., a temperature change, a change in ambient air pressure, light condition, humidity, or any combinations thereof.

In one embodiment, the state-changing cycle refers to a freeze-thaw cycle. In such embodiments, the composition described herein when stored or transported can be subjected to at least one freeze-thaw cycle, at least two freeze-thaw cycles, at least three freeze-thaw cycles, at least four freeze-thaw cycles, at least five freeze-thaw cycles, at least six freeze-thaw cycles, at least seven freeze-thaw cycles, at least eight freeze-thaw cycles, at least nine freeze-thaw cycles, at least ten free-thaw cycles or more. The term "freeze-thaw cycles" is used herein to describe a series of alternating freezing and thawing, and also encompasses a series of alternating frozen (solid) and fluid state. For example, one freeze-thaw cycle involves a change of state between a frozen (solid) state and a fluid state. The time interval between freezing and thawing, or frozen and fluid state, can be any period of time, e.g., hours, days, weeks or months. For example, once an active agent composition has been frozen or is in a frozen state, it can be continually stored in the frozen state at sub-zero temperatures, e.g., between about −20° C. and −80° C., until it needs to be thawed for use again. Freezing of a composition can be performed rapidly, e.g., in liquid nitrogen, or gradually, e.g., in a freezing temperature, e.g., between about −20° C. and −80° C. Thawing of a frozen composition can be performed at any temperature above 0° C. rapidly, e.g., at room temperature, or gradually, e.g., on ice. Typically, an active agent in non-silk fibroin matrix can lose its bioactivity over one or more freeze-thaw cycles. As described herein, distributing an active agent in a silk fibroin matrix can increase the stability of the active agent and thus retain its bioactivity during one or more freeze-thaw cycles.

Embodiments of various aspects described herein provide for stabilized active agents, in which stabilization of an active agent is achieved by distributing, mixing, or embedding an active agent in the silk fibroin compositions disclosed herein. The silk fibroin can be a silk fibroin solution or a solid-state silk fibroin matrix, e.g., a silk fibroin article. This approach provides for the active agent to retain bioactivity regardless of the cold chain and/or environmental conditions under which the active agent is stored and/or transported. Exemplary environmental conditions include, but are not limited to, temperatures, air pressures, humidity, and light exposure. For example, the cold chain is a standard practice for stabilizing active agents in the pharmaceutical industry: maintaining the cold chain ensures that active agents are transported and stored according to the manufacturer's recommended temp range (e.g., 2° C. to 8° C. or sub-zero temperatures) until time of use.

In some embodiments, a silk fibroin composition comprising an active agent is in form of an implant or an implantable drug delivery device. The active agent in such a composition can retain at least 30% (including at least about 40%, at least about 60%, at least about 80% or higher) of its original bioactivity or higher for a period of time. In some embodiments, an active agent a silk fibroin composition which is in the form of an implantable drug device can retain at least about 30% of its original bioactivity or higher for at least about 6 hours, at least about 12 hours, at least about 24 hours, at least about 36 hours, at least about 48 hours, at least 3 days, at least about 4 days, at least about 5 days, at least about 6 days, at least about 1 week, at least about 2 weeks, at least about 3 weeks, at least about 4 weeks, at least about 2 months, at least about 3 months, at least about 4 months, at least about 5 months, at least about 6 months, or at least after 1 year or longer, after implantation.

In some embodiments, one or more active agents encapsulated in an injectable silk fibroin composition can be administered to a subject (e.g., by injection such as subcutaneous injection) as a depot of the active agent (e.g., a vaccine depot) such that the active agent (e.g., a vaccine) can be released, continuously or intermittently, from the depot for an extended period of time, e.g., for a period of hours, days, weeks, or months. In some embodiments, the active agent (e.g., a vaccine) can be released at a rate at which at least about 1% (including at least about 5%, at least about 10%, at least about 20%, at least about 30%, at least about 40%, at least about 50%, at least about 60%, at least about 70%, at least about 80%, at least about 90%, at least about 95%, or more) of the encapsulated active agent is released over a period of at least 1 hour, at least 2 hours, at least 3 hours, at least about 4 hours, at least about 5 hours, at least about 6 hours, at least about 12 hours, at least about 24 hours or longer. In some embodiments, the active agent (e.g., a vaccine) can be released at a rate at which at least about 10% (including at least about 20%, at least about 30%, at least about 40%, at least about 50%, at least about 60%, at least about 70%, at least about 80%, at least about 90%, at least about 95%, or more) of the encapsulated active agent is released over a period of 5 days, a period of 1 week, at least about 2 weeks, at least about 3 weeks, at least about 1 month, at least about 2 months, at least about 3 months or longer.

In some embodiments, the active agent in the silk fibroin composition retains at least about 30% of its original bioactivity e.g., at least about 40%, at least about 50%, at least about 60%, at least about 70%, at least about 80%, at least about 90%, at least about 95% of the original bioactivity or higher activity at about 4° C., at about 25° C., at about 37° C., at about 45° C., or greater, for at least up to 6 months. In some embodiments, the active agent retains at least about 8% of the original bioactivity at temperatures of about 37° C. or greater, for at least 6 months.

Particular aspects described herein are storage-stable compositions, which comprise silk fibroin compositions (e.g., low molecular weight silk fibroin compositions) and an active agent distributed, mixed or embedded therein, wherein the active agent retains at least about 30% of its original bioactivity (e.g., at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, etc.) when the composition is subjected to at least one state-changing cycle, and/or is maintained for a period of time under one or more conditions specified herein. In some embodiments, the active agent can covalently or non-covalently fused or linked to the silk fibroin fragments in the composition. In one embodiment, the state-changing cycle is a freeze-thaw cycle. In one embodiment, the period of time for maintaining the active agent is at least about 24 hours. In some embodiments, the specified condition can be an environmental condition under which an active agent is stored and/or transported. Non-limiting examples of environmental conditions include temperatures, air pressures, humidity, and light exposure. In some embodiments, the compositions described herein can be immunogenic. In some such embodiments, the active agent is an immunogen. In some embodiments, the active agent is a vaccine.

In some aspects, as described herein, the present invention provides methods of stabilizing a biological sample or an active agent. Generally, the method comprises contacting, combining, or mixing the biological sample or the active agent with a a silk fibroin composition disclosed herein thereby providing a mixture comprising the silk fibroin and the biological sample or active agent. In some embodiments, the method further comprises forming a silk-based material (e.g., silk fibroin article) from the mixture. Accordingly, in some embodiments, the method for stabilization of a biological sample or active agent comprises providing a low molecular weight silk fibroin composition comprising the biological sample or the active agent and forming a silk-based article from the composition. In some embodiments, when a silk fibroin composition comprising an active agent/sample/component is in a solid state, it can be further processed to induce formation of beta-sheet secondary structure in the silk fibroin.

In some embodiments, a provided method comprises contacting the biological sample or the active agent with silk fibroin composition, wherein the composition is in the form of a powder. In some further embodiments of this, the method further comprises forming a solution from the composition.

In some embodiments, the method comprises contacting the biological sample or the active agent with a silk fibroin composition, wherein the composition is in the form of a solution.

In some embodiments, the solution composition comprising the biological sample or the active agent can be formed into a silk fibroin article. The resultant article can be soluble in an aqueous solution (e.g., water, a buffered solution, or a combination thereof).

The amounts of silk fibroin to a biological sample within compositions described herein can be adjusted for a number of factors including, e.g., but not limited to, volume and/or type of the biological sample, silk fibroin concentrations, solubility of the resultant silk-based materials, abundance of a target component to be stabilized and/or detected, recovery efficiency of the components present in the biological sample, detection sensitivity of the detection/characterization methods selected for a specific component. For example, as already described, in some embodiments, the ratio (e.g., mass ratio, volume ratio or molar ratio) of the silk fibroin to the biological sample can range from about 1:10000 to about 10000:1, or from about 1:1000 to about 1000:1. In some embodiments, the ratio (e.g., mass ratio, volume ratio or molar ratio) of the silk fibroin to the biological sample is about 1:1 to about 1000:1. By way of example only, in some embodiments, the volume ratio of silk fibroin to a blood sample can range from about 1:1 to about 1000:1, or from about 1:1 to about 100:1, or from about 1:1: to about 50:1, or from about 1:1 to about 25:1.

Active Agents/Components

Silk compositions (e.g., low molecular weight silk fibroin compositions described herein) can include/incorporate any of a variety of active and/or labile agents.

Non-limiting examples of biological samples that can be stored, stabilized, analyzed, and/or recovered from silk fibroin compositions described herein include, but are not limited to: bodily fluid samples such as blood samples, including, e.g., whole blood samples, plasma samples, and serum samples; urine samples; cerebrospinal fluid samples, saliva samples, and any combinations thereof. In some embodiments, such samples can be collected from a patient for medical or clinical purposes. In some embodiments, such samples can be collected for forensic purposes.

In some embodiments, unique properties of provided silk fibroin compositions (e.g., low molecular weight silk compositions) described herein in the context of, e.g., agent incorporation, stabilization and recovery, enable fully reconstitution of various entrapped blood components (e.g., cells, circulating factors such as hormones, growth factors, cytokines, antibodies and other proteins, nucleic acids such as DNAs or RNAs, etc.). For example, a blood draw equivalent to a finger prick volume can be mixed with a silk fibroin solution to form an at least partially dried silk-based material, and thereafter, the at least partially dried silk-based material can be readily procured containing stabilized blood components, which can be stored until ready for use and/or analysis.

In addition to a blood sample, other biological samples used for diagnostic purposes including, e.g., but not limited to, urine, blood, feces, cerumen, nucleic acids (e.g., DNA/RNA, modified nucleic acids) antibodies, whole cells, therapeutics, can be interfaced with silk fibroin in a similar manner, depending on performance needs and sample availability. Provided silk fibroin compositions comprising a biological sample can stabilize one or more components of the biological sample for a period of time, which allows subsequent analysis and/or characterization of the biological sample or a component thereof. Accordingly, embodiments of various aspects described herein also relate to silk fibroin based compositions for stabilization of at least one component of a biological sample mixed therewith or entrapped therewith, which permit detection of the component at a later time, as well as methods of making and using the same.

In accordance with various embodiments described herein, a biological sample to be mixed or entrapped within low molecular silk fibroin include any fluid or specimen (processed or unprocessed) that is intended to be stabilized for at least one component thereof and/or evaluated for the presence of the component. The biological sample can be liquid, supercritical fluid, solutions, suspensions, gases, gels, slurries, solids, and combinations thereof.

In some embodiments, the biological sample can comprise an aqueous fluid. As used herein, the term "aqueous fluid" refers to any flowable water-containing material.

In some embodiments, a biological sample can be obtained from a subject, e.g., a mammalian subject such as a human subject. Exemplary biological samples obtained from a subject can include, but are not limited to, a biological cell, a tissue, blood (including whole blood, plasma, cord blood and serum), lactation products (e.g., milk), amniotic fluids, sputum, saliva, urine, semen, cerebrospinal fluid, bronchial aspirate, perspiration, mucus, liquefied feces, synovial fluid, lymphatic fluid, tears, tracheal aspirate, and fractions thereof. In some embodiments, a biological sample can include a homogenate of a tissue specimen (e.g., biopsy) from a subject. In one embodiment, a biological sample can comprise a suspension obtained from homogenization of a solid sample obtained from a solid organ or a fragment thereof. The biological sample can be obtained from a subject by any means known in the art, which can vary with the biological sample types. By way of example only, a blood sample can be obtained from a subject, e.g., by finger prick, a microneedle, a venous draw, or any known methods for collecting a blood sample.

In some embodiments, the biological sample can comprise a biological cell selected from the group consisting of living or dead cells (prokaryotic and eukaryotic, including mammalian), viruses, bacteria, fungi, yeast, protozoan, microbes, and parasites. The biological cell can be a normal cell or a diseased cell, e.g., a cancer cell. Mammalian cells include, without limitation; primate, human and a cell from any animal of interest, including without limitation; mouse, hamster, rabbit, dog, cat, avian, domestic animals, such as equine, bovine, murine, ovine, canine, and feline. In some embodiments, the cells can be derived from a human subject. In other embodiments, the cells are derived from a domesticated animal, e.g., a dog or a cat. Exemplary mammalian cells include, but are not limited to, stem cells, cancer cells, progenitor cells, immune cells, blood cells, fetal cells, and any combinations thereof. The cells can be derived from a wide variety of tissue types without limitation such as; hematopoietic, neural, mesenchymal, cutaneous, mucosal, stromal, muscle, spleen, reticuloendothelial, epithelial, endothelial, hepatic, kidney, gastrointestinal, pulmonary, cardiovascular, T-cells, and fetus. Stem cells, embryonic stem (ES) cells, ES-derived cells, induced pluripotent stem cells, and stem cell progenitors are also included, including without limitation, hematopoietic, neural, stromal, muscle, cardiovascular, hepatic, pulmonary, and gastrointestinal stem cells. Yeast cells may also be used as cells in some embodiments described herein. In some embodiments, the cells can be ex vivo or cultured cells, e.g. in vitro. For example, for ex vivo cells, cells can be obtained from a subject, where the subject is healthy and/or affected with a disease.

In some embodiments, the biological sample can comprise a tissue derived from animal parts, e.g., but not limited to, one or more organs (including skin), muscle, beaks, claws, feathers, wings, and/or tails.

In some embodiments, the biological sample can include a fluid or specimen obtained from a source, e.g., but not limited to, a research laboratory, an animal colony, a crime scene, a cell bank or depository, a blood bank, a tissue bank, a biological specimen depository, a diagnostic testing facility, a clinical setting, and/or any combinations thereof.

In some embodiments, the biological sample can include a fluid (e.g., culture medium) and/or a cell from a biological culture. Examples of a fluid (e.g., culture medium) and/or a cell obtained from a biological culture includes the one obtained from culturing or fermentation, for example, of single- or multi-cell organisms, including prokaryotes (e.g., bacteria) and eukaryotes (e.g., animal cells, plant cells, yeasts, fungi), and including fractions thereof.

In some embodiments, a biological sample comprises at least one component or a mixture of components. Examples of components that can be stabilized, e.g., for subsequent detection and/or characterization, can include, but are not limited to, a peptide, a protein, an antibody, an enzyme, an antigen, an amino acid, a nucleic acid (e.g., DNA, RNA, siRNA, miRNA, non-coding RNAs, or any variants of RNAs that can be found endogenously in a subject), a nucleotide, a metabolite, a lipid, a sugar, a glycoprotein, a peptidoglycan, a microbe, a cell, and any combinations thereof. Using the compositions and/or methods described herein, at least one component, including, e.g., at least two components, at least three components, at least four components, at least five components, or more can be stabilized for a period of time and be also detected after the period time. In some embodiments, the silk-based material can stabilize at least one or more (e.g., 1, 2, 3, 4, 5, or more) proteins in a biological sample (e.g., plasma or serum proteins in a blood sample), which can be detected at a later time. In some embodiments, the silk-based material can stabilize at least one or more (e.g., 1, 2, 3, 4, 5, or more) cell-free or circulating DNA or RNA in a blood sample. In some embodiments, the silk-based material can stabilize at least one or more (e.g., 1, 2, 3, 4, 5, or more) diagnostic biomarkers present in a biological sample.

In some embodiments, the silk-based materials can stabilize the activity and/or integrity of RNA, it is contemplated that the silk fibroin compositions and methods described herein can be used to stabilize any nucleic acid including, but not limited to, DNA, RNA, and modified DNA or RNA. Some exemplary nucleic acids include peptide plasmid DNA, genomic DNA, mRNA, siRNA, pre-miRNA, miRNA, antisense oligonucleotides, shRNA, activating RNA, decoy oligonucleotides, peptide nucleic acid (PNA), oligonucleotides, and/or any nucleic acid that can be administered to a subject for therapeutic purposes.

In some embodiments, it can be desirable to stabilize the state of at least one component (e.g., at least one detectable entity) of a biological sample, upon incorporation of the biological sample into one or more embodiments of silk fibroin compositions described herein. By way of example only, a protein present in a biological sample can be in an active or inactive state. In some embodiments, the active or native state, e.g., a phosphorylated protein, or a glycosylated protein, of a protein of a biological sample can be stabilized or maintained in the silk fibroin material. These embodiments can be useful, for example, where the activity or state of a component plays a role in diagnosis of a disease or disorder. For example, certain states or levels of post-translational modifications correlate with a disease state so as to aid in diagnosis. In some embodiments, post-translational modifications include, but are not limited to: phosphorylation, myristoylation, palmitoylation, isoprenylation or prenylation, farnesylation, geranylgeranylation, glypiation, glycosylphosphotidylinositol anchor formation, lipoylation, attachmet of flavin moiety, attachment of heme C, phosphopantetheinylation, retinylidene Schiff base formation, diphthamide formation, ethanolamine phosphoglycerol attachment, hypusine formation, acylation, acetylation, formylation, alkylation, methylation, amide bond formation, amidation at C-terminus, amino acid addition, arginylation, polyglutamylation, polyglycylation, butyrylation, gamma-carboxylation, glycosylation, polysialylation, malonylation, hydroxylation, iodination, nucleotide addition, oxidation, phosphate ester or phosphoramidate formation, phosphorylation, adenylylation, propionylation, pyroglutamate formation, S-glutathionylation, S-nitrosylation, succinylation, sulfation, selenoylation, glycation, biotinylation, pegylaiton, ISGylation, SUMOylation, ubiquitination, Neddylation, Pupylation, citrullination, deamidation, eliminylation, carbamylation, disulfide bridges, proteolytic cleavage, and racemization of proline.

In general, for incorporating the biological sample or agent in a silk fibroin article, the biological sample or the active agent can be included in a silk fibroin solution used for producing the silk fibroin article. Alternatively, or in addition, a preformed silk fibroin article can be added to a solution comprising the biological sample or the active agent and letting the biological sample (or a component thereof) or the active agent absorb in/on the silk fibroin article.

In some embodiments, the biological sample/agent can be distributed, homogenously or non-homogenously (e.g., in a gradient) in the silk-based material. In some embodiments, the biological sample can be encapsulated or entrapped by silk fibroin in the silk-based material. In some embodiments, the biological sample can be mixed or blended with silk fibroin in the silk-based material.

After forming the silk-based material, the material can be treated, e.g., to induce formation of beta-sheet secondary structure in the silk fibroin. Methods of inducing formation of beta-sheet secondary structure in the silk fibroin are described elsewhere herein.

In accordance with embodiments of various aspects described herein, a silk fibroin composition comprising a biological sample can stabilize at least one component of the biological sample, which allows detection and/or analysis of the component at a later time. In some embodiments, these silk-based materials comprising a biological sample can be stored and/or transported without the need for refrigeration or freezing, which are typical methods to currently store and handle biological samples to maintain/retain sample quality for diagnostic evaluation of human health. Accordingly, in some embodiments, the silk-based materials and methods described herein can be useful in diagnostic applications. For example, the silk-based materials and methods can be used to maintain and/or retain the quality of a biological sample during storage and/or transportation, or in some developing countries or in remote field conditions where minimum infrastructure to support continuous cold storage does not exist, such that at least one component of the biological sample can be assayed for diagnostic applications. In some embodiments, the silk-based material and methods described herein can be used to maintain and/or retain the quality of biological sample under at least one or any combinations of the following conditions described earlier, namely: (a) a temperature above 0° C. (e.g., at least about room temperature or higher) during storage and/or transportation; (b) light exposure (e.g., UV, infra-red, and/or visible lights) during storage and/or transportation; and (c) a relative humidity of at least about 10% or higher during storage and/or transportation.

Accordingly, yet another aspect provided herein relates to methods for using the silk-based material described herein. The method comprises (a) providing one or more embodiments of the silk fibroin (e.g., a low molecular weight silk fibroin) composition comprising a active agent/sample component; and (b) dissolving at least a portion of the composition in water, whereby forming a sample solution comprising silk fibroin and a detectable amount of the at least one active agent.

In some embodiments, a subject or patient in need of a diagnosis of a disease or disorder can provide a biological sample and contact the biological sample with a silk fibroin composition, which is then sent to a diagnostic testing laboratory for analyses. In some embodiments, a biological sample can be collected from a subject by a skilled practitioner at a clinical setting, where the biological sample can be then contacted with a silk fibroin (e.g., a low molecular weight silk fibroin) and sent to a diagnostic testing laboratory for analyses.

While in some embodiments, at least one component of a biological sample can be detected and/or analyzed without isolating the component from the biological sample, in alternative embodiments, the component can be extracted or recovered from at least a portion of the silk fibroin composition before detection and/or analysis using any methods known in the art. In accordance with some embodiments of the silk-based materials described herein, the composition can be soluble in an aqueous solution (e.g., water, a buffered solution, or a combination thereof). Unlike cellulose-based technologies, e.g., dried blood spots, where blood is absorbed on a filter paper and is difficult to be recovered thereafter, at least a portion of the silk fibroin composition described herein can be solubilized in an aqueous solution (e.g., water, a buffered solution, or a combination thereof). The final silk/biological sample solution can then be amenable to routine liquid assays, e.g., ELISA and Luminex™ assay as described in the Examples, without additional purification. Accordingly, in some embodiments, the method can further comprise contacting at least a portion of the silk fibroin composition with an aqueous solution (e.g., water, a buffered solution, or a combination thereof) prior to subjecting said at least one component of the biological sample to at least one analysis.

Various types of analyses can be performed on the target component of a biological sample, e.g., depending on the nature of the target component. Non-limiting examples of analyses can include, but are not limited to, genotyping, nucleic acid sequencing, expression analysis (e.g., protein level, or transcript level), binding affinity, enzymatic activity, transfection efficiency, cell counting, cell identification, cell viability, immunogenicity, infectivity, metabolite profiling, and any combinations thereof. In some embodiments, at least one component of the biological sample can be subjected to at least one genotyping or nucleic acid sequencing analysis, expression analysis (e.g., protein level and/or transcript level), metabolite profiling, or any combinations thereof. Various methods to perform these analyses can include, but are not limited to, polymerase chain reaction (PCR), real-time quantitative PCR, microarray, western blot, immunohistochemical analysis, enzyme linked immunosorbent assay (ELISA), mass spectrometry, nucleic acid sequencing, flow cytometry, gas chromatography, high performance liquid chromatography, nuclear magnetic resonance (NMR) spectroscopy, or any combinations thereof. Techniques for nucleic acid sequencing are known in the art and can be used to assay the component to determine nucleic acid or gene expression measurements, for example, but not limited to, DNA sequencing, RNA sequencing, de novo sequencing, next-generation sequencing such as massively parallel signature sequencing (MPSS), polony sequencing, pyrosequencing, Illumina (Solexa) sequencing, SOLiD sequencing, ion semiconductor sequencing, DNA nanoball sequencing, Heliscope single molecule sequencing, single molecule real time (SMRT) sequencing), nanopore DNA sequencing, sequencing by hybridization, sequencing with mass spectrometry, microfluidic Sanger sequencing, microscopy-based sequencing techniques, RNA polymerase (RNAP) sequencing, or any combinations thereof.

In some embodiments, the at least one analysis can be performed in a format that can interface with a readout instrument or system. In some embodiments, the at least one analysis can be performed on a system.

In some embodiments, prior to the analysis or contacting the biological sample comprising composition with an aqueous solution, the composition can be reduced or aliquoted into smaller portions, e.g., some of which can be saved for later analyses, and/or can be analyzed for different target components (e.g., proteins, nucleic acid, and/or metabolites). The aliquoting into smaller portions can be by weight or by volume.

Recovery of at least one agent from a silk fibroin composition generally depends, in part, on solubility of the silk fibroin composition in which the agent is encapsulated, stability of an agent when present in the silk fibroin composition, and/or ease of processing the silk fibroin solution containing the agent for subsequent analysis. As noted herein, the inventors have surprisingly discovered that, unlike other silk compositions in which there is a larger portion of silk fibroin fragments having a molecular weight exceeding 200 kDa (e.g., silk compositions produced from a silk solution obtained by degumming silk cocoons for less than 30 minutes), the low molecular weight silk fibroin compositions described herein be readily dissolved or resolubilized in water at an ambient temperature, without any additive (e.g., salt) or heating, to form a silk fibroin solution. For example, in some embodiments, silk fibroin particles (including powder) and films described herein can be readily dissolved or resolubilized at room temperature in deionized water. Thus, in some embodiments, the resultant silk fibroin solution can be ready for use without any subsequent dialysis, which is usually otherwise needed. In some embodiments, the inventors have shown that the silk fibroin solution reconstituted from low molecular weight silk fibroin compositions described herein can be directly injected into a fluidics-based analytical machine for subsequent analysis. Further, the resultant silk fibroin solution can also be used to re-form other low molecular weight silk fibroin compositions described herein.

In addition to their unique features of resolubility and ability to re-form an article from a resultant silk solution, low molecular weight silk fibroin compositions described herein can also stabilize at least one or more agents in a sample for an extended period of time, e.g., as described in the International Application No. PCT/US12/34643 and U.S. Provisional Application Nos. 61/792,161 and 61/830,950, when compared to stability of an agent in the absence of a silk fibroin composition. Accordingly, in some embodiments, the low molecular weight silk fibroin compositions described herein are suitable for any applications where an agent or a sample is desired to be stabilized for a period of time in order to be recovered or retrieved for future use and/or analysis. By way of example only, in some embodiments, an agent or a sample encapsulated in one or more embodiments of the low molecular weight silk fibroin articles, e.g., a low molecular silk fibroin film or powder, can be stored at room temperature without refrigeration for a period of time until it is ready for use and/or analysis. In these embodiments, at least a portion of the low molecular weight silk fibroin articles comprising the agent or sample can be dissolved in water at room temperature to recover the agent or sample in a usable form, while the rest of the sample can be saved for later use and/or other analysis.

In some embodiments, at least a desirable or detectable amount of an agent or sample encapsulated in the low molecular weight silk fibroin compositions described herein can be recovered in a usable form. As used herein, the term "usable form" refers to a form of an agent or sample that is amenable for a specific application. For example, an agent or sample can be recovered in a solution for assay analysis. In some embodiments, the term "usable form" can encompass the agent or sample isolated from the solution, e.g., by any art-recognized purification method. Since the low molecular weight silk fibroin compositions can stabilize an agent and be readily dissolvable, a smaller aliquot of the low molecular weight silk fibroin composition can generally be sufficient to provide the desirable or detectable amount of the agent or sample, when compared to recovery of the agent or sample from a non-silk fibroin composition. Stated another way, with an aliquot containing the same loading of an agent or sample, recovery of an agent or a sample from the low molecular silk fibroin composition described herein can be increased by at least about 10% or more, including, e.g., at least about 20%, at least about 30%, at least about 40%, at least about 50%, at least about 60%, at least about 70%, at least about 80%, at least about 90%, or more, as compared to recovery from a non-silk fibroin composition.

In some embodiments, at least about 50% or higher of the original loading of an agent or sample in a silk fibroin composition (e.g., a low molecular weight composition) can be recovered. In some embodiments, more than 50%, including, e.g., at least about 60%, at least about 70%, at least about 80%, at least about 90% or higher, of the original loading of an agent or sample in the low molecular silk fibroin composition can be recovered. In some embodiments, the agent or sample can be recovered by dissolving the low molecular weight silk fibroin article encapsulating the same in water (e.g., deionized water) at room temperature. In some embodiments, the dissolved silk fibroin article comprising the agent or sample can be subjected to further processing, e.g., analysis of the agent, and/or purification of the agent from the silk fibroin solution.

Due to ease of manipulation and/or handling of low molecular weight silk fibroin compositions described herein, the compositions described herein can be applied in military field setting, in clinic setting, during paramedic transportation, and/or for home use. By way of example only, in order to stabilize a blood sample, e.g., for transportation to a laboratory facility from home or a remote field area, a home user or a military personnel can reconstitute a shelf-stable low molecular weight silk fibroin powder to make a silk fibroin solution, with which the blood sample can then be mixed together. The sample solution mixture, in which components of the blood sample is stabilized in the presence of silk fibroin, can then be sent to the laboratory facility. In some embodiments, the silk fibroin solution comprising the blood sample can be air-dried to form an article, e.g., a film, in which components of the blood sample can be stabilized for a longer period of time, e.g., at least 1 week, at least 2 weeks, at least 3 weeks, at least 4 weeks or longer, at an ambient temperature. Preserving the activity and/or level of one or more desirable components in a sample using the low molecular silk fibroin compositions and/or methods described herein can help discovery of a new biomarker for a disease or disorder, increase sensitivity of a diagnostic test and/or provide a more accurate diagnostic test readout.

Compositions and methods for stabilizing biological samples using silk fibroin are described in inventor's U.S. provisional application Ser. No. 61/792,161 filed Mar. 15, 2013 and No. 61/830,950 filed Jun. 4, 2013, contents of both of which are incorporated herein by reference in their entireties.

Exemplary Composition Formats

Without limitation, a silk fibroin composition as described herein (e.g., a low molecular weight silk fibroin composition and/or a silk fibroin composition comprising a biological sample or active agent for stabilization) can be in any form, shape or size. For example, the composition can be a solution, a fiber, a film, a sheet, a fiber, a mat, a non-woven mat, a mesh, a fabric, a sponge, a foam, a gel, a hydrogel, a tube, a particle (e.g., a nano- or micro-particle, a gel-like particle), a powder, a scaffold, a 3D construct, a coating layer on a substrate, or any combinations thereof.

Methods for producing different formats of the silk-based materials are known in the art, including, e.g., but not limited to drying, solution casting, salt leaching, freeze-drying, gas forming, electrospinning, gelling (e.g., electrogellation), shear stress, sonication, pH reduction, water annealing, water vapor annealing, alcohol immersion, fiber drawing, coating, spraying, micronizing, or any combination thereof. In some particular embodiments, a silk fibroin composition (e.g., a low molecular weight composition and/or a stabilizing composition) is produced by a method that involves during a solution of the silk fibroin, optionally with an active agent/sample/component; in some embodiments the drying comprises lyophilization or air-drying.

In some embodiments, for example depending on, e.g., the water content remained in the silk-based material, in some embodiments, the silk-based material (e.g., in a solid-state) can comprise at least about 10% or more silk fibroin by weight. For example, the silk-based material (e.g., in a solid-state) can comprise at least about 20%, at least about 30%, at least about 40%, at least about 50%, at least about 60%, at least about 70%, at least about 80%, at least about 90%, at least about 95% or more silk fibroin by weight.

In some embodiments, a silk fibroin composition as described herein (e.g., a low molecular weight silk fibroin composition and/or a stabilizing silk composition) is in form of a particle. For example, a silk fibroin article can be in the form of a silk nanosphere or a silk microsphere. As used herein, the term "particle" includes spheres; rods; shells; prisms; and powder; and, in some embodiments, these particles can be part of a network or an aggregate. Without limitations, the particle can have any size from nanometers (nm) to millimeters (mm). In some embodiments, the particles can have a size ranging from about 0.01 µm to about 1000 µm, about 0.05 µm to about 500 µm, about 0.1 µm to about 250 µm, about 0.25 µm to about 200 µm, or about 0.5 µm to about 100 µm. As used herein, the term "nanoparticle" refers to particle having a particle size of about 0.1 nm to about 1000 nm. Certain embodiments of micro- to nano-scale silk fibroin particles and related technology are also provided in U.S. Provisional Application concurrently filed herewith, entitled "SYNTHESIS OF SILK FIBROIN MICRO-AND SUBMICRON SPHERES USING A CO-FLOW METHOD."

It will be understood by one of ordinary skill in the art that particles usually exhibit a distribution of particle sizes around the indicated "size." Unless otherwise stated, the term "particle size" as used herein refers to the mode of a size distribution of particles, i.e., the value that occurs most frequently in the size distribution. Methods for measuring the particle size are known to a skilled artisan, e.g., by dynamic light scattering (such as photocorrelation spectroscopy, laser diffraction, low-angle laser light scattering (LALLS), and medium-angle laser light scattering (MALLS), light obscuration methods (such as Coulter analysis method), or other techniques (such as rheology, and light or electron microscopy).

In some embodiments, the particles can be substantially spherical. What is meant by "substantially spherical" is that the ratio of the lengths of the longest to the shortest perpendicular axes of the particle cross section is less than or equal to about 1.5. Substantially spherical does not require a line of symmetry. Further, the particles can have surface texturing, such as lines or indentations or protuberances that are small in scale when compared to the overall size of the particle and still be substantially spherical. In some embodiments, the ratio of lengths between the longest and shortest axes of the particle is less than or equal to about 1.5, less than or equal to about 1.45, less than or equal to about 1.4, less than or equal to about 1.35, less than or equal to about 1.30, less than or equal to about 1.25, less than or equal to about 1.20, less than or equal to about 1.15 less than or equal to about 1.1. Without wishing to be bound by a theory, surface contact is minimized in particles that are substantially spherical, which minimizes the undesirable agglomeration of the particles upon storage. Many crystals or flakes have flat surfaces that can allow large surface contact areas where agglomeration can occur by ionic or non-ionic interactions. A sphere permits contact over a much smaller area.

In some embodiments, the particles have substantially the same particle size. Particles having a broad size distribution where there are both relatively big and small particles allow for the smaller particles to fill in the gaps between the larger particles, thereby creating new contact surfaces. A broad size distribution can result in larger spheres by creating many contact opportunities for binding agglomeration. The particles described herein are within a narrow size distribution, thereby minimizing opportunities for contact agglomeration. What is meant by a "narrow size distribution" is a particle size distribution that has a ratio of the volume diameter of the 90th percentile of the small spherical particles to the volume diameter of the 10th percentile less than or equal to 5. In some embodiments, the volume diameter of the 90th percentile of the small spherical particles to the volume diameter of the 10th percentile is less than or equal to 4.5, less than or equal to 4, less than or equal to 3.5, less than or equal to 3, less than or equal to 2.5, less than or equal to 2, less than or equal to 1.5, less than or equal to 1.45, less than or equal to 1.40, less than or equal to 1.35, less than or equal to 1.3, less than or equal to 1.25, less than or equal to 1.20, less than or equal to 1.15, or less than or equal to 1.1.

Geometric Standard Deviation (GSD) can also be used to indicate the narrow size distribution. GSD calculations involved determining the effective cutoff diameter (ECD) at the cumulative less than percentages of 15.9% and 84.1%. GSD is equal to the square root of the ratio of the ECD less than 84.17% to ECD less than 15.9%. The GSD has a narrow size distribution when GSD<2.5. In some embodiments, GSD is less than 2, less than 1.75, or less than 1.5. In one embodiment, GSD is less than 1.8.

Without wishing to be bound by a theory, particle size can greatly determine microscopic and macroscopic properties of the final product. Particle size is dependent on a number of process parameters, including, but not limited to, the size of the ceramic balls used, the amount of silk placed in each ball mill cup, the rotational speed (RPM) of the machine, and the duration of ball milling. Particle size in the powder can be predicted based on some of these process parameters, e.g., with mathematical modeling and/or experimentation to determine the correlation. For example, this can be done by milling a given volume of silk fibroin for varying ball mill speeds and durations. Scanning Electron Microscopy (SEM) can be performed on representative samples from each experiment to determine particle size. Additional tests can be run on each sample to determine the effect of process parameters on the color, molecular weight, viscosity in a solution, and solubility in water of the resulting constructs.

Various methods of producing silk particles (e.g., nanoparticles and microparticles) are known in the art. In some embodiments, the silk particles can be produced by a polyvinyl alcohol (PVA) phase separation method as described in, e.g., International App. No. WO 2011/041395, the content of which is incorporated herein by reference in its entirety. Other methods for producing silk fibroin particles are described, for example, in U.S. App. Pub. No. U.S. 2010/0028451 and PCT App. Pub. No.: WO 2008/118133 (using lipid as a template for making silk microspheres or nanospheres), and in Wenk et al., J Control Release, 2008; 132: 26-34 (using spraying method to produce silk microspheres or nanospheres), content of all of which is incorporated herein by reference in its entirety.

Without limitation, there are at least six types of particles that can be formulated with silk fibroin and an additive or active agent/sample: (1) particles comprising a core formed by silk fibroin to which the additive/agent/sample absorbs/adsorbs or forms a coating on the particle core; (2) particles comprising a core formed by the additive/agent/sample, which is coated with one or more layers of silk fibroin; (3) particles comprising a generally homogeneous mixture of silk fibroin and the additive/agent/sample; (4) particles comprising a core comprising a mixture of silk fibroin and the additive/agent/sample with a coating over the core of silk fibroin; (5) a particle comprising a core of a material other than silk fibroin or biological sample, which is coated with one more layers comprising biological sample or silk fibroin or any combination of biological sample and silk fibroin; and (6) particle comprising any of the particles of (1)-(5) and further comprising one or more layers of a material other than silk fibroin or biological sample, e.g., a polymer. Silk fibroin particles (e.g., microspheres, nanospheres, or gel like particles) and methods of preparing the same are described, for example, in U.S. Pat. No. 8,187,616; and U.S. Pat. App. Pub. Nos. US 2008/0085272, US 2010/0028451, US 2012/0052124, US 2012/0070427, US 2012/0187591, the content of all of which is incorporated herein by reference. Without limitations, the biological sample can be distributed in the silk fibroin matrix of the film, present on a surface of the film, coated by the film, or any combination thereof.

In some embodiments, silk particles can be produced using a freeze-drying method as described in U.S. Provisional Application Ser. No. 61/719,146, filed Oct. 26, 2012, content of which is incorporated herein by reference in its entirety. Specifically, silk foam can be produced by freeze-drying a silk solution. The foam then can be reduced to particles. For example, a silk solution can be cooled to a temperature at which the liquid carrier transforms into a plurality of solid crystals or particles and removing at least some of the plurality of solid crystals or particles to leave a porous silk material (e.g., silk foam). After cooling, liquid carrier can be removed, at least partially, by sublimation, evaporation, and/or lyophilization. In some embodiments, the liquid carrier can be removed under reduced pressure. After formation, the silk fibroin foam can be subjected to grinding, cutting, crushing, or any combinations thereof to form silk particles. For example, the silk fibroin foam can be blended in a conventional blender or milled in a ball mill to form silk particles of desired size. Accordingly, in some embodiments, the low molecular weight silk fibroin composition is in form of lyophilized powder.

In some embodiments, provided silk fibroin compositions (e.g., articles) can be in the form of a gel or hydrogel. The term "hydrogel" is used herein to mean a silk-based material which exhibits the ability to retain a significant portion of water or other liquid within its structure without dissolution. Exemplary methods for preparing silk fibroin gels and hydrogels include, but are not limited to, sonication, vortexing, pH titration, exposure to electric field, solvent immersion, water annealing, water vapor annealing, and the like. Exemplary methods for preparing silk fibroin gels and hydrogels are described in, for example, PCT publication no. WO 2005/012606, no. WO 2008/150861, no. WO 2010/036992, and no. WO 2011/005381, contents of all of which are incorporated herein by reference in their entireties. Gels formed by exposure to electric field are also referred to as e-gels herein. Methods for forming e-gels are described in, for example, US Patent Application Publication No. US2011/0171239, content of which is incorporated herein by reference in its entirety. Without limitations, an additive/agent/sample can be distributed in the silk fibroin matrix of a gel or hydrogel, absorbed on a surface of a gel or hydrogel or sponge, present in a pore of the gel or hydrogel, or any combination thereof.

In some embodiments, silk fibroin compositions described herein (e.g., articles) can be in the form of a sponge or foam. In some embodiments, the foam or sponge is a patterned foam or sponge, e.g., nanopatterned foam or sponge. Exemplary methods for preparing silk foams and sponges are described in, for example, PCT application publication no. WO 2004/000915, no. WO 2004/000255, and no. WO 2005/012606, content of all of which are incorporated herein by reference in their entireties. Without limitations, an additive/active/sample can be distributed in the silk fibroin matrix of the foam or sponge, absorbed on a surface of the foam or sponge, present in a pore of the foam or sponge, or any combination thereof.

In some embodiments, silk fibroin compositions as described herein (e.g., articles) are in the form of a fiber. As used herein, the term "fiber" means a relatively flexible, unit of matter having a high ratio of length to width across its cross-sectional perpendicular to its length. Methods for preparing silk fibroin fibers are well known in the art. A fiber can be prepared by electrospinning a silk solution, drawing a silk solution, and the like. Electrospun silk materials, such as fibers, and methods for preparing the same are described, for example in WO2011/008842, content of which is incorporated herein by reference in its entirety. Micron-sized silk fibers (e.g., 10-600 μm in size) and methods for preparing the same are described, for example in Mandal et al., PNAS, 2012, doi: 10.1073/pnas.1119474109; U.S. Provisional Application No. 61/621,209, filed Apr. 6, 2012; and PCT application no. PCT/US13/35389, filed Apr. 5, 2013, contents of all of which are incorporated herein by reference in their entireties.

In some embodiments, silk fibroin compositions as described herein (e.g., articles) can be in the form of a film, e.g., a silk film. As used herein, the term "film" refers to a substantially flat structure and can also encompass a structure formed from a substantially flat structure. For example, the term "film" can encompass tubular structures or any structure that can be formed by manipulating (e.g., rolling up, and/or folding) a substantially flat film into a desired form. It is to be noted that the term "film" is used in a generic sense to include a web, sheet, a laminate, or the like. In some embodiments, the film is a patterned film, e.g., nanopatterned film. Exemplary methods for preparing silk fibroin films are described in, for example, PCT application publication no. WO 2004/000915 and no. WO 2005/012606, contents of both of which are incorporated herein by reference in their entireties. In some embodiments, where an additive and/or an agent/sample is included, it can be distributed in the film, present on a surface of the film, coated by the film, or any combination thereof.

A film can have any desired thickness. For example, the film thickness can range from about 1 nm to about 10 mm. In some embodiments, the film has a thickness in the range of from about 1 nm to about 1000 nm or from about 1 μm to about 1000 μm.

In some embodiments, silk fibroin compositions as described herein can be in the form of a coating layer. In some embodiments, such a coating layer can be on a substrate surface. Without limitation, a silk fibroin coating layer can comprise one or more layers. Further, if two or more layers are present, each layer can be single layer comprising a silk fibroin composition (e.g., low molecular weight silk fibroin) or a plurality of layers, wherein at least one or more layers comprise low molecular silk fibroin fragments. In some embodiments, the coating layer is an ultrathin coating layer. In some embodiments, a silk fibroin composition disclosed herein can form a portion of a substrate.

Examples of a substrate can include, but are not limited to, a dipstick, a cellulose-based product, a micro-titer plate, a specimen container (e.g., but not limited to, a blood collection container), medical devices, implants, and any combinations thereof. Methods of forming coating layers comprising silk fibroin are described in, for example, U.S. patent application Ser. No. 11/997,193, content of which is incorporated herein by reference in its entirety.

In some embodiments, silk fibroin compositions (e.g., articles) as disclosed herein can be in the form of a cylindrical matrix, e.g., a silk tube. The silk tubes can be made using any method known in the art. For example, tubes can be made using molding, dipping, electrospinning, gel spinning, and the like. Gel spinning is described in Lovett et al., Biomaterials 2008, 29(35):4650-4657 and the construction of gel-spun silk tubes is described in PCT application no. PCT/US2009/039870, filed Apr. 8, 2009, contents of both of which are incorporated herein by reference in their entireties. Construction of silk tubes using the dip-coating method is described in PCT application no. PCT/US2008/072742, filed Aug. 11, 2008, content of which is incorporated herein by reference in its entirety. Construction of silk fibroin tubes using the film-spinning method is described in PCT application No. PCT/US2013/030206, filed Mar. 11, 2013; U.S. Provisional application No. 61/613,185, filed Mar. 20, 2012; and PCT application publication no. WO 2013126799, contents of all of which are incorporated herein by references in their entireties. Without wishing to be bound by a theory, it is believed that the inner and outer diameter of the silk tube can be controlled more readily using film-spinning or gel-spinning than dip-coating technique.

In some embodiments, a provided silk-based material is in the form of a matrix comprising a lumen or cavity therein. In some such embodiments, at least a portion of an additive and/or active agent/sample is distributed in the silk fibroin network. In some embodiments, it can be present in the lumen or cavity. In some embodiments, the silk fibroin is in the form of a matrix comprising a lumen or cavity therein and at least a partial amount of the additive/agent/sample is present in the lumen or cavity and at least a partial amount is distributed in the silk fibroin network itself. In some embodiments, when the matrix comprises a lumen or cavity, at least 5%, (e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 98%) of an additive or agent/can be present in the lumen or cavity. In some embodiments, the entire amount is present in the lumen/cavity. In some embodiments, at least 5%, (e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 98%) of can be present in the silk fibroin network of the matrix (e.g., non-lumen portion of the silk-based material).

In some embodiments, silk fibroin compositions (e.g., articles) disclosed herein can be porous (e.g., a porous matrix or scaffold). For example, the porous scaffold can have a porosity of at least about 10%, at least about 20%, at least about 30%, at least about 40%, at least about 50%, at least about 60%, at least about 70%, at least about 80%, at least about 90%, or higher. As used herein, the term "porosity" is a measure of void spaces in a material and is a fraction of volume of voids over the total volume, as a percentage between 0 and 100% (or between 0 and 1). Determination of porosity is well known to a skilled artisan, e.g., using standardized techniques, such as mercury porosimetry and gas adsorption, e.g., nitrogen adsorption. As used herein, the term "porosity" is a measure of void spaces in a material and is a fraction of volume of voids over the total volume, as a percentage between 0 and 100% (or between 0 and 1). Determination of porosity is well known to a skilled artisan, e.g., using standardized techniques, such as mercury porosimetry and gas adsorption, e.g., nitrogen adsorption.

The porous scaffold can have any pore size. As used herein, the term "pore size" refers to a diameter or an effective diameter of the cross-sections of the pores. The term "pore size" can also refer to an average diameter or an average effective diameter of the cross-sections of the pores, based on the measurements of a plurality of pores. The effective diameter of a cross-section that is not circular equals the diameter of a circular cross-section that has the same cross-sectional area as that of the non-circular cross-section.

In some embodiments, the pores of the silk-based material can have a size distribution ranging from about 50 nm to about 1000 nm, from about 250 nm to about 500 nm, from about 500 nm to about 250 nm, from about 1 nm to about 200 nm, from about 10 nm to about 150 nm, or from about 50 nm to about 100 nm. In some embodiments, the silk-based material can be swellable when hydrated. The sizes of the pores can then change depending on the water content in the silk-based material. In some embodiment, the pores can be filled with a fluid such as water or air.

Methods for forming pores in silk fibroin-based scaffolds are known in the art and include, but are not limited, porogen-leaching methods, freeze-drying methods, and/or gas-forming method. Exemplary methods for forming pores in a silk-based material are described, for example, in U.S. Pat. App. Pub. No. US 2010/0279112 and No. US 2010/0279112; U.S. Pat. No. 7,842,780; and WO2004062697, contents of all of which are incorporated herein by reference in their entireties.

Though not meant to be bound by a theory, a porous scaffold's porosity, structure, and mechanical properties can be controlled via different post-spinning processes such as vapor annealing, heat treatment, alcohol treatment, air-drying, lyophilization and the like. Additionally, any desirable release rates, profiles or kinetics of a molecule encapsulated in the matrix can be controlled by varying processing parameters, such as matrix thickness, silk molecular weight, concentration of silk in the matrix, beta-sheet conformation structures, silk II beta-sheet crystallinity, or porosity and pore sizes. In some embodiments, a low molecular weight silk fibroin scaffold can provide sufficient mechanical strength/stability at an implant site, while permitting degradation of the scaffold over a desirable period of time (e.g., a month or longer). Without wishing to be bound by theory, in some embodiments, porosity of the silk-based material can be controlled for desired dissolution rate. For example, higher porosity of the silk-based material can generally allow an aqueous solution to permeate into the silk-based material faster and thus accelerate the process of dissolution. One of skill in the art can adjust the porosity accordingly, based on a number of factors such as, but not limited to, desired dissolution rates; molecular size and/or diffusion coefficient of the component present in the silk-based material, and/or concentrations, amounts of silk fibroin in the silk-based material, and/or desired physical or mechanical properties of the silk-based material.

For incorporating an additive/agent/sample into a silk fibroin matrix, it can be included in a silk fibroin solution used for producing the silk-based material. Alternatively, or in addition, a preformed silk-based material can be added to a solution comprising the additive/agent/sample and letting additive/agent/sample absorb in/on the silk-based material.

In some embodiments, the additive/agent/sample can be distributed, homogenously or non-homogenously (e.g., in a gradient) in the silk-based material. In some embodiments, the additive/agent/sample can be encapsulated or entrapped by silk fibroin in the silk-based material. In some embodiments, the additive/agent/sample can be mixed or blended with silk fibroin in the silk-based material.

In some embodiments, a silk fibroin composition disclosed herein is osteoconductive. Osteoconductivity is generally defined as the ability of a material to facilitate the migration of osteogenic cells to the surfaces of a scaffold through the fibrin clot established immediately after implantation the material. The porosity of a material affects the osteoconductivity of that material.

In some embodiments, a silk fibroin composition disclosed herein is osteoinductive. Osteoinductivity is generally defined as the ability to induce non-differentiated stem cells or osteoprogenitor cells (osteoblasts), which is a component of osseous (bone) tissue, to differentiate into osteoblasts. The simplest test of osteoinductivity is the ability to induce the formation of bone in tissue locations such as muscle, which do not normally form bone (ectopic bone growth). It is generally understood that article of manufacture described herein can be made osteoinductive by adding growth factors such as rhBMP-2 (recombinant human bone morphogenic protein-2) to them. The mineralization and the addition of growth factors can affect the osteoinductivity of a material.

In some embodiments, a silk fibroin composition disclosed herein is osteogenic and shows new bone formation after implantation in vivo. Osteogenesis is the process of laying down new bone material using osteoblasts. Osteoblasts build bone by producing osteoid to form an osteoid matrix, which is composed mainly of Type I collagen. Osseous tissue comprises the osteoid matrix and minerals (mostly with calcium phosphate) that form the chemical arrangement termed calcium hydroxyapatite. Osteoblasts are typically responsible for mineralization of the osteoid matrix to form osseous tissue. Without wishing to be bound by a theory, the osteoconductivity and osteoinductivity of the material has an impact on osteogenesis. The material can show new bone formation within 6 months of implantation in vivo. In some embodiments, the material shows new bone formation within 8 weeks of implantation in vivo.

In some embodiments, a silk fibroin article disclosed herein can be sterilized using conventional sterilization process such as radiation-based sterilization (i.e. gamma-ray), chemical based sterilization (ethylene oxide), autoclaving, or other appropriate procedures. In some embodiments, sterilization process can be with ethylene oxide at a temperature between from about 52° C. to about 55° C. for a time of 8 or less hours. In some embodiments, the silk fibroin article described herein can also be processed aseptically. Sterile silk fibroin articles described herein can be packaged in an appropriate sterilize moisture resistant package for shipment. In some embodiments, a silk fibroin composition containing an active agent is not subject to sterilization that significantly harms or degrades the active agent. In some embodiments, the silk fibroin composition protects an active agent from sterilization harm In some embodiments, s silk fibroin article described herein is in form of an implant or an implantable drug delivery device.

In some embodiments, a provided silk fibroin composition is in form of an injectable composition. As used herein, the term "injectable composition" generally refers to a composition that can be delivered or administered into a tissue with a minimally invasive procedure. The term "minimally invasive procedure" refers to a procedure that is carried out by entering a subject's body through the skin or through a body cavity or an anatomical opening, but with the smallest damage possible (e.g., a small incision, injection). In some embodiments, the injectable composition can be administered or delivered into a tissue by injection. In some embodiments, the injectable composition can be delivered into a tissue through a small incision on the skin followed by insertion of a needle, a cannula, and/or tubing, e.g., a catheter. Without wishing to be limited, the injectable composition can be administered or placed into a tissue by surgery, e.g., implantation. Some exemplary injectable compositions include, but are not limited to, solutions, hydrogels, gel-like particles, and/or microspheres.

To be clear, term "injectable" as in an "injectable formulation" and "injectables" refers to physical properties of a solution (e.g., formulation) suitable for administration by injection, such that there is a sufficient flow of the solution to pass through a needle or any other suitable means, and that such flow is generated with reasonable ease by a user. Syringes are commonly employed for delivering injections to subjects. In some embodiments, the injectable formulation can be provided as pre-filled syringes. In some embodiments, the injectable formulation can be provided as a ready-to-use formulation. In some embodiments, the injectable formulation can be provided as a kit.

In some embodiments, provided compositions such as injectable compositions can further comprise a pharmaceutically acceptable carrier. For example, in some embodiments, compositions suitable for injection include sterile aqueous solutions or dispersions. The carrier can be a solvent or dispersing medium containing, for example, water, cell culture medium, buffers (e.g., phosphate buffered saline), polyol (for example, glycerol, propylene glycol, liquid polyethylene glycol, and the like), suitable mixtures thereof. In some embodiments, the pharmaceutical carrier can be a buffered solution (e.g. PBS).

Alternatively or additionally, various additives which enhance the stability, sterility, and isotonicity of the injectable compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it may be desirable to include isotonic agents, for example, sugars, sodium chloride, and the like. The injectable compositions can also contain auxiliary substances such as wetting or emulsifying agents, pH buffering agents, gelling or viscosity enhancing additives, preservatives, colors, and the like, depending upon the preparation desired.

Viscosity of provided liquid compositions (e.g., injectable compositions) can be modulated by controlling the weight percentage of silk fibroin fragments having a molecular weight sub-range (i) to (xviii). In some embodiments, the viscosity of a composition can be further maintained at the selected level using a pharmaceutically acceptable thickening agent. In one embodiment, methylcellulose can be used because it is readily and economically available and is easy to work with. Other suitable thickening agents include, for example, xanthan gum, carboxymethyl cellulose, hydroxypropyl cellulose, carbomer, and the like. The preferred concentration of the thickener may depend upon the agent selected, and the desired viscosity for injection. The important point is to use an amount which will achieve the selected viscosity, e.g., addition of such thickening agents into some embodiments of the injectable compositions.

In some embodiments, a provided silk fibroin composition is in form of a sprayable composition.

In some embodiments, a provided silk fibroin composition (e.g., a low molecular weight silk composition) described herein can be in a form of an aerogel or an aerogel-like material. Methods forming aerogels or aerogel-like materials, e.g., comprising silk fibroin, are described in a U.S. Provisional Patent Application No. 61/902,145, entitled "PEPTIDE-BASED NANOFIBRILLAR MATERIALS" and filed Nov. 8, 2013, the entire contents of which are incorporated herein by reference Without wishing to be bound by a theory, properties (e.g., but not limited to solubility) of the silk-based materials (including those containing an active agent or biological sample as described herein) can be altered by varying the molecular weight of silk fibroin fragments in the silk-based materials. In some embodiments, silk fibroin of different molecular weights can be produced using different time periods for degumming cocoons to provide degummed fibroin. Accordingly, in some embodiments to produce low molecular weight silk fibroin compositions, cocoons are boiled (e.g., in a salt solution such as $Na_2CO_3$) for a period of about 1 minute to 2 hours, about 5 minutes to about 2 hours, about 10 minutes to about 60 minutes, about 60 minutes to 4 hours, about 60 minutes to 3 hours, about 60 minutes to 2 hours, about 60 minutes to 90 minutes, or about 4 hours or longer. In some embodiments, the cocoons can be boiled (e.g., in a salt solution such as $Na_2CO_3$) for about 10 minutes, about 20 minutes, about 30 minutes, about 45 minutes, about 60 minutes, about 90 minutes, about 100 minutes or longer. By controlling the degumming time, the solubility of the silk-based material (e.g., in an aqueous solution) can be optimized for extraction or recovery of an agent present in the low molecular weight silk fibroin composition. Without wishing to be bound by theory, longer boiling time generally yields silk fibroin of lower molecular weight (MW)/chain length, and thus a silk-based material produced from lower MW silk fibroin can is generally more soluble (e.g., in an aqueous solution) than the one produced from higher MW silk fibroin.

In some embodiments, a dissolvable silk-based material can be produced from a silk solution, in which cocoons have been boiled or degummed for a period of time sufficient to yield lower MW silk fibroin, e.g., at least about 30 minutes, at least about 60 minutes, or at least about 90 minutes or longer. In some embodiments, a dissolvable silk-based material is a lyophilized silk-based material produced from a silk solution, in which cocoons have been boiled or degummed for at least about 30 minutes, at least about 60 minutes, or at least about 90 minutes or longer. In some embodiments, a dissolvable silk-based material is a silk-based film produced from a silk solution, in which cocoons have been boiled or degummed for at least about 30 minutes, at least about 60 minutes, or at least about 90 minutes or longer. The silk-based material can be in any other form as described herein, e.g., produced by electrospinning, gelling or other rapid solidification technique known in the art.

Other methods to alter solubility of the silk-based material described herein can also be employed alone or in combination with degumming time control. For example, the solubility of the silk-based material can be improved by means of accelerating the rate of drying of a silk-based material, e.g., either by forced air, decreased humidity (lower than ambient), and/or increased temperature, etc. Additionally or alternatively, the solubility of silk-based material can be improved by subjecting the silk-based material to lyophilization conditions and/or decreasing time of exposure to conditions which can induce crystallinity in the silk fibroin. In some embodiments, the solubility of the silk-based material can be improved by selectively removing high molecular weight fractions of the silk (e.g., heavy chain and/or long hydrophobic sequences) during purification, e.g., via enzymatic digestion, filtration, chromatography, etc. In some embodiments, the solubility of the silk-based material can be improved by means of sterilization, including, e.g., autoclaving and sterile filtration, which can serve to continue to decrease molecular weight and/or remove insoluble particulates.

In various embodiments, at least a portion of the silk fibroin a silk fibroin composition as described herein (e.g., in a low molecular weight silk fibroin composition and/or in a stabilizing composition) can be modified for different uses, e.g., biomedical applications, and/or different desired mechanical or chemical properties. One of skill in the art can select appropriate methods to modify silk fibroins, e.g., depending on the side groups of the silk fibroins, desired reactivity of the silk fibroin and/or desired charge density on the silk fibroin.

For instance, to maintain the stability of an active agent distributed in a silk fibroin composition when implanted in vivo for tissue engineering or drug delivery purposes, at least a portion of the the silk fibroin can be genetically modified, which provides for further modification of the silk such as the inclusion of a fusion polypeptide comprising a fibrous protein domain and a mineralization domain, which can be used to form an organic-inorganic composite. See for example, WO 2006/076711, content of which is incorporated herein by reference in its entirety. In some embodiments, the silk fibroin can be chemically modified, for example through diazonium or carbodiimide coupling reactions, avidin-biotin interaction, or gene modification and the like, to alter the physical properties and functionalities of the silk protein. Chemically modified silk fibroin and methods of there preparation are described in, for example, PCT application publication no. WO 2011/011347 and no. WO 2010/057142; and U.S. patent application Ser. No. 12/192, 588, contents of all of which are incorporated herein by reference in their entireties.

In one embodiment, modification of silk fibroin can use the amino acid side chain chemistry, such as chemical modifications through covalent bonding, or modifications through charge-charge interaction. Exemplary chemical modification methods include, but are not limited to, carbodiimide coupling reaction (see, e.g. U.S. Patent Application. No. US 2007/0212730), diazonium coupling reaction (see, e.g., U.S. Patent Application No. US 2009/0232963), avidin-biotin interaction (see, e.g., International Application No.: WO 2011/011347) and pegylation with a chemically active or activated derivatives of the PEG polymer (see, e.g., International Application No. WO 2010/057142). Silk fibroin can also be modified through gene modification to alter functionalities of the silk protein (see, e.g., International Application No. WO 2011/006133). For instance, the silk fibroin can be genetically modified, which can provide for further modification of the silk such as the inclusion of a fusion polypeptide comprising a fibrous protein domain and a mineralization domain, which can be used to form an organic-inorganic composite. See WO 2006/076711. In some embodiments, the silk fibroin can be genetically modified to be fused with a protein, e.g., a therapeutic protein.

In some embodiments, at least a portion of the silk fibroin in compositions described herein can be derivatized or modified with positively/negatively charged molecules. In some embodiments, the silk fibroin can be modified with positively/negatively charged peptides or polypeptides, such poly-lysine and poly-glutamic acid. While possible, it is not required that every single silk fibroin molecule in the composition be modified with a positively/negatively charged molecule. Methods of derivatizing or modifying silk fibroin with charged molecules are described in, for example, PCT application publication no. WO2011109691A2, content of which is incorporated herein by reference in its entirety.

Ratio of modified silk fibroin to unmodified silk fibroin can be adjusted to optimize one or more desired properties of the low molecular weight silk fibroin composition or an article formed therefrom. Accordingly, in some embodiments, ratio of modified to unmodified silk fibroin in the composition can range from about 1000:1 (w/w) to about 1:1000 (w/w), from about 500:1 (w/w) to about 1:500 (w/w), from about 250:1 (w/w) to about 1:250 (w/w), from about 200:1 (w/w) to about 1:200 (w/w), from about 25:1 (w/w) to about 1:25 (w/w), from about 20:1 (w/w) to about 1:20 (w/w), from about 10:1 (w/w) to about 1:10 (w/w), or from about 5:1 (w/w) to about 1:5 (w/w).

In some embodiments, the composition comprises a molar ratio of modified to unmodified silk fibroin of, e.g., at least 1000:1, at least 900:1, at least 800:1, at least 700:1, at least 600:1, at least 500:1, at least 400:1, at least 300:1, at least 200:1, at least 100:1, at least 90:1, at least 80:1, at least 70:1, at least 60:1, at least 50:1, at least 40:1, at least 30:1, at least 20:1, at least 10:1, at least 7:1, at least 5:1, at least 3:1, at least 1:1, at least 1:3, at least 1:5, at least 1:7, at least 1:10, at least 1:20, at least 1:30, at least 1:40, at least 1:50, at least 1:60, at least 1:70, at least 1:80, at least 1:90, at least 1:100, at least 1:200, at least 1:300, at least 1:400, at least 1:500, at least 600, at least 1:700, at least 1:800, at least 1:900, or at least 1:100.

In some embodiments, the composition comprises a molar ratio of modified to unmodified silk fibroin of, e.g., at most 1000:1, at most 900:1, at most 800:1, at most 700:1, at most 600:1, at most 500:1, at most 400:1, at most 300:1, at most 200:1, 100:1, at most 90:1, at most 80:1, at most 70:1, at most 60:1, at most 50:1, at most 40:1, at most 30:1, at most 20:1, at most 10:1, at most 7:1, at most 5:1, at most 3:1, at most 1:1, at most 1:3, at most 1:5, at most 1:7, at most 1:10, at most 1:20, at most 1:30, at most 1:40, at most 1:50, at most 1:60, at most 1:70, at most 1:80, at most 1:90, at most 1:100, at most 1:200, at most 1:300, at most 1:400, at most 1:500, at most 1:600, at most 1:700, at most 1:800, at most 1:900, or at most 1:1000.

In some embodiments, the composition comprises a molar ratio of modified to unmodified silk fibroin of e.g., from about 1000:1 to about 1:1000, from about 900:1 to about 1:900, from about 800:1 to about 1:800, from about 700:1 to about 1:700, from about 600:1 to about 1:600, from about 500:1 to about 1:500, from about 400:1 to about 1:400, from about 300:1 to about 1:300, from about 200:1 to about 1:200, from about 100:1 to about 1:100, from about 90:1 to about 1:90, from about 80:1 to about 1:80, from about 70:1 to about 1:70, from about 60:1 to about 1:60, from about 50:1 to about 1:50, from about 40:1 to about 1:40, from about 30:1 to about 1:30, from about 20:1 to about 1:20, from about 10:1 to about 1:10, from about 7:1 to about 1:7, from about 5:1 to about 1:5, from about 3:1 to about 1:3, or about 1:1

In some embodiments, the silk fibroin is substantially depleted of its native sericin content (e.g., 5% (w/w) or less residual sericin in the final extracted silk). Alternatively, higher concentrations of residual sericin can be left on the silk following extraction or the extraction step can be omitted. In some embodiments, the sericin-depleted silk fibroin has, e.g., about 1% (w/w) residual sericin, about 2% (w/w) residual sericin, about 3% (w/w) residual sericin, about 4% (w/w), or about 5% (w/w) residual sericin. In some embodiments, the sericin-depleted silk fibroin has, e.g., at most 1% (w/w) residual sericin, at most 2% (w/w) residual sericin, at most 3% (w/w) residual sericin, at most 4% (w/w), or at most 5% (w/w) residual sericin. In some other embodiments, the sericin-depleted silk fibroin has, e.g., about 1% (w/w) to about 2% (w/w) residual sericin, about 1% (w/w) to about 3% (w/w) residual sericin, about 1% (w/w) to about 4% (w/w), or about 1% (w/w) to about 5% (w/w) residual sericin. In some embodiments, the silk fibroin is entirely free of its native sericin content. As used herein, the term "entirely free" (i.e. "consisting of" terminology) means that within the detection range of the instrument or process being used, the substance cannot be detected or its presence cannot be confirmed. In some embodiments, the silk fibroin is essentially free of its native sericin content. As used herein, the term "essentially free" (or "consisting essentially of") means that only trace amounts of the substance can be detected, is present in an amount that is below detection, or is absent.

Without wishing to be bound by a theory, properties of a provided silk fibroin composition can be modified through controlled partial removal of silk sericin or deliberate enrichment of source silk with sericin. This can be accomplished by varying the conditions, such as time, temperature, concentration, and the like for the silk degumming process.

Degummed silk can be prepared by any conventional method known to one skilled in the art. For example, *B. mori* cocoons are boiled for a period of pre-determined time in an aqueous solution. Generally, longer degumming time generate low molecular weight silk fibroin. In some embodiments, the silk cocoons are boiled for at least 60 minutes, at least 70 minutes, at least 80 minutes, at least 90 minutes, at least 100 minutes, at least 110 minutes, at least 120 minutes, or longer, to generate low molecular weight silk fibroin fragments. Additionally or alternatively, in some embodiments, silk cocoons can be heated or boiled at an elevated temperature. For example, in some embodiments, silk cocoons can be heated or boiled at about 101.0° C., at about 101.5° C., at about 102.0° C., at about 102.5° C., at about 103.0° C., at about 103.5° C., at about 104.0° C., at about 104.5° C., at about 105.0° C., at about 105.5° C., at about 106.0° C., at about 106.5° C., at about 107.0° C., at about 107.5° C., at about 108.0° C., at about 108.5° C., at about 109.0° C., at about 109.5° C., at about 110.0° C., at about 110.5° C., at about 111.0° C., at about 111.5° C., at about 112.0° C., at about 112.5° C., at about 113.0° C., 113.5° C., at about 114.0° C., at about 114.5° C., at about 115.0° C., at about 115.5° C., at about 116.0° C., at about 116.5° C., at about 117.0° C., at about 117.5° C., at about 118.0° C., at about 118.5° C., at about 119.0° C., at about 119.5° C., at about 120.0° C., or higher. In some embodiments, such elevated temperature can be achieved by carrying out at least portion of the heating process (e.g., boiling process) under pressure.

For example, suitable pressure under which silk fibroin fragments described herein can be produced are typically between about 10-40 psi, e.g., about 11 psi, about 12 psi, about 13 psi, about 14 psi, about 15 psi, about 16 psi, about 17 psi, about 18 psi, about 19 psi, about 20 psi, about 21 psi, about 22 psi, about 23 psi, about 24 psi, about 25 psi, about 26 psi, about 27 psi, about 28 psi, about 29 psi, about 30 psi, about 31 psi, about 32 psi, about 33 psi, about 34 psi, about 35 psi, about 36 psi, about 37 psi, about 38 psi, about 39 psi, or about 40 psi.

In one embodiment, the aqueous solution used in the process of degumming silk cocoons is about 0.02M $Na_2CO_3$. The cocoons are rinsed, for example, with water to extract the sericin proteins. The degummed silk can be dried and used for preparing silk powder. Alternatively, the extracted silk can dissolved in an aqueous salt solution. Salts useful for this purpose include lithium bromide, lithium thiocyanate, calcium nitrate or other chemicals capable of solubilizing silk. In some embodiments, the extracted silk can be dissolved in about 8M-12 M LiBr solution. The salt is consequently removed using, for example, dialysis.

If necessary, the solution can then be concentrated using, for example, dialysis against a hygroscopic polymer, for example, PEG, a polyethylene oxide, amylose or sericin. In some embodiments, the PEG is of a molecular weight of 8,000-10,000 g/mol and has a concentration of about 10% to about 50% (w/v). A slide-a-lyzer dialysis cassette (Pierce, MW CO 3500) can be used. However, any dialysis system can be used. The dialysis can be performed for a time period sufficient to result in a final concentration of aqueous silk solution between about 10% to about 30%. In most cases dialysis for 2-12 hours can be sufficient. See, for example, International Patent Application Publication No. WO 2005/012606, the content of which is incorporated herein by reference in its entirety.

Another method to generate a concentrated silk solution comprises drying a dilute silk solution (e.g., through evaporation or lyophilization). The dilute solution can be dried partially to reduce the volume thereby increasing the silk concentration. The dilute solution can be dried completely and then dissolving the dried silk fibroin in a smaller volume of solvent compared to that of the dilute silk solution. In some embodiments, a silk fibroin solution can optionally, at a suitable point, be filtered and/or centrifuged. For example, in some embodiments, a silk fibroin solution can optionally be filtered and/or centrifuged following the heating or boiling step. In some embodiments, a silk fibroin solution can optionally be filtered and/or centrifuged following the dialysis step. In some embodiments, a silk fibroin solution can optionally be filtered and/or centrifuged following the step of adjusting concentrations. In some embodiments, a silk fibroin solution can optionally be filtered and/or centrifuged following the step of reconstitution. In any of such embodiments, the filtration and/or centrifugation step(s) can be carried out to remove insoluble materials. In any of such embodiments, the filtration and/or centrifugation step(s) can be carried out to selectively enrich silk fibroin fragments of certain molecular weight(s).

In some embodiments, the silk fibroin solution can be produced using organic solvents. Such methods have been described, for example, in Li, M., et al., *J. Appl. Poly Sci.* 2001, 79, 2192-2199; Min, S., et al. *Sen'I Gakkaishi* 1997, 54, 85-92; Nazarov, R. et al., *Biomacromolecules* 2004 5, 718-26, contents of all which are incorporated herein by reference in their entireties. An exemplary organic solvent that can be used to produce a silk solution includes, but is not limited to, hexafluoroisopropanol (HFIP). See, for example, International Application No. WO2004/000915, content of which is incorporated herein by reference in its entirety. In some embodiments, the silk solution is entirely free or essentially free of organic solvents; in some embodiments it is substantially free of solvents other than water.

A silk fibroin composition disclosed herein can comprise any amount/ratio of silk fibroin to the total volume/weight of the composition. Without wishing to be bound by a theory, amount of silk fibroin in the solution used for making a silk fibroin composition (e.g., a low molecular weight silk fibroin composition and/or a stabilizing composition), itself can be varied to vary properties of the silk fibroin composition. Generally, any amount of silk fibroin can be present in the solution used for making the a silk fibroin composition. For example, amount of silk fibroin in the solution can be from about 0.1% (w/v) to about 90% (w/v). In some embodiments, the amount of silk fibroin in the solution can be from about 1% (w/v) to about 75% (w/v), from about 1% (w/v) to about 70% (w/v), from about 1% (w/v) to about 65% (w/v), from about 1% (w/v) to about 60% (w/v), from about 1% (w/v) to about 55% (w/v), from about 1% (w/v) to about 50% (w/v), from about 1% (w/v) to about 35% (w/v), from about 1% (w/v) to about 30% (w/v), from about 1% (w/v) to about 25% (w/v), from about 1% (w/v) to about 20% (w/v), from about 1% (w/v) to about 15% (w/v), from about 1% (w/v) to about 10% (w/v), from about 5% (w/v) to about 25% (w/v), from about 5% (w/v) to about 20% (w/v), from about 5% (w/v) to about 15% (w/v). In some embodiments, the silk fibroin in the solution is about 25% (w/v). In some embodiments, the silk fibroin in the solution is about 0.5 (w/v) to about 30% (w/v), about 4% (w/v) to about 16% (w/v), about 4% (w/v) to about 14% (w/v), about 4% (w/v) to about 12% (w/v), about 4% (w/v) to about 0% (w/v), about 6% (w/v) to about 8% (w/v). Exact amount of silk in the silk solution can be determined by drying a known amount of the silk solution and measuring the mass of the residue to calculate the solution concentration.

Amount of silk fibroin in a provided composition or article (e.g., in a low molecular weight silk composition and/or a stabilizing composition) can be from about 1% (w/v) to about 90% (w/v). In some embodiments, the amount of silk fibroin in the silk fibroin composition can be from about 0.1% (w/v) to about 75% (w/v), from about 1% (w/v) to about 70% (w/v), from about 1% (w/v) to about 65% (w/v), from about 1% (w/v) to about 60% (w/v), from about 1% (w/v) to about 55% (w/v), from about 1% (w/v) to about 50% (w/v), from about 1% (w/v) to about 45% (w/v), from about 1% (w/v) to about 40% (w/v), from about 1% (w/v) to about 35% (w/v), from about 1% (w/v) to about 30% (w/v), from about 1% (w/v) to about 25% (w/v), from about 1% (w/v) to about 20% (w/v), from about 1% (w/v) to about 15% (w/v), from about 1% (w/v) to about 10% (w/v), from about 5% (w/v) to about 25% (w/v), from about 5% (w/v) to about 20% (w/v), from about 5% (w/v) to about 15% (w/v). In some embodiments, the silk fibroin in the low molecular weight silk fibroin composition is about 25% (w/v). In some embodiments, the silk in a silk fibroin composition is about 0.5 (w/v) to about 30% (w/v), about 2% (w/v) to about 8% (w/v), about 2% (w/v) to about 7% (w/v), about 2% (w/v) to about 6% (w/v), about 2% (w/v) to about 5% (w/v), about 3% (w/v) to about 4% (w/v).

In some embodiments, a solution has a silk fibroin concentration of from about 0.25% to about 50% (w/v) or from about 0.5% to about 15% (w/v), or from about 0.5% to about 10% (w/v). In some embodiments, the silk fibroin solution has a silk fibroin concentration of from about 10% to about 40% or from 15% to about 35% (w/v). In one embodiment, the silk fibroin solution has a silk fibroin concentration of from about 20% to about 30% (w/v). In one embodiment, the silk fibroin solution has a silk fibroin concentration of about 30% (w/v). In some embodiments, the silk fibroin solution has a silk fibroin concentration of about 0.1% to about 30% (w/v), about 0.5% to about 15% (w/v), about 1% to about 8% (w/v), or about 1.5% to about 5% (w/v). In some embodiments, the silk fibroin solution has a silk fibroin concentration of about 5% to about 30% (w/v), about 10% to about 25% (w/v), or about 15 to about 20% (w/v). In some embodiments, the silk solution has a silk fibroin concentration of about 0.5% to 10% (w/v).

Depending on the applications in some embodiment, a conformational change can be induced in the silk fibroin in a provided composition to control the solubility of the silk fibroin composition/article. In some embodiments, the conformational change can induce the silk fibroin at least partially insoluble. Without wishing to be bound by a theory, the induced conformational change alters the crystallinity of the silk fibroin, e.g., Silk II beta-sheet crystallinity. The conformational change can be induced by any methods known in the art, including, but not limited to, alcohol immersion (e.g., ethanol, methanol), water annealing, shear stress, ultrasound (e.g., by sonication), pH reduction (e.g., pH titration and/or exposure to an electric field) and any combinations thereof. For example, the conformational change can be induced by one or more methods, including but not limited to, controlled slow drying (Lu et al., Biomacromolecules 2009, 10, 1032); water annealing (Jin et al., Adv. Funct. Mats. 2005, 15, 1241; Hu et al., Biomacromolecules 2011, 12, 1686); stretching (Demura & Asakura, Biotech & Bioengin. 1989, 33, 598); compressing; solvent immersion, including methanol (Hofmann et al., J Control Release. 2006, 111, 219), ethanol (Miyairi et al., J. Fermen. Tech. 1978, 56, 303), glutaraldehyde (Acharya et al., Biotechnol J. 2008, 3, 226), and 1-ethyl-3-(3-dimethyl aminopropyl) carbodiimide (EDC) (Bayraktar et al., Eur J Pharm Biopharm. 2005, 60, 373); pH adjustment, e.g., pH titration and/or exposure to an electric field (see, e.g., U.S. Patent App. No. US2011/0171239); heat treatment; shear stress (see, e.g., International App. No.: WO 2011/005381), ultrasound, e.g., sonication (see, e.g., U.S. Patent Application Publication No. U.S. 2010/0178304 and International App. No. WO2008/150861); and any combinations thereof. Contents of all of the references listed above are incorporated herein by reference in their entireties.

In some embodiments, the material can be treated by annealing. As used herein, the process of annealing involves inducing formation of beta-sheet secondary structure in the silk fibroin. This can be due to increased non-covalent interactions of silk fibroin. Such non-covalent interactions can include intra-molecular interactions, inter-molecular interactions, or both. Typically, non-covalent interactions are mediated by hydrogen bonds, which lead to increased beta sheet formation. Upon reaching a certain critical level of beta sheet secondary structure, silk fibroin is rendered insoluble, e.g., in an aqueous environment. This phenomenon is generally referred to as crystallinity and the status of such silk fibroin is referred to as Silk II. Thus, "annealing" involves a conformation change of silk fibroin to beta-sheet dominated (silk II) conformation, such that silk fibroin is crystallized and thus insoluble. Without wishing to be bound by a theory, it is believed that this conformational change is due to hydrogen-bonding and/or hydrophobic interactions mediated structural shift of silk fibroin to a higher beta sheet content.

In some embodiments, the conformation of silk fibroin can be altered by water annealing. There are a number of different methods for water annealing. One method of water annealing involves treating solidified but soluble forms of silk fibroin with water vapor. Without wishing to be bound by a theory, it is believed that water molecules act as a plasticizer, which allows chain mobility of fibroin molecules to promote the formation of hydrogen bonds, leading to increased beta sheet secondary structure. This process is also referred to as "water vapor annealing" herein.

Without wishing to be bound by a theory, it is believed that physical temperature-controlled water vapor annealing (TCWVA) provides a simple and effective method to obtain refined control of the molecular structure of silk biomaterials. The silk materials can be prepared with control of crystallinity, from a low beta-sheet content using conditions at 4° C. ($\alpha$ helix dominated silk I structure), to higher beta-sheet content of ~60% crystallinity at 100° C. ($\beta$-sheet dominated silk II structure). This physical approach covers the range of structures previously reported to govern crystallization during the fabrication of silk materials, yet offers a simpler, green chemistry, approach with tight control of reproducibility. Water or water vapor annealing is described, for example, in PCT application no. PCT/US2004/011199, filed Apr. 12, 2004 and no. PCT/US2005/020844, filed Jun. 13, 2005; and Jin et al., Adv. Funct. Mats. 2005, 15: 1241 and Hu et al., Biomacromolecules, 2011, 12(5): 1686-1696, contents of all of which are incorporated herein by reference in their entireties.

Another way of annealing is by slow, controlled evaporation of water from silk fibroin in the silk material/matrix. Slow, controlled, drying is described in, for example, Lu et al., Acta. Biomater. 2010, 6(4): 1380-1387.

The annealing step can be performed within a water vapor environment, such as in a chamber filled with water vapor, for different periods of time. Without wishing to be bound by a theory, length of annealing effects the amount of beta-sheet crystallinity obtained in silk fibroin within the silk-based material. Accordingly, typical annealing time periods can range from seconds to days. In some embodiments, the annealing is for a period of seconds to hours. For example, annealing time can range from a few seconds (e.g., about 5, 10, 15, 20, 25, 30, 35, 40, 45, 50, 55, or 60 seconds) to about 2, 6, 12, 24, 36, or 48 hours.

The temperature of the water vapor used in the annealing process effects the amount of beta-sheet crystallinity obtained. See HU et al., Biomacromolecules, 12: 1686-1696. Accordingly, the annealing can be performed at any desired temperature. For example, the annealing can be performed with a water vapor temperature from about 4° C. to about 120° C. Optimal water vapor to obtain a required amount of beta-sheet crystallinity in silk fibroin within the silk-based material can be calculated based on equation (I):

$$C=a(1-\exp(-kT)) \qquad (I)$$

wherein C is beta-sheet crystallinity, a is 62.59, k is 0.028 and T is annealing temperature. See Hu et al., Biomacromolecules, 12: 1686-1696.

Without wishing to be bound by a theory, the pressure under which the annealing takes place can also influence the degree or amount of beta-sheet crystallinity. In some embodiments, the contacting can be performed in a vacuum environment.

Relative humidity under which the annealing takes place can also influence the degree or amount of beta-sheet crystallinity. Relative humidity under which the silk-based material is contacted with water or water vapor can range from about 5% to 100%. For example, relative humidity can be from about 5% to about 95%, from about 10% to about 90%, or from about 15% to about 85%. In some embodiments, relative humidity is 90% or higher.

Another useful method for annealing the silk fibroin is to subject the silk-based material to dehydration by the use of organic solvent, such as alcohols, e.g., methanol, ethanol, isopropyl, acetone, etc. Such solvent has an effect of dehydrating silk fibroin, which promotes "packing" of silk fibroin molecules to form beta sheet structures. In some embodiments, a silk-based material can be treated with an alcohol, e.g., methanol, ethanol, etc. The alcohol concentration can be at least 10%, at least 20%, at least 30%, at least 40%, at least 50%, at least 60%, at least 70%, at least 80%, at least 90% or 100%. In some embodiment, alcohol concentration is about 90%.

Thus, in some embodiments, alteration in the conformation of silk fibroin can be induced by immersing in alcohol, e.g., methanol, ethanol, etc. The alcohol concentration can be at least 10%, at least 20%, at least 30%, at least 40%, at least 50%, at least 60%, at least 70%, at least 80%, at least 90% or 100%. In some embodiment, alcohol concentration is 100%. If the alteration in the conformation is by immersing in a solvent, the silk composition can be washed, e.g., with solvent/water gradient to remove any of the residual solvent that is used for the immersion. The washing can be repeated one, e.g., one, two, three, four, five, or more times.

Alternatively, alteration in the conformation of the silk fibroin can be induced with shear stress. The shear stress can be applied, for example, by passing the silk composition through a needle. Other methods of inducing conformational changes include applying an electric field, applying pressure, or changing the salt concentration.

The treatment time for inducing the conformational change can be any period of time to provide a desired silk II (beta-sheet crystallinity) content. In some embodiments, the treatment time can range from about 1 hour to about 12 hours, from about 1 hour to about 6 hours, from about 1 hour to about 5 hours, from about 1 hour to about 4 hours, or from about 1 hour to about 3 hours. In some embodiments, the sintering time can range from about 2 hours to about 4 hours or from 2.5 hours to about 3.5 hours.

When inducing the conformational change is by solvent immersion, treatment time can range from minutes to hours. For example, immersion in the solvent can be for a period of at least about 15 minutes, at least about 30 minutes, at least about 1 hour, at least about 2 hours, at least 3 hours, at least about 6 hours, at least about 18 hours, at least about 12 hours, at least about 1 day, at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 13 days, or at least about 14 days. In some embodiments, immersion in the solvent can be for a period of about 12 hours to about seven days, about 1 day to about 6 days, about 2 to about 5 days, or about 3 to about 4 days.

After the treatment to induce the conformational change, silk fibroin can comprise a silk II beta-sheet crystallinity content of at least about 5%, at least about 10%, at least about 20%, at least about 30%, at least about 40%, at least about 50%, at least about 60%, at least about 70%, at least about 80%, at least about 90%, or at least about 95% but not 100% (i.e., all the silk is present in a silk II beta-sheet conformation). In some embodiments, the silk fibroin in silk-based material comprises beta-sheet crystallinity of at least 10%, e.g., 15%, 20%, 25%, 30%, 35%, 40%, 45%, 50%, 55%, 60%, 65%, 70%, 75%, 70%, 85%, 90%, 95% or more, but not 100% (i.e., not all the silk fibroin is in a beta-sheet conformation). In some embodiments, silk is present completely in a silk II beta-sheet conformation, i.e., 100% silk II beta-sheet crystallinity.

Regardless of the annealing method employed, the end result of the annealing process is often that annealed silk fibroin has high degree of crystallinity such that it becomes insoluble. In some embodiments, "high degrees of crystallinity" refers to beta sheet contents of between about 20% and about 70%, e.g., about 20%, about 25%, about 30%, about 35%, about 40%, about 45%, about 50%, about 55%, about 60%, about 65% and about 75%.

In some embodiments, the annealing process can provide silk-based material can comprising a silk II beta-sheet crystallinity content of at least about 20%, at least about 30%, at least about 40%, at least about 50%, at least about 60%, at least about 70%, at least about 80%, at least about 90%, or at least about 95% but not 100% (i.e., all the silk is present in a silk II beta-sheet conformation). In some embodiments, the silk-based material can have a silk II beta-sheet crystallinity of 100%.

In some embodiments, the silk fibroin in a provided silk fibroin composition has a protein structure that substantially includes β-turn and β-strand regions. Without wishing to be bound by a theory, the silk β sheet content can impact gel function and in vivo longevity of the composition. It is to be understood that composition including non-β sheet content (e.g., e-gels) can also be utilized. In aspects of these embodiments, the silk fibroin in a provided composition has a protein structure including, e.g., about 5% β-turn and β-strand regions, about 10% β-turn and β-strand regions, about 20% β-turn and β-strand regions, about 30% β-turn and β-strand regions, about 40% β-turn and β-strand regions, about 50% β-turn and β-strand regions, about 60% β-turn and β-strand regions, about 70% β-turn and β-strand regions, about 80% β-turn and β-strand regions, about 90% β-turn and β-strand regions, or about 100% β-turn and β-strand regions. In other aspects of these embodiments, the silk fibroin in the low molecular weight silk fibroin composition has a protein structure including, e.g., at least 10% β-turn and β-strand regions, at least 20% β-turn and β-strand regions, at least 30% β-turn and β-strand regions, at least 40% β-turn and β-strand regions, at least 50% β-turn and β-strand regions, at least 60% β-turn and β-strand regions, at least 70% β-turn and β-strand regions, at least 80% β-turn and β-strand regions, at least 90% β-turn and β-strand regions, or at least 95% β-turn and β-strand regions. In yet other aspects of these embodiments, the silk fibroin in the low molecular weight silk fibroin composition has a protein structure including, e.g., about 10% to about 30% β-turn and β-strand regions, about 20% to about 40% β-turn and β-strand regions, about 30% to about 50% β-turn and β-strand regions, about 40% to about 60% β-turn and β-strand regions, about 50% to about 70% β-turn and β-strand regions, about 60% to about 80% β-turn and β-strand regions, about 70% to about 90% β-turn and β-strand regions, about 80% to about 100% β-turn and β-strand regions, about 10% to about 40% β-turn and β-strand regions, about 30% to about 60% β-turn and β-strand regions, about 50% to about 80% β-turn and β-strand regions, about 70% to about 100% β-turn and β-strand regions, about 40% to about 80% β-turn and β-strand regions, about 50% to about 90% β-turn and β-strand regions, about 60% to about 100% β-turn and β-strand regions, or about 50% to about 100% β-turn and β-strand regions. In some embodiments, silk β sheet content, from less than 10% to ~55% can be used in silk fibroin compositions disclosed herein.

In some embodiments, the silk fibroin in a silk fibroin composition provided herein has a protein structure that is substantially-free of α-helix and random coil regions. In aspects of these embodiments, the silk fibroin has a protein structure including, e.g., about 5% α-helix and random coil regions, about 10% α-helix and random coil regions, about 15% α-helix and random coil regions, about 20% α-helix and random coil regions, about 25% α-helix and random coil regions, about 30% α-helix and random coil regions, about 35% α-helix and random coil regions, about 40% α-helix and random coil regions, about 45% α-helix and random coil regions, or about 50% α-helix and random coil regions. In other aspects of these embodiments, the silk fibroin has a protein structure including, e.g., at most 5% α-helix and random coil regions, at most 10% α-helix and random coil regions, at most 15% α-helix and random coil regions, at most 20% α-helix and random coil regions, at most 25% α-helix and random coil regions, at most 30% α-helix and random coil regions, at most 35% α-helix and random coil regions, at most 40% α-helix and random coil regions, at most 45% α-helix and random coil regions, or at most 50% α-helix and random coil regions. In yet other aspects of these embodiments, the silk fibroin has a protein structure including, e.g., about 5% to about 10% α-helix and random coil regions, about 5% to about 15% α-helix and random coil regions, about 5% to about 20% α-helix and random coil regions, about 5% to about 25% α-helix and random coil regions, about 5% to about 30% α-helix and random coil regions, about 5% to about 40% α-helix and random coil regions, about 5% to about 50% α-helix and random coil regions, about 10% to about 20% α-helix and random coil regions, about 10% to about 30% α-helix and random coil regions, about 15% to about 25% α-helix and random coil regions, about 15% to about 30% α-helix and random coil regions, or about 15% to about 35% α-helix and random coil regions.

In another aspect, the disclosure provides a method for modulating at least one property of a silk fibroin article or article of manufacture described herein. Generally, the method comprises varying the weight ratio of the various silk fibroin fragments in the low molecular weight silk in the silk fibroin article or article of manufacture. In some embodiments, the method comprises varying the weight ratio of silk fibroin fragments having a molecular weight within a first specified range between about 3.5 kDa and about 120 kDa, to silk fibroin fragments having a molecular weight within a second specified range between about 3.5 kDa and about 120 kDa, wherein first and second specified ranges do not overlap. In some embodiments, the method comprises varying the weight ratio of silk fibroin fragments having a molecular weight exceeding 200 kDa to silk fibroin fragments having a molecular weight within a specified range between about 3.5 kDa and about 120 kDa.

Without limitation, the property that can be modulated using the method described herein can be selected from the group consisting of: release rate of an agent present in the article, release kinetics of an agent present in the article, resolubility, degradation, mechanical property, optical property, porosity, pore size, viscosity, biocompatibility, bioresorbablity, net charge of the article, particle size, and any combinations thereof.

In another aspect, the disclosure provides a method of controlling size of a silk particle. The method generally comprises varying the weight ratio of the various silk fibroin fragments of low molecular weight silk in a solution and forming the silk particle from the solution. In some embodiments, the method comprises varying the weight ratio of silk fibroin fragments having a molecular weight within a first specified range between about 3.5 kDa and about 120 kDa to silk fibroin fragments having a molecular weight within a second specified range between about 3.5 kDa and about 120 kDa, wherein first and second specified ranges do not overlap. In some embodiments, the method comprises varying the weight ratio of silk fibroin fragments having a molecular weight exceeding 200 kDa to silk fibroin fragments having a molecular weight within a specified range between about 3.5 kDa and about 120 kDa. Methods for preparing silk particles are described in, for example, Int. App. No. WO 2011/041395; Int. App. Pub. No.: WO 2008/118133; U.S. App. Pub. No. U.S. 2010/0028451; U.S. Provisional Application Ser. No. 61/719,146, filed Oct. 26, 2012; and Wenk et al. J Control Release, 2008; 132: 26-34, contents of all of which are incorporated herein by reference in their entirety.

In any of the embodiments described herein, low molecular weight silk fibroin fragments can be derived from portion or portions of a full-length silk fibroin polypeptide, such that amino acid sequences of the low molecular weight silk fibroin collectively represent less than 100% of the full-length silk fibroin polypeptide. For example, one or more recombinantly produced silk fibroin polypeptides can be used to carry out some embodiments of any aspects described herein. Such recombinant silk fibroin polypeptides can contain a fragment or fragments of a full-length counterpart. In some embodiments, silk fibroin polypeptides that correspond to a fragment or fragments of the full-length counterpart can be produced from transgenic organisms that carry a transgene to produce such fragments.

In any of the embodiments described herein, low molecular weight silk fibroin fragments can include one or more mutations and/or modifications, relative to a naturally occurring (e.g., wild type) sequence of silk fibroin. Such mutation and/or modification in the silk fibroin fragment can be spontaneously occurring or introduced by design. For example, in some embodiments, such mutation and/or modification in the silk fibroin fragment can be introduced using recombinant techniques, chemical modifications, etc.

Silk fibroin is an example of polypeptides having a portion or portions of an amino acid sequence that can adopt bet-sheet secondary structure. For example, silk fibroin structure generally comprises a sequence of amino acids, in which a portion or portions of the sequence are generally characterized by alternating glycine and alanine, or alanine alone. Without wishing to be bound by theory, such configuration allows fibroin molecules to self-assemble into a beta-sheet conformation. Accordingly, in yet another aspect, provided herein is a composition comprising a population of polypeptide fragments having a portion or portions of an amino acid sequence that is characterized by alternating glycine and alanine or alanine alone, and having a range of molecular weights ranging between about 3.5 kDa and about 120 kDa or between about 5 kDa and about 125 kDa. In some embodiments, the compositions is characterized in that: no more than 15% of the total number of polypeptide fragments in the population has a molecular weight exceeding 200 kDa, and at least 50% of the total number of the polypeptide fragments in the population has a molecular weight within a specified range, wherein the specified range is between about 3.5 kDa and about 120 kDa, or between about 5 kDa and about 125 kDa.

In another aspect, the silk fibroin in the compositions and/or methods described herein can be replaced with or used in combination with other non-silk polypeptides comprising a beta sheet structure or having a propensity for forming such a structure based on the amino acid sequence. Thus, provided herein also include polypeptide compositions comprising a population of beta-sheet forming polypeptide fragments. In some embodiments, the population of beta-sheet forming polypeptide fragments described herein can have a range of molecular weights, characterized in that: no more than 15% of the total number of the beta-sheet forming polypeptide fragments in the population has a molecular weight exceeding 200 kDa, and at least 50% of the total number of the beta-sheet forming polypeptide fragments in the population has a molecular weight within a specified range, wherein the specified range is between about 3.5 kDa and about 120 kDa or between about 5 kDa and about 125 kDa.

As used herein, the term "beta-sheet forming polypeptide" refers to a polypeptide having a portion or portions of an amino acid sequence that adopt the beta-sheet secondary structure. In some embodiments, the beta-sheet forming polypeptides can be selected on the basis of having a beta sheet structure or a propensity for forming such a structure based on the amino acid sequence.

In some embodiments, the beta-sheet forming polypeptides can have an amphiphilic nature (i.e., having both hydrophilic and hydrophobic portions). The amphiphilic polypeptide can be obtained from a single source (e.g., naturally occurring proteins) and contain both a hydrophobic module or stretch and a hydrophilic module or stretch within the polypeptide, such that the single polypeptide itself is naturally amphiphilic. In some embodiments, a hydrophobic module or stretch and a hydrophilic module or stretch can be fused or coupled together to form an amphiphilic entity. Such "fusion" or "chimeric" polypeptides can be produced using recombinant techniques, chemical coupling, or both.

In some embodiments, the beta-sheet forming polypeptides can comprise a portion or portions of an amino acid sequence of polypeptides selected from the following list: fibroins, actins, collagens, catenins, chitosans, claudins, coilins, elastins, elaunins, extensins, fibrillins, lamins, laminins, keratins, tublins, viral structural proteins, zein proteins (seed storage protein) and any combinations thereof.

In some embodiments, the beta-sheet forming polypeptides can comprise a regenerated (e.g., purified) protein from natural sources, recombinant proteins produced in heterologous systems, synthetic or chemically produced peptides, or combination of these.

In some embodiments, the beta-sheet forming polypeptides can comprise a portion or portions of an amino acid sequence of polypeptides corresponding to any one of the list provided above, with or without one or more sequence variations, as compared to the native or wild type counterpart. For example, in some embodiments, such variants may show at least 85% overall sequence identity as compared to a wild type sequence, e.g., at least 86%, 87%, 88%, 89%, 90%, 91%, 92%, 93%, 94%, 95%, 96%, 97%, 98%, 99% overall sequence identity.

Certain Exemplary Methods of Preparation

Without wishing to be bound by a theory, treatment with heat or high pressure, before processing into a final desire shape, can reduce or limit a number of problems associated with forming articles comprising silk fibroin. This provides the ability to manufacture articles of consistent geometries without significant bubbles, shrinkage, and deformation. This leads to reproducible, providing consistent samples for testing and implantation. Furthermore, the article can be machined, which allows exact replication of biological geometries, e.g., computer numerical control (CNC) mill to machine silk blank to desired construct. Methods comprising treatment with heat or high pressure before processing a silk fibroin article into a final desired shape are described in, for example, U.S. provisional application No. 61/808,768 filed Apr. 5, 2013, No. 61/719,146, filed Oct. 26, 2012, No. 61/809,535, filed Apr. 8, 2013, and No. 61/881,653, filed Sep. 24, 2013, contents of all of which are incorporated herein by reference in their entireties.

Accordingly, in one aspect, the disclosure provides a method for preparing a silk fibroin article. Generally, the method comprises incubating a silk fibroin composition (e.g., a low molecular weight silk fibroin composition) under elevated temperature and/or elevated pressure. The silk fibroin in the composition can be in an at least partially insoluble state. After incubation, the composition can be processed into a desired final shape. Without limitations, the silk fibroin composition for preparing the article of manufacture can be in the form of solutions, slurries, suspensions, colloids, mixtures, dispersions, pastes, and the like.

As used herein the term "insoluble state" when used in reference to silk fibroin refers to the formation of or state of being in a substantially amorphous, primarily beta-sheet conformation. The term "formed into an insoluble state" is not intended to reflect polymerization of silk monomers into a silk polymer. Rather, it is intended to reflect the conversion of soluble silk fibroin to a water insoluble state. As used herein, silk fibroin is in an "insoluble state" if it can be pelleted by centrifugation or if it cannot be dissolved by immersion in or rinsing with water at 37° C. or less.

In some embodiments, the silk fibroin composition can comprise an organic solvent. In one embodiment, the organic solvent can be hexafluoroisopropanol (HFIP). In some other embodiments, silk fibroin composition is free or essentially free of organic solvents, i.e., free of solvents other than water. Without wishing to be bound by a theory, an organic solvent in the silk fibroin composition provides for a more even drying of the composition leading to more uniform mechanical and structural properties in the final silk fibroin article of manufacture. Further, using an organic solvent also provides better mechanical and structural properties for processing into the final shape.

In some embodiments, the method comprises: (i) providing a silk fibroin composition, wherein the silk fibroin is at least partially in an insoluble state; (ii) incubating the composition under an elevated temperature and/or an elevated pressure; (iii) optionally repeating step (ii); and (iv) processing the composition to a desired shape. As used herein, the term "incubating" means subjecting the composition to the elevated temperature and/or pressure.

In some embodiments, the silk fibroin composition is in a mold. As used herein, the term "mold" is intended to encompass any mold, container or substrate capable of shaping, holding or supporting the silk fibroin composition. Thus, the mold in its simplest form could simply comprise a supporting surface. The mold can be of any desired shape, and can be fabricated from any suitable material including polymers (such as polysulphone, polypropylene, polyethylene), metals (such as stainless steel, titanium, cobalt chrome), ceramics (such as alumina, zirconia), glass ceramics, and glasses (such as borosilicate glass). In some embodiments, the mold can provide a scaffold of simple geometry, which can be processed into the final desired shape, i.e., the mold can be used to provide a blank which can be processed to the final shape.

Accordingly, in some embodiments, the method comprises: (i) providing a mold comprising a silk fibroin composition, wherein the silk fibroin in the composition is in an at least partially insoluble state; (ii) incubating the composition at an elevated temperature or under pressure; (iii) optionally repeating step (ii) one or more times; and (iv) processing the composition to a desired shape.

In some embodiments, the step of providing a mold comprising the silk fibroin composition comprises transferring a solution comprising silk fibroin to the mold and inducing a conformation change in the silk fibroin.

As used herein, the term "elevated temperature" means a temperature higher that room temperature. Generally, the elevated temperature is a temperature higher than about 25° C. For example, the elevated temperature can be temperature of about 30° C. or higher, about 35° C. or higher, about 40° C. or higher, about 45° C. or higher, about 50° C. or higher, about 55° C. or higher, about 60° C. or higher, about 65° C. or higher, about 70° C. or higher, about 75° C. or higher, about 80° C. or higher, about 85° C. or higher, about 90° C. or higher, about 95° C. or higher, about 100° C. or higher, about 105° C. or higher, about 110° C. or higher, about 115° C. or higher, about 120° C. or higher, about 125° C. or higher, about 130° C. or higher, about 135° C. or higher, about 140° C. or higher, about 145° C. or higher, or about 150° C. or higher. In some embodiments, the elevated temperature is at least about 121° C.

As used herein, the term "elevated pressure" means a pressure of about 0.05 bar, about 0.1 bar, about 0.15 bar, about 0.2 bar, about 0.25 bar, about 0.3 bar, about 0.35 bar, about 0.4 bar, about 0.45 bar, about 0.5 bar, about 0.55 bar, about 0.6 bar, about 0.65 bar, about 0.7 bar, about 0.75 bar or higher. For example, the elevated pressure can be about 1 bar, 1.25 bar, 1.5 bar, 1.75 bar, 2 bar, 2.25 bar, 2.5 bar, 2.75 bar, 3 bar, 3.25 bar, 3.5 bar, 3.75 bar, 4 bar, 4.25 bar, 4.5 bar, 4.75 bar, 5 bar, 5.25 bar, 5.5 bar, 5.75 bar, 6 bar, 7.25 bar, 7.5 bar, 7.75 bar, 8 bar, 8.25 bar, 8.5 bar, 8.75 bar, 9 bar, 9.25 bar, 9.5 bar, 9.75 bar, 10 bar, or higher. In some embodiments, the elevated pressure is about 1 bar or higher. In some embodiments, said incubating is under vacuum.

In some embodiments, said incubating is in the presence of water vapor.

Without limitation, incubation can be for any desired period of time. For example, the incubation can be for a period of about 1 minute, about 2 minutes, about 3 minute, about 4 minutes, about 5 minutes, about 6 minutes, about 7 minutes, about 8 minutes, about 8 minutes, about 10 minutes or longer. In some embodiments, the incubation can be for a period of from about 10 minutes to about 5 hours, from about 15 minutes to about 2.5 hours, from about 20 minutes to about 2 hours, from about 25 minutes to about 1.5 hours. In some embodiments, said incubating is for about 25 minutes.

A number of properties of the manufactured article (e.g., strength, molecular weight, degradation profile, swellability, density, color, and the like) can be controlled by repeating the incubating step. Accordingly, in some embodiments, the incubating step can be repeated one, e.g., one, two, three, four, five, six, seven, eight, nine, ten, or more times.

In some embodiments, a silk fibroin composition can optionally be dried before repeating the incubating step. Without limitation, drying can be for any desired period of time. For example, the drying can be for a period of about 1 minute, about 2 minutes, about 3 minute, about 4 minutes, about 5 minutes or longer. In some embodiments, the incubation can be for a period of from about 5 minutes to about 5 hours, from about 10 minutes to about 2.5 hours, from about 15 minutes to about 2 hours, from about 20 minutes to about 1.5 hours. In some embodiments, said drying is for about 15 minutes. Further, said drying can be at room temperature or an elevated temperature. For example, such drying can be at temperature of about 4° C. to about 100° C., about 10° C. to about 95° C., about 15° C. to about 90° C., about 20° C. to about 85° C., about 25° C. to about 80° C., about 30° C. to about 75° C., about 35° C. to about 60° C., or about 45° C. to about 65° C.

In some embodiments, said incubating comprises autoclaving. By "autoclaving" is meant heat treatment in the presence or absence of water vapor (e.g., saturated steam) at superatmospheric pressure. For purposes of this disclosure, the term, autoclaving, represents a process that elevates the composition temperature at a sufficient pressure and for a sufficient period of time. Generally, autoclaving relates to a standardized thermal heating procedure characterized by the following parameters: heating to 120° C. or more for a period of 15 minutes or more under pressure. Temperature for autoclaving can range from 120-150° C., more preferably from 120-140° C.; and the pressure can range from 1-20 bar, more preferably from 1-10 bar, and even more preferably form 1-5 bar. The time needed can range from 15-120 minutes, more preferably from 15-60 minutes. In some embodiments, the autoclaving can be repeated one, e.g., one, two, three, four, five, six, seven, eight, nine, ten, or more times.

Without wishing to be bound by a theory, it is believed that steam, high heat, and/or pressure forces the water into the samples during autoclaving, wherein the water acts as a plasticizer and allows mobility of the chains. During the drying cycle, the mobile chains are compacted to create a denser, stronger material. With time and heat the protein chains can get degraded. This can able a more tight packing due to avoidance of some chain entanglements. Thus, changes in the parameters of the autoclaving process, such as slow or rapid venting, temperature, pressure, and duration can affect the mechanical, physical, or structural properties of the material produced.

In some embodiments, the silk fibroin composition can be optionally dried after incubating but before processing into the desired shape or geometry. Without limitation, drying before processing into the desired shape can be for any desired period of time. For example, the drying can be for a period of about few minutes to days. In some embodiments, the drying can be for a period of about at least 12 hours, at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, or at least 14 days. In some embodiments, said drying before processing to the final shape is for about at least seven days. Further, said drying can be at room temperature or an elevated temperature. For example, such drying can be at temperature of about 4° C. to about 100° C., about 10° C. to about 95° C., about 15° C. to about 90° C., about 20° C. to about 85° C., about 25° C. to about 80° C., about 30° C. to about 75° C., about 35° C. to about 60° C., or about 45° C. to about 65° C. In some embodiments, drying is at a temperature of about 60° C.

After optionally drying the silk fibroin composition, the composition can be processed into the final desired shape. As used herein, the term "processing" with reference to processing into the desired shape should be understood to include any method or process used to provide the final shape of the manufactured article. Without limitation, such processing can include, but is not limited to, mechanical and chemical means. For example, processing can be selected from the group consisting of machining, turning (lathe), rolling, thread rolling, drilling, milling, sanding, punching, die cutting, blanking, broaching, extruding, chemical etching, and any combinations thereof. As used herein, the term "machining" should be understood to include all types of machining operations including, but not limited to, CNC machining, cutting, milling, turning, drilling, shaping, planing, broaching, sawing, burnishing, grinding, and the like. One or more of the processing methods can be used in combination to obtain more complex, intricate geometries. The term "machinable" means a material which can be readily subjected to machining.

After processing into the desired shape, the manufactured article can be further post-processed. For example, the manufactured article can be incubated at an elevated temperature or under pressure. Post processing of the article can be used to control a number of properties (e.g., strength, molecular weight, degradation profile, swellability, density, color, and the like) of the manufactured article. In some embodiments, post-processing comprises autoclaving the article in its final shape for one, e.g., one, two, three, four, five, six, seven, eight, nine, ten, or more times.

As discussed herein above, the silk fibroin composition can optionally be dried after the incubating step. Accordingly, in some embodiments, the method comprises: (i) providing a mold comprising a silk fibroin composition, wherein the silk fibroin in the composition is in an at least partially insoluble state; (ii) incubating the composition at an elevated temperature or under pressure; (iii) drying the composition; (iv) optionally repeating steps (ii) and (iii) one or more times; and (iv) processing the composition to a desired shape.

The disclosure also provides silk fibroin articles prepared by the method disclosed herein. Without limitations, the article can be used for medical applications, e.g. medical devices, or the article can be for non-medical applications. As used herein, the term medical device is intended to encompass all types of medical devices, including those used in connection with either external or internal treatment of a mammal. Medical devices used in the external treatment of a mammal include, but are not limited to, wound dressings, burn dressings or other skin coverings, and surgical thread. Medical devices used in the internal treatment of a mammal include, but are not limited to, vascular grafts, stents, catheters, valves, artificial joints, artificial organs, surgical thread, and the like.

Exemplary medical devices include, but are not limited to, an orthopedic implant, a facial implant, a nasal implant (e.g., for nasal reconstruction), a suture anchor, a dental implant, a Swanson prosthetic, and any combinations thereof. In some embodiments, the article of manufacture is a continuous, one-phase suture anchor.

As used herein, the term "orthopedic implant" includes within its scope any device intended to be implanted into the body of a vertebrate animal, in particular a mammal such as a human, for preservation and restoration of the function of the musculoskeletal system, particularly joints and bones, including the alleviation of pain in these structures. Exemplary orthopedic implants include, but are not limited to, orthopedic screws, orthopedic plates, orthopedic rods, orthopedic tulips, or any combinations thereof.

In some embodiments, the article of manufacture can be a tapping screw, e.g., self-tapping screw.

In some embodiments, the article of manufacture can be a suture anchor. Suture anchors are composed of an anchor, eyelet, and suture. The anchor is inserted to the bone which can be a screw mechanism or interference fit and the eyelet is the hole or loop in the anchor through which the suture passes.

In some embodiments, the article of manufacture can be a dental implant. As used herein, the term "dental implant" includes within its scope any device intended to be implanted into the oral cavity of a vertebrate animal, in particular a mammal such as a human, in tooth restoration procedures. Dental implants can also be denoted as dental prosthetic devices. Generally, a dental implant is composed of one or several implant parts. For instance, a dental implant usually comprises a dental fixture coupled to secondary implant parts, such as an abutment and/or a dental restoration such as a crown, bridge or denture. However, any device, such as a dental fixture, intended for implantation can alone be referred to as an implant even if other parts are to be connected thereto. Dental implants are presently preferred embodiments.

In some embodiments, dental implants are composed of a crown and screw implant. The implant is inserted into the bone using a screwing mechanism for stabilization of the crown.

In some embodiments, the article of manufacture can be a bone screw and/or a bone plate. Bone screws consist of a thread portion and head used for insertion and stabilization of associated equipment such as bone plates.

In some embodiments, the article of manufacture can be Swanson prosthesis. The Swanson Finger Joint Implant is a flexible intramedullary-stemmed one-piece implant that helps restore function to hands and wrists disabled by rheumatoid, degenerative or traumatic arthritis. It is composed of a silicone elastomer and its primary function is to help maintain proper joint space and alignment with good lateral stability and minimal flexion-extensional restriction. These implants bear minimal load as the majority of the compressive loads are distributed to the bones.

In some embodiments, the article of manufacture can be used for nasal reconstruction. A nasal reconstruction is performed in order to create an aesthetically inconspicuous nose while maintaining function. Structural grafts are often required to provide rigidity to the sidewall and resist lateral collapse and establish nasal contour and projection. Current materials include alloplasts such as silicone and porous high density polyethylene as well has homografts such as alloderm or rib cartilage.

The method disclosed herein allows for silk to be used for this application due to the ability of the silk to be manufactured into a variety of different shapes. For instance, the silk can be extruded into a rod then turned (lathe) to remove any deformations and obtain the desired size. Moreover, the construct can be molded in situ to conform to the natural geometry of the nose.

In some embodiments, the article of manufacture can be used for otoplasty. Otoplasty is the process of reconstructing partial or total ear defects typically resulting from congenital hypoplasia, trauma, cancer ablation, and prominent ears. The ears can be reconstructed by using cartilage from the rib cage or an artificial ear can be created. The rib cartilage is carved and wired together using fine stainless steel wire to create a very detailed framework.

The method disclosed herein allows silk to be extruded, drawn and molded in situ into a fine wire network that could be used to create the framework of the new ear. Moreover, due to numerous processes which can create intricate geometries, the silk could be manufactured based on patient specific needs.

In addition to the above-discussed specific medical devices and implants, the method disclosed herein can be used for facial implants (dermal fillers, cheek implants, eye socket), occuloplasty, lip enhancement, reproductive organ plastic surgeries (penile implant, vaginaplasty, sex conversion), buttock augmentation, and other soft tissue "plastys."

Non-medical applications include manufacturing of dice, thumbtacks, bullets, children's toys (e.g., building blocks, Legos, Checkers, etc. . . . ), and biodegradable plastic alternatives.

Additives

In some embodiments, a silk fibroin composition described herein can comprise at least one additive (e.g., as an alternative to or in addition to an active agent/sample/component as discussed herein; or in some embodiments an active agent/sample/component may be an "additive" as that term is used herein). In some embodiments of various aspects described herein, the silk composition can further comprise one or more (e.g., one, two, three, four, five or more) additives. Without wishing to be bound by a theory additive can provide one or more desirable properties, e.g., strength, flexibility, ease of processing and handling, biocompatibility, bioresorability, surface morphology, release rates and/or kinetics of one or more active agents present in the composition, and the like. The additive can be covalently or non-covalently linked with silk fibroin and can be integrated homogenously or heterogeneously within the silk composition.

For example, the silk material can be prepared from a fibroin solution comprising one or more (e.g., one, two, three, four, five or more) additives.

Without limitations, an additive can be selected from small organic or inorganic molecules; saccharides; oligosaccharides; polysaccharides; polymers; proteins; peptides; peptide analogs and derivatives; peptidomimetics; nucleic acids; nucleic acid analogs; and the like. In some embodiments, additives are or comprise immunogens; antigens; an extract made from biological materials such as bacteria, plants, fungi, or animal cells; animal tissues; naturally occurring or synthetic compositions; and any combinations thereof. Furthermore, the additive can be in any physical form. For example, the additive can be in the form of a particle, a fiber, a film, a gel, a mesh, a mat, a non-woven mat, a powder, a liquid, or any combinations thereof. In some embodiments, the additive is a particle.

In one embodiment, said at least one additive is a stabilizer, which can be used to stabilize one or more aspects of the composition, and/or of an active agent/sample/component included therein, and/or to increase dissolvability of the silk fibroin. One example of a stabilizer that can be added for stabilization of at least RNA or protein present in a biological sample includes a nuclease inhibitor (e.g., a RNAse inhibitor) or proteinase inhibitor, respectively.

Additional examples of a stabilizer can include, but are not limited to, amino acids, such as sodium glutamate, arginine, lysine, and cysteine; monosaccharides, such as glucose, galactose, fructose, and mannose; disaccharides, such as sucrose, maltose, and lactose; sugar alcohols such as sorbitol and mannitol; polysaccharides, such as oligosaccharide, starch, cellulose, and derivatives thereof; human serum albumin and bovine serum albumin; gelatin, and gelatin derivatives, such as hydrolyzed gelatin; and ascorbic acid as an antioxidant; and ions (e.g., cationic or anionic stabilizers); and surfactants; and any combinations thereof. These materials are described in publications, e.g., "Toketsu-Kanso To Hogo Busshitsu (Lyophilization And Protective Materials)" written by Nei, p. 1-176, published by Tokyo Daigaku Shuppan Kai (Publishing Association of the University of Tokyo), Japan in 1972; and "Shinku Gijutsu Koza (8): Sinku Kanso (Lecture on Vacuum Technology (8): Vacuum Drying)" written by Ota et al., p. 176-182, published by Nikkan Kogyo Shimbun Co., Ltd., Japan in 1964.

In some embodiments, an additive is a biocompatible polymer. Exemplary biocompatible polymers include, but are not limited to, a poly-lactic acid (PLA), poly-glycolic acid (PGA), poly-lactide-co-glycolide (PLGA), polyesters, poly(ortho ester), poly(phosphazine), poly(phosphate ester), polycaprolactone, gelatin, collagen, fibronectin, keratin, polyaspartic acid, alginate, chitosan, chitin, hyaluronic acid, pectin, polyhydroxyalkanoates, dextrans, and polyanhydrides, polyethylene oxide (PEO), poly(ethylene glycol) (PEG), triblock copolymers, polylysine, alginate, polyaspartic acid, any derivatives thereof and any combinations thereof. Other exemplary biocompatible polymers amenable to use according to the present disclosure include those described, for example, in U.S. Pat. Nos. 6,302,848; 6,395,734; 6,127,143; 5,263,992; 6,379,690; 5,015,476; 4,806,355; 6,372,244; 6,310,188; 5,093,489; 387,413; 6,325,810; 6,337,198; 6,267,776; 5,576,881; 6,245,537; 5,902,800; and 5,270,419, content of all of which is incorporated herein by reference.

In one embodiment, the additive is glycerol, which can affect the flexibility and/or solubility of the silk-based. Silk-based materials, e.g., silk films comprising glycerol are described in WO 2010/042798, content of which is incorporated herein by reference in its entirety.

Examples of other additives include, but are not limited to: cell attachment mediators, such as collagen, elastin, fibronectin, vitronectin, laminin, proteoglycans, or peptides containing known integrin binding domains e.g. "RGD" integrin binding sequence, or variations thereof, that are known to affect cellular attachment (Schaffner P & Dard 2003 Cell Mol Life Sci. January; 60(1):119-32; Hersel U. et al. 2003 Biomaterials. November; 24(24):4385-415); biologically active ligands; and substances that enhance or exclude particular varieties of cellular or tissue ingrowth. Other examples of additive agents that enhance proliferation or differentiation include, but are not limited to, osteoinductive substances, such as bone morphogenic proteins (BMP); cytokines, growth factors such as epidermal growth factor (EGF), platelet-derived growth factor (PDGF), insulin-like growth factor (IGF-I and II) TGF-$\beta$1, and the like.

Total amount of additives in the composition can be from about 0.01 wt % to about 99 wt %, from about 0.01 wt % to about 70 wt %, from about 5 wt % to about 60 wt %, from about 10 wt % to about 50 wt %, from about 15 wt % to about 45 wt %, or from about 20 wt % to about 40 wt %, of the total silk composition. In some embodiments, ratio of silk fibroin to additive in the composition can range from about 1000:1 (w/w) to about 1:1000 (w/w), from about 500:1 (w/w) to about 1:500 (w/w), from about 250:1 (w/w) to about 1:250 (w/w), from about 200:1 (w/w) to about 1:200 (w/w), from about 25:1 (w/w) to about 1:25 (w/w), from about 20:1 (w/w) to about 1:20 (w/w), from about 10:1 (w/w) to about 1:10 (w/w), or from about 5:1 (w/w) to about 1:5 (w/w).

In some embodiments, total amount of additives in the silk-based material can be from about 0.1 wt % to about 70 wt %, from about 5 wt % to about 60 wt %, from about 10 wt % to about 50 wt %, from about 15 wt % to about 45 wt %, or from about 20 wt % to about 40 wt %, of the total silk fibroin in the silk-based material. One of skill in the art can determine appropriate ratio of the silk fibroin to the additive, e.g., by measuring the property of the component or the silk-based material that is affected by the addition of the additive at various ratios described herein.

In some embodiments, the composition comprises a molar ratio of silk fibroin to the additive of, e.g., at least 1000:1, at least 900:1, at least 800:1, at least 700:1, at least 600:1, at least 500:1, at least 400:1, at least 300:1, at least 200:1, at least 100:1, at least 90:1, at least 80:1, at least 70:1, at least 60:1, at least 50:1, at least 40:1, at least 30:1, at least 20:1, at least 10:1, at least 7:1, at least 5:1, at least 3:1, at least 1:1, at least 1:3, at least 1:5, at least 1:7, at least 1:10, at least 1:20, at least 1:30, at least 1:40, at least 1:50, at least 1:60, at least 1:70, at least 1:80, at least 1:90, at least 1:100, at least 1:200, at least 1:300, at least 1:400, at least 1:500, at least 600, at least 1:700, at least 1:800, at least 1:900, or at least 1:100.

In some embodiments, the composition comprises a molar ratio of silk fibroin to the additive of, e.g., at most 1000:1, at most 900:1, at most 800:1, at most 700:1, at most 600:1, at most 500:1, at most 400:1, at most 300:1, at most 200:1, 100:1, at most 90:1, at most 80:1, at most 70:1, at most 60:1, at most 50:1, at most 40:1, at most 30:1, at most 20:1, at most 10:1, at most 7:1, at most 5:1, at most 3:1, at most 1:1, at most 1:3, at most 1:5, at most 1:7, at most 1:10, at most 1:20, at most 1:30, at most 1:40, at most 1:50, at most 1:60, at most 1:70, at most 1:80, at most 1:90, at most 1:100, at most 1:200, at most 1:300, at most 1:400, at most 1:500, at most 1:600, at most 1:700, at most 1:800, at most 1:900, or at most 1:1000.

In some embodiments, the composition comprises a molar ratio of silk fibroin to the additive of e.g., from about 1000:1 to about 1:1000, from about 900:1 to about 1:900, from about 800:1 to about 1:800, from about 700:1 to about 1:700, from about 600:1 to about 1:600, from about 500:1 to about 1:500, from about 400:1 to about 1:400, from about 300:1 to about 1:300, from about 200:1 to about 1:200, from about 100:1 to about 1:100, from about 90:1 to about 1:90, from about 80:1 to about 1:80, from about 70:1 to about 1:70, from about 60:1 to about 1:60, from about 50:1 to about 1:50, from about 40:1 to about 1:40, from about 30:1 to about 1:30, from about 20:1 to about 1:20, from about 10:1 to about 1:10, from about 7:1 to about 1:7, from about 5:1 to about 1:5, from about 3:1 to about 1:3, or about 1:1.

In some embodiments, the additive is a biologically active agent. The term "biologically active agent" as used herein refers to any molecule which exerts at least one biological effect in vivo. For example, the biologically active agent can be a therapeutic agent to treat or prevent a disease state or condition in a subject. Biologically active agents include, without limitation, organic molecules, inorganic materials, proteins, peptides, nucleic acids (e.g., genes, gene fragments, gene regulatory sequences, and antisense molecules), nucleoproteins, polysaccharides, glycoproteins, and lipoproteins. Classes of biologically active compounds that can be incorporated into the composition described herein include, without limitation, anticancer agents, antibiotics, analgesics, anti-inflammatory agents, immunosuppressants, enzyme inhibitors, antihistamines, anti-convulsants, hormones, muscle relaxants, antispasmodics, ophthalmic agents, prostaglandins, anti-depressants, anti-psychotic substances, trophic factors, osteoinductive proteins, growth factors, and vaccines.

In some embodiments, the additive is a therapeutic agent. As used herein, the term "therapeutic agent" means a molecule, group of molecules, complex or substance administered to an organism for diagnostic, therapeutic, preventative medical, or veterinary purposes. As used herein, the term "therapeutic agent" includes a "drug" or a "vaccine." This term include externally and internally administered topical, localized and systemic human and animal pharmaceuticals, treatments, remedies, nutraceuticals, cosmeceuticals, biologicals, devices, diagnostics and contraceptives, including preparations useful in clinical and veterinary screening, prevention, prophylaxis, healing, wellness, detection, imaging, diagnosis, therapy, surgery, monitoring, cosmetics, prosthetics, forensics and the like. This term can also be used in reference to agriceutical, workplace, military, industrial and environmental therapeutics or remedies comprising selected molecules or selected nucleic acid sequences capable of recognizing cellular receptors, membrane receptors, hormone receptors, therapeutic receptors, microbes, viruses or selected targets comprising or capable of contacting plants, animals and/or humans. This term can also specifically include nucleic acids and compounds comprising nucleic acids that produce a therapeutic effect, for example deoxyribonucleic acid (DNA), ribonucleic acid (RNA), nucleic acid analogues (e.g., locked nucleic acid (LNA), peptide nucleic acid (PNA), xeno nucleic acid (XNA)), or mixtures or combinations thereof, including, for example, DNA nanoplexes, siRNA, microRNA, shRNA, aptamers, ribozymes, decoy nucleic acids, antisense nucleic acids, RNA activators, and the like. Generally, any therapeutic agent can be included in the composition described herein.

The term "therapeutic agent" also includes an agent that is capable of providing a local or systemic biological, physiological, or therapeutic effect in the biological system to which it is applied. For example, the therapeutic agent can act to control infection or inflammation, enhance cell growth and tissue regeneration, control tumor growth, act as an analgesic, promote anti-cell attachment, and enhance bone growth, among other functions. Other suitable therapeutic agents can include anti-viral agents, hormones, antibodies, or therapeutic proteins. Other therapeutic agents include prodrugs, which are agents that are not biologically active when administered but, upon administration to a subject are converted to biologically active agents through metabolism or some other mechanism. Additionally, a silk-based drug delivery composition can contain one therapeutic agent or combinations of two or more therapeutic agents.

A therapeutic agent can include a wide variety of different compounds, including chemical compounds and mixtures of chemical compounds, e.g., small organic or inorganic molecules; saccharines; oligosaccharides; polysaccharides; biological macromolecules, e.g., peptides, proteins, and peptide analogs and derivatives; peptidomimetics; antibodies and antigen binding fragments thereof; nucleic acids; nucleic acid analogs and derivatives; an extract made from biological materials such as bacteria, plants, fungi, or animal cells; animal tissues; naturally occurring or synthetic compositions; and any combinations thereof. In some embodiments, the therapeutic agent is a small molecule.

As used herein, the term "small molecule" can refer to compounds that are "natural product-like," however, the term "small molecule" is not limited to "natural product-like" compounds. Rather, a small molecule is typically characterized in that it contains several carbon-carbon bonds, and has a molecular weight of less than 5000 Daltons (5 kDa), preferably less than 3 kDa, still more preferably less than 2 kDa, and most preferably less than 1 kDa. In some cases it is preferred that a small molecule have a molecular weight equal to or less than 700 Daltons.

Exemplary therapeutic agents include, but are not limited to, those found in *Harrison's Principles of Internal Medicine,* 13$^{th}$ Edition, Eds. T. R. Harrison et al. McGraw-Hill N.Y., NY; Physicians' Desk Reference, 50$^{th}$ Edition, 1997, Oradell N.J., Medical Economics Co.; Pharmacological Basis of Therapeutics, 8$^{th}$ Edition, Goodman and Gilman, 1990; United States Pharmacopeia, The National Formulary, USP XII NF XVII, 1990, the complete contents of all of which are incorporated herein by reference.

Therapeutic agents include the herein disclosed categories and specific examples. It is not intended that the category be limited by the specific examples. Those of ordinary skill in the art will recognize also numerous other compounds that fall within the categories and that are useful according to the present disclosure. Examples include a radiosensitizer, a steroid, a xanthine, a beta-2-agonist bronchodilator, an anti-inflammatory agent, an analgesic agent, a calcium antagonist, an angiotensin-converting enzyme inhibitors, a beta-blocker, a centrally active alpha-agonist, an alpha-1-antagonist, an anticholinergic/antispasmodic agent, a vasopressin analogue, an antiarrhythmic agent, an antiparkinsonian agent, an antiangina/antihypertensive agent, an anticoagulant agent, an antiplatelet agent, a sedative, an ansiolytic agent, a peptidic agent, a biopolymeric agent, an antineoplastic agent, a laxative, an antidiarrheal agent, an antimicrobial agent, an antifungal agent, a vaccine, a protein, or a nucleic acid. In a further aspect, the pharmaceutically active agent can be coumarin, albumin, steroids such as betamethasone, dexamethasone, methylprednisolone, prednisolone, prednisone, triamcinolone, budesonide, hydrocortisone, and pharmaceutically acceptable hydrocortisone derivatives; xanthines such as theophylline and doxophylline; beta-2-agonist bronchodilators such as salbutamol, fenterol, clenbuterol, bambuterol, salmeterol, fenoterol; antiinflammatory agents, including antiasthmatic anti-inflammatory agents, antiarthritis antiinflammatory agents, and non-steroidal antiinflammatory agents, examples of which include but are not limited to sulfides, mesalamine, budesonide, salazopyrin, diclofenac, pharmaceutically acceptable diclofenac salts, nimesulide, naproxene, acetaminophen, ibuprofen, ketoprofen and piroxicam; analgesic agents such as salicylates; calcium channel blockers such as nifedipine, amlodipine, and nicardipine; angiotensin-converting enzyme inhibitors such as captopril, benazepril hydrochloride, fosinopril sodium, trandolapril, ramipril, lisinopril, enalapril, quinapril hydrochloride, and moexipril hydrochloride; beta-blockers (i.e., beta adrenergic blocking agents) such as sotalol hydrochloride, timolol maleate, esmolol hydrochloride, carteolol, propanolol hydrochloride, betaxolol hydrochloride, penbutolol sulfate, metoprolol tartrate, metoprolol succinate, acebutolol hydrochloride, atenolol, pindolol, and bisoprolol fumarate; centrally active alpha-2-agonists such as clonidine; alpha-1-antagonists such as doxazosin and prazosin; anticholinergic/antispasmodic agents such as dicyclomine hydrochloride, scopolamine hydrobromide, glycopyrrolate, clidinium bromide, flavoxate, and oxybutynin; vasopressin analogues such as vasopressin and desmopressin; antiarrhythmic agents such as quinidine, lidocaine, tocainide hydrochloride, mexiletine hydrochloride, digoxin, verapamil hydrochloride, propafenone hydrochloride, flecainide acetate, procainamide hydrochloride, moricizine hydrochloride, and disopyramide phosphate; antiparkinsonian agents, such as dopamine, L-Dopa/Carbidopa, selegiline, dihydroergocryptine, pergolide, lisuride, apomorphine, and bromocryptine; anti-angina agents and antihypertensive agents such as isosorbide mononitrate, isosorbide dinitrate, propranolol, atenolol and verapamil; anticoagulant and antiplatelet agents such as Coumadin, warfarin, acetylsalicylic acid, and ticlopidine; sedatives such as benzodiazepines and barbiturates; ansiolytic agents such as lorazepam, bromazepam, and diazepam; peptidic and biopolymeric agents such as calcitonin, leuprolide and other LHRH agonists, hirudin, cyclosporin, insulin, somatostatin, protirelin, interferon, desmopressin, somatotropin, thymopentin, pidotimod, erythropoietin, interleukins, melatonin, granulocyte/macrophage-CSF, and heparin; antineoplastic agents such as etoposide, etoposide phosphate, cyclophosphamide, methotrexate, 5-fluorouracil, vincristine, doxorubicin, cisplatin, hydroxyurea, leucovorin calcium, tamoxifen, flutamide, asparaginase, altretamine, mitotane, and procarbazine hydrochloride; laxatives such as senna concentrate, casanthranol, bisacodyl, and sodium picosulphate; antidiarrheal agents such as difenoxine hydrochloride, loperamide hydrochloride, furazolidone, diphenoxylate hdyrochloride, and microorganisms; vaccines such as bacterial and viral vaccines; antimicrobial agents such as penicillins, cephalosporins, and macrolides, antifungal agents such as imidazolic and triazolic derivatives; and nucleic acids such as DNA sequences encoding for biological proteins, and antisense oligonucleotides.

Anti-cancer agents include alkylating agents, platinum agents, antimetabolites, topoisomerase inhibitors, antitumor antibiotics, antimitotic agents, aromatase inhibitors, thymidylate synthase inhibitors, DNA antagonists, farnesyl-transferase inhibitors, pump inhibitors, histone acetyltransferase inhibitors, metalloproteinase inhibitors, ribonucleoside reductase inhibitors, TNF alpha agonists/antagonists, endothelinA receptor antagonists, retinoic acid receptor agonists, immuno-modulators, hormonal and anti-hormonal agents, photodynamic agents, and tyrosine kinase inhibitors.

Antibiotics include aminoglycosides (e.g., gentamicin, tobramycin, netilmicin, streptomycin, amikacin, neomycin), bacitracin, corbapenems (e.g., imipenem/cislastatin), cephalosporins, colistin, methenamine, monobactams (e.g., aztreonam), penicillins (e.g., penicillin G, penicillinV, methicillin, natcillin, oxacillin, cloxacillin, dicloxacillin, ampicillin, amoxicillin, carbenicillin, ticarcillin, piperacillin, mezlocillin, azlocillin), polymyxin B, quinolones, and vancomycin; and bacteriostatic agents such as chloramphenicol, clindanyan, macrolides (e.g., erythromycin, azithromycin, clarithromycin), lincomyan, nitrofurantoin, sulfonamides, tetracyclines (e.g., tetracycline, doxycycline, minocycline, demeclocyline), and trimethoprim. Also included are metronidazole, fluoroquinolones, and ritampin.

Enzyme inhibitors are substances which inhibit an enzymatic reaction. Examples of enzyme inhibitors include edrophonium chloride, N-methylphysostigmine, neostigmine bromide, physostigmine sulfate, tacrine, tacrine, 1-hydroxy maleate, iodotubercidin, p-bromotetramii sole, 10-(alpha-diethylaminopropionyl)-phenothiazine hydrochloride, calmidazolium chloride, hemicholinium-3,3,5-dinitrocatechol, diacylglycerol kinase inhibitor I, diacylglycerol kinase inhibitor II, 3-phenylpropargylamine, N°-monomethyl-Larginine acetate, carbidopa, 3-hydroxybenzylhydrazine, hydralazine, clorgyline, deprenyl, hydroxylamine, iproniazid phosphate, 6-MeO-tetrahydro-9H-pyrido-indole, nialamide, pargyline, quinacrine, semicarbazide, tranylcypromine, N,N-diethylaminoethyl-2,2-diphenylvalerate hydrochloride, 3-isobutyl-1-methylxanthne, papaverine, indomethacind, 2-cyclooctyl-2-hydroxyethylamine hydrochloride, 2,3-dichloro-a-methylbenzylamine (DCMB), 8,9-dichloro-2,3,4,5-tetrahydro-1H-2-benzazepine hydrochloride, p-amino glutethimide, p-aminoglutethimide tartrate, 3-iodotyrosine, alpha-methyltyrosine, acetazolamide, dichlorphenamide, 6-hydroxy-2-benzothiazolesulfonamide, and allopurinol.

Antihistamines include pyrilamine, chlorpheniramine, and tetrahydrazoline, among others.

Anti-inflammatory agents include corticosteroids, non-steroidal anti-inflammatory drugs (e.g., aspirin, phenylbutazone, indomethacin, sulindac, tolmetin, ibuprofen, piroxicam, and fenamates), acetaminophen, phenacetin, gold salts, chloroquine, D-Penicillamine, methotrexate colchicine, allopurinol, probenecid, and sulfinpyrazone.

Muscle relaxants include mephenesin, methocarbomal, cyclobenzaprine hydrochloride, trihexylphenidyl hydrochloride, levodopa/carbidopa, and biperiden.

Anti-spasmodics include atropine, scopolamine, oxyphenonium, and papaverine.

Analgesics include aspirin, phenybutazone, idomethacin, sulindac, tolmetic, ibuprofen, piroxicam, fenamates, acetaminophen, phenacetin, morphine sulfate, codeine sulfate, meperidine, nalorphine, opioids (e.g., codeine sulfate, fentanyl citrate, hydrocodone bitartrate, loperamide, morphine sulfate, noscapine, norcodeine, normorphine, thebaine, norbinaltorphimine, buprenorphine, chlomaltrexamine, funaltrexamione, nalbuphine, nalorphine, naloxone, naloxonazine, naltrexone, and naltrindole), procaine, lidocain, tetracaine and dibucaine.

Ophthalmic agents include sodium fluorescein, rose bengal, methacholine, adrenaline, cocaine, atropine, alpha-chymotrypsin, hyaluronidase, betaxalol, pilocarpine, timolol, timolol salts, and combinations thereof.

Prostaglandins are art recognized and are a class of naturally occurring chemically related long-chain hydroxy fatty acids that have a variety of biological effects.

Anti-depressants are substances capable of preventing or relieving depression. Examples of anti-depressants include imipramine, amitriptyline, nortriptyline, protriptyline, desipramine, amoxapine, doxepin, maprotiline, tranylcypromine, phenelzine, and isocarboxazide.

Trophic factors are factors whose continued presence improves the viability or longevity of a cell. trophic factors include, without limitation, platelet-derived growth factor (PDGP), neutrophil-activating protein, monocyte chemoattractant protein, macrophage-inflammatory protein, platelet factor, platelet basic protein, and melanoma growth stimulating activity; epidermal growth factor, transforming growth factor (alpha), fibroblast growth factor, platelet-derived endothelial cell growth factor, insulin-like growth factor, glial derived growth neurotrophic factor, ciliary neurotrophic factor, nerve growth factor, bone growth/cartilage-inducing factor (alpha and beta), bone morphogenetic proteins, interleukins (e.g., interleukin inhibitors or interleukin receptors, including interleukin 1 through interleukin 10), interferons (e.g., interferon alpha, beta and gamma), hematopoietic factors, including erythropoietin, granulocyte colony stimulating factor, macrophage colony stimulating factor and granulocyte-macrophage colony stimulating factor; tumor necrosis factors, and transforming growth factors (beta), including beta-1, beta-2, beta-3, inhibin, and activin.

Hormones include estrogens (e.g., estradiol, estrone, estriol, diethylstibestrol, quinestrol, chlorotrianisene, ethinyl estradiol, mestranol), anti-estrogens (e.g., clomiphene, tamoxifen), progestins (e.g., medroxyprogesterone, norethindrone, hydroxyprogesterone, norgestrel), antiprogestin (mifepristone), androgens (e.g, testosterone cypionate, fluoxymesterone, danazol, testolactone), anti-androgens (e.g., cyproterone acetate, flutamide), thyroid hormones (e.g., triiodothyronne, thyroxine, propylthiouracil, methimazole, and iodixode), and pituitary hormones (e.g., corticotropin, sumutotropin, oxytocin, and vasopressin). Hormones are commonly employed in hormone replacement therapy and/or for purposes of birth control. Steroid hormones, such as prednisone, are also used as immunosuppressants and anti-inflammatories.

In some embodiments, the additive is an agent that stimulates tissue formation, and/or healing and regrowth of natural tissues, and any combinations thereof. Agents that increase formation of new tissues and/or stimulates healing or regrowth of native tissue at the site of injection can include, but are not limited to, fibroblast growth factor (FGF), transforming growth factor-beta (TGF-β, platelet-derived growth factor (PDGF), epidermal growth factors (EGFs), connective tissue activated peptides (CTAPs), osteogenic factors including bone morphogenic proteins, heparin, angiotensin II (A-II) and fragments thereof, insulin-like growth factors, tumor necrosis factors, interleukins, colony stimulating factors, erythropoietin, nerve growth factors, interferons, biologically active analogs, fragments, and derivatives of such growth factors, and any combinations thereof.

In some embodiments, the silk composition can further comprise at least one additional material for soft tissue augmentation, e.g., dermal filler materials, including, but not limited to, poly(methyl methacrylate) microspheres, hydroxylapatite, poly(L-lactic acid), collagen, elastin, and glycosaminoglycans, hyaluronic acid, commercial dermal filler products such as BOTOX® (from Allergan), DYSPORT®, COSMODERM®, EVOLENCE®, RADIESSE®, RESTYLANE®, JUVEDERM® (from Allergan), SCULPTRA®, PERLANE®, and CAPTIQUE®, and any combinations thereof.

In some embodiments, the additive is a wound healing agent. As used herein, a "wound healing agent" is a compound or composition that actively promotes wound healing process. Exemplary wound healing agents include, but are not limited to dexpanthenol; growth factors; enzymes, hormones; povidon-iodide; fatty acids; anti-inflammatory agents; antibiotics; antimicrobials; antiseptics; cytokines; thrombin; angalgesics; opioids; aminoxyls; furoxans; nitrosothiols; nitrates and anthocyanins; nucleosides, such as adenosine; and nucleotides, such as adenosine diphosphate (ADP) and adenosine triphosphate (ATP); neutotransmitter/neuromodulators, such as acetylcholine and 5-hydroxytryptamine (serotonin/5-HT); histamine and catecholamines, such as adrenalin and noradrenalin; lipid molecules, such as sphingosine-1-phosphate and lysophosphatidic acid; amino acids, such as arginine and lysine; peptides such as the bradykinins, substance P and calcium gene-related peptide (CGRP); nitric oxide; and any combinations thereof.

In certain embodiments, the active agents described herein are immunogens. In one embodiment, the immunogen is a vaccine. Most vaccines are sensitive to environmental conditions under which they are stored and/or transported. For example, freezing may increase reactogenicity (e.g., capability of causing an immunological reaction) and/or loss of potency for some vaccines (e.g., HepB, and DTaP/IPV/HIB), or cause hairline cracks in the container, leading to contamination. Further, some vaccines (e.g., BCG, Varicella, and MMR) are sensitive to heat. Many vaccines (e.g., BCG, MMR, Varicella, Meningococcal C Conjugate, and most DTaP-containing vaccines) are light-sensitive. See, e.g., Galazka et al., *Thermostability of vaccines, in* Global Programme for Vaccines & Immunization (World Health Organization, Geneva, 1998); Peetermans et al., *Stability of freeze-dried rubella virus vaccine (Cendehill strain) at various temperatures,* 1 J. Biological Standardization 179 (1973). Thus, the compositions and methods described herein also provide for stabilization of vaccines regardless of the cold chain and/or other environmental conditions.

In some embodiments, the additive is a cell, e.g., a biological cell. Cells useful for incorporation into the composition can come from any source, e.g., mammalian, insect, plant, etc. In some embodiments, the cell can be a human, rat or mouse cell. In general, cells to be used with the compositions described herein can be any types of cells. In general, the cells should be viable when encapsulated within compositions. In some embodiments, cells that can be used with the composition include, but are not limited to, mammalian cells (e.g. human cells, primate cells, mammalian cells, rodent cells, etc.), avian cells, fish cells, insect cells, plant cells, fungal cells, bacterial cells, and hybrid cells. In some embodiments, exemplary cells that can be can be used with the compositions include platelets, activated platelets, stem cells, totipotent cells, pluripotent cells, and/or embryonic stem cells. In some embodiments, exemplary cells that can be encapsulated within compositions include, but are not limited to, primary cells and/or cell lines from any tissue. For example, cardiomyocytes, myocytes, hepatocytes, keratinocytes, melanocytes, neurons, astrocytes, embryonic stem cells, adult stem cells, hematopoietic stem cells, hematopoietic cells (e.g. monocytes, neutrophils, macrophages, etc.), ameloblasts, fibroblasts, chondrocytes, osteoblasts, osteoclasts, neurons, sperm cells, egg cells, liver cells, epithelial cells from lung, epithelial cells from gut, epithelial cells from intestine, liver, epithelial cells from skin, etc, and/or hybrids thereof, can be included in the silk/platelet compositions disclosed herein. Those skilled in the art will recognize that the cells listed herein represent an exemplary, not comprehensive, list of cells. Cells can be obtained from donors (allogenic) or from recipients (autologous). Cells can be obtained, as a non-limiting example, by biopsy or other surgical means known to those skilled in the art.

In some embodiments, the cell can be a genetically modified cell. A cell can be genetically modified to express and secrete a desired compound, e.g. a bioactive agent, a growth factor, differentiation factor, cytokines, and the like. Methods of genetically modifying cells for expressing and secreting compounds of interest are known in the art and easily adaptable by one of skill in the art.

Differentiated cells that have been reprogrammed into stem cells can also be used. For example, human skin cells reprogrammed into embryonic stem cells by the transduction of Oct3/4, Sox2, c-Myc and Klf4 (Junying Yu, et. al., *Science,* 2007, 318, 1917-1920 and Takahashi K. et. al., *Cell,* 2007, 131, 1-12).

In some embodiments, the additive can be silk fibroin particles. Silk fibroin particles and methods of making them are described herein above.

In some embodiments, the additive can be a silk-based material. The silk-based material can be selected from the group consisting of silk fibers, micro-sized silk fibers, unprocessed silk fibers, silk particles, and any combinations thereof. In some embodiments, the additive is a silk fiber. Use of silk fibers is described in for example, US patent application publication no. US20110046686, the content of which is incorporated herein by reference in its entirety.

In some embodiments, the silk fibers are microfibers or nanofibers. In some embodiments, the additive is micron-sized silk fiber (10-600 μm). Micron-sized silk fibers can be obtained by hydrolyzing the degummed silk fibroin or by increasing the boing time of the degumming process. Alkali hydrolysis of silk fibroin to obtain micron-sized silk fibers is described for example in Mandal et al., PNAS, 2012, doi: 10.1073/pnas.1119474109; U.S. Provisional Application No. 61/621,209, filed Apr. 6, 2012; and PCT application no. PCT/US13/35389, filed Apr. 5, 2013, content of all of which are incorporated herein by reference in their entireties. Because regenerated silk fibers made from HFIP silk solutions are mechanically strong, the regenerated silk fibers can also be used as additive.

In some embodiments, the silk fiber is an unprocessed silk fiber, e.g., raw silk or raw silk fiber. The term "raw silk" or "raw silk fiber" refers to silk fiber that has not been treated to remove sericin, and thus encompasses, for example, silk fibers taken directly from a cocoon Thus, by unprocessed silk fiber is meant silk fibroin, obtained directly from the silk gland. When silk fibroin, obtained directly from the silk gland, is allowed to dry, the structure is referred to as silk I in the solid state. Thus, an unprocessed silk fiber comprises silk fibroin mostly in the silk I conformation. A regenerated or processed silk fiber on the other hand comprises silk fibroin having a substantial silk II or beta-sheet crystallinity.

In some embodiments, the additive is a biocompatible polymer. Exemplary biocompatible polymers include, but are not limited to, a poly-lactic acid (PLA), poly-glycolic acid (PGA), poly-lactide-co-glycolide (PLGA), polyesters, poly(ortho ester), poly(phosphazine), poly(phosphate ester), polycaprolactone, gelatin, collagen, fibronectin, keratin, polyaspartic acid, alginate, chitosan, chitin, hyaluronic acid, pectin, polyhydroxyalkanoates, dextrans, and polyanhydrides, polyethylene oxide (PEO), poly(ethylene glycol) (PEG), triblock copolymers, polylysine, alginate, polyaspartic acid, any derivatives thereof and any combinations thereof. Other exemplary biocompatible polymers amenable to use according to the present disclosure include those described for example in U.S. Pat. Nos. 6,302,848; 6,395,734; 6,127,143; 5,263,992; 6,379,690; 5,015,476; 4,806,355; 6,372,244; 6,310,188; 5,093,489; 387,413; 6,325,810; 6,337,198; 6,267,776; 5,576,881; 6,245,537; 5,902,800; and 5,270,419, contents of all of which are incorporated herein by reference in their entireties. As used herein, the term "biocompatible" refers to a material that does not elicit a substantial immune response in the host.

In some embodiments, the biocompatible polymer is PEG or PEO. As used herein, the term "polyethylene glycol" or "PEG" means an ethylene glycol polymer that contains about 20 to about 2000000 linked monomers, typically about 50-1000 linked monomers, usually about 100-300. PEG is also known as polyethylene oxide (PEO) or polyoxyethylene (POE), depending on its molecular weight. Generally PEG, PEO, and POE are chemically synonymous, but historically PEG has tended to refer to oligomers and polymers with a molecular mass below 20,000 g/mol, PEO to polymers with a molecular mass above 20,000 g/mol, and POE to a polymer of any molecular mass. PEG and PEO are liquids or low-melting solids, depending on their molecular weights. PEGs are prepared by polymerization of ethylene oxide and are commercially available over a wide range of molecular weights from 300 g/mol to 10,000,000 g/mol. While PEG and PEO with different molecular weights find use in different applications, and have different physical properties (e.g. viscosity) due to chain length effects, their chemical properties are nearly identical. Different forms of PEG are also available, depending on the initiator used for the polymerization process—the most common initiator is a monofunctional methyl ether PEG, or methoxypoly(ethylene glycol), abbreviated mPEG. Lower-molecular-weight PEGs are also available as purer oligomers, referred to as monodisperse, uniform, or discrete PEGs are also available with different geometries.

As used herein, the term PEG is intended to be inclusive and not exclusive. The term PEG includes poly(ethylene glycol) in any of its forms, including alkoxy PEG, difunctional PEG, multiarmed PEG, forked PEG, branched PEG, pendent PEG (i.e., PEG or related polymers having one or more functional groups pendent to the polymer backbone), or PEG With degradable linkages therein. Further, the PEG backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, pentaerythritol and sorbitol. The central branch moiety can also be derived from several amino acids, such as lysine. The branched poly(ethylene glycol) can be represented in general form as R(-PEG-OH)m in which R represents the core moiety, such as glycerol or pentaerythritol, and m represents the number of arms. Multiarmed PEG molecules, such as those described in U.S. Pat. No. 5,932,462, which is incorporated by reference herein in its entirety, can also be used as biocompatible polymers.

Some exemplary PEGs include, but are not limited to, PEG20, PEG30, PEG40, PEG60, PEG80, PEG100, PEG115, PEG200, PEG 300, PEG400, PEG500, PEG600, PEG1000, PEG1500, PEG2000, PEG3350, PEG4000, PEG4600, PEG5000, PEG6000, PEG8000, PEG11000, PEG12000, PEG15000, PEG 20000, PEG250000, PEG500000, PEG100000, PEG2000000 and the like. In some embodiments, PEG is of MW 10,000 Dalton. In some embodiments, PEG is of MW 100,000, i.e. PEO of MW 100,000.

In some embodiments, the additive is an enzyme that hydrolyzes silk fibroin. Without wishing to be bound by a theory, such enzymes can be used to control the degradation of the article of manufacture.

In some embodiment, the additive is a plasticizer. Without wishing to be bound by a theory, inclusion of a plasticizer can affect the flexibility and/or solubility of the silk-based article, e.g., a silk fibroin film. In one embodiment, the plasticizer is glycerol. Silk-based materials, e.g., silk films comprising glycerol are described in WO 2010/042798, content of which is incorporated herein by reference in its entirety.

Examples of other additives include, but are not limited to: cell attachment mediators, such as collagen, elastin, fibronectin, vitronectin, laminin, proteoglycans, or peptides containing known integrin binding domains e.g. "RGD" integrin binding sequence, or variations thereof, that are known to affect cellular attachment (Schaffner P & Dard, Cell Mol Life Sci., 2003, 60(1):119-32 and Hersel U. et al., Biomaterials, 2003, 24(24):4385-415); biologically active ligands; and substances that enhance or exclude particular varieties of cellular or tissue ingrowth.

In some embodiments, release of active agents from the silk fibroin composition can be controlled by adding additives to the composition that can disrupt interactions between silk fibroin and the active agent. Accordingly, in some embodiments, the additive is an agent that disrupts, inhibits, or reduces protein-active agent interactions. For example, silk fibroin has a net negative charge. Thus, active agents having a net positive charge can interact with silk fibroin through ionic/electrostatic interactions and be retained in the composition. Altering the ionic/electrostatic interactions can change the release rate of the factor from the composition. One way of altering ionic/electrostatic interactions can be by adding a cationic molecule to the composition. Some other agents can interact with silk fibroin through hydrophobic interactions. Without wishing to be bound by a theory, such factors can be released using additives that disrupt, inhibit, or reduce non-ionic interactions. Thus, in some embodiments, the additive can be a surfactant. As used herein, the term "surfactant" refers to a natural or synthetic amphiphilic compound. A surfactant can be non-ionic, zwitterionic, or ionic. Non-limiting examples of surfactants include polysorbates like polysorbate 20 (TWEEN® 20), polysorbate 40 (TWEEN® 40), polysorbate 60 (TWEEN® 60), polysorbate 61 (TWEEN® 61), polysorbate 65 (TWEEN® 65), polysorbate 80 (TWEEN® 80), and polysorbate 81 (TWEEN® 81); poloxamers (polyethylene-polypropylene copolymers), like Poloxamer 124 (PLURONIC® L44), Poloxamer 181 (PLURONIC® L61), Poloxamer 182 (PLURONIC® L62), Poloxamer 184 (PLURONIC® L64), Poloxamer 188 (PLURONIC® F68), Poloxamer 237 (PLURONIC® F87), Poloxamer 338 (PLURONIC® L108), Poloxamer 407 (PLURONIC® F127), polyoxyethyleneglycol dodecyl ethers, like BRIJ® 30, and BRIJ® 35; 2-dodecoxyethanol (LUBROL®-PX); polyoxyethylene octyl phenyl ether (TRITON® X-100); sodium dodecyl sulfate (SDS); 3-[(3-Cholamidopropyl)dimethylammonio]-1-propanesulfonate (CHAPS); 3-[(3-Cholamidopropyl)dimethylammonio]-2-hydroxy-1-propanesulfonate (CHAPSO); sucrose monolaurate; and sodium cholate. Other non-limiting examples of surfactant excipients can be found in, e.g., Pharmaceutical Dosage Forms and Drug Delivery Systems (Howard C. Ansel et al., eds., Lippincott Williams & Wilkins Publishers, 7$^{th}$ ed. 1999); Remington: The Science and Practice of Pharmacy (Alfonso R. Gennaro ed., Lippincott, Williams & Wilkins, 20$^{th}$ ed. 2000); Goodman & Gilman's The Pharmacological Basis of Therapeutics (Joel G. Hardman et al., eds., McGraw-Hill Professional, 10$^{th}$ ed. 2001); and Handbook of Pharmaceutical Excipients (Raymond C. Rowe et al., APhA Publications, 4$^{th}$ edition 2003), each of which is hereby incorporated by reference in its entirety. In some embodiments, the surfactant is a cationic polymer. In one embodiment, the cationic polymer is polylysine, e.g., ε-poly-L-lysine. In alternative embodiments, the surfactant is an anionic polymer. In one embodiment, the anionic polymer is polyglutamate, e.g., poly-L-glutamate.

For administration to a subject, a provided silk fibroin composition can be formulated in pharmaceutically acceptable compositions which comprise the silk fibroin composition disclosed herein, formulated together with one or more pharmaceutically acceptable carriers (additives) and/or diluents. For administering to a subject, the pharmaceutical composition can be generally formulated in a unit dosage form. Further, the pharmaceutical composition can be specially formulated for administration in solid or liquid form, such as, tablets, capsules, powders, solutions, suspensions, or emulsions including those adapted for the following: (1) topical application, for example, as a cream, ointment, a controlled-release patch, or spray applied to the skin; (2) parenteral administration, for example, by subcutaneous, intramuscular, intravenous, or epidural injection as, for example, a sterile solution or suspension, or sustained-release formulation; (3) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (4) intravaginally or intrarectally, for example, as a pessary, cream or foam; (5) sublingually; (6) ocularly; (7) transdermally; (8) transmucosally; or (9) nasally. Additionally, compositions can be implanted into a patient or injected using a drug delivery composition. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

Pharmaceutically-acceptable antioxidants include, but are not limited to, (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lectithin, propyl gallate, alpha-tocopherol, and the like; and (3) metal chelating agents, such as citric acid, ethylenediamine tetraacetic acid (EDTA), sorbitol, tartaric acid, phosphoric acids, and the like.

As used herein, the term "administered" refers to the placement of a drug delivery composition into a subject by a method or route which results in at least partial localization of the pharmaceutically active agent at a desired site.

The composition can be administered by any appropriate route which results in effective treatment in the subject, i.e. administration results in delivery to a desired location in the subject where at least a portion of the pharmaceutically active agent is delivered. Exemplary modes of administration include, but are not limited to, topical, implant, injection, infusion, instillation, implantation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebrospinal, and intrasternal injection and infusion.

Injectables require that the composition meets certain physical criteria suitable for administration by injection. For example, such formulations require a sufficient level of so-called syringeability. The term syringeability refers to time and force required for a manual injection (or time required for an injection using an autoinjector), which is an important parameter because it may impact the usability of the product by the end-user and thus compliance. The force required for the injection of a solution at a given injection rate via a needle of predetermined gauge and length is referred to as syringeability (Burckbuchler, V et al., Eur. J. Pharm. Biopharm. 2010, 76 (3): 351-356). The Hagen-Poiseuille equation can be utilized to estimate the travel (or glide) force, which can be expressed as $$F=8Q\mu L/\pi R4 \times A \qquad \text{(Equation 1)}$$

wherein Q=Volumetric flow rate; μ=Fluid viscosity; L=Needle length; R=Needle inner diameter; A=Cross sectional area of syringe plunger; F=Frictionless travel force The viscosity of a solution is dependent on the protein itself, the protein concentration, the temperature and the formulation, e.g. pH, type of excipients and excipient concentrations. Besides the protein itself, protein concentration is another important factor for viscosity. Subcutaneous injections are generally limited to an injection volume of approx. <1.5 mL (see for example, Adler (2012) Am. Pharmaceutical Rev. pp. 1-9).

In some embodiments, a silk fibroin composition disclosed herein can be implanted in a subject. As used herein, the term "implanted," and grammatically related terms, refers to the positioning of the composition in a particular locus in the subject, either temporarily, semi-permanently, or permanently. The term does not require a permanent fixation of the composition in a particular position or location. Exemplary in vivo loci include, but are not limited to site of a wound, trauma or disease.

For administering to a subject, a silk fibroin composition can be generally formulated in a unit dosage injectable form. The compositions and preparations suitable for injection include sterile aqueous solutions or dispersions. The carrier can be a solvent or dispersing medium containing, for example, water, cell culture medium, buffers (e.g., phosphate buffered saline), polyol (for example, glycerol, propylene glycol, liquid polyethylene glycol, and the like), suitable mixtures thereof. In some embodiments, the pharmaceutical carrier can be a buffered solution (e.g. PBS).

In some embodiments, pharmaceutical composition can be administered with a delivery device, e.g., a syringe. Accordingly, an additional aspect described herein provides for delivery devices comprising at least one chamber with an outlet, wherein the at least one chamber comprises a predetermined amount of any composition described herein and the outlet provides an exit for the composition enclosed inside the chamber. In some embodiments, a delivery device described herein can further comprise an actuator to control release of the composition through the outlet. Such delivery device can be any device to facilitate the administration of any composition described herein to a subject, e.g., a syringe, a dry powder injector, a nasal spray, a nebulizer, or an implant such as a microchip, e.g., for sustained-release or controlled release of any composition described herein.

Kits

Sample collection devices and kits, which can be employed in the compositions and methods described herein, are also provided. Accordingly, another aspect provided herein is a sample collection device comprising a chamber for collecting a sample, e.g., a biological sample or an active agent, wherein the chamber comprises a silk fibroin composition. Upon contacting the biological sample or the active agent with a silk fibroin solution, at least one property of at least one component of the biological sample or bioactivity of the active agent can be stabilized for a period of time. In some embodiments, a silk fibroin composition present in the chamber can be present in a form of a solution, powder, a suspension, or a gel.

Any sample, e.g., biological sample, collection device known in the art can be applied herein. Non-limiting examples of the device can include a biological specimen collection tube (e.g., a blood collection tube), a vial, a syringe, a centrifuge tube, a microtiter plate, a dipstick, a biological specimen collection bag, a sponge, and any combinations thereof. In one embodiment, the device can be a blood collection tube or bag.

In some embodiments, the chamber of the device can further comprise an additive as described herein. In some embodiments, the chamber of the device can further comprise an anti-coagulation agent, a stabilizer, a gelation-inducing agent, a protease or digestive enzyme, or any combinations thereof. Stabilizers that can be used to further enhance stabilization of a target component of a biological sample can include, but are not limited to, a saccharide, a sugar alcohol, an ion, a surfactant, an amino acid, human serum albumin, bovine serum albumin, gelatin, and gelatin derivatives, an antioxidant, any stabilizers described herein, or any combinations thereof. In some embodiments, the stabilizer can be a nuclease inhibitor or proteinase inhibitor. In some embodiments, where RNA is to be detected from the biological sample, the stabilizer can include RNase inhibitor and/or DEPC.

A gelation-inducing agent can be any agent that can induce gelation of silk fibroin to form a silk-based material, e.g., functionally-activated PEGs disclosed in the International Application No. WO/2012/031144, the content of which are incorporated herein by reference. For example, in one embodiment, the chamber can further comprise a first functionally activated PEG component as disclosed in the International Application No. WO/2012/031144. In this embodiment, the biological sample collection device can further comprise an additional chamber comprising a second functionally activated PEG component capable of reacting with the first functionally activated PEG component to form a solid-state silk-based material.

In some embodiments where the device is a blood collection tube, the chamber can further comprise at least one additive commonly found in a conventional blood collection tube, including, e.g., but not limited to, clot activator, sodium heparin, lithium heparin, thrombin-based clot activator, $K_2$EDTA, liquid $K_3$EDTA, $Na_2$EDTA, potassium oxalate, sodium fluoride, sodium polyanethol sulfonate (SPS), acid citrate dextrose additives (ACD) (comprising trisodium citrate and citric acid), sodium citrate, a mixture comprising citrate, theophylline, adenosine, dipyridamole (CTAD), or any combinations thereof.

Kits comprising one or more embodiments of the biological sample collection device described herein are also provided. In some embodiments, the kit can further comprise at least one container containing a gelation-inducing agent, e.g., comprising a functionally activated PEG component disclosed in the International Application No. WO/2012/031144, a pH-reducing agent (e.g., an acid), or a combination thereof.

In some embodiments, the kit can further comprise a container containing a silk-solubilizing agent. Examples of a silk-solubilizing agent can include water, a buffered solution, or a combination thereof. In some embodiments where a target component to be detected is not a protein or peptide, the silk-solubilizing agent can include a proteinase to degrade silk fibroin.

In some embodiments, the kit can further comprise a container containing a stabilizer, wherein the stabilizer stabilizes at least one component of the biological sample. For example, the stabilizer can include, but are not limited to, a saccharide, a sugar alcohol, an ion, a surfactant, an amino acid, human serum albumin, bovine serum albumin, gelatin, and gelatin derivatives, an antioxidant, any stabilizer described herein or any combinations thereof. In one embodiment, the stabilizer can be a nuclease inhibitor or proteinase inhibitor. In one embodiment where RNA is to be detected from the biological sample, the stabilizer can include a RNase inhibitor.

In some embodiments, the kit can further comprise a container containing an agent for detecting said at least one component of the biological sample. Depending on the purpose of the kit, e.g., for genotyping or expression analyses, one of skill in the art can determine appropriate agents for performing the analysis. By way of example only, the agent can comprise component-purifying agents (e.g., an agent to purify a target component such as RNA from a non-target component such as genomic DNA; or to extract proteins from the biological sample); nucleic acid amplification agents (e.g., but not limited to, primers, polymerase, oligonucleotides); immuno-affinity-based detection agents (e.g., but not limited to, primary and/or secondary antibodies, and aptamers), labeling agents (e.g., fluorescent dyes, agents for colorimetric enzyme-substrate reactions such as horseradish peroxidase (HRP) and respective chromogenic substrates (e.g., TMB, DAB, ABTS), or any combinations thereof.

In some embodiments of the compositions described herein, the silk fibroin can be modified to control its degradation and thus the release of active agents, e.g. such that release occurs over a period of time ranging from hours to days, or months. In some embodiments, the compositions described herein can be combined with other types of delivery systems available and known to those of ordinary skill in the art. They include, for example, polymer-based systems such as polylactic and/or polyglycolic acids, polyanhydrides, polycaprolactones, copolyoxalates, polyesteramides, polyorthoesters, polyhydroxybutyric acid, and/or combinations thereof. Microcapsules of the foregoing polymers containing drugs are described in, for example, U.S. Pat. No. 5,075,109. Other examples include nonpolymer systems that are lipid-based including sterols such as cholesterol, cholesterol esters, and fatty acids or neukal fats such as mono-, di- and triglycerides; hydrogel release systems; liposome-based systems; phospholipid based-systems; silastic systems; peptide based systems; or partially fused implants. Specific examples include, but are not limited to, erosional systems in which the composition is contained in a form within a matrix (for example, as described in U.S. Pat. Nos. 4,452,775, 4,675,189, 5,736,152, 4,667,014, 4,748,034 and—29 5,239,660), or diffusional systems in which an active component controls the release rate (for example, as described in U.S. Pat. Nos. 3,832,253, 3,854,480, 5,133,974 and 5,407,686). The formulation may be as, for example, microspheres, hydrogels, polymeric reservoirs, cholesterol matrices, or polymeric systems. In some embodiments, the system may allow sustained or controlled release of the composition to occur, for example, through control of the diffusion or erosion/degradation rate of the formulation containing the composition. In addition, a pump-based hardware delivery system can be used to deliver one or more embodiments of the compositions or preparations described herein. Use of a long-term sustained release formulations or implants can be particularly suitable for treatment of chronic conditions, such as diabetes. Long-term release, as used herein, means that a formulation or an implant is made and arranged to deliver compositions or preparations described herein at a therapeutic level for at least 30 days, or at least 60 days. In some embodiments, the long-term release refers to a formulation or an implant being configured to deliver an active agent at a therapeutic level over several months.

Certain Exemplary Applications

In accordance with embodiments of various aspects described herein, forming a silk-based material comprising silk fibroin and a biological sample can stabilize at least one component of the biological sample, which allows detection and/or analysis of the component at a later time. In some embodiments, these silk-based materials comprising a biological sample can be stored and/or transported without the need for refrigeration or freezing, which are typical methods to currently store and handle biological samples to maintain/retain sample quality for diagnostic evaluation of human health. Accordingly, in some embodiments, the silk-based materials and methods described herein can be useful in diagnostic applications. For example, the silk-based materials and methods can be used to maintain and/or retain the quality of a biological sample during storage and/or transportation, or in some developing countries or in remote field conditions where minimum infrastructure to support continuous cold storage does not exist, such that at least one component of the biological sample can be assayed for diagnostic applications. In some embodiments, the silk-based material and methods described herein can be used to maintain and/or retain the quality of biological sample under at least one or any combinations of the following conditions described earlier, namely: (a) a temperature above 0° C. (e.g., at least about room temperature or higher) during storage and/or transportation; (b) light exposure (e.g., UV, infra-red, and/or visible lights) during storage and/or transportation; and (c) a relative humidity of at least about 10% or higher during storage and/or transportation.

Accordingly, yet another aspect provided herein relates to methods for using the silk-based material described herein. The method comprises (a) providing one or more embodiments of the silk-based material comprising silk fibroin and a biological sample; and (b) subjecting at least one component of the biological sample to at least one analysis.

In some embodiments, the silk-based material can be formed by contacting a biological sample with silk fibroin. Methods of forming the silk-based material is described hereon. In some embodiments, the silk-based material can be in liquid state. In other embodiments, the silk-based material can be a dissolvable solid-state material (e.g., but not limited to, a dissolvable silk-based film, or foam). In some embodiments, a subject or patient in need of a diagnosis of a disease or disorder can provide a biological sample and contact the biological sample with silk fibroin to form the silk-based material, which is then sent to a diagnostic testing laboratory for analyses. In some embodiments, a biological sample can be collected from a subject by a skilled practitioner at a clinical setting, where the biological sample is then in contact with silk fibroin to form the silk-based material and sent to a diagnostic testing laboratory for analyses.

While in some embodiments, at least one component of the biological sample can be detected and/or analyzed without isolating the component from the biological sample, in alternative embodiments, the component can be extracted or recovered from at least a portion of the silk-based material before detection and/or analysis using any methods known in the art. In accordance with some embodiments of the silk-based materials described herein, the silk-based material can be soluble in an aqueous solution (e.g., water, a buffered solution, or a combination thereof). Unlike cellulose-based technologies, e.g., dried blood spots, where blood is absorbed on a filter paper and is difficult to be recovered thereafter, at least a portion of the dissolvable silk-based material described herein can be solubilized in an aqueous solution (e.g., water, a buffered solution, or a combination thereof). The final silk/biological sample solution can then be amenable to routine liquid assays, e.g., ELISA and Luminex™ assay as described in the Examples, without additional purification. Accordingly, in some embodiments, the method can further comprise contacting at least a portion of the silk-based material with an aqueous solution (e.g., water, a buffered solution, or a combination thereof) prior to subjecting said at least one component of the biological sample to at least one analysis.

Various types of analyses can be performed on the active agent/target component of a biological sample, e.g., depending on the nature of the agent/component. Non-limiting examples of analyses can include, but are not limited to, genotyping, nucleic acid sequencing, expression analysis (e.g., protein level, or transcript level), binding affinity, enzymatic activity, transfection efficiency, cell counting, cell identification, cell viability, immunogenicity, infectivity, metabolite profiling, and any combinations thereof. In some embodiments, at least one component of the biological sample can be subjected to at least one genotyping or nucleic acid sequencing analysis, expression analysis (e.g., protein level and/or transcript level), metabolite profiling, or any combinations thereof. Various methods to perform these analyses can include, but are not limited to, polymerase chain reaction (PCR), real-time quantitative PCR, microarray, western blot, immunohistochemical analysis, enzyme linked absorbance assay (ELISA), mass spectrometry, nucleic acid sequencing, flow cytometry, gas chromatography, high performance liquid chromatography, nuclear magnetic resonance (NMR) spectroscopy, or any combinations thereof. Techniques for nucleic acid sequencing are known in the art and can be used to assay the component to determine nucleic acid or gene expression measurements, for example, but not limited to, DNA sequencing, RNA sequencing, de novo sequencing, next-generation sequencing such as massively parallel signature sequencing (MPSS), polony sequencing, pyrosequencing, Illumina (Solexa) sequencing, SOLiD sequencing, ion semiconductor sequencing, DNA nanoball sequencing, Heliscope single molecule sequencing, single molecule real time (SMRT) sequencing), nanopore DNA sequencing, sequencing by hybridization, sequencing with mass spectrometry, microfluidic Sanger sequencing, microscopy-based sequencing techniques, RNA polymerase (RNAP) sequencing, or any combinations thereof.

In some embodiments, the at least one analysis can be performed in a format that can interface with a readout instrument or system. In some embodiments, the at least one analysis can be performed on a system.

In some embodiments, prior to the analysis or contacting the silk-based material with an aqueous solution, the silk-based material can be reduced or aliquoted into smaller portions, e.g., some of which can be saved for later analyses, and/or can be analyzed for different target components (e.g., proteins, nucleic acid, and/or metabolites). The silk-based material can be aliquoted into smaller portions by weight or by volume.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

Example 1

Exemplary Materials and Methods Used for Generating a Composition Comprising Silk Fibroin and its Characterizations Silk Fibroin Solution. Silkworm *Bombyx mori* cocoons were degummed through a modified extraction process as described in Sofia S et al. (2001) Journal of Biomedical Materials Research, 54, 139-148. Provided herein is an exemplary protocol to produce a composition of low molecular weight silk fibroin.

- Cut cocoons and remove the pupae, pupae skins and any other dirt from the inside of the cocoon;
- Degum the cocoon pieces in a ~0.02M boiling sodium carbonate ($Na_2CO_3$) solution using a degumming time of about 60 minutes or more;
- Rinse the degummed silk fibroin in water (e.g., Milli-Q water) at least thrice, for at least half an hour each time.
- Air dry the rinsed silk fibroin.
- Dissolve the silk fibroin in a 9.3 M lithium bromide solution (Sigma Aldrich, Mo., USA, ReagentPlus >99%) at 60° C. and dialyze against water (e.g., Milli-Q water), e.g., with Slide-a-Lyzer dialysis cassettes (Thermo Scientific, IL, USA, MWCO 3,500) for about 2 days, regularly changing the water, e.g., every 6 hours.
- Centrifuge the resulting aqueous silk solution twice, at approximately 11,000 rpm, for 20 minutes each time.
- The resulting aqueous low molecular weight silk fibroin solution has a concentration between 7% wt/vol and 9% wt/vol silk fibroin. Up to this point, the silk fibroin solution is called an as-purified solution. The as-purified silk fibroin solution can be further subjected to an autoclaving step, and the silk fibroin solution is then called an autoclaved solution.
- Store the silk fibroin solution at 4° C.

Solid-State Silk Fibroin Preparation. The as-purified or autoclaved silk fibroin solutions are subjected to the freezing step, and primary drying or a combination of primary and secondary drying steps as outlined in FIG. 1. For the freezing step, the silk fibroin solution is frozen from room temperature to −40° C. at a rate of 0.8° C./min at atmospheric pressure, and held at −40° C. for 480 minutes. For primary drying, the silk fibroin solution is dried from −40° C. to −20° C. at a ramp rate of 0.2° C./min at 100 mtorr, and held at −20° C. for 2400 minutes. For secondary drying, the silk fibroin solution is dried from −20° C. to 4° C. at a ramp rate of 0.2° C./min at 100 mtorr, and held at 4° C. for 620 minutes. Silk fibroin foams formed at the end of the freezing step and primary drying step are called Primary Dry Only Foams (P). Silk fibroin foams formed at the end of the freezing step and primary drying and secondary drying steps are called Primary+Secondary Dry Foams (P+S). The silk foams are stored at 4° C., 22° C., or 37° C. Silk fibroin solutions can then be produced by dissolving the silk foams, following the flow diagram in FIG. 1.

Figure 2A:
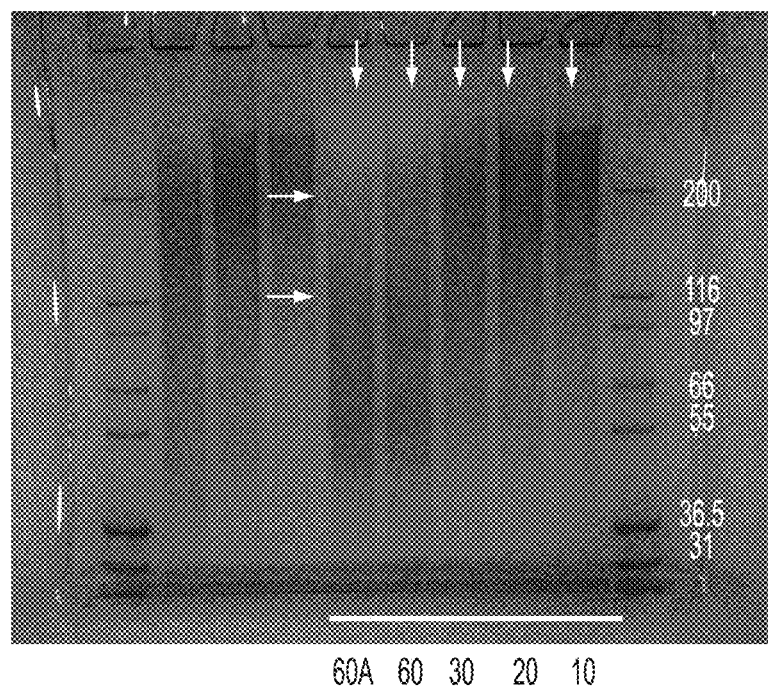
FIGS. 2A and 2B show the method used to calculate the percentages of four molecular weight bands (above 200 kDa, 200 to 116.3 kDa, 116.3 to 66.3 kDa, and 66.3 to 36.5 kDa). For this gel, 7.5 µg of protein in solution was run under reducing conditions on a NuPAGE® Novex® 3-8% Tris-Acetate Gel (Invitrogen), using a Mark12™ Unstained Standard (range 31-200 kDa, Invitrogen).
Figure 2B:
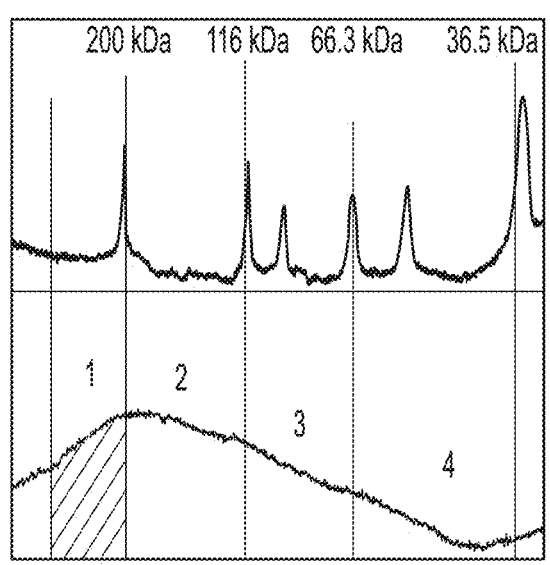

Characterizations. Gel electrophoresis is used to determine the molecular weight distribution of silk fibroin solutions produced from silk foams under different temperature storage conditions and boiling time. FIGS. 2A-2B show the method used to quantify the molecular weight distribution. The electrophoretic mobility of the fibroin molecules was determined using sodium dodecyl sulfate polyacrylamide gel electrophoresis (SDS-PAGE)(FIG. 2A). For each condition of interest, 0.15% (1.5 mg/mL) silk fibroin solution is loaded into a 3-8% Tris Acetate gel (NuPAGE, Life Technologies, Grand Island, N.Y.). The gel was run with a high molecular weight ladder as a reference (Mark12 Protein Standard, Life Technologies) and stained with a Colloidal Blue staining kit (Life Technologies). The molecular weight distribution of the silk solutions was determined by imaging the gels, performing pixel density analysis and normalizing across all the lanes for a peak intensity value of one (ImageJ, NIH, Bethesda, Md.). A rectangular bracket was applied to each lane, including the molecular weight ladder, which was used as a reference frame. The bracket was placed just above the start of the smear and extended beyond the bounds of the protein smear at the bottom, at the point of the 21.5 kDa marker.

The ImageJ software automatically averages the pixel intensity horizontally across the rectangle, and then plots this average down the length of the smear (top of smear=left, bottom of smear=right). The ladder positions are used to create brackets as follows:

1) Above 200 kDa (from the top of the smear to 200 kDa ladder position)
2) 200 kDa–116 kDa
3) 116 kDa–66.3 kDa
4) 66.3 kDa–36.5 kDa (the lowest resolvable molecular weight location)

The area under the curve (above a minimum background threshold) within each bracket is normalized to the total area between the top and bottom of the smear bounds in order to define the percentage molecular weight distribution in the respective molecular weight brackets. The bracketed ranges are then plotted across samples generated from different boil times in order to semi-quantitate changes in molecular weight. For example, in FIG. 2B, the percentage of silk fibroin having molecular weight above 200 kDa can be calculated using the following formula:

$$\%MolecularWeightAbove\ 200\,kDa = \frac{Area1}{Area(1+2+3+4)} \times 100$$

Figure 3A:
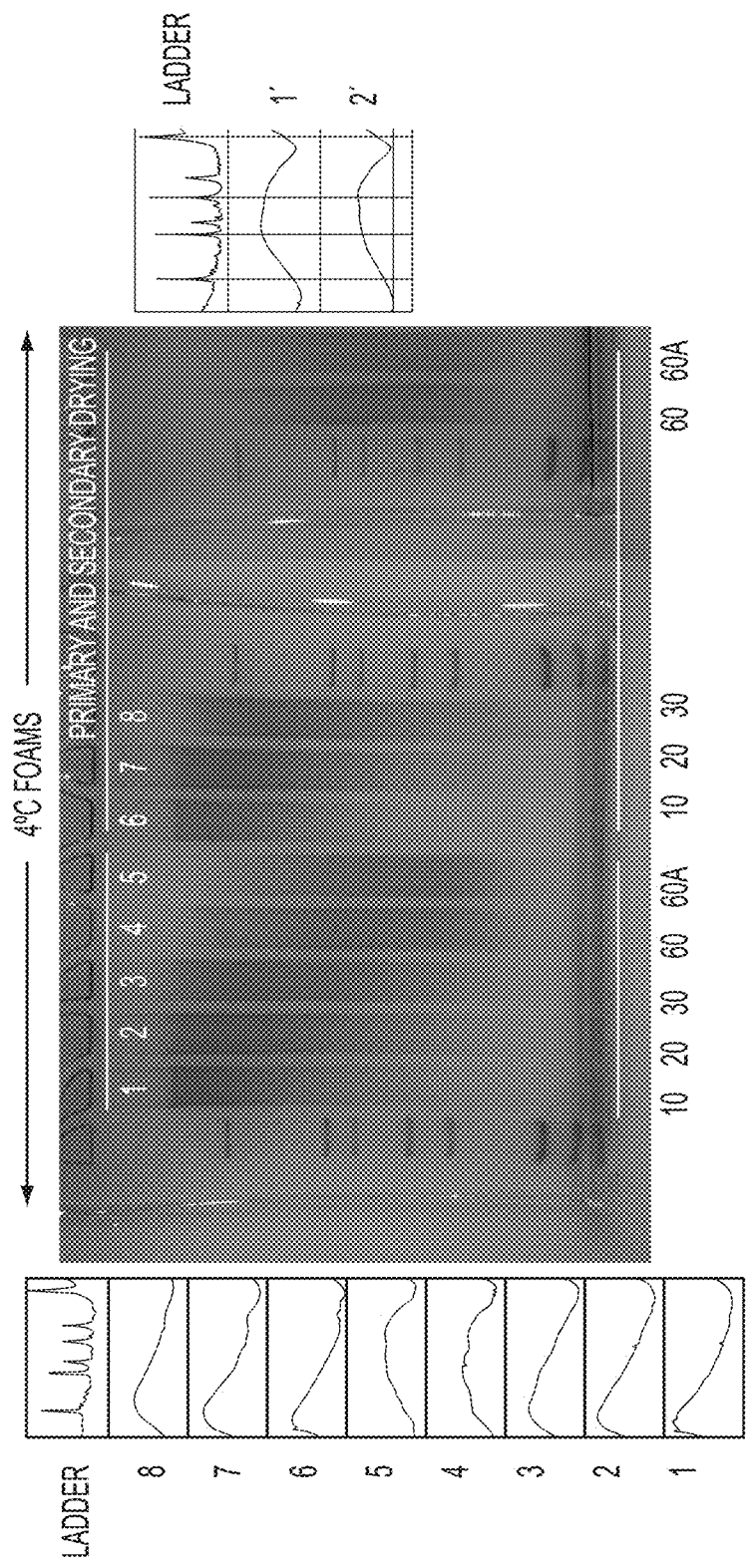
FIG. 3A is an image of SDS-PAGE gel for silk fibroin solutions produced from silk foams stored at 4° C.
Figure 3B:
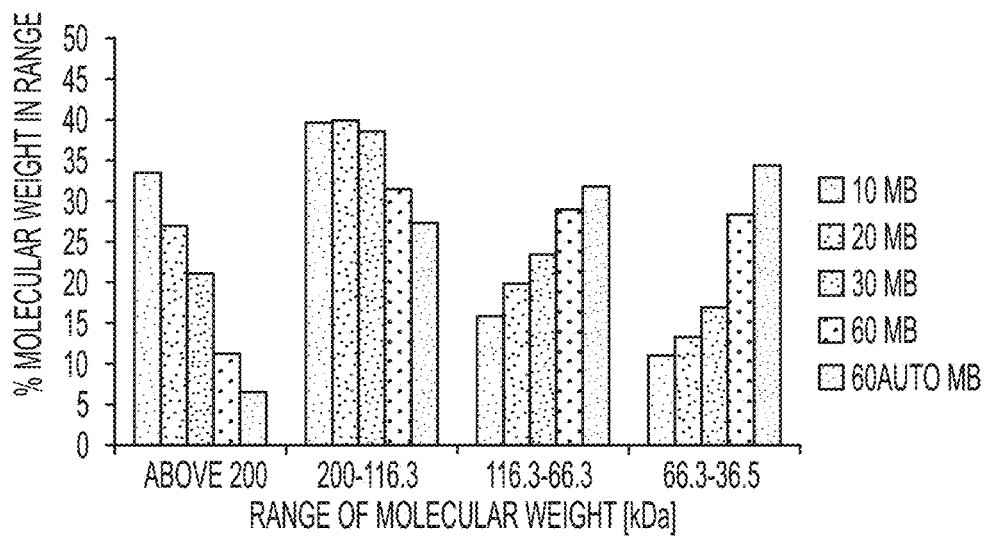
FIG. 3B shows the molecular weight distribution of silk fibroin that undergoes primary drying from the gel data in FIG. 3A.
Figure 3C:
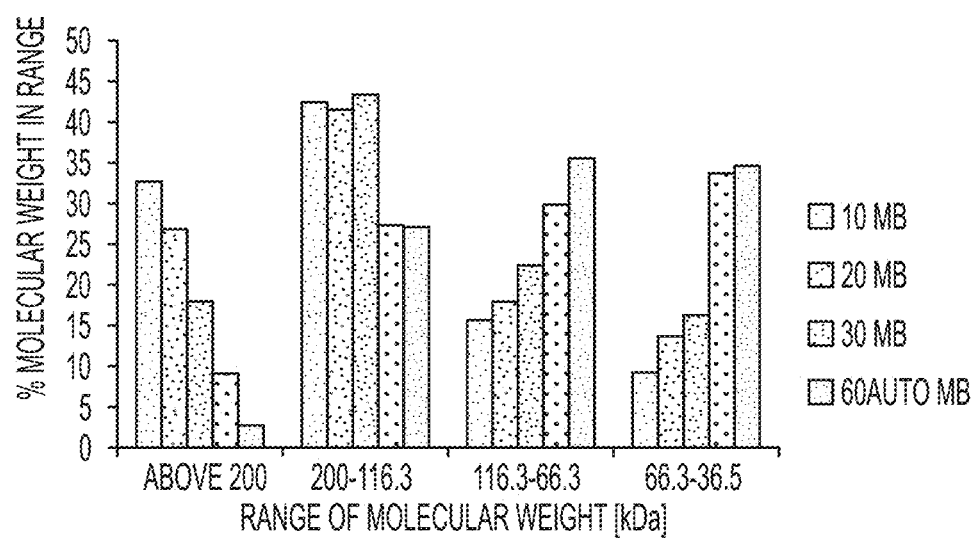
FIG. 3C shows the molecular weight distribution of silk fibroin that undergoes primary and secondary drying from the gel data in FIG. 3A.
Figure 4A:
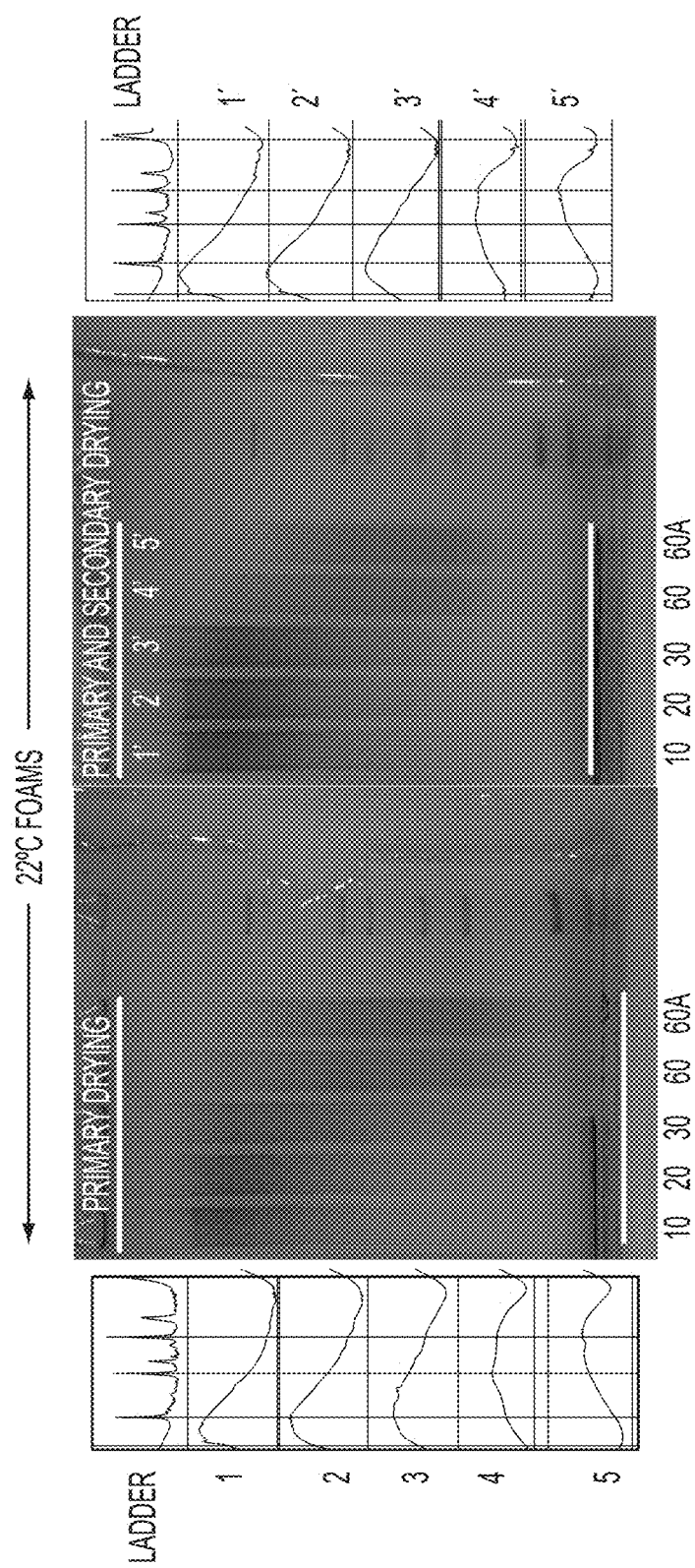
FIG. 4A is an image of SDS-PAGE gel for silk fibroin solutions produced from silk foams stored at 22° C.
Figure 4B:
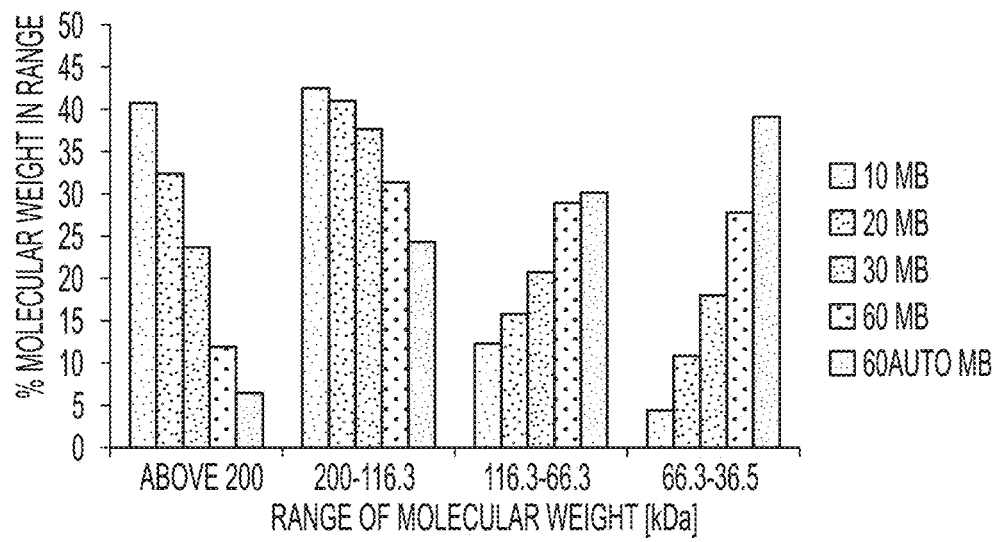
FIG. 4B shows the molecular weight distribution of silk fibroin that undergoes primary drying from the gel data in FIG. 4A.
Figure 4C:
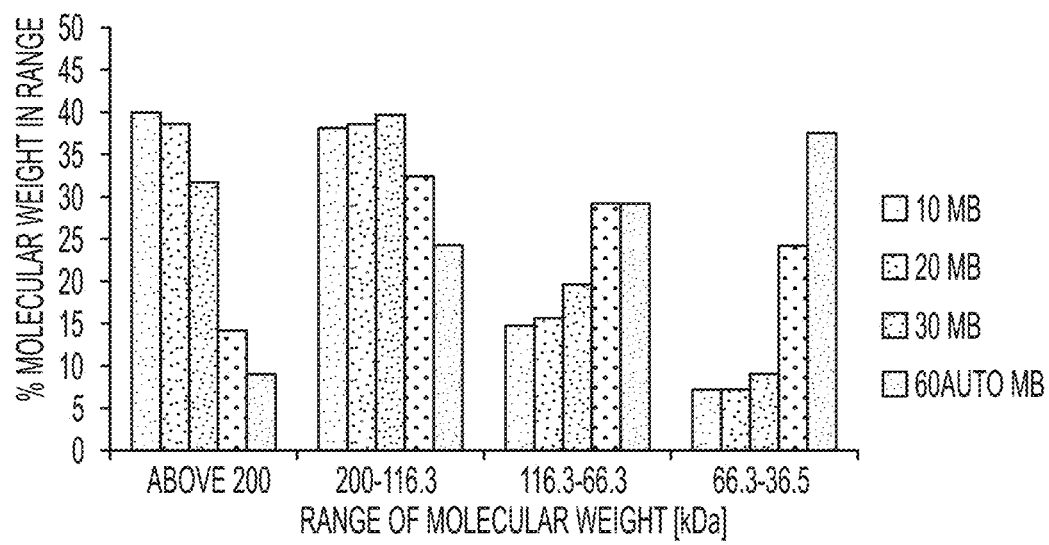
FIG. 4C shows the molecular weight distribution of silk fibroin that undergoes primary and secondary drying from the gel data in FIG. 4A.
Figure 5A:
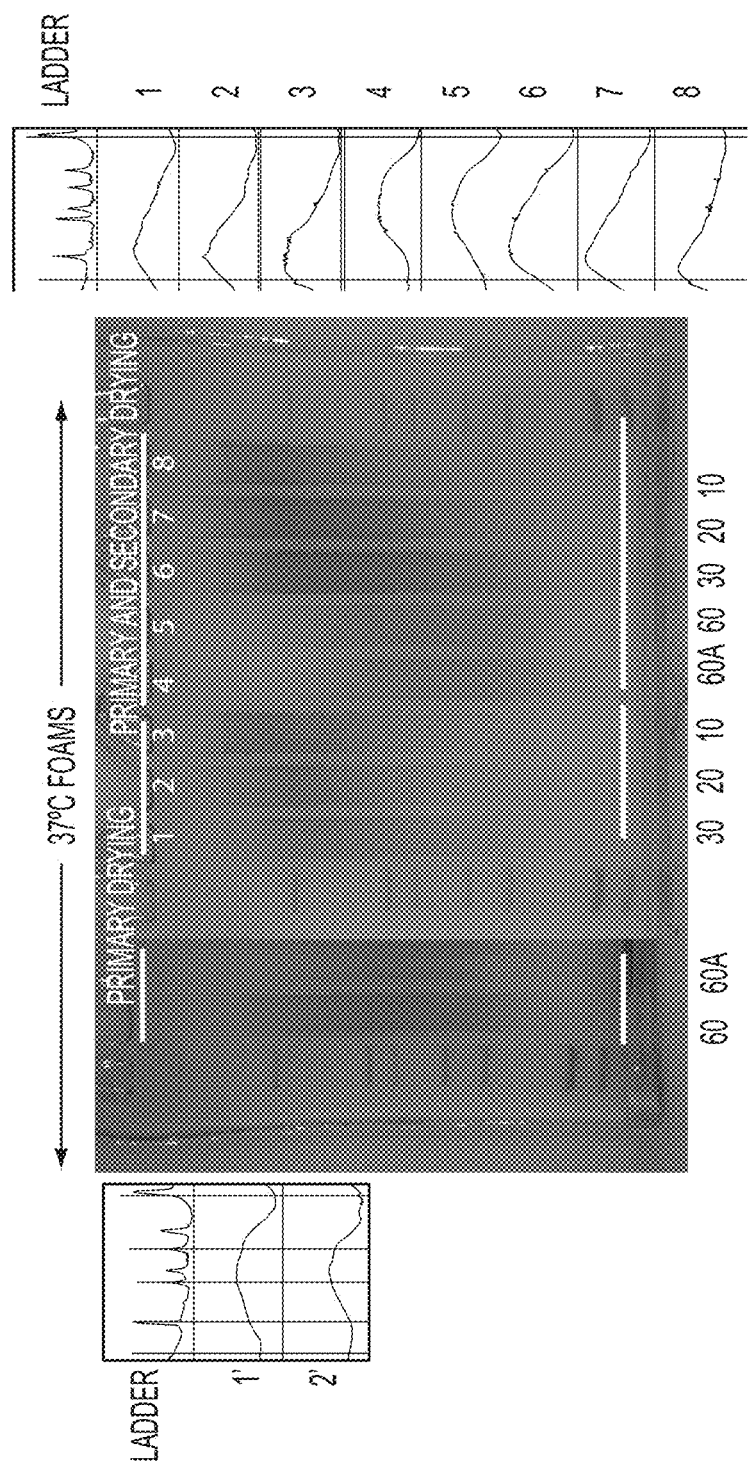
FIG. 5A is an image of SDS-PAGE gel for silk fibroin solutions produced from silk foams stored at 37° C.
Figure 5B:
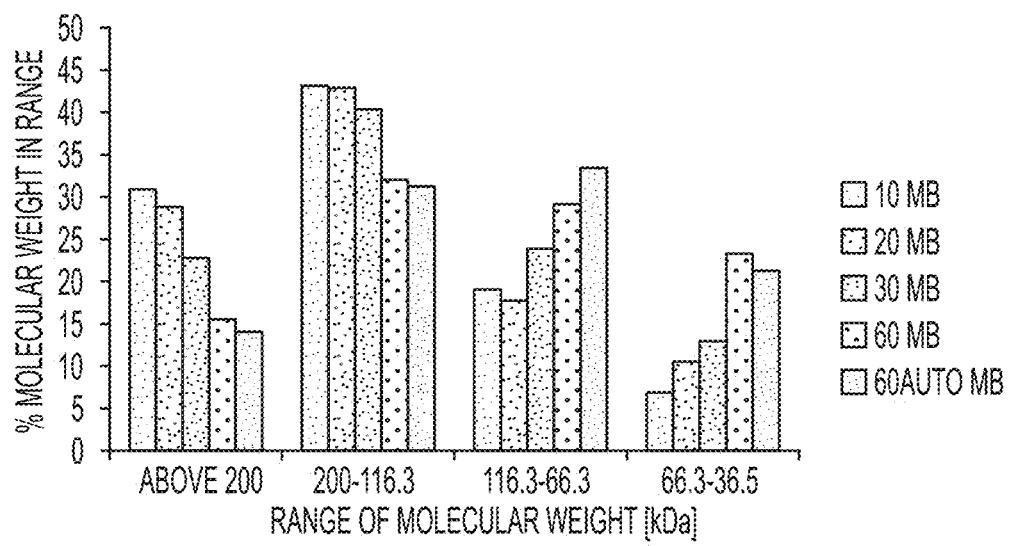
FIG. 5B shows the molecular weight distribution of silk fibroin that undergoes primary drying from the gel data in FIG. 5A.
Figure 5C:
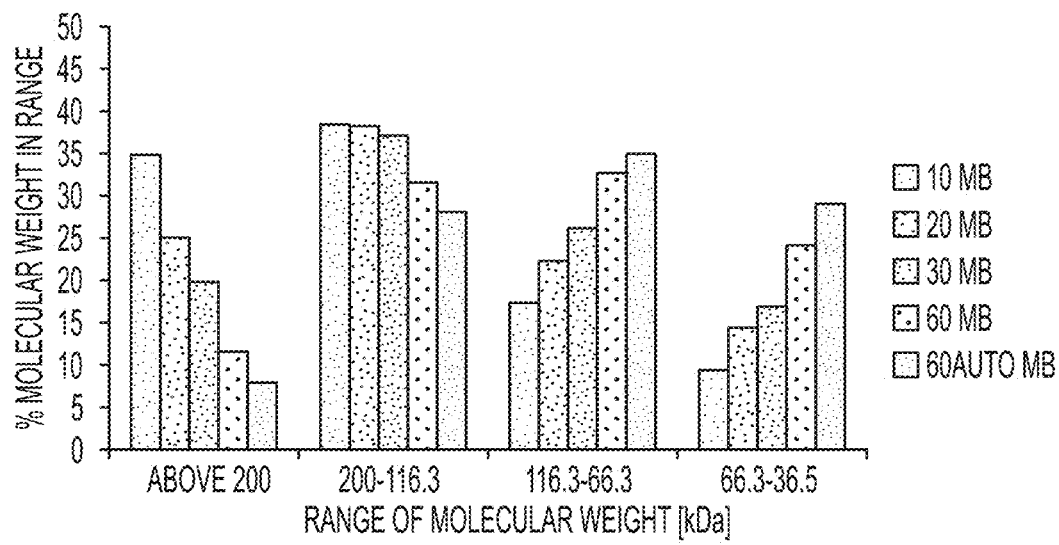
FIG. 5C shows the molecular weight distribution of silk fibroin that undergoes primary and secondary drying from the gel data in FIG. 5A.
Figure 6A:
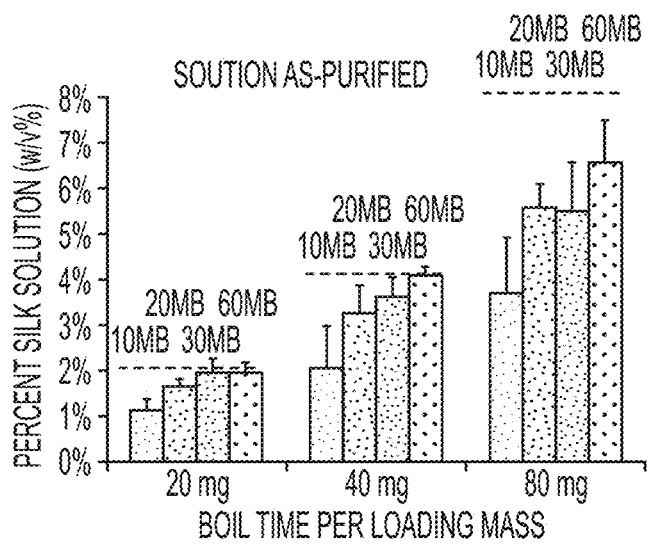
FIGS. 6A-6E show silk foam solubility versus loading. Silk fibroin solutions produced from various cocoon boiling times (10-60 minutes boiling, MB) were lyophilized using as-purified solutions (6A, 6B) and autoclaved solutions (6C, 6D) following the process flow diagram shown in FIG. 1. Either 20, 40, or 80 mg of milled powder was added to deionized water to a final volume of 1 mL. Following centrifugation of this mixture at 1000 rpm, insoluble protein was pelleted and the supernatant was removed and films cast for weight over volume (w/v %) concentration measurement.
Figure 6B:
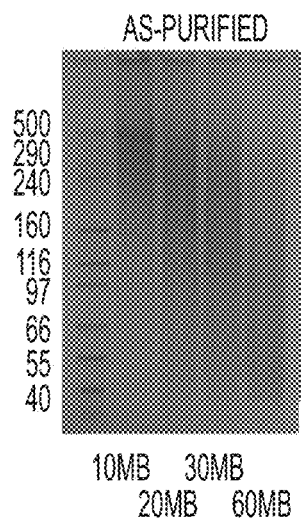
Figure 6C:
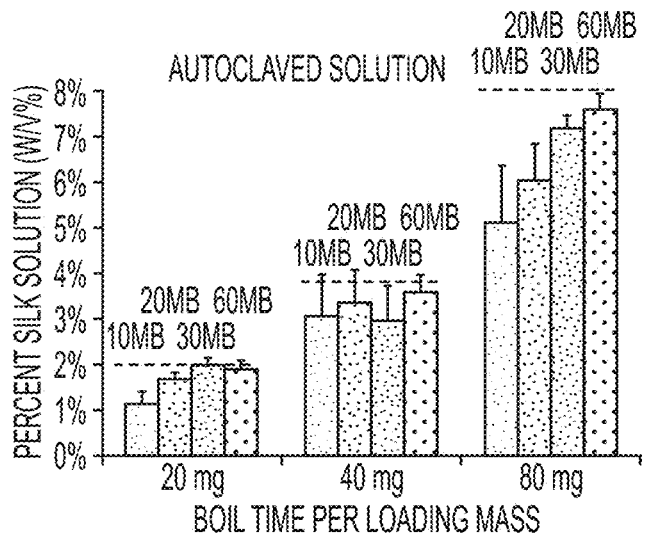
Figure 6D:
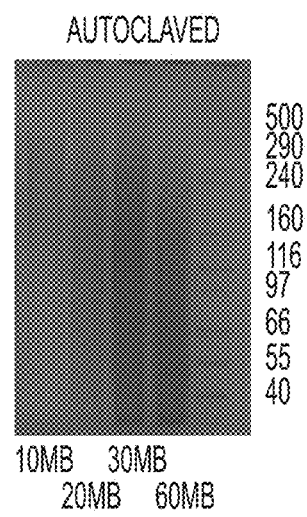
Figure 6E:
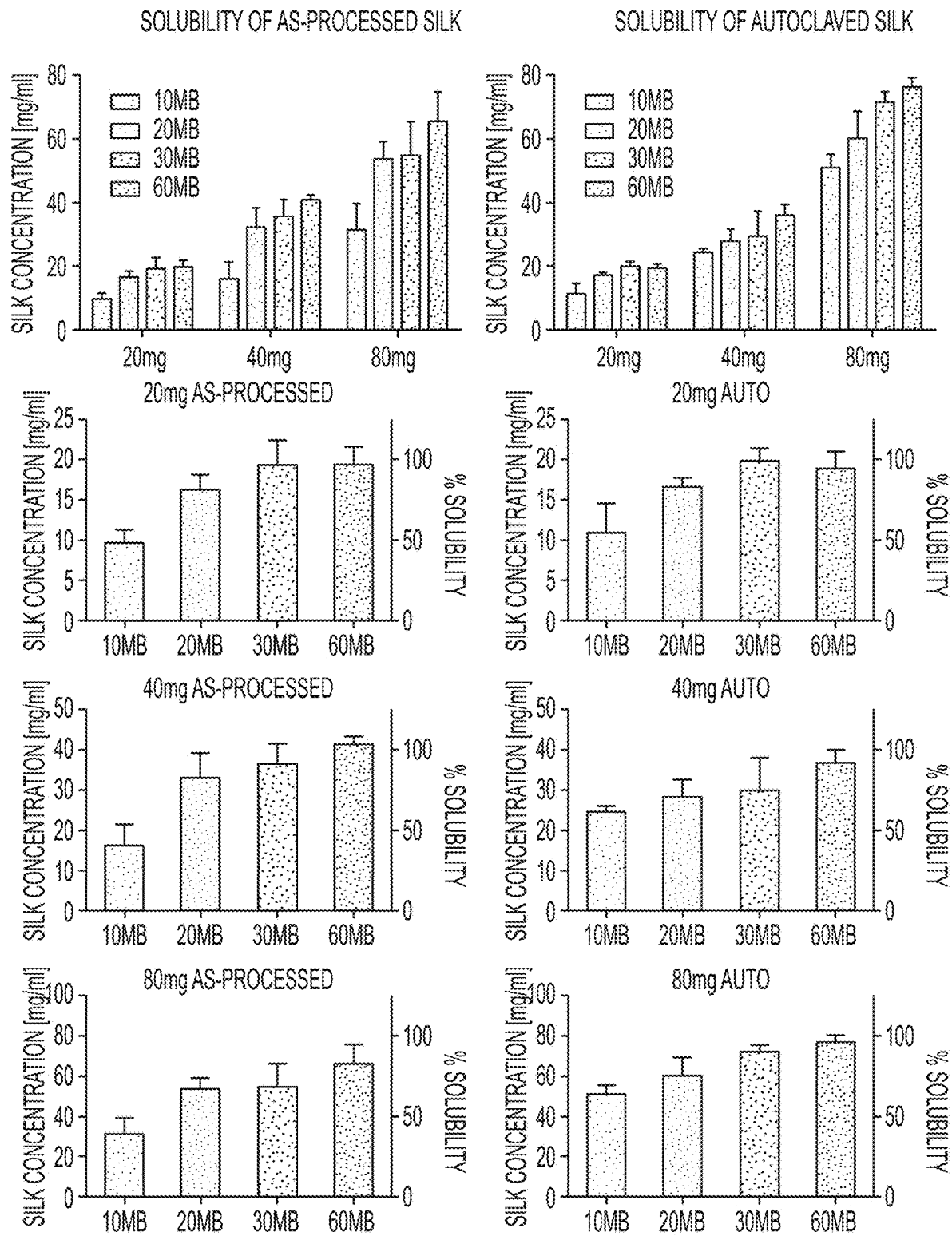

FIGS. 3, 4 and 5 show the molecular weight distribution of silk fibroin solutions obtained from silk foams stored at 4° C., 22° C., and 37° C., respectively. Two types of silk foams were used for each storage temperature: silk foams through primary drying, and silk foams through both primary and secondary dryings. For all silk foam samples examined, the percentage of silk fibroin having molecular weight of 200 kDa or higher decreases as the degumming time increases. Meanwhile, the percentage of silk fibroin having molecular weight of no more than 120 kDa increases as the degumming time increases. As the result of long degumming time (60 minutes or more), low molecular weight silk fibroin described herein comprises a population of silk fibroin fragments having a range of molecular weights, characterized in that: no more than 15% of total number (or total moles) or total weight of the silk fibroin fragments in the population has a molecular weight exceeding 200 kDa, and at least 50% of the total number (or total moles) or total weight of the silk fibroin fragments in the population has a molecular weight within a specified range, wherein the specified range is between about 3.5 kDa and about 120 kDa, or between about 5 kDa and about 125 kDa.

Studies were carried out to compare the differential solubility of milled silk powder from the lyophilized systems depicted in FIG. 1, while varying i) boiling time and ii) mass of powder loading according to the Table of Solubilization Ratios in FIG. 1. Films were casted from each recovered solution in order to directly measure the solution's silk concentration in units of weight/volume %. Following complete drying and weighing, the films were then measured for secondary structure using FTIR in order to confirm the absence of any cross-linked conformational states that would make the silk insoluble in water or inhibit utility of downstream solidification techniques. These solid films were treated with methanol to demonstrate their ability to form cross-linked, water-insoluble structures. The measured concentrations of the recovered solutions are shown below in FIGS. 6A-6D, grouped by initial silk powder loading mass. For reference, the molecular weight distributions of both "as-purified" and "autoclaved" silk systems are also included in FIGS. 6A-6D.

Figure 7:
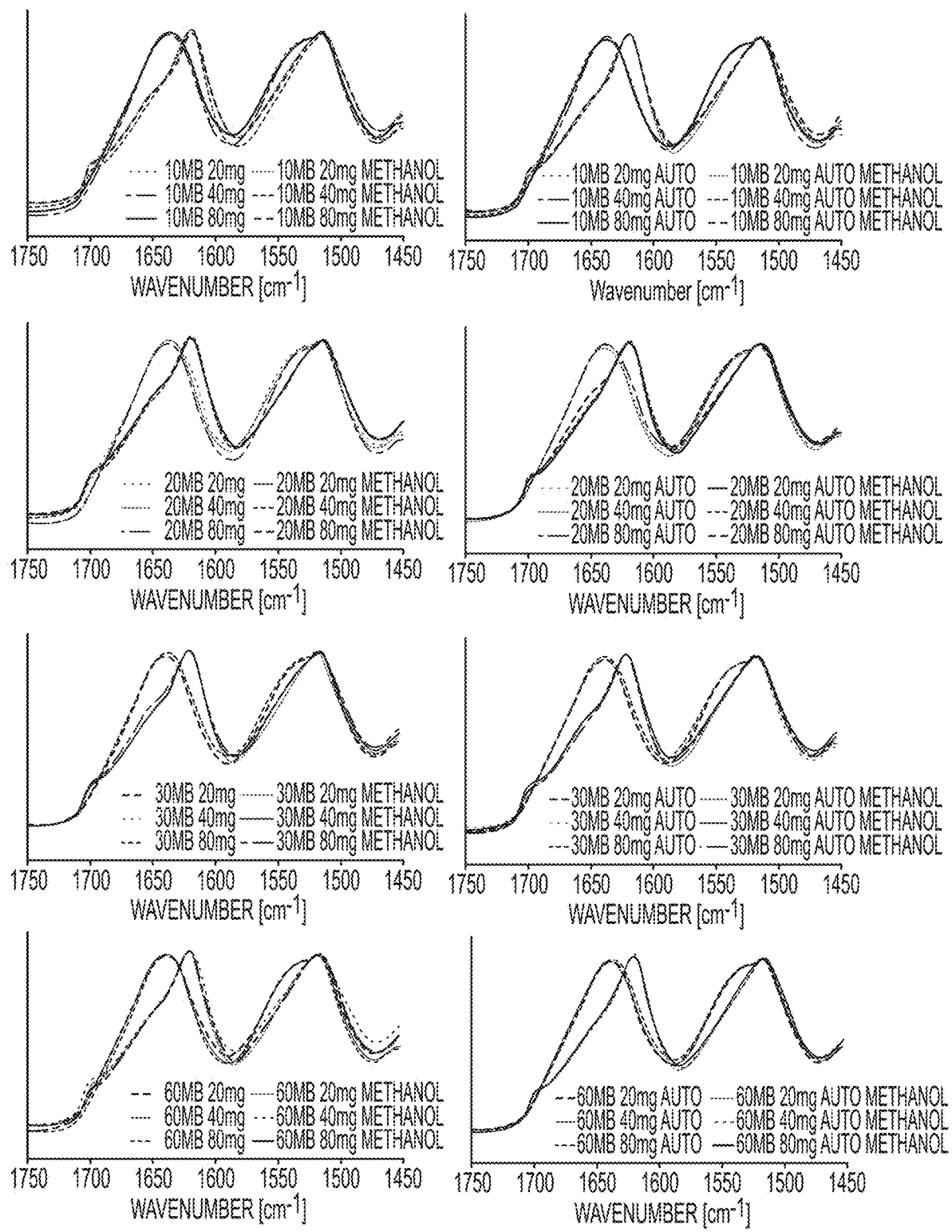
FIG. 7 shows FTIR spectra confirming amorphous-to-β-sheet conversion. Films generated from the recovered as-purified (left) or autoclaved (right) were measured before and after treatment by 90% methanol for one hour. Films formed from various cocoon boiling times (10-60 MB, top-bottom) are shown across all 4 sets of graphs, all with different mass loadings (20, 40, 80 mg) included.

Films generated in FIGS. 6A-6D were evaluated on a Jasco FTIR machine to confirm structure. As shown in FIG. 7, the Amide I and II regions show characteristic peaks centered around 1650 cm$^{-1}$ and 1525 cm$^{-1}$ for the as-cast films, suggesting a largely amorphous "Silk I" conformation (i.e. non-cross-linked). However, following treatment of these films with 90% v/v methanol for 1 hour, the Amide I region is shifted right and includes a small shoulder at 1700 cm$^{-1}$, while Amide II shifts to a broader shoulder at 1535 cm$^{-1}$. These methanol-induced changes are due to the formation of β-sheet structures characteristic of a "Silk II" confirmation.

Figure 8:
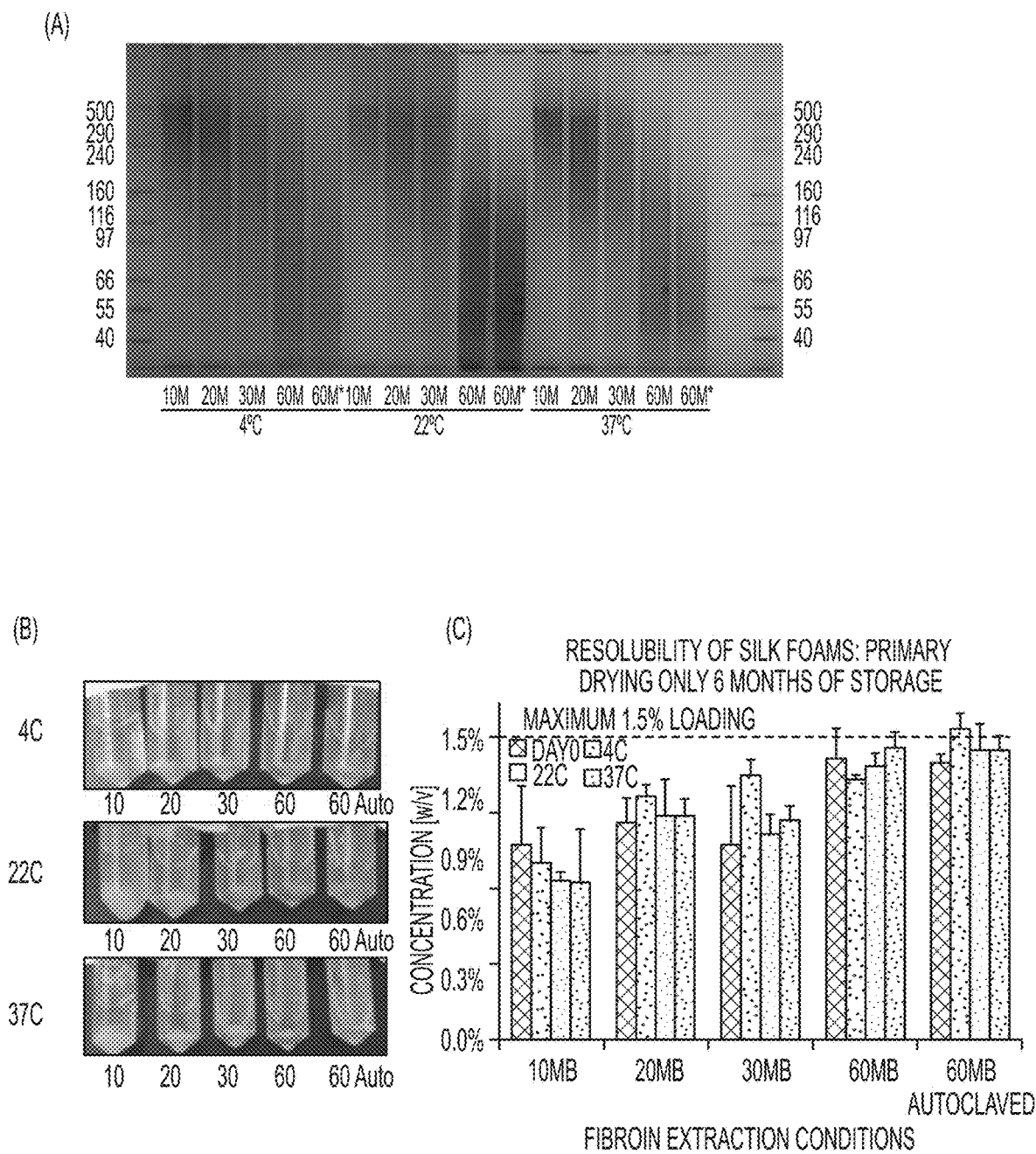
FIG. 8 shows solubility for silk foam formed using only primary drying cycle after 6 months of dry storage. Silk fibroin solutions produced from various cocoon boiling times (10-60 minutes boiling, MB) were lyophilized using a primary drying (only) protocols. After completion of the lyophilization cycle, and storage for 6 months at the indicated temperatures (4° C., 22° C., 37° C.), 15 mg pulverized powder of each foam was then re-solubilized in 985 μL of deionized water. (A) Assuming negligible solubility losses, a 7.5 μg protein loading from each reconstituted solution was run under reducing conditions on a NuPAGE® Novex® 3-8% Tris-Acetate Gel (Invitrogen), using a HiMark™ Pre-Stained Protein Standard (range 30-460 kDa, Invitrogen). Following centrifugation of this mixture at 1000 rpm, insoluble protein was pelleted (B) and the supernatant was removed and films cast for w/v % concentration measurement (C). The dotted line indicates the maximum w/v % concentration possible based on complete theoretical solubility (1.5%).
Figure 9:
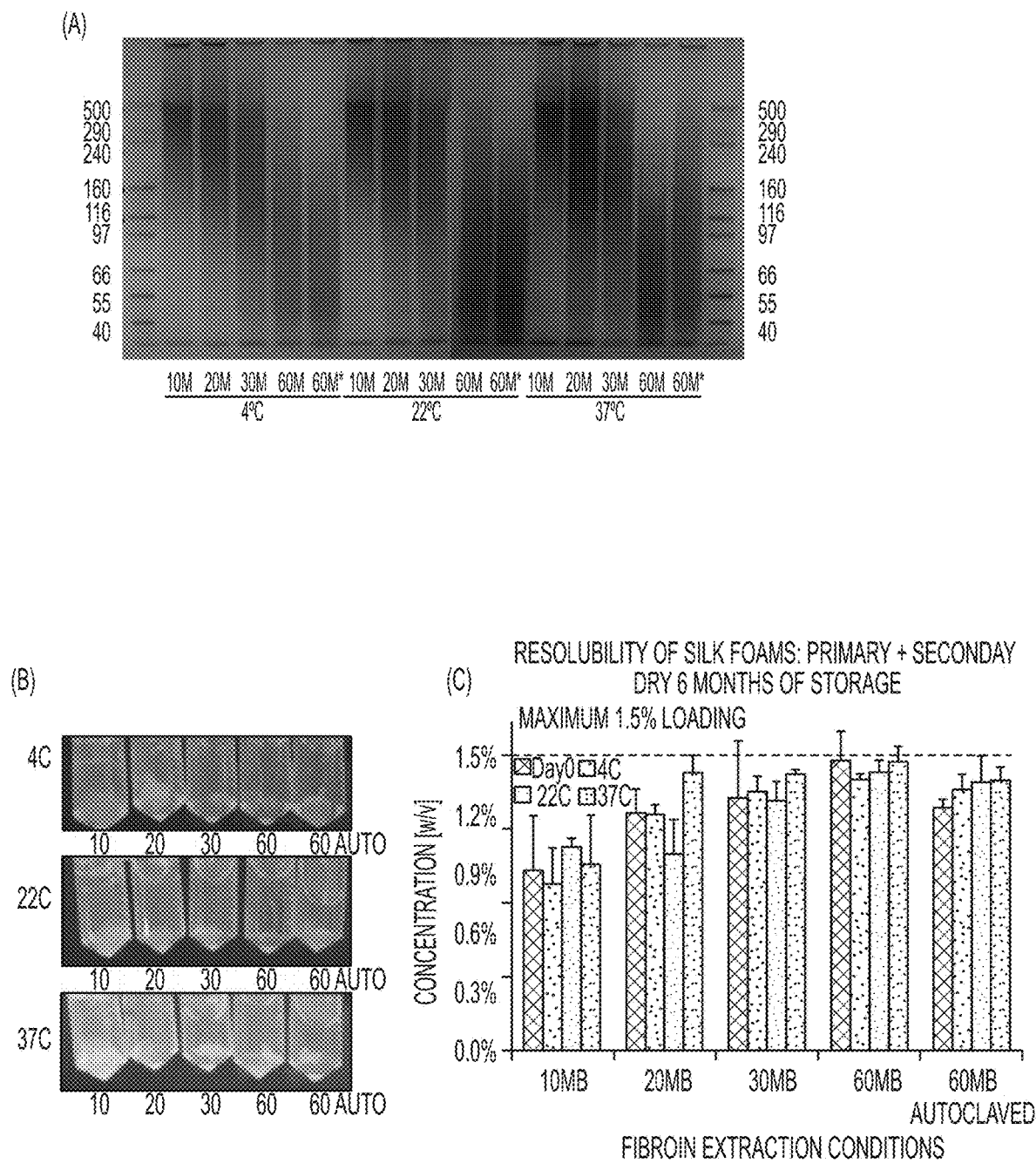
FIG. 9 shows solubility for silk foam formed using both primary and secondary drying cycles after 6 months of dry storage. Silk fibroin solutions produced from various cocoon boiling times (10-60 minutes boiling, MB) were lyophilized using a primary+secondary drying protocols. After completion of the lyophilization cycle, and storage for 6 months at the indicated temperatures (4° C., 22° C., 37° C.), 15 mg pulverized powder of each foam was then re-solubilized in 985 μL of deionized water. (A) Assuming negligible solubility losses, a 7.5 μg protein loading from each reconstituted solution was run under reducing conditions on a NuPAGE® Novex® 3-8% Tris-Acetate Gel (Invitrogen), using a HiMark™ Pre-Stained Protein Standard (range 30-460 kDa, Invitrogen). Following centrifugation of this mixture at 1000 rpm, insoluble protein was pelleted (B) and the supernatant was removed and films cast for w/v % concentration measurement (C). The dotted line indicates the maximum w/v % concentration possible based on complete theoretical solubility (1.5%).

6-Month Foam Stability. Experiments were performed to compare the solubility of the silk powders formed by milling lyophilized silk of varying boil time, after 6 months of storage at various temperature conditions. FIG. 8 shows results from foams formed using Primary Drying only while FIG. 9 shows foams formed using Primary and Secondary Dryings.

Figure 10:
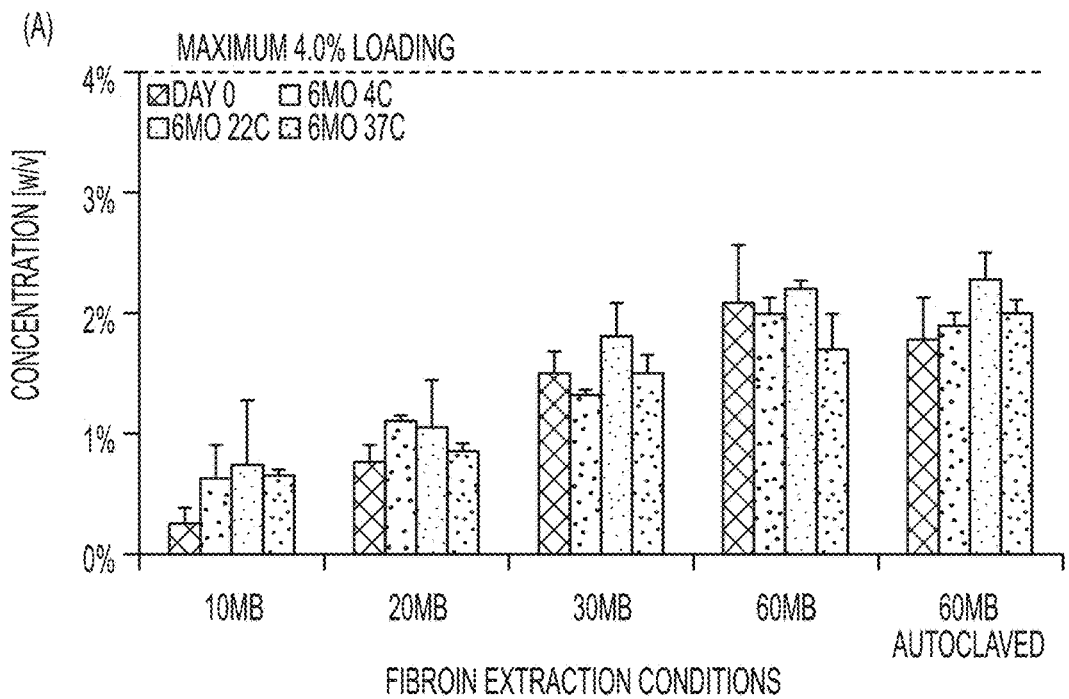
FIG. 10 shows silk film solubility in simulated aging conditions for (A) thick and (B) thin films. Films of varied boiling times (60 MB films also formed from autoclaved solutions) were held at 4° C., 22° C., and 37° C. for 6 months prior to dissolving 40 mg of sample in ultrapure water, as compared to day 0. The dotted line indicates the maximum w/v % concentration possible based on complete theoretical solubility (4%).
Figure 10:
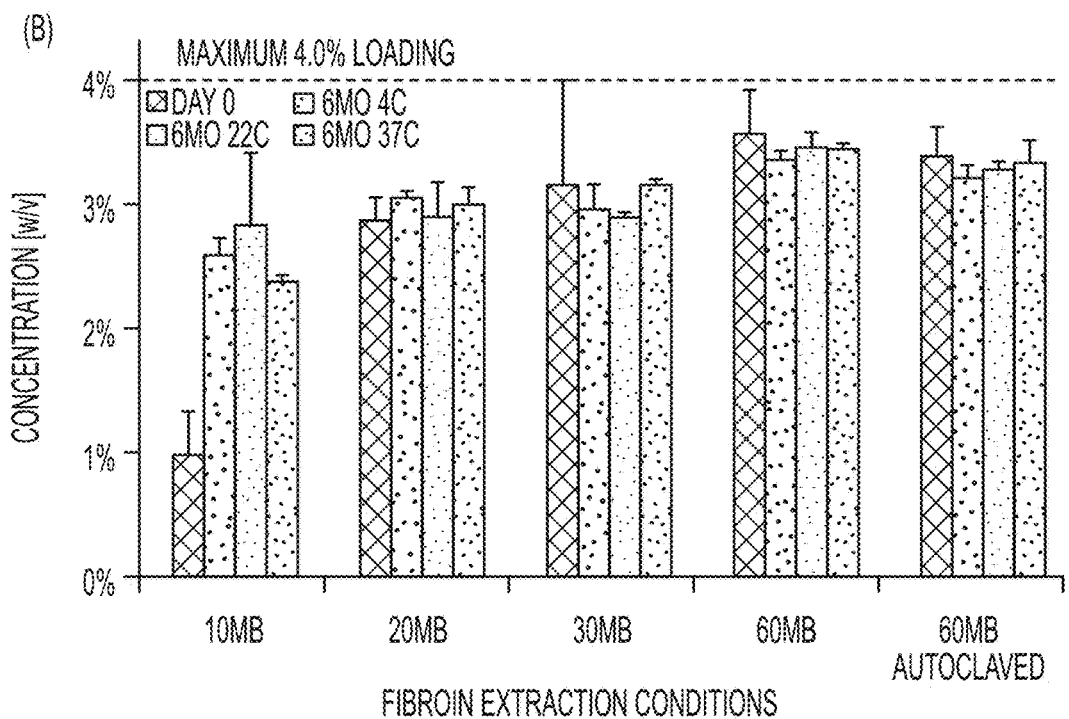
Figure 11A:
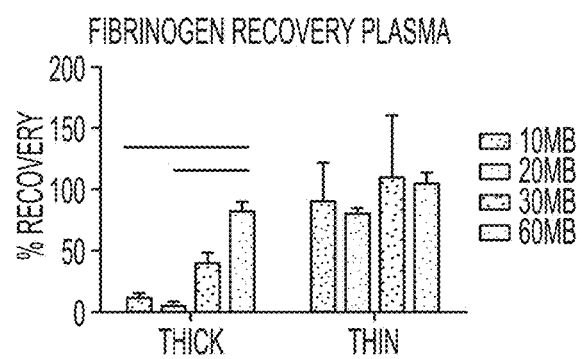
FIGS. 11A-11D show silk recovery tuning based on solution and film design. Using ELISA kits shown in Table 1, silk films weighing 40 mg were dissolved in 1 mL (final volume) of PBS and sample recoveries from films were normalized to theoretical maximum loading values based on frozen plasma aliquots. Silk solutions formed using different boil times (10-60 minutes boiled, MB) were mixed with either plasma or blood and films were cast either in two thicknesses (Thick vs. Thin). Lines indicate significant differences between groups at the α=0.05 level of significance from within two-way ANOVA test.
Figure 11B:
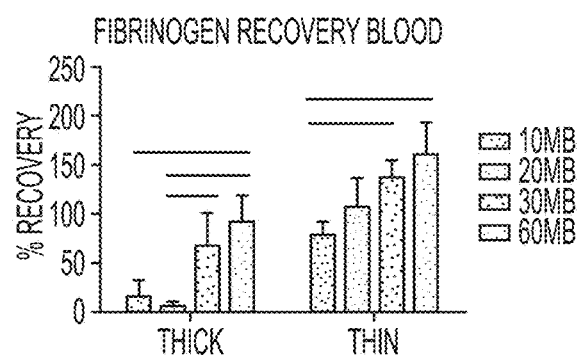
Figure 11C:
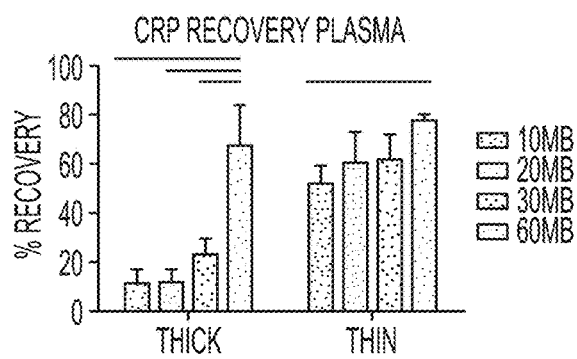
Figure 11D:
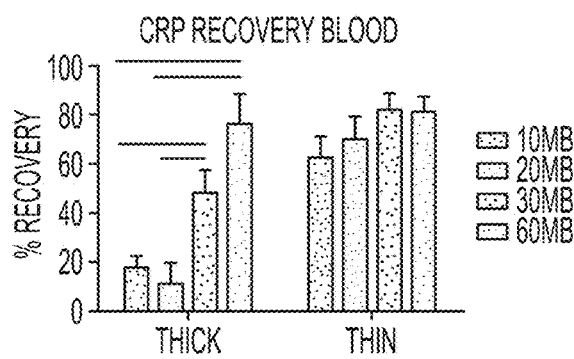

6-Month Film Stability. Experiments were performed to compare solubility of the thick and thin silk films after 6 months of storage at various temperature conditions as shown in FIG. 10.

Example 2

Blood Recovery from Silk-Blood Samples

Materials and methods. Fresh donor blood (Vacutainer tubes, Na-heparin anticoagulant, Research Blood Components, Brighton, Mass.) was delivered from a single donor within 1 hour of draw. Tubes were then immediately centrifuged at 1000×g for plasma isolation. Plasma aliquots were then immediately frozen to serve as positive controls. Silk solution was prepared from the cocoon of the silkworm *Bombyx mori* as previously described. Cocoons were degummed for 10, 20, 30, or 60 minutes by boiling in a solution of 0.02M Na$_2$CO$_3$. Silk films were casted onto polydimethylsiloxane (PDMS) surfaces, in which 100 µL of either blood or plasma was mixed with 1.9 mL of silk solution (~8 wt % in water independent of boil time) prior to casting 2 mL as either thick films (3×2.5 cm diameter casting surface) or thin films (7.5 cm diameter casting on 3× surfaces). After the films dried overnight (8 hrs), samples are sectioned to 40 mg coupons for analysis. In the preliminary experiments, 10 mg and 40 mg coupons were prepared from the plasma and blood films for ELISA readings to tune the mass loading required for analysis within the standard curves, at which point 40 mg was identified as being appropriate for recovery studies (data not shown). Films were added to 960 µL of PBS as diluent, vortexed for 5 seconds, and then immediately assayed using available supernatant. For all ELISAs (abCAM or R&D Systems per Table 1), frozen plasma aliquots were diluted according to manufacturer recommendations (from 1:100 to 1:8000) while the dissolved blood and plasma films were tested at 40× smaller dilution based on theoretical estimates of recovery.

TABLE 1

ELISA markers, protein characteristics, and detection limits

| ELISA Kit | Protein | Molecular weight | ELISA Std (pg/mL) | Tissue subtype/ disease |
|---|---|---|---|---|
| Ab108841, Abcam | Fibrinogen | 340 kDa | 1,250-80,000 | Inflammation, cardiovascular disease (CVD) |
| DCRP00, R&D | C-reactive protein (CRP) | 118-144 kDa | 78,100-500,000 | CVD, diabetes |

Calculating Recovery of Plasma and Blood. In order to accurately convert the values of the recovered proteins from the blood and plasma coupons to the concentrations found in the donor-matched plasma, and thus determine the recovery efficiency, several physical measurements of the blood and plasma were made. The wt/vol fraction (wt %) of blood or plasma (i.e. blood or plasma solids [g] per unit volume [mL]) was determined by drying whole blood or plasma of a known volume in a fume hood for 24 hrs and measuring the residual mass. Then, the weight fraction of plasma solids per volume of blood was estimated by assuming 55% plasma volume of blood. The plasma solids per weight of each film was calculated by the knowledge that ~20 mg of whole blood (depending on Table 2 values) and 144 mg of silk was would be found in every 100 μL of blood casting solution, and the same for plasma casting solution.

$$Wt \; frac \text{ plasma solids in blood } \left[\frac{g}{mL}\right] =$$

$$\text{Plasma } wt \text{ fraction}\left[\frac{g}{mL}\right] \times .55 \left[\frac{\text{plasma vol, mL}}{\text{total blood vol, mL}}\right]$$

$$\text{Plasma solids per weight of blood film } \left[\frac{g}{g}\right] =$$

$$\frac{Wt \; frac \text{ plasma solids in blood } \left[\frac{g}{mL}\right] \times 0.1 \text{ mL blood}}{\left(\text{blood } wt \; frac \left[\frac{g}{mL}\right] \times 0.1 \text{ mL blood}\right) \times \left(\text{Silk mass } frac \left[\frac{g}{mL}\right] \times 1.9 \text{ mL silk}\right)}$$

$$\text{Plasma solids per weight of plasma film } \left[\frac{g}{g}\right] =$$

$$\frac{\text{plasma } wt \; frac \left[\frac{g}{mL}\right] \times 0.1 \text{ mL plasma}}{\left(\text{plasma } wt \; frac \left[\frac{g}{mL}\right] \times 0.1 \text{ mL plasma}\right) + \left(\text{Silk mass } frac \left[\frac{g}{mL}\right] \times 1.9 \text{ mL silk}\right)}$$

TABLE 2

Physical Parameters to Determine Blood/Plasma Loading (three donor averages)

|   |   | Donor A | Donor B | Donor C | Donor |
|---|---|---------|---------|---------|-------|
| I | Blood wt. fraction [g/mL] | 0.2316 | 0.1827 | 0.2298 | 0.2146 |
| II | Plasma wt. fraction [g/mL] | 0.1040 | 0.0994 | 0.1075 | 0.1036 |
| III | Wt. fraction plasma solids in | 0.0572 | 0.0547 | 0.0591 | 0.0570 |
| IV | Plasma solids per wt. of blood | 0.0341 | 0.0335 | 0.0353 | 0.0343 |
| V | Plasma solids per wt. of plasma | 0.0671 | 0.0644 | 0.0693 | 0.0669 |

Finally, the theoretical loading of plasma or blood in the assay could be calculated from the above fractions. The plasma solids in each 20 mg coupon is multiplied by the plasma concentration measured in the assay [mg/mL], which is then normalized to the total plasma solids mass in a given [1.02 mL] PBS resuspension volume. These calculations are shown below in order to illustrate the assumptions made in our analysis, and also to show how physical blood and plasma parameters were incorporated in order to determine accurate recovery estimates from theoretical loading values.

$$\text{Theoretical plasma loading in 20 mg coupon } \left[\frac{mg}{mL}\right] =$$

$$\text{Plasma solids per weight of plasma film } \left[\frac{mg}{mg}\right] \times$$

$$20 \text{ [mg] coupon} \times \frac{\text{Plasma } Conc. \text{ Measured in Assay [mg/mL]}}{Wt. \; Frac \text{ Plasma Solids [mg/mL]} \times 1.02 \text{ [mL]}}$$

-continued $$\text{Theoretical plasma loading in 20 mg coupon } \left[\frac{mg}{mL}\right] =$$

$$\text{Plasma solids per solids of blood film } \left[\frac{mg}{mg}\right] \times 20 \text{ [mg] coupon} \times$$

$$\frac{\text{Plasma } Conc. \text{ Measured in Assay [mg/mL]}}{Wt \; Frac. \text{ Plasma Solids [mg/mL]} \times 1.02 \text{ [mL]}}$$

Sample recoveries were calculated according to the description in section Calculating Recovery of Plasma and Blood. Sample variance was calculated based on triplicate readings from repeat samples from the same donor. Results were compared between films prepared using different boil times and different thicknesses ("thick" vs. "thin") using a two-way ANOVA with multiple comparisons and Tukey's correction testing at the $\alpha=0.05$ family-wise significance level.

Results. The inventors found that for CRP and fibrinogen as model markers, recovery from silk was dependent on both boiling time and film thickness at a statistically-significant level (see FIGS. 11A-11D); furthermore, in the case of CRP, for both the blood and plasma recoveries, the variables of thickness and boil time had strong interactive effects, suggesting additive features in improving recovery from the silk matrix. In terms of specific comparisons, silk boiled for 60 minutes formed matrices that provided maximum recovery, independent of boiling time and thickness, while the lower boiling-time systems decreased in recoverability in a dose-dependent fashion. While not significantly so for every boiling time, thick films were predominantly more effective at releasing stores of analytes compared to their thinner counterparts, independent of sample type (blood vs. plasma).

Example 3

Figure 12:
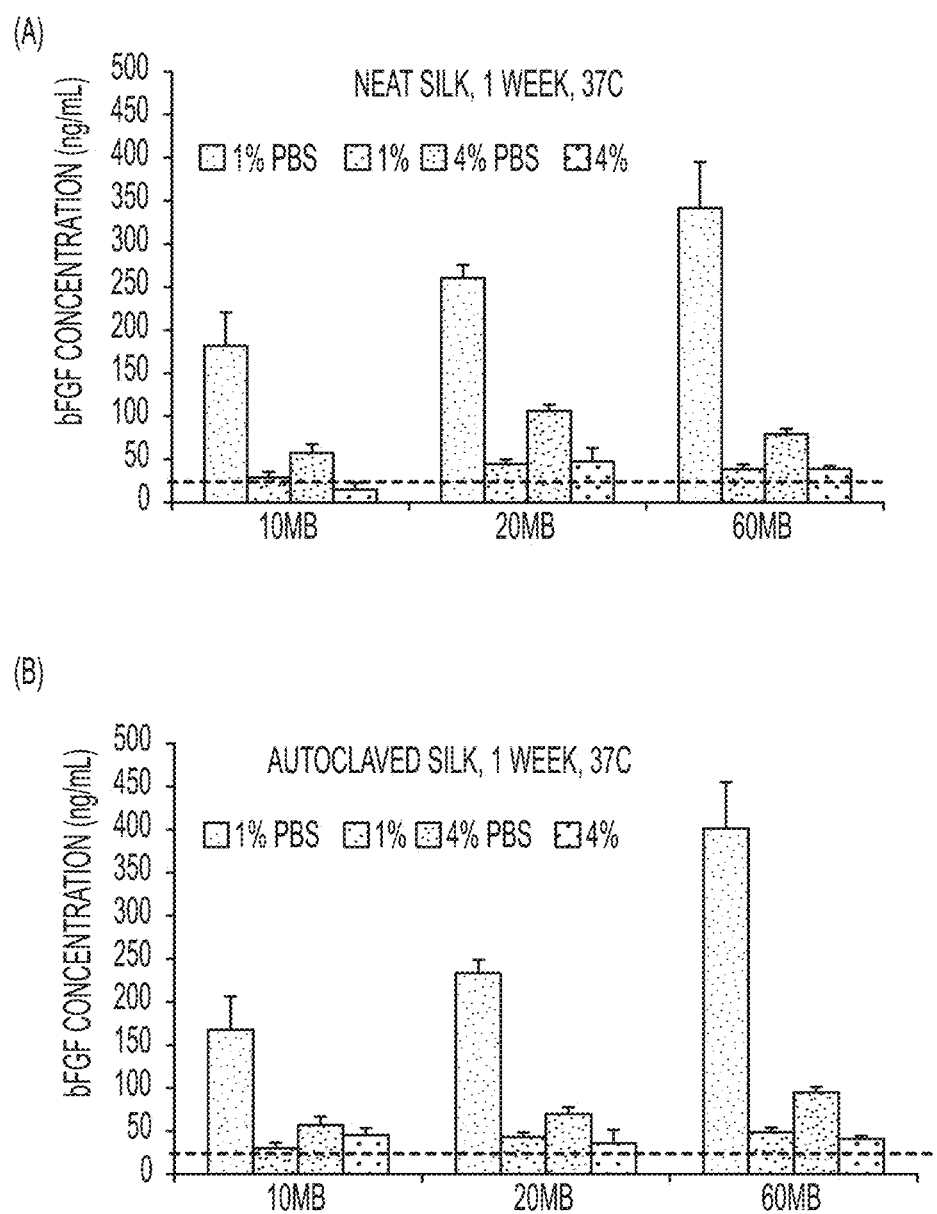
FIG. 12 shows bFGF recovery from (A) as-purified and (B) autoclaved silk fibroin solutions. The addition of PBS improved bFGF, independent of boiling time, concentration or as-purified vs. autoclaved. The solutions were buffered to a final PH of 7.2 by the addition of PBS. bFGF was more stable in 1% solutions than 4% solutions. 60 MB silk solutions had the highest recovery of bFGF for both as-purified and autoclaved conditions. The dotted line indicates PBS alone as the control condition. The as-purified silk, the improved bFGF recovery at 37° C. can be linked to the absorbance data in FIG. 13A, in that the 10 MB groups that gelled had the worse bFGF recovery overall.

Stabilization of Basic Fibroblast Growth Factor (bFGF) in Silk Fibroin Solutions Silk solution was prepared from the cocoon of the silkworm *Bombyx mori* previously described. Cocoons were degummed for 10, 20, or 60 minutes by boiling in a solution of 0.02M $Na_2CO_3$. The silk solution is 1 w/v % or 4 w/v %, including 1×PBS or no buffer. The silk solution is either as purified or autoclaved. The following controls are used: 0.1% BSA in 1×PBS, 1.0% BSA in 1×PBS, and 1×PBS. bFGF is added to each solution to a final concentration of 250 ng/mL. All bFGF-containing solutions are stored at 37° C. for one week before recovery measurement. FIG. 12 shows bFGF recovery from silk fibroin solutions, demonstrating that the low molecular weight silk fibroin can lead to higher recovery and specifically demonstrating that 1% low MW silk in PBS yielded the most promising recovery of bFGF, regardless of whether or not the silk used was autoclaved or used as purified (i.e. "neat silk"). The red dotted line in FIGS. 12A and 12B shows the value of the PBS control.

Figure 13A:
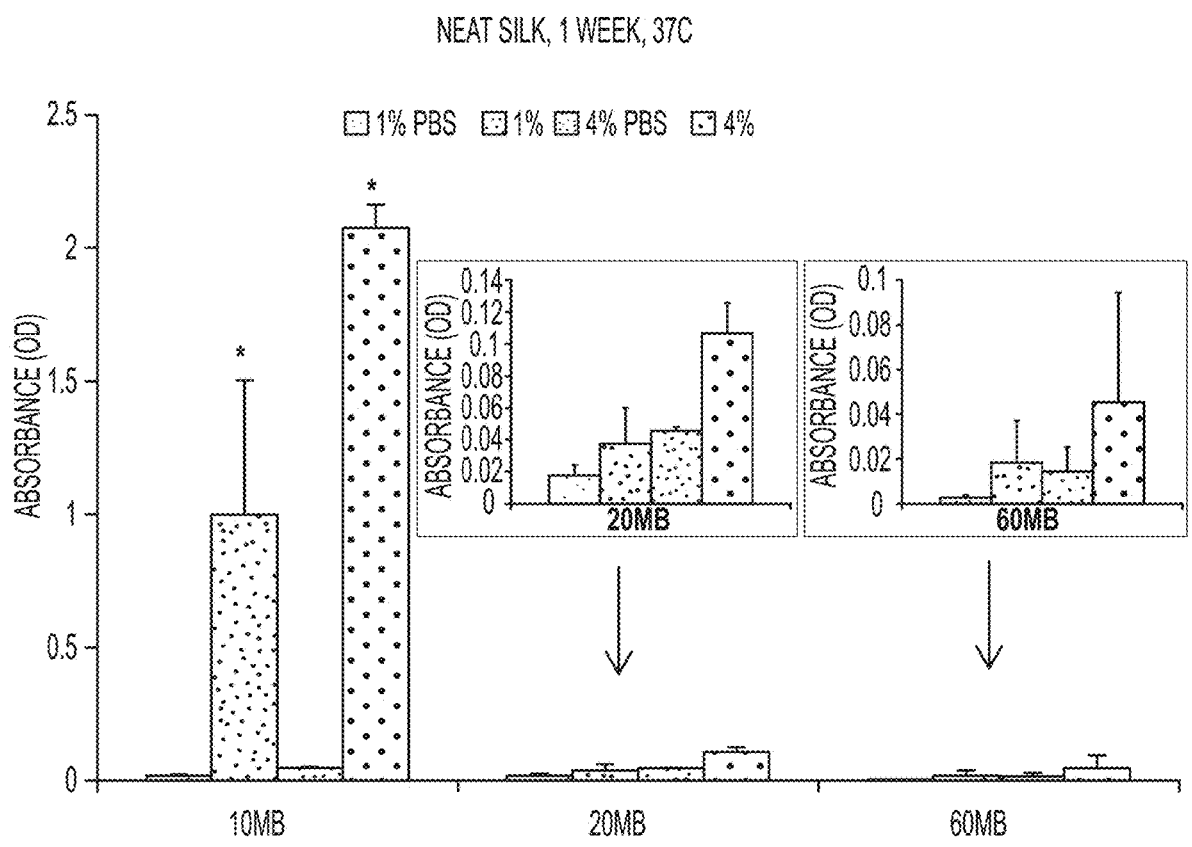
FIGS. 13A and 13B show the gelation results for as-purified and autoclaved silk fibroin solutions stored at 37° C. for a week, respectively. The asterisks in FIG. 13A indicate gelation, showing that only 1% and 4% 10 MB solutions gelled.
Figure 13B:
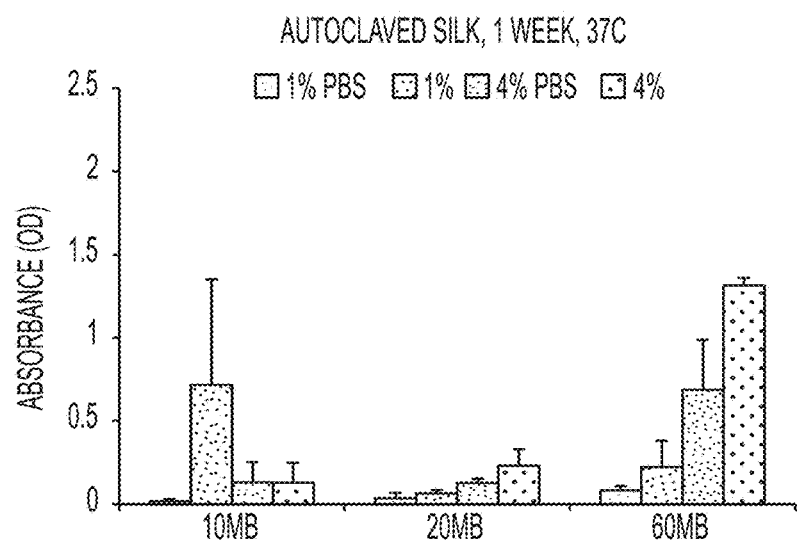
Figure 14A:
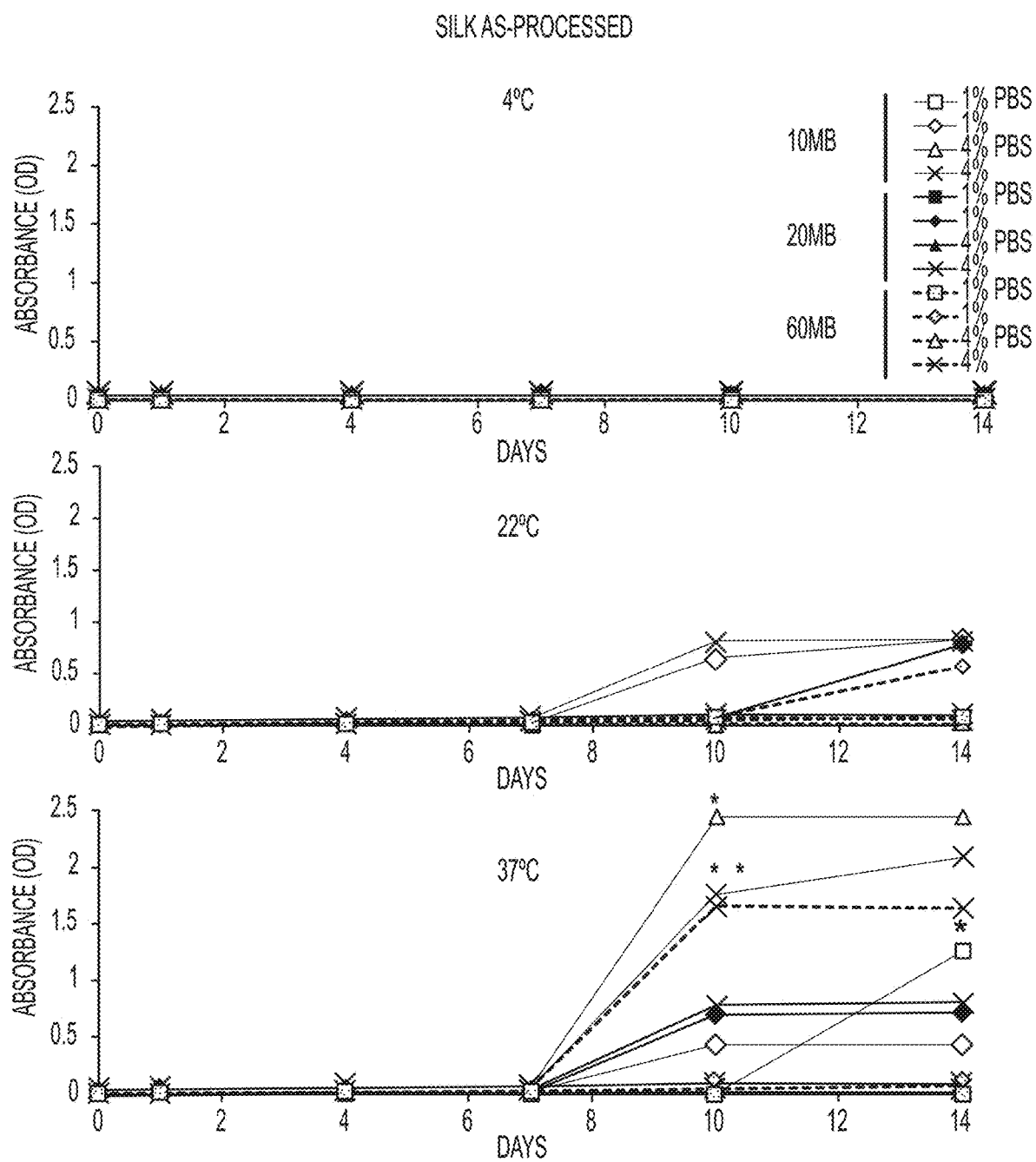
FIG. 14A shows the gelation status for as-purified silk fibroin solutions at 4° C., 22° C., and 37° C. over a period of two weeks, respectively. The asterisks indicate gelation. Samples without an asterisk but rising above the baseline are still pre-gelled solutions. Samples from the 10 MB group tend to gel faster than samples with longer boiling time. Groups at 4% concentration tend to gel faster than the 1% groups. PBS-containing groups gel slower than the un-buffered samples.
Figure 14B:
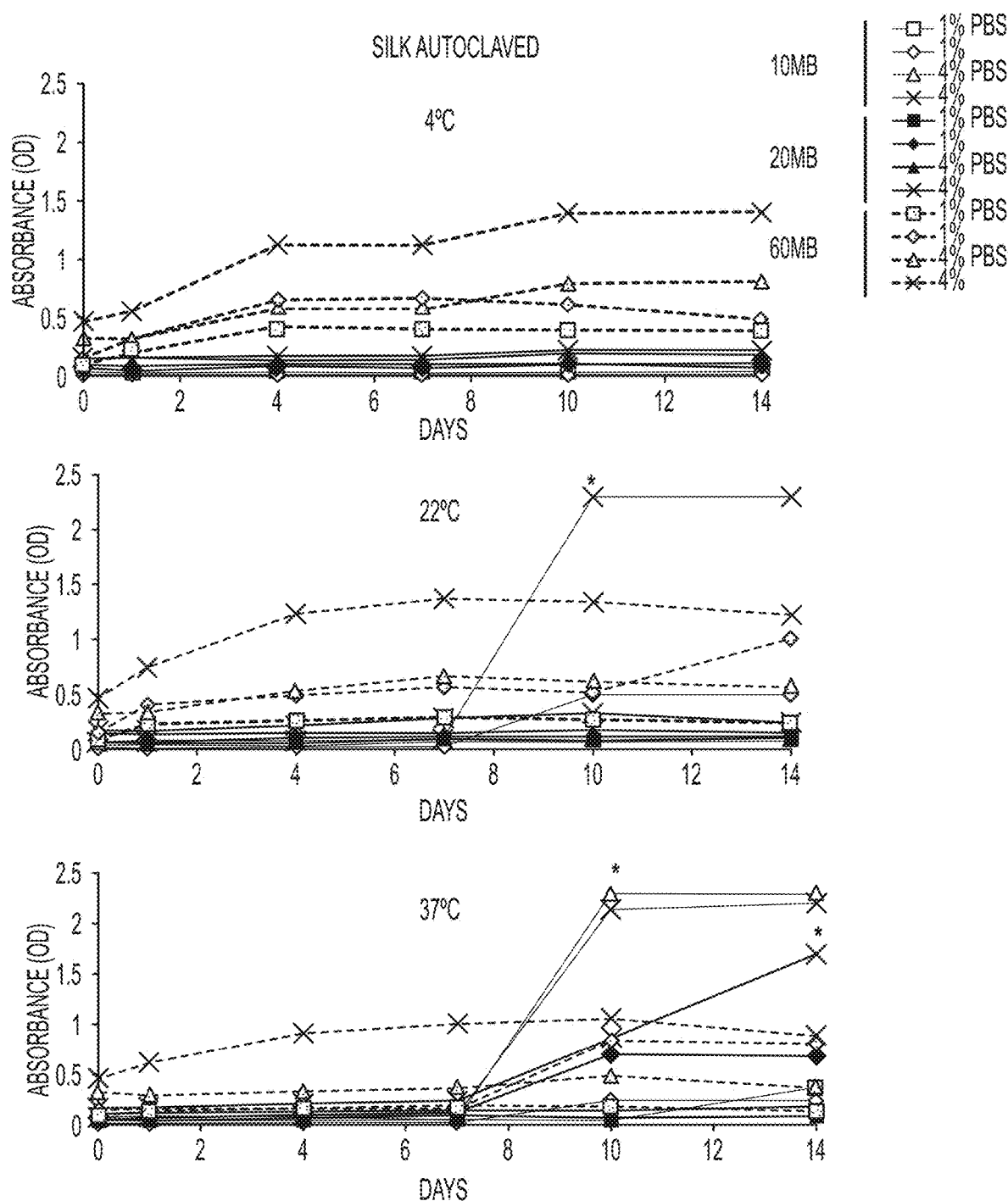
FIG. 14B shows the gelation status for autoclaved silk fibroin solutions at 4° C., 22° C., and 37° C. over a period of two weeks, respectively. The asterisks indicate gelation. The signals from the 60 MB group are a result of a whitish coloration in the samples, giving a false positive for gelation in the absorbance readings, but these samples did not gel. Samples from the 10 MB group tend to gel faster than samples with longer boiling time. Groups at 4% concentration tend to gel faster than the 1% groups. PBS-containing groups gel slower than the un-buffered samples.

For gelation monitoring experiments, no bFGF is added. Absorption at 550 nm (Matsumoto+, 2006) is used to monitor gelation. FIGS. 13A and 13B show the gelation results for as-purified and autoclaved silk fibroin solutions. FIG. 14 shows the gelation status for (A) as-purified and (B) autoclaved silk fibroin solutions at 4° C., 22° C., and 37° C., respectively.

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Example 4

Stabilization of Blood and Blood Components in Silk Fibroin Matrices

Cellulose-based technologies have currently dominated the market space of biospecimen preservation. Dried blood spots (DBS) specimens are collected by applying a few drops of blood, drawn by lancet from the finger, heel or toe, onto specially manufactured absorbent filter paper. These paper matrices may be designed with proprietary chemistries and/or embedded enzyme inhibitors. Once dried and in the laboratory, technicians separate a small disc of saturated paper from the sheet using an automated or manual hole punch, dropping the disc into a flat bottomed microtiter plate. The blood is eluted out in buffered saline overnight at 4° C. The resultant plate containing the eluted material forms the "master" from which dilutions can be made for subsequent testing. Filter paper has thus been used to collect blood for individual diagnostics and public health purposes since the 1960s (Guthrie and Susi, 1963). The CDC maintains an active list of substances that have been stabilized using DBS on their website (www.cdc.gov/labstandards/nsqap_bloodspots.html), compiled from literatures citations over the last 20-30 years, and maintains an independent quality control program for blood spots. The cards were originally manufactured and marketed by Whatman® as the "Whatman FTA card technology" and have since been repackaged and sold by GE Healthcare, GlaxoSmithKline, and Alturas Analytics. Newer companies such as Ahlstrom are also marketing fiber composites with similar liquid filtration and stabilization capabilities (www.ahlstrom.com/en/products/enduseApplication/medicalAndHealthcare/laboratoryAndDiagn osticsFiltration/Pages/Diagnosticfiltration.aspx).

For more than 30 years, researchers have studied the temperature/stability relationships of markers for many disorders in DBS samples and in particular have focused on newborn screening applications because of the demand for low-volume analytics and remote diagnostics. Researchers have hence discovered that no one paper format is appropriate to cover all analytes of interest and that some markers are insufficiently recovered using the chemically-modified cards. Several specific drawbacks of these paper-based systems have also been uncovered upon years of assessment in a broad set of clinical situations. DBS specimens place constraints on the lower limit of detection (LLOD) attainable and the dynamic range over which there is adequate quantitative discrimination (Andreotti et al., 2010). Ensuring specimen integrity also remains a logistical constraint on molecular testing for RNA viruses (Dineva et al., 2007; Puren et al., 2010). Accordingly, there is a need for improved technologies and/or products that can stabilize biological samples and/or components thereof (e.g., at ambient conditions) and permit recovery of various analytes in sufficient amounts from the stabilized samples for detection and/or analyses.

In large-scale screening studies (epidemiological or toxicological), very small capillary blood samples are available from most patients through finger or heel prick, due to the lack of trained phlebotomists on-site or the general aversion to invasive sampling techniques such as venipuncture. Furthermore, human whole blood and blood components can be very labile, hence requiring special handling to maintain/retain sample quality for diagnostic evaluation of human health. The typical method of storing and handling blood draws or fractions of blood (plasma, serum, buffy coat, hematocrit, etc.) is by cold-freezing (−20 C) or, in the case of highly unstable RNA at ultra-low temperatures (−80 C), so as to preserve sample integrity. Shipping biological samples from collection sites (field, clinics, etc.) to the lab for direct analysis or further extraction of plasma proteins/RNA is often a very costly exercise since it requires the use of bulky materials such as styrofoam boxes and dry-ice. Such bulky packaging often results in expensive shipping charges (see Table 3) even for local shipments.

TABLE 3

| Shipment type | Germany | Australia | India | Japan |
|---|---|---|---|---|
| Dry Ice, FedEx* | $178 | $202 | $205 | $172 |
| Ambient, USPS | <$5 | <$5 | <$5 | <$5 |
| Cost savings | >$173 | >$197 | >$200 | >$167 |

*1-10 samples with 10 lb of dry ice

In some developing countries or in remote field conditions, the minimum infrastructure to support continuous cold storage does not exist, thus limiting the scope of diagnostic workup that can be performed. Unfortunately, it is these limited-resource settings that are in dire need of cheap/durable storage formats for pharmacokinetic (PK) screening or to monitor treatment efficacy and to guide an appropriate switch to second line therapy. Furthermore, population-wide epidemiological screening as conducted by federal organizations such as the Center for Disease Control and Prevention (CDC) would greatly benefit from a more streamlined approach at sample stabilization that rely solely on retrieving less-invasive small sample volumes (Mei et al., 2001). If a simple, inexpensive toolset were available for these communities to send away biological materials via existing, albeit limited, infrastructure settings, we could see a shift in the paradigm of global health monitoring and facilitate a greater number of international Phase II/III clinical studies.

In this study, the inventors disclose experiments that demonstrate that appropriately prepared and reconstituted silk fibroin can stabilize whole blood and blood components over time and a range of storage temperatures, and allow recovery of the components for analysis. The silk protein solution is mixed with these components in the liquid state, followed by air-drying the biologic/silk complex into a thin film that acts as the stabilizing format. Alternatively, reconstituted silk solutions containing nucleic acids can be lyophilized in order to provide a rapid solidification technique to demonstrate that labile, low-abundance nucleic acid molecules can likewise be stabilized using the silk protein. These embodiments of silk stabilization described herein further extend a platform based on recent discoveries of the unique features of silk proteins as a protectant for active agents and/or biological samples. In addition to use of silk proteins as a protectant or a stabilizing agent, the inventors herein show that control of silk processing characteristics can, at least in part, determine solubility characteristics of final stabilizing matrices, which in turn can dictate the ability to recover biological samples for analyses used in diagnostic as well as some therapeutic settings.

In one embodiment, the inventors specifically demonstrate that high levels of plasma proteins can be isolated from silk-stabilized whole blood or plasma as compared to the frozen liquid plasma storage format (the gold standard); in the case of several of the markers assessed, the silk stabilization format improved retention of low-abundance plasma proteins when compared to the gold standard. In the case of nucleic acids, it was surprisingly discovered excellent recovery of entrapped stores of RNA in the presence of RNAse-deactivated silk solutions, regardless of storage temperatures. Taken together, these findings indicate that reconstituted silk solutions can be configured for various products, e.g., which can be used in the field of diagnostics, specifically for point of care diagnostics, storage and shipping of samples to other locations, and/or to serve patients in remote areas who require advanced diagnostics performed on preserved biospecimens. In some embodiments, blood samples stabilized in silk can help circumvent the cold-chain (i.e. continuous un-interrupted cold storage) that links remote settings where blood is extracted (via finger prick or venous blood draw) to a centralized lab where blood components can be analyzed for markers of patient health.

The only other technology currently marketed for dry storage of blood is a paper-based technology (Whatman® FTA dried blood spot cards), but this technique is not widely adopted due to its inability to match cold-chain performance metrics. In this sense, the silk stabilization technology can be used to supplant on-paper devices and shift the paradigm away from reliance on cold-chain storage, opening up new markets for silk devices. Further, some embodiments of various aspects presented herein can be applied to other forms of sample collection, such as from urine, saliva and other bodily fluids or cells for similar diagnostic utility.

Example 5

Silk Processing Controls for Enhanced/Optimal Solubility of Silk Fibroin

The effects of different processing conditions on the performance capabilities of materials derived from silk fibroin have been previously evaluated, and these performance metrics include ways to modulate mechanical performance, degradability, and biologic release characteristics (Altman et al., 2003; Pritchard et al., 2013; Vepari and Kaplan, 2007). However, there is no available literature defining strategies to engineer solid matrices derived from silk for the expressed purpose of optimizing their solubility in order to entrap and recover biologics (of any kind) in an on-demand and complete fashion. The inventors have discovered that the solubility characteristics of silk-derived matrices can be manipulated by protein-specific processing parameters, some of which have been previously identified in the literature (but not used for this purpose), and other novel modifications described herein. It is shown herein that the formulae for protein processing control, which augments previously-available techniques, offers an optimal means through which silk materials can be solubilized and entrapped materials meaningfully extracted/analyzed for a variety of purposes. In addition, storage experiments were conducted using representative silk film and lyophilized foam formulations in order to verify their stability against a variety of temperature conditions they may encounter when used in field settings.

Effects of degumming time on silk solubility were evaluated herein. In particular, silk solution was purified as previously described with modifications to boil time (Pritchard et al., 2013). Briefly, cocoons of Bombyx mori silkworm silk were purchased from Tajima Shoji Co., LTD (Sumiyoshicho, Naka-ku, Yokohama, Japan). Cocoons were degummed for 10, 20, 30, or 60 minutes by boiling in a solution of 0.02M $Na_2CO_3$. Degummed fibroin was rinsed and then dried at ambient conditions overnight. The dried fibroin was solubilized in a 9.3 M aqueous LiBr, dialyzed against distilled water for 2.5 d using Slide-a-Lyzer dialysis cassettes (molecular-weight cut off (MWCO) 3.5 kDa (Pierce Thermo Scientific Inc., Rockford, Ill.) and centrifuged. The silk fibroin concentration (in w/v) was determined by evaporating water from a solution sample of known volume. All of the solutions were stored at 4° C. before use.

Figure 15:
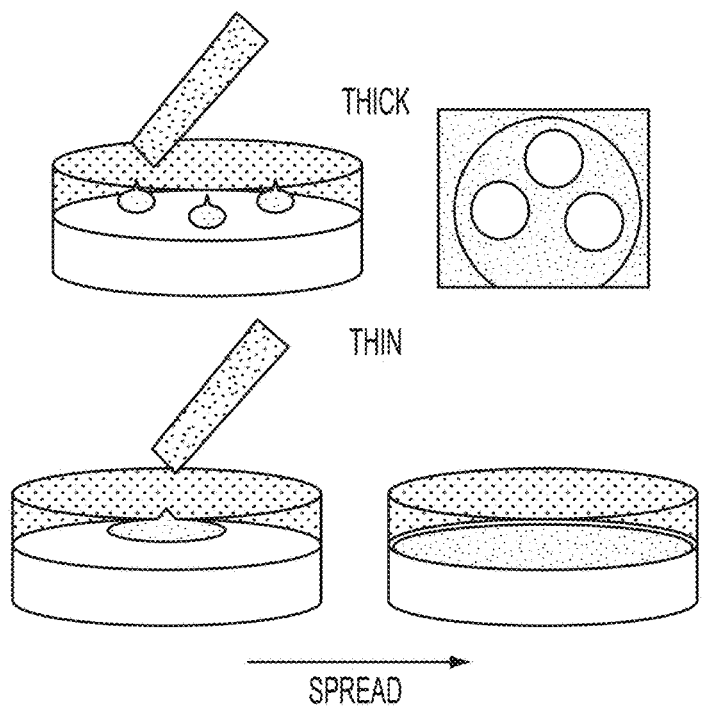
FIG. 15 is a schematic diagram showing preparation of thick and thin silk films. Silk fibroin solutions produced from various cocoon boiling times (10-60 minutes boiling, MB) were purified in parallel, each diluted to 4% wt/v in concentration, and 1.5 mL cast as either thick films (3×2.5 cm diameter casting surface) or thin films (7.5 cm diameter casting on 3× surfaces). Thin films were generated by spreading the 1.5 mL volume as widely as possible, using a pipette tip.

Silk matrices were prepared using the ~10-60 minute-boil (MB) solutions by either film casting or lyophilization methods. 60 MB solutions were also autoclaved using standard 20-minute autoclave conditions as sterilized alternative. Silk films were created by pipetting 4 wt/v % silk solution onto polydimethylsiloxane (PDMS) surfaces in triplicate. Thin films were designed to be as spread as possible on the PDMS surface while still allowing for removal as a continuous film structure. Conversely, thick films were designed as thick as possible under routine pipetting procedures. These two film casting procedures represent practical scenarios one encounters when pipetting samples in multi-well plates, petri dishes, or potentially in field conditions. The casting techniques are shown diagrammatically in FIG. 15.

For lyophilized foam samples, 1.5 mL of 4 w/v % solutions and a VirTis Genesis 25 L Super XL Freeze Dryer was used, utilizing a protocol previously described to stabilize monoclonal antibodies in silk foams (Guziewicz et al., 2011). Samples were first frozen at −20° C. and in a standard lab freezer, then the lyophilizer was used to continue to cool samples to −45° C. before initiating primary drying (vac 100 mT, −20° C.). Half the samples were completed at this point, while half were exposed additionally to secondary drying (vac 100 mT, 35° C.) in an attempt to remove any remaining bound water from the silk.

In the case of both silk films and lyophilized foams, samples were removed at designated time points day 0, 6 months, and 1 year pending) after being held at different storage temperatures (4° C., 25° C., 37° C.). Silk films were cut up and weighed to 40 mg samples using an analytical balance. Silk foams were pulverized using an analytical mill for 15 seconds, and weighed to 15 mg samples using an analytical balance. In both cases, a 60 mg starting mass was assumed per sample. All samples were mixed with 1 mL of ultrapure water (UPW), vortexed for 10 seconds, and centrifuged for 10 minutes at 1000×g in 2 mL Eppendorf tubes. In order to assess re-solubility, 250 μL aliquots were removed and cast onto additional PDMS surfaces for measurement of silk w/v % as had been conducted to assess initial silk concentration.

Results and Discussion

Figure 16:
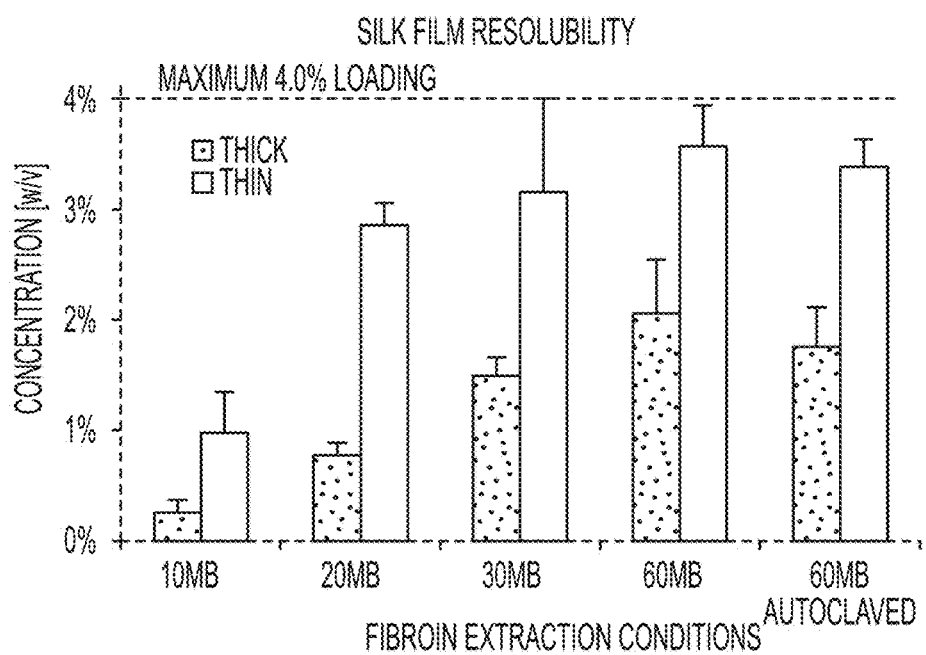
FIG. 16 is a bar graph showing optimization of silk films for complete dissolution. Silk fibroin solutions produced from various cocoon boiling times (10-60 minutes boiling, MB) were cast as either thick films (2.5 cm diameter casting surface) or thin films (7.5 cm diameter casting surface). After air drying overnight, 40 mg coupons of each film were then re-solubilized in 1 mL of deionized water and the wt % of the resultant solution measured. The dotted line indicates the maximum w/v % concentration possible based on complete theoretical solubility (4%).
Figure 17:
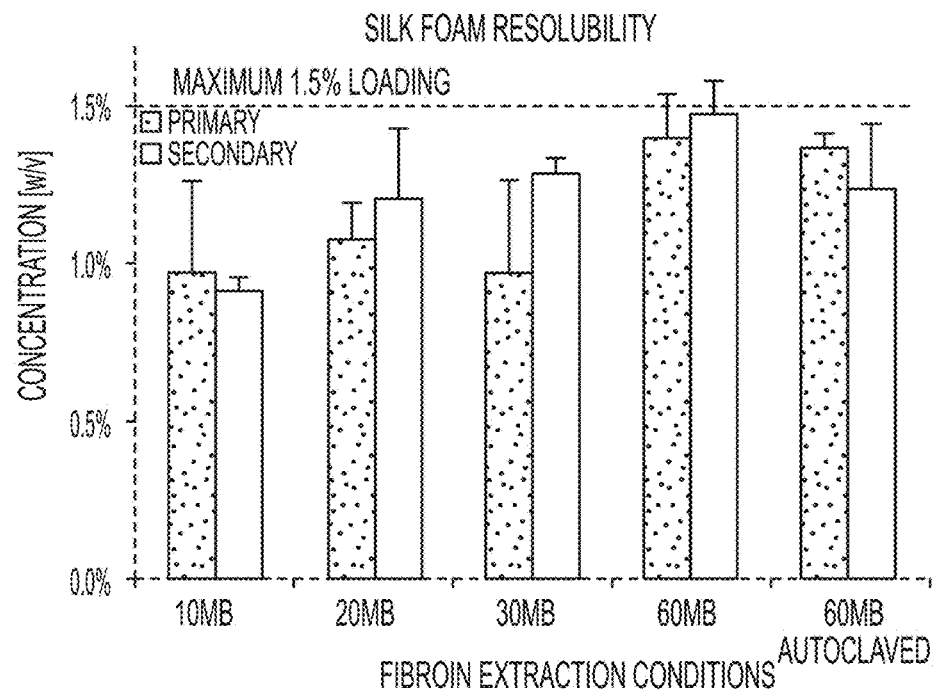
FIG. 17 is a bar graph showing optimization of silk foams for complete dissolution. Silk fibroin solutions produced from various cocoon boiling times (10-60 minutes boiling, MB) were lyophilized using a primary or primary+secondary drying protocols. After completion of the lyophilization cycle, 15 mg pulverized powder of each foam was then re-solubilized in 1 mL of deionized water and the wt % of the resultant solution measured. The dotted line indicates the maximum w/v % concentration possible based on complete theoretical solubility (1.5%).

Before encapsulating biologics, it was sought to identify silk purification techniques and construct preparation methods that can yield a fully-dissolvable silk-based material format. As shown in FIGS. 16 and 17, by boiling the silk cocoons for increasing times (≤60 minutes) at the onset of the purification scheme, the solubility of the films and foams can be effectively increased, respectively.

Figure 18:
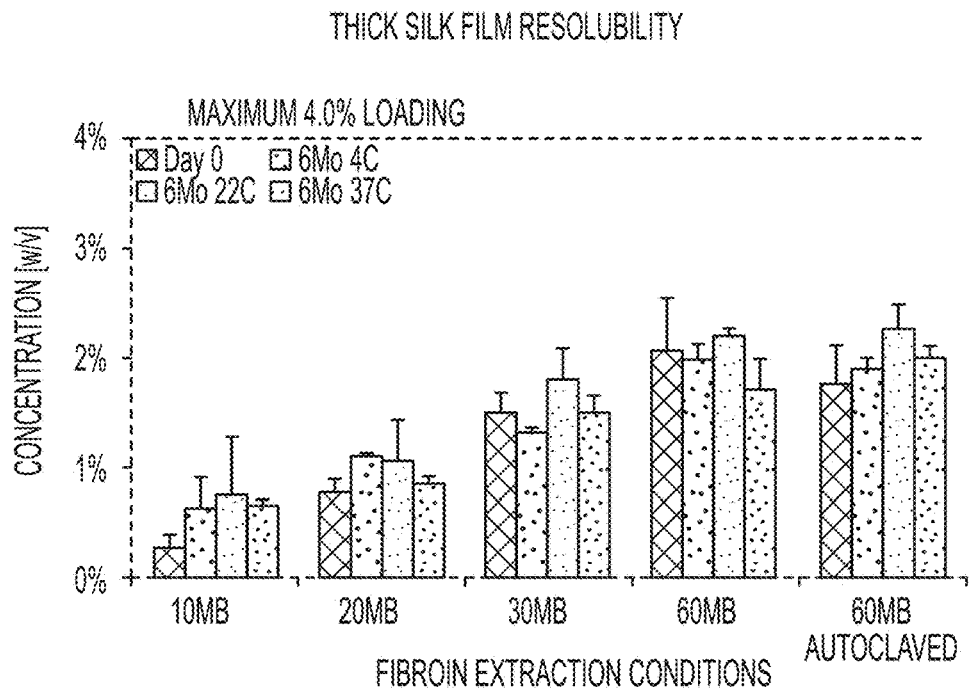
FIG. 18 is a bar graph showing thick silk film solubility in simulated aging conditions. Films of varied boiling times (60 MB films also formed from autoclaved solutions) were held at 4° C., 22° C., and 37° C. for 6 months prior to dissolving 40 mg of sample in ultrapure water (UPW), as compared to data from FIG. 16 (Day 0). The dotted line indicates the maximum w/v % concentration possible based on complete theoretical solubility (4%).
Figure 19:
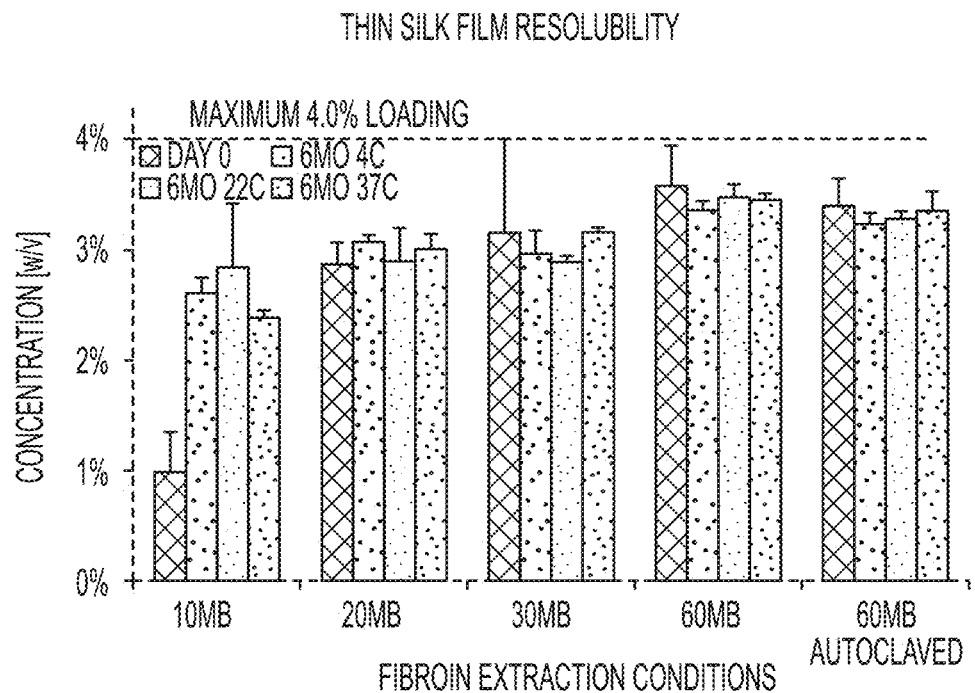
FIG. 19 is a bar graph showing thin silk film solubility in simulated aging conditions. Thin films of varied boiling times (60 MB films also formed from autoclaved solutions) were held at 4° C., 22° C., and 37° C. for 6 months prior to dissolving 40 mg of sample in UPW water, as compared to data from FIG. 2 (Day 0). The dotted line indicates the maximum w/v % concentration possible based on complete theoretical solubility (4%).

The solubility of the thin and thick silk films was also compared after 6 months of storage at various temperature conditions as shown in FIGS. 18 and 19. This finding shows that the solubility characteristics of silk films are very stable, independent of boil time, and that these features will not compromise the ability to recover entrapped biologics if high boil times are selected for use in the field.

After assessment of the behavior of the reconstituted silk fibroin materials, regarding solubility and temperature stability, some practical considerations are summarized below:

Samples formed into solid matrices such as films and foams (or powders thereof) can be utilized as shelf-stable silk formulations for distribution and/or use on-demand, and they are generally much more stable than silk in solutions form (which generally has a 3-4 months shelf life before gelation). Furthermore, solid matrices are much more resilient in the case of long-range shipment conditions, which often encounter agitation in addition to fluctuating temperature profiles.

Long-term temperature stability can be desirable for field condition where the silk material is used as an entrapping matrix and recovery of analytes is, in part, dependent on sustained solubility characteristics.

The solubility of silk in the presence of or in a mixture with other entrapped materials can depend, e.g., on the ratio of entrapped biologic to silk, the type of entrapped material (e.g., but not limited to, urine, blood, feces, cerumen, purified or non-purified DNA/RNA/antibody, therapeutic, etc), and/or buffers/excipients typically employed in aiding in stabilization of these biologics.

Solubility of the silk-based materials or matrices can be optimized, for example, by: decreasing a film or foam's loading in water (e.g., lower than 4% or lower than 1.5% w/v, respectively). While the inventors have used these values for this study, saturation of loading can used for optimizing solubility.

Means of accelerating the rate of drying of the film, e.g., either by forced air, decreased humidity (lower than ambient), increased temperature, etc. Without wishing to be bound by a theory, it is believed that this mechanism is likely, in part, responsible for thin film solubility improvements seen here.

Lyophilization conditions to improve foam quality and/or decreasing time of exposure to conditions which might induce crystallinity in the silk-based material.

Higher boiling times than 60 minutes or methods to selectively remove high molecular weight fractions of the silk (e.g., heavy chain and/or long hydrophobic sequences) during purification via enzymatic digestion, filtration, chromatography, etc.

Means of sterilization, including, e.g., autoclaving and sterile filtration, which can serve to continue to decrease molecular weight and/or remove insoluble particulates.

Example 6

Stabilization of Whole Blood and Plasma in Silk Fibroin-Based Materials

In the application space of diagnostics, it is desirable to demonstrate that the solubility-optimized silk matrices can be further used to stabilize human whole blood and blood components over long durations and in the context of adverse environmental conditions. To this end, the inventors first conducted preliminary studies in order to demonstrate the breadth of clinically-relevant analytical tools that could be used to measure the relative abundance of plasma and blood proteins from a range of donors once recovered from a particular format of reconstituted silk. These measures should be consistent with measurements performed on donor-matched fresh or frozen plasma, which is the format currently used for clinical workups. In order to demonstrate this functionality, plasma was isolated from donor venous blood, and volumes of either whole blood or plasma (in a volume equivalent to a blood prick) were entrapped in silk fibroin. The silk/blood or silk/plasma complex matrices were then allowed to air dry. These matrices were then re-solubilized in buffered saline solution and analytes recovered in solution state.

A standard ELISA well-plate methodology was initially employed to demonstrate an immune-affinity-based technique to identify markers in blood apart from the silk protein or, conversely, to identify certain markers that could be compromised due to silk interference. The ELISA results were then compared to a high-throughput approach for biomarker quantification. In particular, the Luminex™ platform was used as a high-throughput method, as it employs similar antibody-based detection but with the ability to multiplex multiple tags simultaneously in the same sample. In principle, the Luminex™ approach allows for more analytes to be detected, with fewer samples required. In turn, this sample multiplexing enables more rapid detection of diseases (e.g., but not limited to, cardiovascular disease, CVD) where many complementary and confirmatory biomarkers are required for confidence to diagnose. Additionally, these experiments address an issue of practical importance, e.g., whether the presence of a stabilization matrix (e.g., remnants from the solubilized silk film) can compromise utility of the Luminex™ platform because of potential clogging of the fluidics employed by the high molecular weight protein residues.

To perform the experiments as described above, fresh donor blood (Vacutainer tubes, Na-heparin anticoagulant, Research Blood Components, Brighton, Mass.) was delivered from three separate donors within 1 hour of draw. Tubes were then immediately centrifuged at 1000×g for plasma isolation. Plasma aliquots were then immediately frozen to serve as positive controls. Silk solution was prepared from the cocoon of the silkworm Bombyx moni previously described (Lu et al., 2010). Silk films were cast onto polydimethylsiloxane (PDMS) surfaces, in which 100 µL of either blood or plasma from each of the 3 donors was mixed with 1.9 mL of silk solution (7.6 wt % in water) prior to casting over a large surface (8.5 cm diameter petri dish) for purposes of air-drying. After the films dried overnight (8 hrs), samples are punched out for analysis. For example, 10 mg and 40 mg coupons were prepared from the plasma and blood films for ELISA readings to tune the mass loading required for analysis within the standard curves. For all ELISAs (R&D Systems), frozen plasma aliquots were diluted 1:10 and 1:100 while the dissolved blood and plasma in silk-based films were tested without dilution.

TABLE 4

ELISA Markers, Protein Characteristics, and Detection Limits

| R&D Systems # | Protein | Mw | ELISA Std [pg/mL] | Tissue Subtype/ Disease |
|---|---|---|---|---|
| DLP00 | Leptin | 16 kDa | 1,560-100,000 | Diabetes, Stress |
| DCRP00 | C-reactive protein | 118- | 78,100-5,00,000 | CVD, Diabetes |
| DTSP10 | Thrombo-spondin-1 | 150 kDa | 781,000- | Cardiovascular Disease |
| DSE100 | PAI-1 | 45 kDa | 31,200-2,000,000 | Breast Cancer, Asthma |

# = cross-referenced with Luminex results

High-throughput analysis (e.g., using Luminex™ CVD kits, Table 5 below) were performed on dried film samples and plasma aliquots. The Luminex™ assay was run in according to manufacturer instructions (EMD Millipore Corporation, Billerica, Mass.), which required dilution of the frozen plasma aliquots (1:2,000 and 1:20,000) to fall within standard curve detection limits. The 20 mg blood and plasma coupons were each placed in 1 mL Phosphate Buffered Saline (PBS), vortexed for 15 seconds, then allowed to sit for 2 minutes in order to visually confirm dissolution. Similar to the plasma aliquots, dissolved blood and plasma in silk-based coupons (and blank silk controls) were diluted 1:200 and 1:2,000 in kit reagents to account for the potential recovery based on previous findings with the silk film formats.

TABLE 5

Luminex™ Markers, Protein Characteristics, and Detection Limits

| Luminex kit # | Protein | Mw | Luminex Std | Disease Marker |
|---|---|---|---|---|
| HCVD3-67CK-02 | Serum Amyloid P | 25 kDa | 80-250,000 | Diabetes |
| HCVD3-67CK-02 | C-reactive protein | 118- | 80-250,000 | Inflammation, CVD |
| HCVD2-67BK- | Haptoglobin | 43 kDa | 80-250,000 | Hemolytic Anemia |
| HCVD1-67AK-02 | tPAI-1 | 45 kDa | 16-50,000 | Breast Cancer, |
| HCVD1-67AK-02 | sVCAM-1 | 100- | 80-250,000 | CVD |
| HCVD3-67CK-02 | Fibrinogen | 340 kDa | 80-250,000 | Inflammation, CVD |

_ = cross-referenced with ELISA results

Calculating Recovery of Plasma and Blood: In order to accurately convert the values of the recovered proteins from the blood and plasma coupons to the concentrations found in the donor-matched plasma, and thus determine the recovery efficiency, several physical measurements of the blood and plasma were first made, as described above in Example 2.

Statistics for Luminex™ Assay Results: A two-way ANOVA was run in order to compare the sources of sample variance between two sets of independent variables: i) the levels of blood or plasma detected across the three donors and ii) blood or plasma coupon recovery compared to the theoretical coupon recovery as calculated from readings taken of frozen plasma aliquots. Sample variance was calculated based on triplicate readings from the Luminex™ assay, and this error was carried across coupon recovery calculations without adjustment to the variance in physical parameters such as blood and plasma wt fraction. A finding was considered significant at a P value<0.05.

Figure 20:
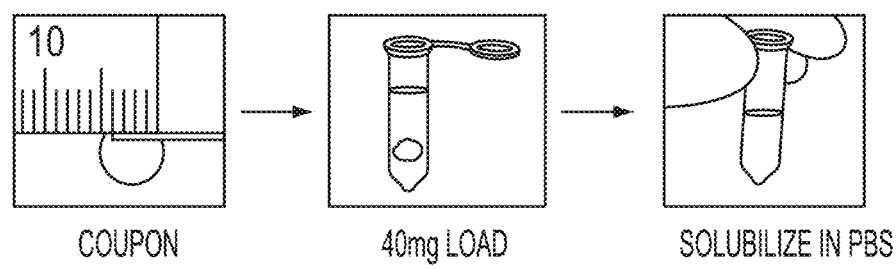
FIG. 20 is a set of photographs showing film preparation and film dissolution according to one embodiment described herein.

These findings indicated that thin films (cast across the entire surface of a PDMS-coated 8.5 cm petri dish) formed from silk boiled for 30 minutes can be ideal for an application where complete solubility is desired. The films formed from silk/blood and silk/plasma mixing resulted in formats that were easily solubilized for further analyses (see FIG. 20). Up to 40 mg of dry matrix was used in this format.

ELISA Results: Recovered liquid aliquots were then tested by ELISA following manufacturer protocol for human plasma (R&D Systems, Table 4 above). Plasma samples from donor-matched blood were diluted 1:10 and 1:100 in PBS, following instructions by the manufacturer, and these used to determine the recovery efficiency from the silk coupons.

Figure 21:
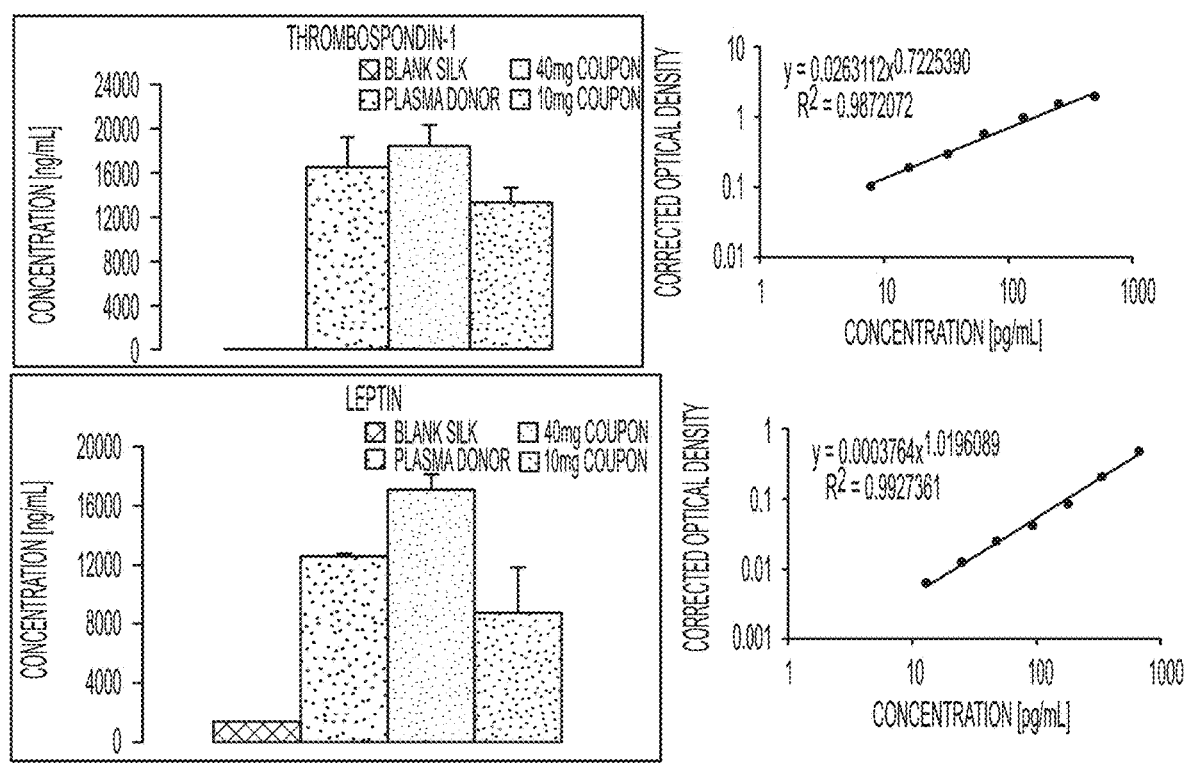
FIG. 21 is a set of data graphs showing measurements of biomarkers by ELISA recovered from blood-stabilizing silk films. Silk solution generated from 30 MB fibroin was formed into films after mixing with whole blood and later air dried at "thin" samples. Coupons weighing 10 mg or 40 mg were dissolved in 1 mL PBS (1% and 4% w/v loading, respectively) and concentration conversions were based on theoretical loading amounts (50 µL in 1 mL blood:silk ratio). Assay standard curves shown to the right. Blank (non-loaded) silk films were also used as a negative assay control.

The graphs in FIG. 21 show that the ELISA kits were able to detect clinically-relevant quantities of selected biomarkers in a range of molecular weight (16-150 kDa) and at range of concentration (5.91 ng/mL-16.7 mg/mL). Notably, these values are consistent with donor profile (Asian, female, 25 yrs of age, asymptomatic), including high Leptin levels and low CRP levels (Table 6), indicating the accuracy of the assay and proper preparation of plasma. More importantly, the values from samples recovered after silk mixing, drying, casting, and re-solubilization were similar to the direct measurements of donor plasma. In cases where both a ~10 mg and ~40 mg coupon (n=6 assay measurements each) resulted in values that fell within the assay standard curve, the mean of the 10 mg and 40 mg groups were averaged and normalized to the theoretic loading values to calculate the % recovery (summarized below in Table 6). For CRP and Serpin E1, only the 40 mg coupons released sufficient blood to fall in the detectable range of the ELISA, and thus % recovery is reported for a single film mass.

TABLE 6

Summary of ELISA Results

| Protein | Mw | Plasma Values (R&D) (ng/mL) | Donor ELISA Values (ng/mL) | % Recovery Silk Films |
|---|---|---|---|---|
| Leptin | 16 kDa | 3877-77,273 (♀) | 12,628.87 | 101.91% (10 mg + 40 mg) |
| C-Reactive Protein | 118-144 kDa | 108-4523 | 233.88 | 53% (40 mg) |
| Thrombo-spondin-1 | 150 kDa | 8,794-28,335 | 16,680.25 | 95.74% (10 mg + 40 mg) |
| SerpinE1, PAI-1 | 45 kDa | 0.98-18.7 | 5.91 | 142.66% (40 mg) |

Figure 22:
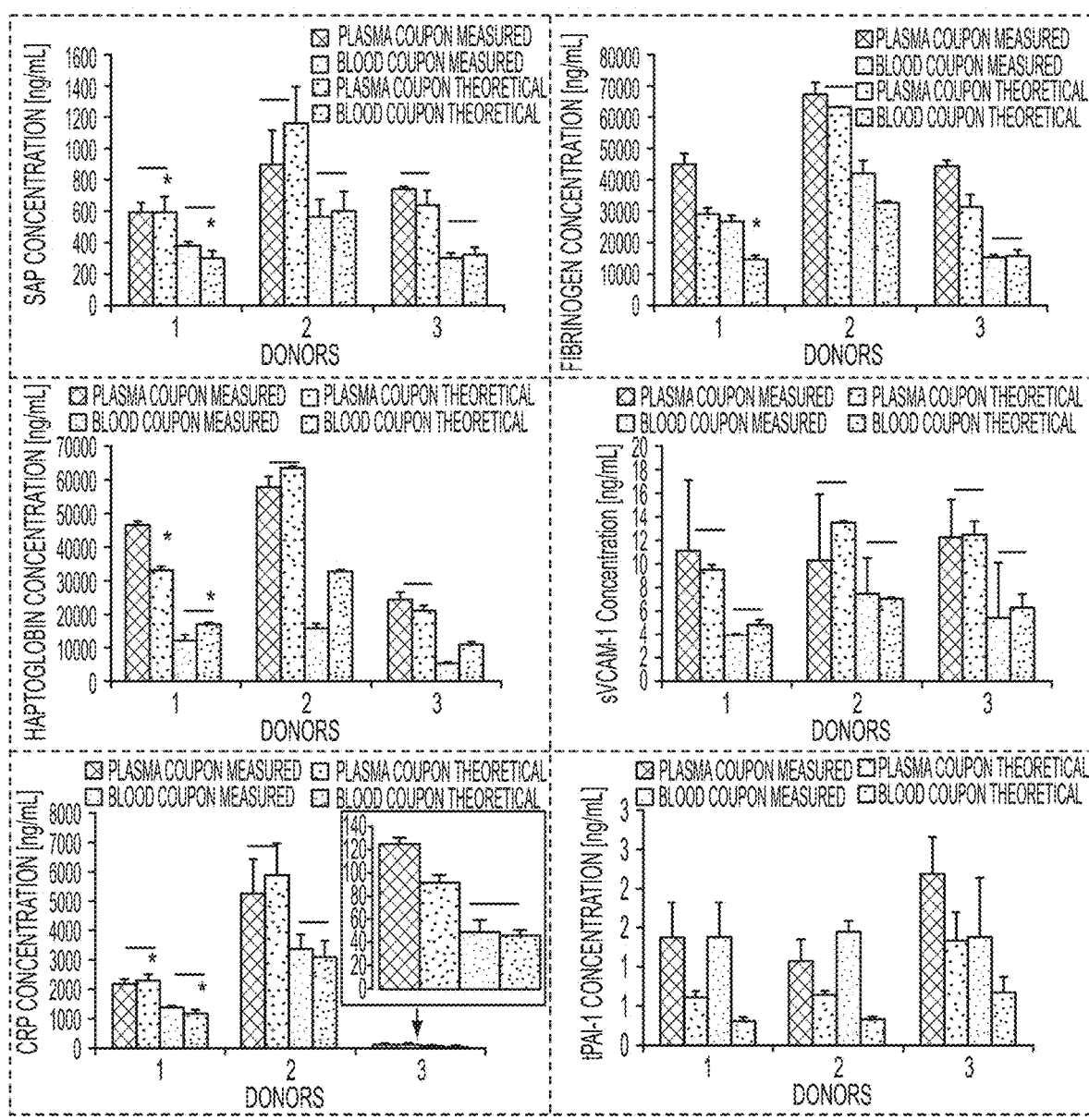
FIG. 22 is a set of data graphs showing measurements of various biomarkers by Luminex™ recovered from blood- and plasma-stabilizing silk films. Silk film coupons weighing 20 mg were dissolved in 1 mL PBS and 25 µL aliquots run on a Luminex 200™ instrument using 3 separate CVD biomarker kits. Samples (Plasma Coupons and Blood Coupons Measured) were taken after 1:200 and 1:2000 dilutions and compared to frozen donor-matched plasma aliquots after 1:2,000 dilution. Internal standards provided absolute quantitation and conversions necessary to calculate plasma and blood coupon theoretical loading amounts were based on the above calculations. Blank (non-loaded) silk films were also solubilized and used as a negative assay control. All samples were run in triplicate and average±SD shown. * indicates significant differences detected when compared to donors 2 & 3 (at p<0.05 level). Bars indicate agreement between calculated loading values based on frozen plasma aliquots and matched coupon recoveries.

Luminex Experiments: The Luminex™ system was run on 6 markers across three different kits and between three different donor blood samples, and results of these assays are shown in FIG. 22.

Prior to entrapment in the silk films, differences in the physical appearance of blood from the three donors were observed—after venous draw and transportation, donor 3 showed obvious signs of hemolysis (i.e. a reddening of the isolated plasma and RBC smearing on the inside of the Vacutainer tube). The Luminex assay appeared sensitive to both variations between donors and to the relative amounts of blood proteins isolated from whole blood vs. proteins isolated from purified plasma across all donors. All values for theoretical and measured plasma were approximately 60-100% larger than the actual blood concentration (due to the removal of the cellular fraction).

The two-way ANOVA indicated a significant (and in most cases highly significant) variation between donors for both blood and plasma comparisons as measured by the Luminex system, with the exception of the sVCAM marker for blood and plasma coupons and the tPAI-1 markers for the blood coupons. This was due partly to the sensitivity of the tPAI-1, sVCAM-1, and Haptoglobin assays and the standard curves employed. For instance, donor 2 had plasma Haptoglobin levels that exceeded the highest assay standard [50 ng/mL], even for a 1:20,000× dilution, making theoretical comparisons less accurate. Conversely, detection of sVCAM-1 and tPAI-1 suffered from a low-end sensitivity problem, whereby all plasma values at the 1:20,000× dilution were at or below the lowest assay standard (0.08 and 0.016 ng/mL, respectively); this, in turn, led to difficulty in quantifying coupon recovery with high confidence (CV values >20% for most donors and coupon types). The lack of any measurable background from the silk indicates that silk protein does not interfere with the Luminex™ instrument.

Two of the markers in the CVD panel, namely SAP and CRP, showed excellent agreement between theoretical loading levels (based on frozen plasma aliquots) and the levels recovered from the blood and plasma coupons (with silk fibroin). In the case of these two markers, the two-way ANOVA resulted in significant sources of variation from donors but no significant differences between frozen plasma and either the blood or plasma coupons ($p<0.05$). The differences between donor Fibrinogen and Haptoglobin levels were also far greater than the respective differences between matched blood and plasma coupon levels, as the donor differences accounted for >60% of the variation in the sample sets. These findings corroborate the earlier results with the ELISA kits, indicating adequate recovery of the analytes provided by the casting/drying/resolubilization methodology. Furthermore, the CRP test in particular showed excellent fidelity between coupons and frozen plasma controls, despite the donor levels ranging over 2 orders of magnitude. The above issues with the sVCAM-1, tPAI-1, and Haptoglobin assays reduced our ability to detect differences between donors; therefore, in these three cases, the variation from donor-donor differences were not considered statistically more significant contributors to the overall sample variation than the fidelity between plasma and frozen aliquots. Taken together, these six different CVD markers demonstrated that, while some donor-level calibration is necessary, the Luminex platform can be used for stabilized blood detection in our silk system.

Figure 23:
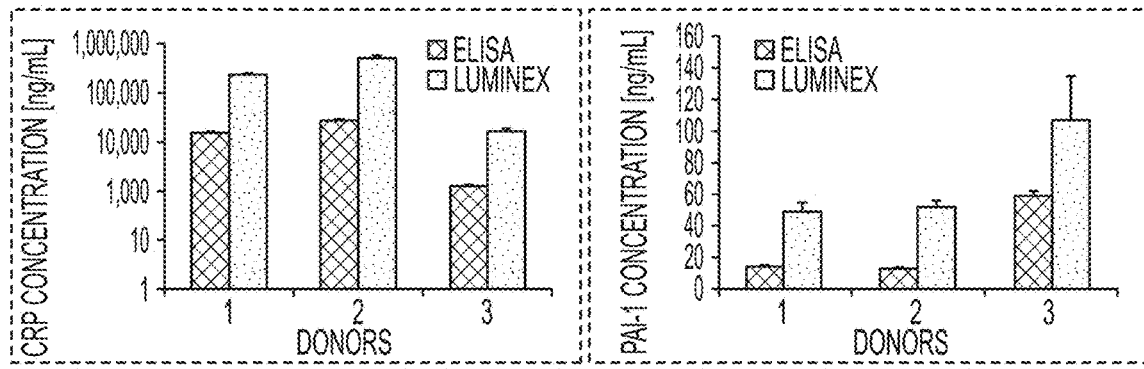
FIG. 23 is a set of bar graphs comparing plasma concentrations determined by Luminex and ELISA assay formats. Frozen plasma aliquots were run on the Luminex 200 system and Millipore EMD CVD1 panel at a 1:200× dilution (see Table 5) and were run on ELISA kits produced by R&D Systems (see Table 2) at a 1:10× dilution in order to compare absolute detection levels. Note the log axis used for the CRP assay (left) and the linear axis used for the PAI-1 assay (right).

When the absolute levels of plasma calculated from the ELISA format were compared to the Luminex format, lower concentration for all markers using ELISA was consistently found, as compares to the Luminex assay (see FIG. 23). These differences were observed independent of the markers used (CRP and PAI-1 are shown as examples) and the position along the dynamic range of each assay (from 10-100,000 ng/mL). The differences observed between ELISA and Luminex varied in magnitude depending on the analytes (e.g., 10-fold differences for CRP but only 2-3-fold differences for PAI-1).

Surprisingly, the greatest differences was found across all markers between the plasma isolated from donors 1 and 2 and the hemolyzed plasma from donor 3, and this was strikingly so for CRP. The physiological role of CRP is to bind to phosphocholine expressed on the surface of dead or dying cells or the their nuclear components in order to activate the complement system (Chang et al., 2002); therefore, it is possible that disruptions to the cellular fraction (WBCs or RBCs) upon drawing blood caused CRP to associate with the cell lysate that was pelleted during plasma preparation, and thus was unavailable for detection in the plasma. However, since the blood coupons also showed very low CRP levels, it is also possible that in vitro damage to RBCs during draw or handling caused an overall dilution of CRP levels for the donor, or simply that donor CRP levels were intrinsically low. The ELISA screen for CRP confirmed the low values corresponding to donor 3 as reported by the Luminex kit as shown in FIG. 22. Additionally, the ELISA results indicated that donor 3 contained high lipid levels from the two-fold increase in Leptin as compared to donors 1 and 2 (data not shown). Without wishing to be bound by theory, lipolysis can be a source of inaccurate CRP readings by ELISA methods (Martinez-Subiela and Ceron, 2005), whereby doping of virgin plasma with various lipids such as bilirubin resulted in dose-dependent decreases in measured CRP.

Figure 24:
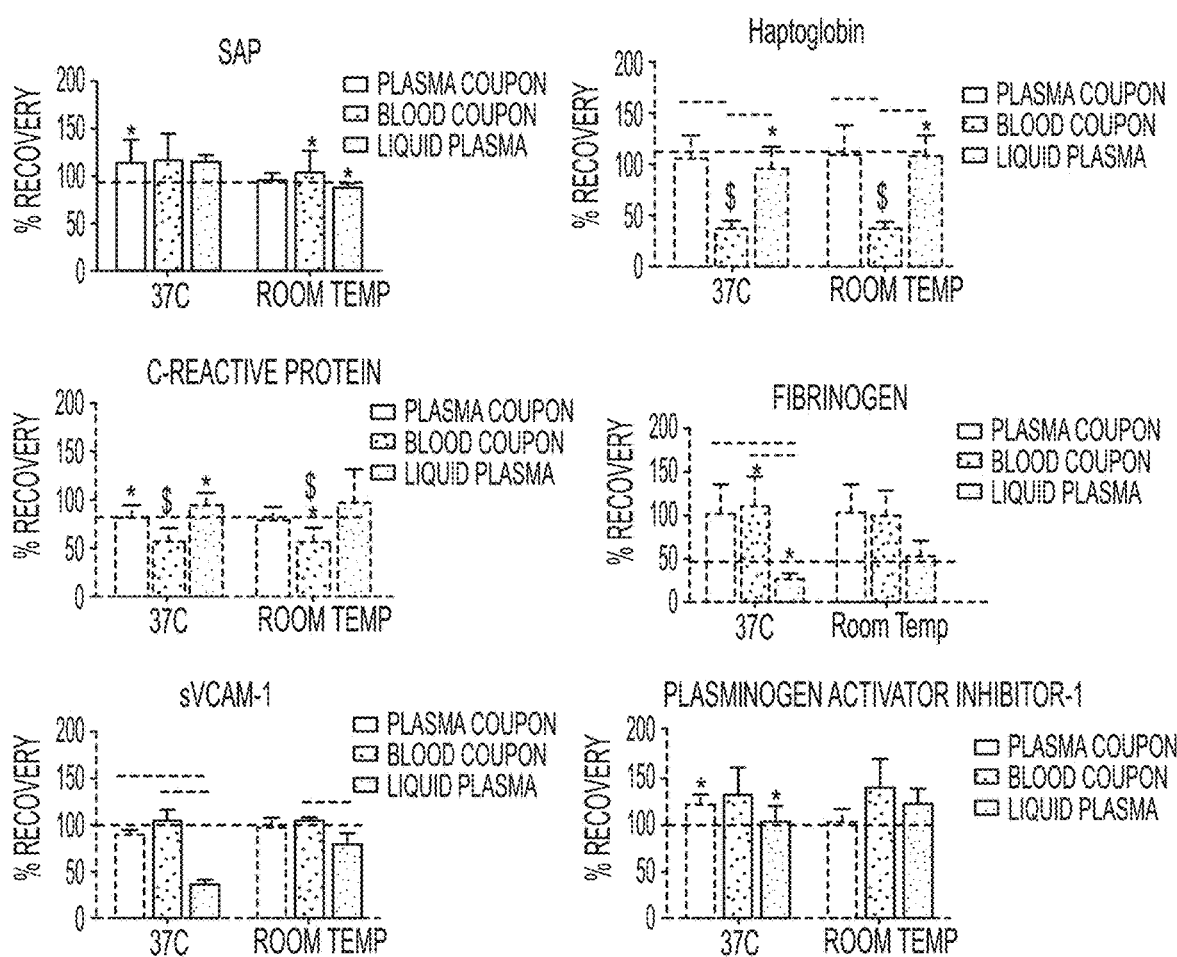
FIG. 24 is a set of bar graphs showing percents of recovery of various biomarkers, as determined by Luminex™, from blood- and plasma-stabilizing silk films at Day 30 after exposure to different temperatures. Silk film coupons weighing 20 mg were dissolved in 1 mL PBS, and 25 µL aliquots run on a Luminex 200™ instrument for N=3 donors. Liquid plasma aliquots stored at the same conditions were similarly analyzed. Internal standards provided absolute quantitation and conversions necessary to calculate plasma and blood coupon theoretical loading amounts were based on previous calculations (April Report). The three donor % Recovery values were averaged and ±SD shown. % Recovery defined by analyte level divided by day zero plasma levels×100%. Bars indicate significant differences between groups (at p<0.05 level). Dotted line indicates −20 C stored day 30 values. $ indicates coupon levels that deviate from 100%. * indicates % CV values in the range 20-30% from the Luminex system.

Time Course Results: The Luminex™ system was run on 6 markers between three different donor blood samples, after being stored for 30 days at 37° C. or room temperature, and results of these assays are shown in FIG. 24. Similar trends at day 30 as observed originally at day zero were determined (FIG. 22). The Luminex™ assay was sensitive to both variations between donors and to the relative amounts of blood proteins isolated from whole blood vs. proteins isolated from purified plasma across all donors (data not shown). In some embodiments, the tPAI-1 and VCAM-1 markers were detected by reducing the amount of dilution of those samples. Some background from the blank silk controls in the tPAI-1 assay was determined, indicating that some cross-talk between the antibodies used for this marker, which is exacerbated with such low analyte levels. The baseline silk film negative controls were subtracted from all film-containing samples in the case of tPAI-1, but nonetheless the coupon tPAI-1 levels were still inflated compared to the 100% baseline.

All values of analytes measured from coupons and converted to theoretical loading levels indicated complete 100% recovery, except for the blood coupon measurements for CRP and haptoglobin. The possible biological basis for these discrepancies was discussed above. The two-way ANOVA indicated significant (and in some cases highly significant, $P<0.01$) variance between the different storage formats. Specifically, fibrinogen and sVCAM-1 levels measured from silk-based coupons appeared insensitive to the storage conditions, whereas the respective liquid plasma levels decreased, and significantly so at 37° C.

As shown in FIG. 24, the frozen plasma aliquot levels measured at day 30, as indicated by the dotted grey line on each graph therein, did not always match the day zero baseline values. Specifically, while CRP levels were 80% of day zero baseline, fibrinogen levels were only 48% of their respective baseline. This indicates a significant degradation of fibrinogen using the gold standard freezing/thawing technique, which appears to be avoided using the film stabilization technique. Indeed, previous reports have indicated that small precipitates can form in plasma isolated from heparinized blood at frozen at temperatures below −80° C. (for instance the −20° C. conditions used herein), and that this is a major contributor to the loss of viability/recoverability of clotting factors in general (Palmer et al., 1993). This behavior is underscored by the degradation of the corresponding fibrinogen markers taken from liquid plasma levels at room temperature and 37° C. Susceptibility of fibrinogen and other clotting factors can be evaluated as a function of the choice of anticoagulant used and storage temperature in comparison to the silk systems.

Figure 25:
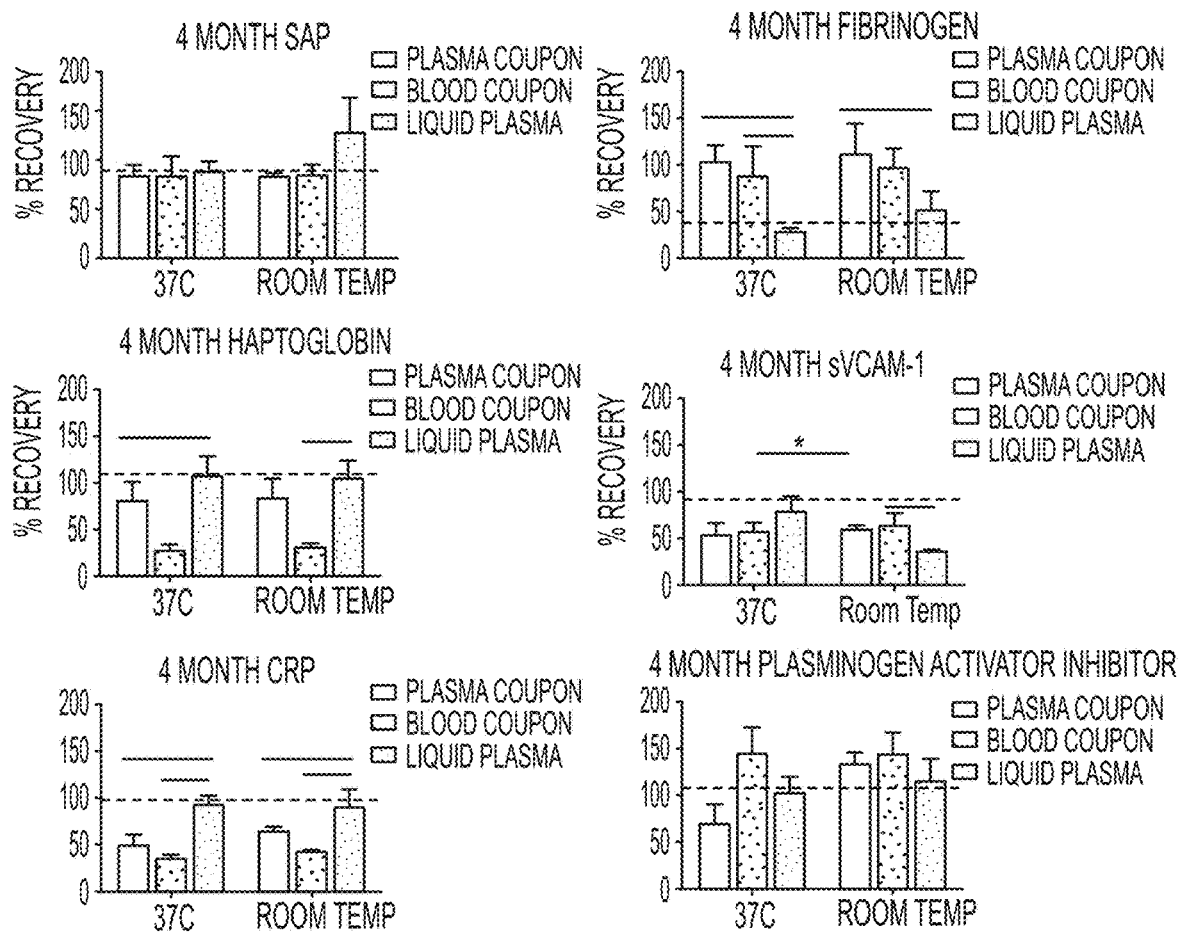
FIG. 25 is a set of bar graphs showing percents of recovery of various biomarkers, as determined by Luminex™, from blood- and plasma-stabilizing silk films at 4 months after exposure to different temperatures. Silk film coupons weighing 20 mg were dissolved in 1 mL PBS, and 25 µL aliquots run on a Luminex 200™ instrument for N=3 donors. All conditions are the same as at day 30. Liquid plasma aliquots stored at the same conditions were similarly analyzed. Internal standards provided absolute quantitation. The three donor % Recovery values were averaged and ±SD shown. % Recovery defined by analyte level divided by day zero plasma levels×100%. Bars indicate significant differences between groups (at p<0.05 level). Dotted line indicates −20 C stored day 30 values. $ indicates coupon levels that deviate from 100%. * indicates % CV values in the range 20-30% from the Luminex system.

At 4 months (FIG. 25), protein marker levels recovered from the silk systems were diminished in many cases, but still showed significant performance enhancement over gold standard cold storage conditions for fibrinogen and maintenance of very high levels for other markers such as SAP.

Example 7

Stabilization of RNA in Silk Fibroin-Based Materials

This Example shows that RNA can be entrapped and recovered in a lyophilized silk solution without loss of function. A series of experiments were performed to establish optimal solution conditions in order to maximize recovery of RNA. For example, Green Fluorescent Protein (GFP)-encoding mRNA was mixed with silk solutions which underwent a 3-day mixing, lyophilization, and recovery protocol. Following this protocol, mRNA was recovered by re-solubilization in ultrapure water, and an RNA-specific fluorometric assay used to quantitate encapsulation and recovery efficiency. Furthermore, the incorporation of a commercially-available RNAse inhibitor was employed in order to mitigate damage to the RNA in the solutions while undergoing to the lyophilization protocol. Using these inhibitor/silk systems, the retention of RNA function after retrieval from the silk was assessed by transfecting a model cell line with the recovered fraction of mRNA molecules. In some embodiments, the methods and/or compositions described herein can remain stable over longer (e.g., 30-120 day) time frames.

To perform the experiments, GFP-encoding RNA was purchased from a commercial source (Stemgent® eGFP mRNA, www.stemgent.com/products/show/222). This RNA sequence was originally developed by Warren et al to provide a simple, non-integrating (i.e. non-viral or DNA-based) strategy for reprogramming cells based on administration of synthetic RNA modified to overcome innate antiviral responses (Warren et al., 2010). The sequence contains 3 important components: i) a 5' guanine cap for improved stability in cell cytoplasm, ii) a strong Kozak consensus sequence to initiate translation and, iii) a terminating sequence required for mRNA polyadenylation. The GFP sequence is synthetically manufactured into this construct using in vitro transcription reactions template by PCR amplicons. The stock solution is sold by Stemgent® at a high concentration (100 jig/mL) and previous results from Warren et al suggest translation of sufficient GFP can occur in short time frames (8-12 hrs), making it ideal for encapsulation and retrieval studies requiring assays on RNA-specific function.

Silk solutions were prepared using 20 minutes of boiling and dissolving conditions (9.3M LiBr, dialysis against diH2O for 48 hrs) and final concentration was 6 wt % in ultrapure water assessed by drying a measured volume of solution. This solution was diluted to 2%, 1% or 0.5% wt/v using certified RNAse-free water. Tris-EDTA (TE) was added in order to generate a final working concentration 10 mM-1 mM, respectively. In some embodiments where the silk purification process cannot be used with DEPC-based RNAse treatments, e.g., due to the required autoclaving step that can alter the silk protein, other methods of eliminating the presence or activity of RNAse during mRNA handing can be used. For example, certified RNAse/DNAse-free pipette tips, tubes, and solutions were utilized as purchased from Ambion® and RNAzap was used on all external surfaces. 60 jig of stock GFP mRNA solution (supplied in 1×TE) was stored at −80° C. until use, at which point it was thawed on ice and then mixed as a final step in a v/v ratio 20jiL mRNA/80 jiL (silk+TE) solution in each container for a final mRNA concentration 20×10$^3$ ng/mL. The mRNA pipetting process lasted less than 5 minutes for all samples. Matched controls without mRNA loading were also prepared using blank 1×TE buffer. In addition, these conditions were fully replicated (silk alone and silk/RNA) with the addition of a SUPERase.In™ RNase Inhibitor (Ambion®) to further protect the RNA during handling.

Lyophilization of Silk/RNA Solutions: Following mixing steps, all 100 µL samples stored in 2 mL tubes were immediately transferred to a VirTis Genesis 25 L Super XL Freeze Dryer, utilizing a protocol previously described to stabilize monoclonal antibodies in silk foams (Guziewicz et al., 2011). Samples were placed with caps open on their sides to promote rapid drying, and tubes were in direct contact with a cooling plate to facilitate more accurate and homogeneous thermal regulation. The process initiates by ramping from −20° C. frozen conditions, in which the samples are slowly cooled on the plate to −45° C. over 63 minutes and held at that temperature for an additional 8 hrs before warming back to −20° C. Primary drying followed under 100 mT vacuum at −20° C. for 40 hrs to remove unbound water. The samples were warmed again to 35° C. and held for 620 minutes as a secondary drying phase to remove bound water. The samples were then stored at −4° C. at 800 mT pressure until the recovery protocol was initiated, typically 2-3 hrs.

Figure 26:
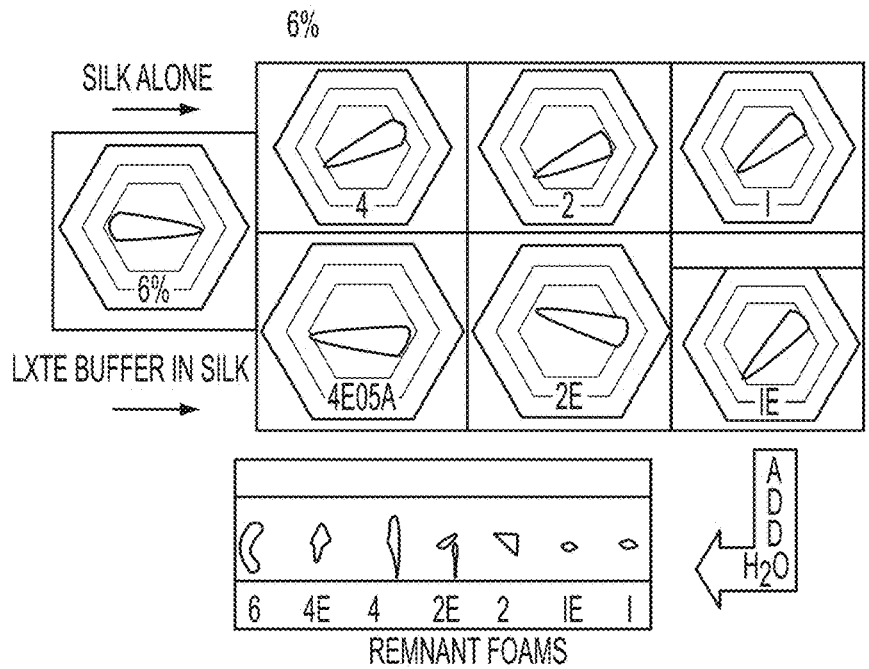
FIG. 26 is a set of photographs showing form and solubilization of lyophilized silk solutions. (Upper) Silk solutions formed from 20 MB silk fibroin, at concentrations from 6% to 1%, with or without TE buffer (EDTA), underwent lyophilization using primary and secondary drying. Solutions yielded shape profiles that matched their 1.5 mL storage conicals. (Lower) After water was added to the lyophilized solutions and mixed by vortexing, the silk re-solubilized, leaving behind small remnant foam fragments, the mass of which depended on the mass of silk loading.

Concentrations of silk solution (silk w/v 6-1%) were optimized such that silk fibroin-based materials can re-solubilize after the freeze-dry protocol. As shown below in FIG. 26, free-standing foams were generated from each solution, with or without EDTA (in TE buffer). Upon re-solubilizing in water, a small fraction of non-dissolved silk remnant was found with size dependent on the initial silk loading. The size/solubility, however, was not dependent on TE buffering. Based on these findings, 2% w/v were selected as a starting point to investigate concentration effects on solubility.

Recovery and Measurement of RNA Content: Following the screening study, 2%, 1%, and 0.5% silk solutions were selected as lead candidates for the RNA recovery study. Following the entrapment and lyophilization protocol described above, samples were removed from −45° C. lyophilizer storage conditions and immediately thawed on ice for 2 hrs (the duration of the assay preparation).

RNA Quantitation of Recovery: The Quant-iT™ Ribogreen® RNA Reagent and Kit were prepared according to manufacturer guidelines from the web at probes.invitrogen.com/media/pis/mp11490.pdf. Ribosomal RNA standard was used to generate the standard curve (ranging from 1000-7.8125 ng/mL) while the stock GFP mRNA stored at −80° C. was likewise thawed on ice, diluted 1:80, and used as an internal control to calibrate the results of the standard curve for the differing sequence biding to the Ribogreen reagent. The assay was run on a 96-well format requiring 25 µL per sample. After standards were prepared, lyophilized silk samples (and 0% controls) were removed from ice, 200 µL DNAase/RNAse free water added, vortexed for 15 seconds, and 25 µL of the sample immediately pipetted into each well (duplicate assay readings on N=3 biological replicates).

Transfection of Eukaryotic Cells Using Recovered mRNA: ~10 µL per sample was reserved immediately following re-solubilization of the silk/inhibitor complex in order to probe the stability of the recovered mRNA and potential for continued use as a translation template in vitro. Prior to recovery of the mRNA, 293 fibroblasts were seeded into 96-well plate at a density of $5 \times 10^4$ cells/cm$^2$ and allowed to adhere in the presence of 15% serum, 1% antibiotic/antimycotic in Dulbecco's Modified Eagle's Medium (DMEM, Invitrogen). Cells were maintained at 37° C., 5% $CO_2$.

Following manufacturer's recommendations, the Stemfect™ Transfection Kit was used according to published user protocols (Stemgent, www.stemgent.com/products/show/221). The Transfection Reagent was combined with the Transfection Buffer to generate as a stock solution, which was then split to 7.33 µL aliquots prior to combination with 10 µL of recovered mRNA. This Buffer/Reagent/mRNA solution was allowed to equilibrate for 15 minutes at room temperature before 15 µL was taken from each aliquot and added dropwise to an individual well in the 96-well plate. The cells were then returned to incubation as above for 12 hrs, at which point they were imaged on an Axiovert CFL fluorescent microscope with filters set for 488 nm (blue) excitation and 510 nm (green) emission.

Results and Discussion

Figure 27:
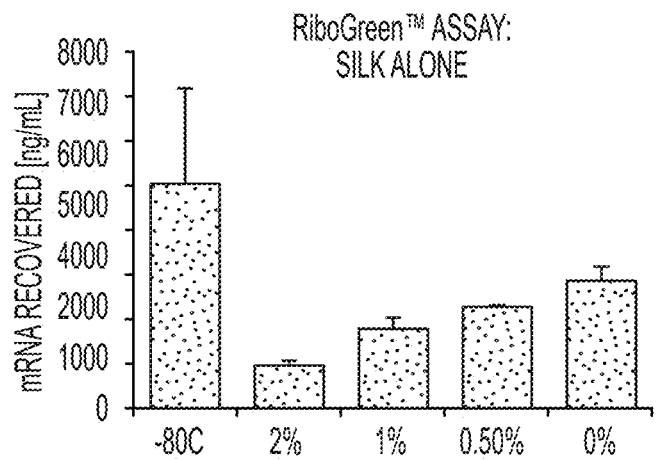
FIG. 27 is a bar graph showing mRNA recovery, as measured by RiboGreen™ assay, from lyophilized silk solutions at various concentrations. Silk solutions formed from 20 MB silk fibroin, ranging from 2% to 0.05% concentration as well as non-silk-loaded group (0%), were lyophilized using primary and secondary drying and resolubilized in ultrapure water prior to mixing with the RiboGreen reagent and fluorometric analysis. Recovered samples were compared to the frozen stock solution of mRNA (−80° C.). Duplicate assay reads were performed for every sample. Absolute quantitation was performed against standard curve generated by ribosomal RNA (provided by manufacturer) and data represents the average of N=3 samples±st dev.

The results of the initial study are shown in FIG. 27. The RiboGreen assay indicated both a small but significant background from the silk protein (fluorometrically active at 480 nm) apparent in the silk-only groups, as well as large readings from the recovered RNA in every group. The non-loaded groups were therefore used to normalize against the silk-RNA samples from every respective concentration. RNA recovered from the 1% and 0.5% groups were comparable to the non-silk 0% groups but all these lyophilized systems were far below the virgin frozen stock.

Figure 28:
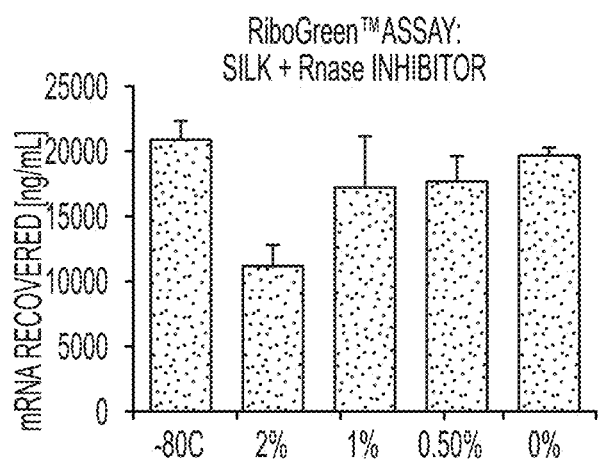
FIG. 28 is a bar graph showing mRNA recovery, as measured by RiboGreen™ assay, from various concentrations of lyophilized silk solutions containing an RNAse inhibitor. Silk solutions formed from 20 MB silk fibroin, ranging from 2% to 0.05% concentration as well as non-silk-loaded group (0%), were mixed with SUPERase*In™ RNase Inhibitor, lyophilized using primary and secondary drying, and resolubilized in ultrapure water prior to mixing with the RiboGreen reagent and fluorometric analysis. Recovered samples were compared to the frozen stock solution of mRNA (−80° C.). Duplicate assay reads were performed for every sample. Absolute quantitation was performed against standard curve generated by ribosomal RNA (provided by manufacturer) and data represents the average of N=3 samples±st dev.

Following these results, it was sought to improve the efficiency of RNA recovery, e.g., by manipulating the solution storage conditions. It was speculated that RNAse was present at low quantities in the silk solution and mRNA recovered in all conditions was susceptible to degradation after recovery during assay preparation, so a SUPERase.In™ RNase Inhibitor (tools.invitrogen.com/content/sfs/manuals/sp_2694.pdf) at a working concentration of 1 U/µL was included in the assay and results are shown in FIG. 28. Compared to the previous assay run using silk/TE alone (FIG. 27), the presence of the inhibitor markedly improved the recovery of mRNA as compared to the −80° C. storage condition. Additionally, the interference of the silk component was minimized, as values for the 1% and 0.5% groups were comparable to the non-silk 0% group.

Figure 29:
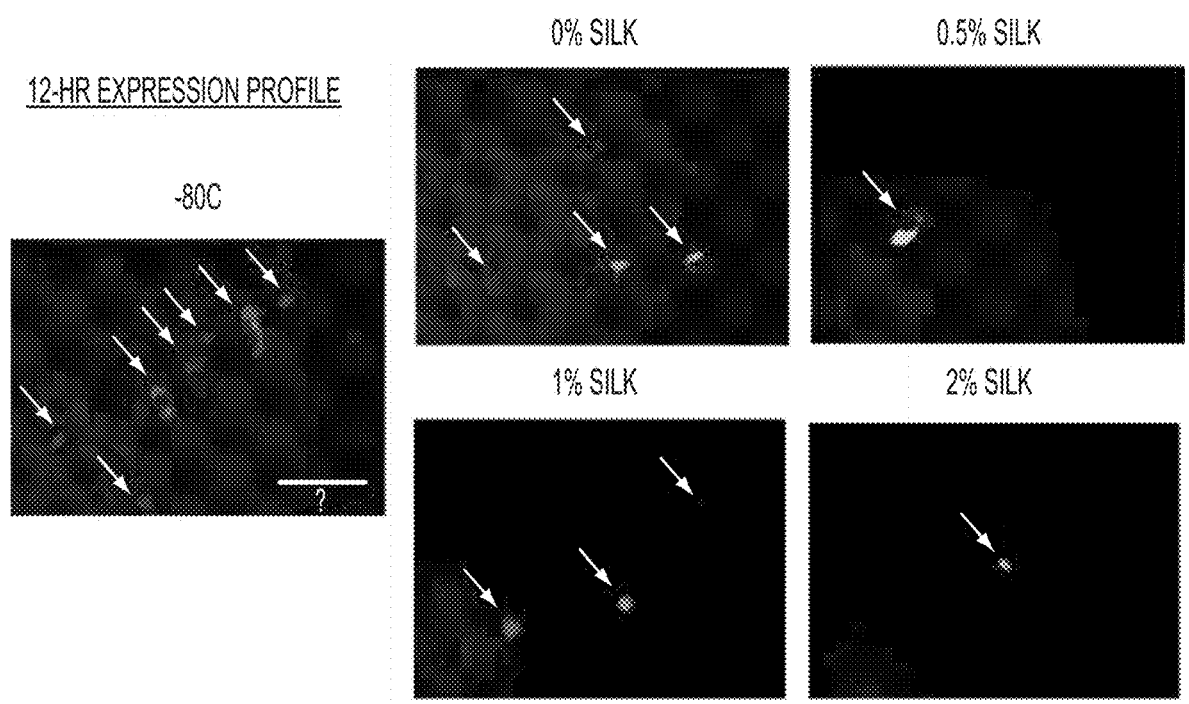
FIG. 29 is a set of fluorescent images showing fibroblast transfection using frozen and recovered mRNA with the Stemfect™ Transfection Kit. Silk solutions used for FIG. 28 were also mixed with the reagents of the Stemfect™ Transfection Kit. The Transfection Reagent was combined with either the frozen stock (−80° C.) or recovered mRNA, and added to the cells for a 12-hr treatment prior to fluorescence imaging with GFP filters. White arrows indicate positive GFP expression.
Figure 30B:
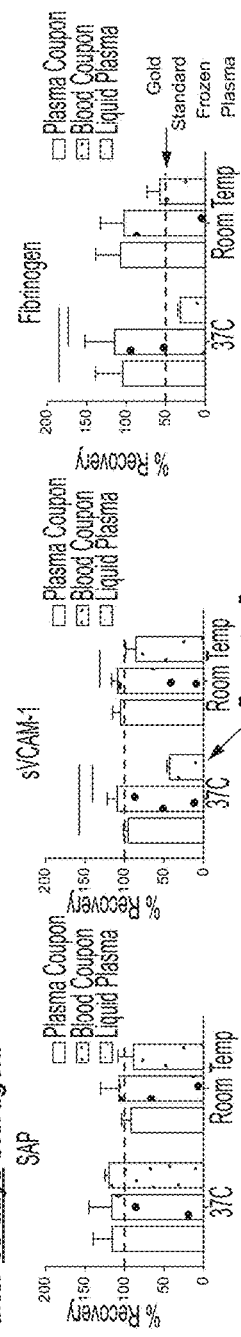
Figure 30B:
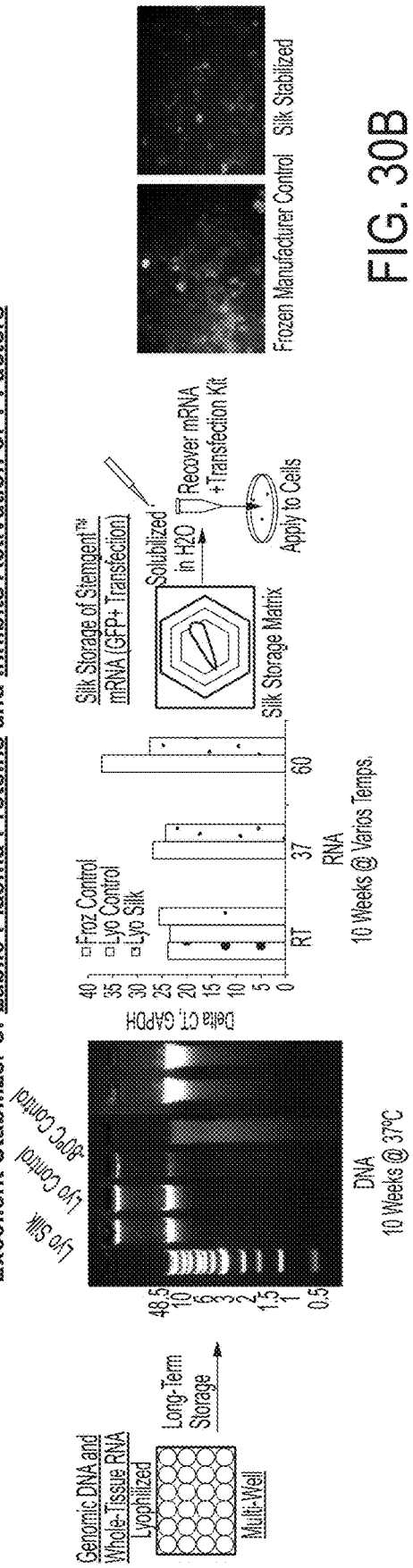

As shown below in FIG. 29, cells in every media condition containing the transfection reagent and mRNA, including frozen stocks (−80° C. storage) and all recovered silk groups, induced GFP expression by the 293 fibroblasts by 12 hours of incubation. It was also found that the −80° C. group produced more widespread expression patterns to the cell colonies in the inoculated wells, likely due to the dose-dependent nature of mRNA-based transfection and the limited dilution of the −80° C. stock. It is likely that the recovered mRNA from the silk groups (0-2%) were at the minimum titer necessary to observe a positive transfection result.

While the recovery of the RNA from the lyophilized silk solutions in this Example was sufficient for the purposes of transfection, the absolute levels were less than the frozen controls. However, the formulation of silk and/or methods of silk processing can be optimized to increase the recovery of RNA from the lyophilized silk solutions. For example, the pre-solubilization cocoon boiling time can be modified to select the most soluble solution sub-type. FIG. 17 indicates that 60 minutes of boiling or more can be used for recovery of RNA from lyophilized silk solutions with improved resolubility.

CERTAIN REFERENCES

Altman, G. H., Diaz, F., Jakuba, C., Calabro, T., Horan, R. L., Chen, J., Lu, H., Richmond, J., and Kaplan, D. L. (2003). Silk-based biomaterials. Biomaterials 24, 401-416.

Andreotti, M., Pirillo, M., Guidotti, G., Ceffa, S., Paturzo, G., Germano, P., Luhanga, R., Chimwaza, D., Mancini, M. G., Marazzi, M. C., et al. (2010). Correlation between HIV-1 viral load quantification in plasma, dried blood spots, and dried plasma spots using the Roche COBAS Taqman assay. Journal of clinical virology: the official publication of the Pan American Society for Clinical Virology 47, 4-7.

Chang, M. K., Binder, C. J., Torzewski, M., and Witztum, J. L. (2002). C-reactive protein binds to both oxidized LDL and apoptotic cells through recognition of a common ligand: Phosphorylcholine of oxidized phospholipids. Proceedings of the National Academy of Sciences of the United States of America 99, 13043-13048.

Dineva, M. A., MahiLum-Tapay, L., and Lee, H. (2007). Sample preparation: a challenge in the development of point-of-care nucleic acid-based assays for resource-limited settings. The Analyst 132, 1193-1199.

Guthrie, R., and Susi, A. (1963). A SIMPLE PHENYLALANINE METHOD FOR DETECTING PHENYLKETONURIA IN LARGE POPULATIONS OF NEWBORN INFANTS. Pediatrics 32, 338-343.

Guziewicz, N., Best, A., Perez-Ramirez, B., and Kaplan, D. L. (2011). Lyophilized silk fibroin hydrogels for the sustained local delivery of therapeutic monoclonal antibodies. Biomaterials 32, 2642-2650.

Lu, Q., Wang, X., Hu, X., Cebe, P., Omenetto, F., and Kaplan, D. L. (2010). Stabilization and release of enzymes from silk films. Macromol Biosci 10, 359-368.

Martinez-Subiela, S., and Ceron, J. J. (2005). Effects of hemolysis, lipemia, hyperbilirrubinemia, and anticoagulants in canine C-reactive protein, serum amyloid A, and ceruloplasmin assays. Can Vet J 46, 625-629.

Mei, J. V., Alexander, J. R., Adam, B. W., and Hannon, W. H. (2001). Use of filter paper for the collection and analysis of human whole blood specimens. The Journal of nutrition 131, 1631S-1636S.

Palmer, D. S., Rosborough, D., Perkins, H., Bolton, T., Rock, G., and Ganz, P. R. (1993). Characterization of factors affecting the stability of frozen heparinized plasma. Vox sanguinis 65, 258-270.

Pritchard, E. M., Hu, X., Finley, V., Kuo, C. K., and Kaplan, D. L. (2013). Effect of Silk Protein Processing on Drug Delivery from Silk Films. Macromolecular bioscience.

Puren, A., Gerlach, J. L., Weigl, B. H., Kelso, D. M., and Domingo, G. J. (2010). Laboratory operations, specimen processing, and handling for viral load testing and surveillance. The Journal of infectious diseases 201 Suppl 1, S27-36.

Scott, C. T., Caulfield, T., Borgelt, E., and Illes, J. (2012). Personal medicine—the new banking crisis. Nature biotechnology 30, 141-147.

Vepari, C., and Kaplan, D. L. (2007). Silk as a biomaterial. Prog Polym Sci 32, 991.

Warren, L., Manos, P. D., Ahfeldt, T., Loh, Y.-H., Li, H., Lau, F., Ebina, W., Mandal, P. K., Smith, Z. D., Meissner, A., et al. (2010). Highly Efficient Reprogramming to Pluripotency and Directed Differentiation of Human Cells with Synthetic Modified mRNA. Cell Stem Cell 7, 618630.

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

EQUIVALENTS

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

What is claimed is:

1. A composition comprising
    a population of silk fibroin fragments;
    wherein between 5% and 35% of silk fibroin fragments in the population has a molecular weight between 120 kDa and 200 kDa, and
    wherein at least 50% by weight of the silk fibroin fragments have a molecular weight within the range of 3.5 to 120 kDa; wherein the composition is lyophilized and the silk fibroin fragments of the lyophilized composition are soluble in an aqueous solution.

2. The composition of claim 1, further comprising at least one additive.

3. The composition of claim 2, wherein the ratio of silk fibroin fragments to the additive is between 1:1 and 1:10000, inclusive.

4. The composition of claim 2, wherein the additive comprises at least 5% wt of the composition.

5. The composition of claim 1, wherein the composition comprises between about 0.1% to 90% silk fibroin by weight.

6. The composition of claim 1, wherein at least 50% by weight of the silk fibroin fragments have a molecular weight within the range of about 19 kDa to 50 kDa.

7. The composition of claim 2, wherein the composition is characterized in that the at least one additive is shelf stable for at least 1 month.

8. The composition of claim 2, wherein the composition is characterized in that at least one property of the at least one additive is stabilized for at least one week.

9. The composition of claim 1, wherein the silk fibroin fragments have a continuous molecular weight distribution within the range of about 3.5 to about 120 kDa.

10. The composition of claim 1, wherein the silk fibroin fragments have a discrete molecular weight distribution within the range of about 3.5 to about 120 kDa.

11. The composition of claim 2, wherein the at least one additive is selected from the group consisting of small organic or inorganic molecules, saccharides, oligosaccharides, polysaccharides, polymers, proteins, peptides, peptide analogs, peptide derivatives, peptidomimetics, nucleic acids, nucleic acid analogs, and combinations thereof.

12. The composition of claim 2, wherein the additive is or comprises an immunogen, cell attachment mediator, stabilizer, biocompatible polymer, growth factor, anti-inflammatory agent, antimicrobial agent, a vaccine, biological sample, or combination thereof.

13. The composition of claim 12, wherein the cell attachment mediator is selected from the group consisting of collagen, elastin, fibronectin, vitronectin, laminin, proteoglycans, a peptide comprising a known integrin binding domain, and combinations thereof.

14. The composition of claim 12, wherein the biological sample is selected from the group consisting of tissue, blood, plasma, serum, urine, cerebrospinal fluid, saliva, hormones, growth factors, cytokines, antibodies, and any combination thereof.

15. The composition of claim 1, further comprising at least one additional material for soft tissue augmentation.

16. The composition of claim 15, wherein the at least one additional material for soft tissue augmentation is or comprises at least one of poly(methyl methacrylate), microspheres, hydroxyapatite, poly(L-lactic acid), collagen, elastin, a glycosaminoglycan, hyaluronic acid, BOTOX®, DYSPORT®, COSMODERM®, EVOLENCE®, RADIESSE®, RESTYLANE®, JUVEDERM®, SCULPTRA®, PERLANE®, CAPTIQUE®, and combinations thereof.

17. The composition of claim 1, wherein the composition has a solubility of at least 5% in an aqueous solution.

18. The composition of claim 1, wherein the composition can be resolubilized in an aqueous solution at room temperature.

19. The composition of claim 1, wherein the composition does not comprise silk fibroin particles.

20. The composition of claim 1, wherein the composition comprises a beta sheet content less than about 20%.

21. The composition of claim 1, wherein at least 50% by weight of the silk fibroin fragments have a molecular weight within the range of about 55 kDa to 120 kDa.

* * * * *

```
                        SEQUENCE LISTING

<160> NUMBER OF SEQ ID NOS: 24

<210> SEQ ID NO 1
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(90)
<223> OTHER INFORMATION: This sequence may encompass 5-15 'Gly Ala Gly
      Ala Gly Ser' repeating units, wherein some positions may be absent
<220> FEATURE:
<223> OTHER INFORMATION: See specification as filed for detailed
      description of substitutions and preferred embodiments

<400> SEQUENCE: 1

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
            20                  25                  30

Gly Ala Gly Ser Gly Ala Gly Ala Gly Ser Gly Ala Gly Ala Gly Ser
        35                  40                  45

Gly Ala Gly Ala Gly Ser Gly Ala Gly Ala Gly Ser Gly Ala Gly Ala
    50                  55                  60

Gly Ser Gly Ala Gly Ala Gly Ser Gly Ala Gly Ala Gly Ser Gly Ala
65                  70                  75                  80

Gly Ala Gly Ser Gly Ala Gly Ala Gly Ser
                85                  90

<210> SEQ ID NO 2
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Val, Ile or Ala
<220> FEATURE:
<221> NAME/KEY: MOD_RES
<222> LOCATION: (4)..(4)
```

```
<223> OTHER INFORMATION: Val, Ile or Ala
<220> FEATURE:
<221> NAME/KEY: MOD_RES
<222> LOCATION: (6)..(6)
<223> OTHER INFORMATION: Val, Ile or Ala
<220> FEATURE:
<221> NAME/KEY: MOD_RES
<222> LOCATION: (8)..(8)
<223> OTHER INFORMATION: Val, Ile or Ala
<220> FEATURE:
<221> NAME/KEY: MOD_RES
<222> LOCATION: (10)..(10)
<223> OTHER INFORMATION: Val, Ile or Ala
<220> FEATURE:
<221> NAME/KEY: MOD_RES
<222> LOCATION: (12)..(12)
<223> OTHER INFORMATION: Val, Ile or Ala
<220> FEATURE:
<221> NAME/KEY: MOD_RES
<222> LOCATION: (14)..(14)
<223> OTHER INFORMATION: Val, Ile or Ala
<220> FEATURE:
<221> NAME/KEY: MOD_RES
<222> LOCATION: (16)..(16)
<223> OTHER INFORMATION: Val, Ile or Ala
<220> FEATURE:
<221> NAME/KEY: MOD_RES
<222> LOCATION: (18)..(18)
<223> OTHER INFORMATION: Val, Ile or Ala
<220> FEATURE:
<221> NAME/KEY: MOD_RES
<222> LOCATION: (20)..(20)
<223> OTHER INFORMATION: Val, Ile or Ala
<220> FEATURE:
<221> NAME/KEY: MOD_RES
<222> LOCATION: (22)..(22)
<223> OTHER INFORMATION: Val, Ile or Ala
<220> FEATURE:
<221> NAME/KEY: MOD_RES
<222> LOCATION: (24)..(24)
<223> OTHER INFORMATION: Val, Ile or Ala
<220> FEATURE:
<221> NAME/KEY: MOD_RES
<222> LOCATION: (26)..(26)
<223> OTHER INFORMATION: Val, Ile or Ala
<220> FEATURE:
<221> NAME/KEY: MOD_RES
<222> LOCATION: (28)..(28)
<223> OTHER INFORMATION: Val, Ile or Ala
<220> FEATURE:
<221> NAME/KEY: MOD_RES
<222> LOCATION: (30)..(30)
<223> OTHER INFORMATION: Val, Ile or Ala
<220> FEATURE:
<221> NAME/KEY: MISC_FEATURE
<222> LOCATION: (1)..(30)
<223> OTHER INFORMATION: This sequence may encompass 5-15 'Gly Xaa'
      repeating units, wherein some positions may
      be absent
<220> FEATURE:
<223> OTHER INFORMATION: See specification as filed for detailed
      description of substitutions and preferred embodiments

<400> SEQUENCE: 2

Gly Xaa Gly Xaa Gly Xaa Gly Xaa Gly Xaa Gly Xaa Gly Xaa Gly Xaa
1               5                   10                  15

Gly Xaa Gly Xaa Gly Xaa Gly Xaa Gly Xaa Gly Xaa Gly Xaa
            20                  25                  30

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 3

Gly Ala Ala Ser
1

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: May or may not be present
<220> FEATURE:
<221> NAME/KEY: MOD_RES
<222> LOCATION: (14)..(15)
<223> OTHER INFORMATION: May or may not be present

<400> SEQUENCE: 4

Ser Ser Ala Ala Ala Ala Ala Ala Ala Ala Ala Ala Ala
1               5                   10                  15

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(5)
<223> OTHER INFORMATION: Any amino acid and this region may encompass
      1-4 residues, wherein some positions may be absent
<220> FEATURE:
<221> NAME/KEY: MOD_RES
<222> LOCATION: (8)..(8)
<223> OTHER INFORMATION: Any amino acid

<400> SEQUENCE: 5

Gly Xaa Xaa Xaa Xaa Gly Gly Xaa
1               5

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ala, Ser, Tyr, Arg, Asp, Val or Trp

<400> SEQUENCE: 6

Gly Gly Gly Xaa
1

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (2)..(2)
<223> OTHER INFORMATION: May or may not be present
<220> FEATURE:
<221> NAME/KEY: MOD_RES
<222> LOCATION: (3)..(6)
<223> OTHER INFORMATION: May or may not be present
<220> FEATURE:
<221> NAME/KEY: MOD_RES
<222> LOCATION: (8)..(8)
<223> OTHER INFORMATION: May or may not be present
<220> FEATURE:
<221> NAME/KEY: MOD_RES
<222> LOCATION: (10)..(12)
<223> OTHER INFORMATION: May or may not be present
<220> FEATURE:
<221> NAME/KEY: MISC_FEATURE
<222> LOCATION: (1)..(12)
<223> OTHER INFORMATION: This sequence may encompass 1-2 '(Ser)1-2
      (Ala)1-4' repeating units, wherein some positions may be absent
<220> FEATURE:
<223> OTHER INFORMATION: See specification as filed for detailed
      description of substitutions and preferred embodiments

<400> SEQUENCE: 7

Ser Ser Ala Ala Ala Ala Ser Ser Ala Ala Ala Ala
1               5                   10

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Leu Gly Gly Leu Gly
1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Leu, Ile, Val or Pro
<220> FEATURE:
<221> NAME/KEY: MOD_RES
<222> LOCATION: (5)..(5)
<223> OTHER INFORMATION: Leu, Ile, Val or Pro

<400> SEQUENCE: 9

Gly Xaa Gly Gly Xaa Gly
1               5

<210> SEQ ID NO 10
<211> LENGTH: 300
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (3)..(14)
<223> OTHER INFORMATION: This region may encompass 1-4 'Gly Gly Xaa'
      repeating units, wherein some positions may be absent
<220> FEATURE:
<221> NAME/KEY: MOD_RES
```

-continued

```
<222> LOCATION: (5)..(5)
<223> OTHER INFORMATION: Tyr, Val, Ser or Ala
<220> FEATURE:
<221> NAME/KEY: MOD_RES
<222> LOCATION: (8)..(8)
<223> OTHER INFORMATION: Tyr, Val, Ser or Ala
<220> FEATURE:
<221> NAME/KEY: MOD_RES
<222> LOCATION: (11)..(11)
<223> OTHER INFORMATION: Tyr, Val, Ser or Ala
<220> FEATURE:
<221> NAME/KEY: MOD_RES
<222> LOCATION: (14)..(14)
<223> OTHER INFORMATION: Tyr, Val, Ser or Ala
<220> FEATURE:
<221> NAME/KEY: MISC_FEATURE
<222> LOCATION: (18)..(29)
<223> OTHER INFORMATION: This region may encompass 1-4 'Gly Gly Xaa'
      repeating units, wherein some positions may be absent
<220> FEATURE:
<221> NAME/KEY: MOD_RES
<222> LOCATION: (20)..(20)
<223> OTHER INFORMATION: Tyr, Val, Ser or Ala
<220> FEATURE:
<221> NAME/KEY: MOD_RES
<222> LOCATION: (23)..(23)
<223> OTHER INFORMATION: Tyr, Val, Ser or Ala
<220> FEATURE:
<221> NAME/KEY: MOD_RES
<222> LOCATION: (26)..(26)
<223> OTHER INFORMATION: Tyr, Val, Ser or Ala
<220> FEATURE:
<221> NAME/KEY: MOD_RES
<222> LOCATION: (29)..(29)
<223> OTHER INFORMATION: Tyr, Val, Ser or Ala
<220> FEATURE:
<221> NAME/KEY: MISC_FEATURE
<222> LOCATION: (33)..(44)
<223> OTHER INFORMATION: This region may encompass 1-4 'Gly Gly Xaa'
      repeating units, wherein some positions may be absent
<220> FEATURE:
<221> NAME/KEY: MOD_RES
<222> LOCATION: (35)..(35)
<223> OTHER INFORMATION: Tyr, Val, Ser or Ala
<220> FEATURE:
<221> NAME/KEY: MOD_RES
<222> LOCATION: (38)..(38)
<223> OTHER INFORMATION: Tyr, Val, Ser or Ala
<220> FEATURE:
<221> NAME/KEY: MOD_RES
<222> LOCATION: (41)..(41)
<223> OTHER INFORMATION: Tyr, Val, Ser or Ala
<220> FEATURE:
<221> NAME/KEY: MOD_RES
<222> LOCATION: (44)..(44)
<223> OTHER INFORMATION: Tyr, Val, Ser or Ala
<220> FEATURE:
<221> NAME/KEY: MISC_FEATURE
<222> LOCATION: (48)..(59)
<223> OTHER INFORMATION: This region may encompass 1-4 'Gly Gly Xaa'
      repeating units, wherein some positions may be absent
<220> FEATURE:
<221> NAME/KEY: MOD_RES
<222> LOCATION: (50)..(50)
<223> OTHER INFORMATION: Tyr, Val, Ser or Ala
<220> FEATURE:
<221> NAME/KEY: MOD_RES
<222> LOCATION: (53)..(53)
<223> OTHER INFORMATION: Tyr, Val, Ser or Ala
<220> FEATURE:
<221> NAME/KEY: MOD_RES
<222> LOCATION: (56)..(56)
<223> OTHER INFORMATION: Tyr, Val, Ser or Ala
<220> FEATURE:
<221> NAME/KEY: MOD_RES
<222> LOCATION: (59)..(59)
<223> OTHER INFORMATION: Tyr, Val, Ser or Ala
<220> FEATURE:
<221> NAME/KEY: MISC_FEATURE
```

```
<222> LOCATION: (63)..(74)
<223> OTHER INFORMATION: This region may encompass 1-4 'Gly Gly Xaa'
      repeating units, wherein some positions may be absent
<220> FEATURE:
<221> NAME/KEY: MOD_RES
<222> LOCATION: (65)..(65)
<223> OTHER INFORMATION: Tyr, Val, Ser or Ala
<220> FEATURE:
<221> NAME/KEY: MOD_RES
<222> LOCATION: (68)..(68)
<223> OTHER INFORMATION: Tyr, Val, Ser or Ala
<220> FEATURE:
<221> NAME/KEY: MOD_RES
<222> LOCATION: (71)..(71)
<223> OTHER INFORMATION: Tyr, Val, Ser or Ala
<220> FEATURE:
<221> NAME/KEY: MOD_RES
<222> LOCATION: (74)..(74)
<223> OTHER INFORMATION: Tyr, Val, Ser or Ala
<220> FEATURE:
<221> NAME/KEY: MISC_FEATURE
<222> LOCATION: (78)..(89)
<223> OTHER INFORMATION: This region may encompass 1-4 'Gly Gly Xaa'
      repeating units, wherein some positions may be absent
<220> FEATURE:
<221> NAME/KEY: MOD_RES
<222> LOCATION: (80)..(80)
<223> OTHER INFORMATION: Tyr, Val, Ser or Ala
<220> FEATURE:
<221> NAME/KEY: MOD_RES
<222> LOCATION: (83)..(83)
<223> OTHER INFORMATION: Tyr, Val, Ser or Ala
<220> FEATURE:
<221> NAME/KEY: MOD_RES
<222> LOCATION: (86)..(86)
<223> OTHER INFORMATION: Tyr, Val, Ser or Ala
<220> FEATURE:
<221> NAME/KEY: MOD_RES
<222> LOCATION: (89)..(89)
<223> OTHER INFORMATION: Tyr, Val, Ser or Ala
<220> FEATURE:
<221> NAME/KEY: MISC_FEATURE
<222> LOCATION: (93)..(104)
<223> OTHER INFORMATION: This region may encompass 1-4 'Gly Gly Xaa'
      repeating units, wherein some positions may be absent
<220> FEATURE:
<221> NAME/KEY: MOD_RES
<222> LOCATION: (95)..(95)
<223> OTHER INFORMATION: Tyr, Val, Ser or Ala
<220> FEATURE:
<221> NAME/KEY: MOD_RES
<222> LOCATION: (98)..(98)
<223> OTHER INFORMATION: Tyr, Val, Ser or Ala
<220> FEATURE:
<221> NAME/KEY: MOD_RES
<222> LOCATION: (101)..(101)
<223> OTHER INFORMATION: Tyr, Val, Ser or Ala
<220> FEATURE:
<221> NAME/KEY: MOD_RES
<222> LOCATION: (104)..(104)
<223> OTHER INFORMATION: Tyr, Val, Ser or Ala
<220> FEATURE:
<221> NAME/KEY: MISC_FEATURE
<222> LOCATION: (108)..(119)
<223> OTHER INFORMATION: This region may encompass 1-4 'Gly Gly Xaa'
      repeating units, wherein some positions may be absent
<220> FEATURE:
<221> NAME/KEY: MOD_RES
<222> LOCATION: (110)..(110)
<223> OTHER INFORMATION: Tyr, Val, Ser or Ala
<220> FEATURE:
<221> NAME/KEY: MOD_RES
<222> LOCATION: (113)..(113)
<223> OTHER INFORMATION: Tyr, Val, Ser or Ala
<220> FEATURE:
<221> NAME/KEY: MOD_RES
<222> LOCATION: (116)..(116)
<223> OTHER INFORMATION: Tyr, Val, Ser or Ala
<220> FEATURE:
```

```
<221> NAME/KEY: MOD_RES
<222> LOCATION: (119)..(119)
<223> OTHER INFORMATION: Tyr, Val, Ser or Ala
<220> FEATURE:
<221> NAME/KEY: MISC_FEATURE
<222> LOCATION: (123)..(134)
<223> OTHER INFORMATION: This region may encompass 1-4 'Gly Gly Xaa'
      repeating units, wherein some positions may be absent
<220> FEATURE:
<221> NAME/KEY: MOD_RES
<222> LOCATION: (125)..(125)
<223> OTHER INFORMATION: Tyr, Val, Ser or Ala
<220> FEATURE:
<221> NAME/KEY: MOD_RES
<222> LOCATION: (128)..(128)
<223> OTHER INFORMATION: Tyr, Val, Ser or Ala
<220> FEATURE:
<221> NAME/KEY: MOD_RES
<222> LOCATION: (131)..(131)
<223> OTHER INFORMATION: Tyr, Val, Ser or Ala
<220> FEATURE:
<221> NAME/KEY: MOD_RES
<222> LOCATION: (134)..(134)
<223> OTHER INFORMATION: Tyr, Val, Ser or Ala
<220> FEATURE:
<221> NAME/KEY: MISC_FEATURE
<222> LOCATION: (138)..(149)
<223> OTHER INFORMATION: This region may encompass 1-4 'Gly Gly Xaa'
      repeating units, wherein some positions may be absent
<220> FEATURE:
<221> NAME/KEY: MOD_RES
<222> LOCATION: (140)..(140)
<223> OTHER INFORMATION: Tyr, Val, Ser or Ala
<220> FEATURE:
<221> NAME/KEY: MOD_RES
<222> LOCATION: (143)..(143)
<223> OTHER INFORMATION: Tyr, Val, Ser or Ala
<220> FEATURE:
<221> NAME/KEY: MOD_RES
<222> LOCATION: (146)..(146)
<223> OTHER INFORMATION: Tyr, Val, Ser or Ala
<220> FEATURE:
<221> NAME/KEY: MOD_RES
<222> LOCATION: (149)..(149)
<223> OTHER INFORMATION: Tyr, Val, Ser or Ala
<220> FEATURE:
<221> NAME/KEY: MISC_FEATURE
<222> LOCATION: (153)..(164)
<223> OTHER INFORMATION: This region may encompass 1-4 'Gly Gly Xaa'
      repeating units, wherein some positions may be absent
<220> FEATURE:
<221> NAME/KEY: MOD_RES
<222> LOCATION: (155)..(155)
<223> OTHER INFORMATION: Tyr, Val, Ser or Ala
<220> FEATURE:
<221> NAME/KEY: MOD_RES
<222> LOCATION: (158)..(158)
<223> OTHER INFORMATION: Tyr, Val, Ser or Ala
<220> FEATURE:
<221> NAME/KEY: MOD_RES
<222> LOCATION: (161)..(161)
<223> OTHER INFORMATION: Tyr, Val, Ser or Ala
<220> FEATURE:
<221> NAME/KEY: MOD_RES
<222> LOCATION: (164)..(164)
<223> OTHER INFORMATION: Tyr, Val, Ser or Ala
<220> FEATURE:
<221> NAME/KEY: MISC_FEATURE
<222> LOCATION: (168)..(179)
<223> OTHER INFORMATION: This region may encompass 1-4 'Gly Gly Xaa'
      repeating units, wherein some positions may be absent
<220> FEATURE:
<221> NAME/KEY: MOD_RES
<222> LOCATION: (170)..(170)
<223> OTHER INFORMATION: Tyr, Val, Ser or Ala
<220> FEATURE:
<221> NAME/KEY: MOD_RES
<222> LOCATION: (173)..(173)
<223> OTHER INFORMATION: Tyr, Val, Ser or Ala
```

```
<220> FEATURE:
<221> NAME/KEY: MOD_RES
<222> LOCATION: (176)..(176)
<223> OTHER INFORMATION: Tyr, Val, Ser or Ala
<220> FEATURE:
<221> NAME/KEY: MOD_RES
<222> LOCATION: (179)..(179)
<223> OTHER INFORMATION: Tyr, Val, Ser or Ala
<220> FEATURE:
<221> NAME/KEY: MISC_FEATURE
<222> LOCATION: (183)..(194)
<223> OTHER INFORMATION: This region may encompass 1-4 'Gly Gly Xaa'
      repeating units, wherein some positions may be absent
<220> FEATURE:
<221> NAME/KEY: MOD_RES
<222> LOCATION: (185)..(185)
<223> OTHER INFORMATION: Tyr, Val, Ser or Ala
<220> FEATURE:
<221> NAME/KEY: MOD_RES
<222> LOCATION: (188)..(188)
<223> OTHER INFORMATION: Tyr, Val, Ser or Ala
<220> FEATURE:
<221> NAME/KEY: MOD_RES
<222> LOCATION: (191)..(191)
<223> OTHER INFORMATION: Tyr, Val, Ser or Ala
<220> FEATURE:
<221> NAME/KEY: MOD_RES
<222> LOCATION: (194)..(194)
<223> OTHER INFORMATION: Tyr, Val, Ser or Ala
<220> FEATURE:
<221> NAME/KEY: MISC_FEATURE
<222> LOCATION: (198)..(209)
<223> OTHER INFORMATION: This region may encompass 1-4 'Gly Gly Xaa'
      repeating units, wherein some positions may be absent
<220> FEATURE:
<221> NAME/KEY: MOD_RES
<222> LOCATION: (200)..(200)
<223> OTHER INFORMATION: Tyr, Val, Ser or Ala
<220> FEATURE:
<221> NAME/KEY: MOD_RES
<222> LOCATION: (203)..(203)
<223> OTHER INFORMATION: Tyr, Val, Ser or Ala
<220> FEATURE:
<221> NAME/KEY: MOD_RES
<222> LOCATION: (206)..(206)
<223> OTHER INFORMATION: Tyr, Val, Ser or Ala
<220> FEATURE:
<221> NAME/KEY: MOD_RES
<222> LOCATION: (209)..(209)
<223> OTHER INFORMATION: Tyr, Val, Ser or Ala
<220> FEATURE:
<221> NAME/KEY: MISC_FEATURE
<222> LOCATION: (213)..(224)
<223> OTHER INFORMATION: This region may encompass 1-4 'Gly Gly Xaa'
      repeating units, wherein some positions may be absent
<220> FEATURE:
<221> NAME/KEY: MOD_RES
<222> LOCATION: (215)..(215)
<223> OTHER INFORMATION: Tyr, Val, Ser or Ala
<220> FEATURE:
<221> NAME/KEY: MOD_RES
<222> LOCATION: (218)..(218)
<223> OTHER INFORMATION: Tyr, Val, Ser or Ala
<220> FEATURE:
<221> NAME/KEY: MOD_RES
<222> LOCATION: (221)..(221)
<223> OTHER INFORMATION: Tyr, Val, Ser or Ala
<220> FEATURE:
<221> NAME/KEY: MOD_RES
<222> LOCATION: (224)..(224)
<223> OTHER INFORMATION: Tyr, Val, Ser or Ala
<220> FEATURE:
<221> NAME/KEY: MISC_FEATURE
<222> LOCATION: (228)..(239)
<223> OTHER INFORMATION: This region may encompass 1-4 'Gly Gly Xaa'
      repeating units, wherein some positions may be absent
<220> FEATURE:
<221> NAME/KEY: MOD_RES
<222> LOCATION: (230)..(230)
```

```
<223> OTHER INFORMATION: Tyr, Val, Ser or Ala
<220> FEATURE:
<221> NAME/KEY: MOD_RES
<222> LOCATION: (233)..(233)
<223> OTHER INFORMATION: Tyr, Val, Ser or Ala
<220> FEATURE:
<221> NAME/KEY: MOD_RES
<222> LOCATION: (236)..(236)
<223> OTHER INFORMATION: Tyr, Val, Ser or Ala
<220> FEATURE:
<221> NAME/KEY: MOD_RES
<222> LOCATION: (239)..(239)
<223> OTHER INFORMATION: Tyr, Val, Ser or Ala
<220> FEATURE:
<221> NAME/KEY: MISC_FEATURE
<222> LOCATION: (243)..(254)
<223> OTHER INFORMATION: This region may encompass 1-4 'Gly Gly Xaa'
      repeating units, wherein some positions may be absent
<220> FEATURE:
<221> NAME/KEY: MOD_RES
<222> LOCATION: (245)..(245)
<223> OTHER INFORMATION: Tyr, Val, Ser or Ala
<220> FEATURE:
<221> NAME/KEY: MOD_RES
<222> LOCATION: (248)..(248)
<223> OTHER INFORMATION: Tyr, Val, Ser or Ala
<220> FEATURE:
<221> NAME/KEY: MOD_RES
<222> LOCATION: (251)..(251)
<223> OTHER INFORMATION: Tyr, Val, Ser or Ala
<220> FEATURE:
<221> NAME/KEY: MOD_RES
<222> LOCATION: (254)..(254)
<223> OTHER INFORMATION: Tyr, Val, Ser or Ala
<220> FEATURE:
<221> NAME/KEY: MISC_FEATURE
<222> LOCATION: (258)..(269)
<223> OTHER INFORMATION: This region may encompass 1-4 'Gly Gly Xaa'
      repeating units, wherein some positions may be absent
<220> FEATURE:
<221> NAME/KEY: MOD_RES
<222> LOCATION: (260)..(260)
<223> OTHER INFORMATION: Tyr, Val, Ser or Ala
<220> FEATURE:
<221> NAME/KEY: MOD_RES
<222> LOCATION: (263)..(263)
<223> OTHER INFORMATION: Tyr, Val, Ser or Ala
<220> FEATURE:
<221> NAME/KEY: MOD_RES
<222> LOCATION: (266)..(266)
<223> OTHER INFORMATION: Tyr, Val, Ser or Ala
<220> FEATURE:
<221> NAME/KEY: MOD_RES
<222> LOCATION: (269)..(269)
<223> OTHER INFORMATION: Tyr, Val, Ser or Ala
<220> FEATURE:
<221> NAME/KEY: MISC_FEATURE
<222> LOCATION: (273)..(284)
<223> OTHER INFORMATION: This region may encompass 1-4 'Gly Gly Xaa'
      repeating units, wherein some positions may be absent
<220> FEATURE:
<221> NAME/KEY: MOD_RES
<222> LOCATION: (275)..(275)
<223> OTHER INFORMATION: Tyr, Val, Ser or Ala
<220> FEATURE:
<221> NAME/KEY: MOD_RES
<222> LOCATION: (278)..(278)
<223> OTHER INFORMATION: Tyr, Val, Ser or Ala
<220> FEATURE:
<221> NAME/KEY: MOD_RES
<222> LOCATION: (281)..(281)
<223> OTHER INFORMATION: Tyr, Val, Ser or Ala
<220> FEATURE:
<221> NAME/KEY: MOD_RES
<222> LOCATION: (284)..(284)
<223> OTHER INFORMATION: Tyr, Val, Ser or Ala
<220> FEATURE:
<221> NAME/KEY: MISC_FEATURE
<222> LOCATION: (288)..(299)
```

```
<223> OTHER INFORMATION: This region may encompass 1-4 'Gly Gly Xaa'
      repeating units, wherein some positions may be absent
<220> FEATURE:
<221> NAME/KEY: MOD_RES
<222> LOCATION: (290)..(290)
<223> OTHER INFORMATION: Tyr, Val, Ser or Ala
<220> FEATURE:
<221> NAME/KEY: MOD_RES
<222> LOCATION: (293)..(293)
<223> OTHER INFORMATION: Tyr, Val, Ser or Ala
<220> FEATURE:
<221> NAME/KEY: MOD_RES
<222> LOCATION: (296)..(296)
<223> OTHER INFORMATION: Tyr, Val, Ser or Ala
<220> FEATURE:
<221> NAME/KEY: MOD_RES
<222> LOCATION: (299)..(299)
<223> OTHER INFORMATION: Tyr, Val, Ser or Ala
<220> FEATURE:
<221> NAME/KEY: MISC_FEATURE
<222> LOCATION: (1)..(300)
<223> OTHER INFORMATION: This sequence may encompass 3-20 'Gly Pro (Gly
      Gly Xaa)1-4 Tyr' repeating units, wherein some
      positions may be absent
<220> FEATURE:
<223> OTHER INFORMATION: See specification as filed for detailed
      description of substitutions and preferred embodiments

<400> SEQUENCE: 10

Gly Pro Gly Gly Xaa Gly Gly Xaa Gly Gly Xaa Gly Gly Xaa Tyr Gly
1               5                   10                  15

Pro Gly Gly Xaa Gly Gly Xaa Gly Gly Xaa Gly Gly Xaa Tyr Gly Pro
            20                  25                  30

Gly Gly Xaa Gly Gly Xaa Gly Gly Xaa Gly Gly Xaa Tyr Gly Pro Gly
        35                  40                  45

Gly Xaa Gly Gly Xaa Gly Gly Xaa Gly Gly Xaa Tyr Gly Pro Gly Gly
    50                  55                  60

Xaa Gly Gly Xaa Gly Gly Xaa Gly Gly Xaa Tyr Gly Pro Gly Gly Xaa
65                  70                  75                  80

Gly Gly Xaa Gly Gly Xaa Gly Gly Xaa Tyr Gly Pro Gly Gly Xaa Gly
                85                  90                  95

Gly Xaa Gly Gly Xaa Gly Gly Xaa Tyr Gly Pro Gly Gly Xaa Gly Gly
            100                 105                 110

Xaa Gly Gly Xaa Gly Gly Xaa Tyr Gly Pro Gly Gly Xaa Gly Gly Xaa
        115                 120                 125

Gly Gly Xaa Gly Gly Xaa Tyr Gly Pro Gly Gly Xaa Gly Gly Xaa Gly
    130                 135                 140

Gly Xaa Gly Gly Xaa Tyr Gly Pro Gly Gly Xaa Gly Gly Xaa Gly Gly
145                 150                 155                 160

Xaa Gly Gly Xaa Tyr Gly Pro Gly Gly Xaa Gly Gly Xaa Gly Gly Xaa
                165                 170                 175

Gly Gly Xaa Tyr Gly Pro Gly Gly Xaa Gly Gly Xaa Gly Gly Xaa Gly
            180                 185                 190

Gly Xaa Tyr Gly Pro Gly Gly Xaa Gly Gly Xaa Gly Gly Xaa Gly Gly
        195                 200                 205

Xaa Tyr Gly Pro Gly Gly Xaa Gly Gly Xaa Gly Gly Xaa Gly Gly Xaa
    210                 215                 220

Tyr Gly Pro Gly Gly Xaa Gly Gly Xaa Gly Gly Xaa Gly Gly Xaa Tyr
225                 230                 235                 240

Gly Pro Gly Gly Xaa Gly Gly Xaa Gly Gly Xaa Gly Gly Xaa Tyr Gly
                245                 250                 255

Pro Gly Gly Xaa Gly Gly Xaa Gly Gly Xaa Gly Gly Xaa Tyr Gly Pro
```

```
              260                 265                 270
Gly Gly Xaa Gly Gly Xaa Gly Gly Xaa Gly Gly Xaa Tyr Gly Pro Gly
            275                 280                 285

Gly Xaa Gly Gly Xaa Gly Gly Xaa Gly Gly Xaa Tyr
        290                 295                 300

<210> SEQ ID NO 11
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(24)
<223> OTHER INFORMATION: May or may not be present

<400> SEQUENCE: 11

Gly Arg Gly Gly Ala Ala Ala Ala Ala Ala Ala Ala Ala Ala Ala Ala
1               5                   10                  15

Ala Ala Ala Ala Ala Ala Ala Ala
            20

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: May or may not be present

<400> SEQUENCE: 12

Gly Ala Gly Ala Ala Ala Ala Ala Ala Ala Gly Gly Ala
1               5                   10

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Gln, Tyr, Leu, Ala, Ser or Arg
<220> FEATURE:
<221> NAME/KEY: MOD_RES
<222> LOCATION: (5)..(5)
<223> OTHER INFORMATION: Gln, Tyr, Leu, Ala, Ser or Arg
<220> FEATURE:
<221> NAME/KEY: MOD_RES
<222> LOCATION: (7)..(8)
<223> OTHER INFORMATION: Gln, Tyr, Leu, Ala, Ser or Arg

<400> SEQUENCE: 13

Gly Gly Xaa Gly Xaa Gly Xaa Xaa
1               5

<210> SEQ ID NO 14
<211> LENGTH: 16
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 14

Thr Gly Ser Ser Gly Phe Gly Pro Tyr Val Asn Gly Gly Tyr Ser Gly
1               5                   10                  15

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Tyr Glu Tyr Ala Trp Ser Ser Glu
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Asp Phe Gly Thr Gly Ser
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Arg Ala Gly Tyr Asp Arg
1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Glu Val Ile Val Ile Asp Asp Arg
1               5

<210> SEQ ID NO 19
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Thr Thr Ile Ile Glu Asp Leu Asp Ile Thr Ile Asp Gly Ala Asp Gly
1               5                   10                  15

Pro Ile
```

```
<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Thr Ile Ser Glu Glu Leu Thr Ile
1               5

<210> SEQ ID NO 21

<400> SEQUENCE: 21

000

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(5)
<223> OTHER INFORMATION: Any amino acid

<400> SEQUENCE: 22

Gly Pro Gly Xaa Xaa
1               5

<210> SEQ ID NO 23
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Leu, Tyr or Ile

<400> SEQUENCE: 23

Gly Pro Xaa
1

<210> SEQ ID NO 24
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(22)
<223> OTHER INFORMATION: Ala, Thr, Val or Ser
<220> FEATURE:
<221> NAME/KEY: MISC_FEATURE
<222> LOCATION: (3)..(22)
<223> OTHER INFORMATION: This region may encompass 3-20 residues,
      wherein some positions may be absent
```

```
<400> SEQUENCE: 24

Gly Gly Xaa Xaa Xaa Xaa Xaa Xaa Xaa Xaa Xaa Xaa Xaa Xaa Xaa
1               5                   10                  15

Xaa Xaa Xaa Xaa Xaa Xaa
            20
```